(12) United States Patent
Abdullah et al.

(10) Patent No.: US 9,984,200 B2
(45) Date of Patent: May 29, 2018

(54) MANTLE PHENOTYPE DETECTION IN PALM

(71) Applicant: Malaysian Palm Oil Board, Kajang (MY)

(72) Inventors: Meilina Ong Abdullah, Seremban (MY); Ooi Siew Eng, Kuala Lumpur (MY); Leslie Low Eng Ti, Kuala Lumpur (MY); Rajinder Singh, Kuala Lumpur (MY); Rajanaidu Nookiah, Kuala Lumpur (MY); Ravigadevi Sambanthamurthi, Selangor (MY); Nan Jiang, St. Louis, MO (US); Steven W. Smith, Fitchburg, WI (US); Nathan D. Lakey, Chesterfield, MO (US); Rob Martienssen, Cold Spring Harbor, NY (US); Jared Ordway, St. Louis, MO (US); Michael Hogan, Ballwin, MO (US)

(73) Assignee: MALAYSIAN PALM OIL BOARD, Kajang (MY)

( * ) Notice: Subject to any disclaimer, the term of this patent is extended or adjusted under 35 U.S.C. 154(b) by 211 days.

(21) Appl. No.: 14/701,425

(22) Filed: Apr. 30, 2015

(65) Prior Publication Data

US 2015/0315662 A1 Nov. 5, 2015

Related U.S. Application Data

(60) Provisional application No. 61/988,132, filed on May 2, 2014, provisional application No. 62/091,471, filed on Dec. 12, 2014.

(51) Int. Cl.
| | |
|---|---|
| *A01H 1/04* | (2006.01) |
| *C12Q 1/68* | (2018.01) |
| *C12N 15/29* | (2006.01) |
| *G06F 19/22* | (2011.01) |
| *C12N 15/113* | (2010.01) |
| *G06F 19/18* | (2011.01) |

(52) U.S. Cl.
CPC ............ *G06F 19/22* (2013.01); *C12N 15/113* (2013.01); *C12Q 1/6895* (2013.01); *C12N 2310/14* (2013.01); *C12Q 2537/164* (2013.01); *C12Q 2600/13* (2013.01); *C12Q 2600/154* (2013.01); *C12Q 2600/158* (2013.01); *C12Q 2600/16* (2013.01); *G06F 19/18* (2013.01)

(58) Field of Classification Search
None
See application file for complete search history.

(56) References Cited

U.S. PATENT DOCUMENTS

| | | |
|---|---|---|
| 4,910,146 A | 3/1990 | Tur-Kaspa et al. |
| 5,786,146 A | 7/1998 | Herman et al. |
| 5,972,602 A | 10/1999 | Hyland et al. |
| 6,033,854 A | 3/2000 | Kurnit et al. |
| 6,180,349 B1 | 1/2001 | Ginzinger et al. |
| 6,307,123 B1 | 10/2001 | Kriz et al. |
| 6,646,264 B1 | 11/2003 | Modiano et al. |
| 6,673,595 B2 | 1/2004 | Barbera-Guillem |
| 6,880,771 B2 | 4/2005 | Deppermann |
| 7,186,512 B2 | 3/2007 | Martienssen et al. |
| 7,367,155 B2 | 5/2008 | Kotyk et al. |
| 7,402,731 B2 | 7/2008 | Penner et al. |
| 7,454,989 B2 | 11/2008 | Deppermann |
| 7,600,642 B2 | 10/2009 | Deppermann |
| 7,673,572 B2 | 3/2010 | Depperman et al. |
| 7,685,768 B2 | 3/2010 | Deppermann |
| 7,901,880 B2 | 3/2011 | Jeddeloh et al. |
| 7,909,276 B2 | 3/2011 | Deppermann et al. |
| 7,910,296 B2 | 3/2011 | Jeddeloh et al. |
| 7,998,669 B2 | 8/2011 | Deppermann et al. |
| 8,076,076 B2 | 12/2011 | Osborn et al. |
| 8,114,669 B2 | 2/2012 | Choo |
| 8,163,485 B2 | 4/2012 | Jeddeloh et al. |
| 8,221,968 B2 | 7/2012 | Becker et al. |
| 8,237,016 B2 | 8/2012 | Ye et al. |
| 8,241,914 B2 | 8/2012 | Durack et al. |
| 8,281,935 B2 | 10/2012 | Depermann |
| 8,312,672 B2 | 11/2012 | Deppermann et al. |
| 8,361,719 B2 | 1/2013 | Jeddeloh et al. |
| 8,362,317 B2 | 1/2013 | Calabotta et al. |
| 8,401,271 B2 | 3/2013 | Depperman et al. |
| 8,443,545 B2 | 5/2013 | Deppermann et al. |
| 2005/0069879 A1 | 3/2005 | Berlin |
| 2006/0112449 A1 | 5/2006 | Van der Linden et al. |
| 2007/0224626 A1 | 9/2007 | Jeddeloh et al. |
| 2013/0247249 A1 | 9/2013 | Singh et al. |
| 2014/0302497 A1 | 10/2014 | Singh et al. |

FOREIGN PATENT DOCUMENTS

| | | |
|---|---|---|
| EP | 2787004 A1 | 10/2014 |
| WO | 00/70090 A1 | 11/2000 |
| WO | 2011/119390 A1 | 9/2011 |
| WO | 2011/119394 A1 | 9/2011 |

OTHER PUBLICATIONS

Jaligot et al (Mar. 2014, PLoS One 9 (3):e91896).*
Rival et al (2009, Acta Horticulturae 829 (Proceedings of the VIth International Symposium on In Vitro Culture and Horticultural Breeding, 2008): 177-181).*
Jaligot et al (Mar. 2014, PLoS One 9 (3) (Year: 2014).*
Adam et al., "Reproductive developmental complexity in the African oil palm (*Elaeis guineensis*, Arecaceae)", *Am J Bot*, 92(11): 1836-1853.

(Continued)

*Primary Examiner* — Lee A Visone
(74) *Attorney, Agent, or Firm* — Kilpatrick Townsend & Stockton LLP

(57) ABSTRACT

Methods, compositions, kits, and computer program code are provided for predicting somaclonal abnormality (e.g., a Mantled phenotype) in a plant and or sorting plants based on the predicted presence or absence of somaclonal abnormality.

14 Claims, 17 Drawing Sheets

(56) References Cited

OTHER PUBLICATIONS

Adam et al., "MADS Box Genes in Oil Palm (*Elaeis guineensis*): Patterns in the Evolution of the Squamosa, Deficiens, Globosa, Agamous, and Sepallata Subfamilies", *J Mol Evol*, 62(1):15-31 (2006).

Adam et al., "Determination of flower structure in *Elaeis guineensis*: do palms use the same homeotic genes as other species?", *Ann Bot*, 100(1): 1-12 (2007).

Adam et al., "Functional characterization of MADS box genes involved in the determination of oil palm flower structure", *J Exp Bot*, 58(6):1245-1259 (2007).

Alwee et al., "Characterization of Oil palm MADS box genes to the mantled flower abnormality", *Plant Cell, Tissue and Organ Culture*, 85:331-344 (2006).

Auyong et al., "'MADS-box directed profiling for the detection of oil palm variations", Proceedings of the Pipoc 2005 International Palm Oil Congress, Agriculture, Biotechnology and Sustainability (2005).

Auyong, "MADS box genes and DNA methylation polymorphisms as markers for tissue culture-induced mantled flower abnormalities in oil palm", M.Sc. thesis. University Putra Malaysia (2006), abstract only.

Castilho et al., "Repetitive DNA and the Chromosomes in the Genome of Oil Palm (*Elaeis guineensis*)", *Annals of Botany*, 85(6):837-844.

Jaligot et al., "Methylation-sensitive RFLPs: characterisation of two oil palm markers showing somaclonal variation-associated polymorphism", *Theor Appl Genet.*, 104(8): 1263-1269 (2002).

Jaligot et al., "Search for methylation-sensitive amplification polymorphisms associated with the mantled variant phenotype in oil palm (*Elaeis guineensis Jacq*).", *Genome*, 47(1): 224-248 (2004).

Jaligot et al., "Somaclonal variation in oil palm (*Elaeis guineensis Jacq.*): the DNY methylation hypothesis", *Plant Cell Reports*, 19:684-690 (2000).

Jaligot et al., "DNA methylation and expression of the EgDEF1 gene and neighboring retrotransposons in mantled somaclonal variants of oil palm", *PLos One*, 9(3):e91896 (2014).

Jiang et al., "Regenerant Arabidopsis lineages display a distinct genome-wide spectrum of mutations conferring variant phenotypes", *Curr Biol*, 21(16):1385-1390 (2011).

Kubis et al., "Retroelements, transposons and methylation status in the genome of oil palm (*Elaeis guineensis*) and the relationship to somaclonal variation", *Plant Mol Biol*, 52(1):69-79 (2003).

Matthes et al., "Variation in oil palm (*Elaeis guineensis Jacq.*) tissue culture-derived regenerants revealed by AFLPs with methylation-sensitive enzymes", *Theoretical and Applied Genetics*, 102: 971-979.

Miguel et al., "An epigenetic view of plant cells cultured in vitro: somaclonal variation and beyond", *J Exp Bot.*, 62(11):3713-3725 (2011).

Miyao et al., "Molecular spectrum of somaclonal variation in regenerated rice revealed by whole-genome sequencing", *Plant Cell Physiol*, 53(1):256-264 (2012).

Stelpflug et al., "Consistent and heritable alterations of DNA methylation are induced by tissue culture in maize", *Genetics*, 198(1):209-218 (2014).

Stroud et al., "Plants regenerated from tissue culture contain stable epigenome changes in rice", *eLife*, 14 pages (2013).

Tanurdzic et al., "Epigenomic consequences of immortalized plant cell suspension culture", *PLos Biol.*, 6(12):2880-2895 (2008).

Van der Linden et al, "Cloning and characterization of four apple MADS box genes isolated from vegetative tissue", *J Exp Bot.*, 53(371):1025-1036 (2002).

GenBank: KF 142646.1, "Elaeis quineensis disrupted DEF1 gene, partial sequence; and retrotransposons RLB_Koala_Eg133H20-1 and RLC-Rider-Eg133H20-1, complete sequence", 28 pages (2014). http://www.ncbi.hlm.nih.gov/nuccore/KF142646 (downloaded Aug. 30, 2015).

International Search Report and Written Opinion dated Nov. 24, 2015, 19 pages.

PCT/US2015/028646, "International Preliminary Report on Patentability", dated Nov. 17, 2016, 12 pages.

PCT/US2015/028646, "Invitation to Pay Additional Fees and Partial Search Report", dated Sep. 9, 2015, 5 pages.

\* cited by examiner

MANTLE PHENOTYPE DETECTION IN PALM

CROSS-REFERENCE TO RELATED PATENT APPLICATIONS

The present application claims the benefit of priority to U.S. Provisional Patent Application No. 61/988,132, filed on May 2, 2014, and U.S. Provisional Patent Application No. 62/091,471, filed on Dec. 12, 2014, the contents of each of which are hereby incorporated by reference in the entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SUBSEQ_96380-941209.txt, created on Jul. 13, 2015, 420,997 bytes, machine format IBM-PC, MS-Windows operating system, is hereby incorporated by reference.

BACKGROUND OF THE INVENTION

The oil palm belongs to the genus *Elaeis* which contains two species, *E. guineensis* and *E. oleifera*. It is regarded as the most efficient oil bearing crop in the world out yielding all other crops of the same genre, e.g., soybean, rapeseed and sunflower. The ability to produce oil at an average yield of 3.74 tonne/ha/year, on land 10 times smaller than the requirement for soybean (Oil World, 2007) and with a productive life cycle of 25-30 years, makes the oil palm a lucrative agricultural crop. However, of late the oil yield has reached stagnation. Nevertheless, demand for edible oils is predicted to escalate to feed the growing world population.

The oil palm has gone through at least two known cycles of yield improvements since its introduction as an oil crop in Malaysia, the first wave being the introduction of the hybrid tenera (DxP), which replaced the dura as commercial planting material. This demonstrated an increase in oil yield of up to 30% by merely manipulating a single gene (Kushairi et al., 2006; Singh et al., 2013). However, the average oil yield in Malaysia has hovered between 3.5 and 3.9 t/ha/yr for the last two decades. Having dropped to the number two spot in palm oil production, Malaysia—and all other palm oil producing countries—is in need of yield improvement. This is further compounded by the fact that agricultural land is becoming a rarity. Therefore increased production by planting larger areas is no longer seen as an alternative.

Through years of breeding and selection, the palm oil industry has already produced palms yielding as high as 13.6 t/ha/yr (Sharma and Tan, 1999) which are close to the theoretical yield of 18.2 t/ha/yr (Corley, 1998). The best experimental plot has produced an average of 9.8 t/ha/yr of palm oil (Musa and Gurmit, 2008) with selected progenies able to achieve up to 12.2 t/ha/yr (Raj anaidu et al., 1990). Cloning these super palms may provide the industry with the much-needed high-yielding planting materials to get it out of the stagnation rut. Hence, clones for commercial use are touted as the second wave of crop improvement for the oil palm.

Due to its biological structure, the oil palm has no natural means of vegetative propagation and conventional hybrid breeding methodology would require at least three generations, or over 20 years, to realize such superior yields (Soh et al., 2005). Successful vegetative propagation of oil palm was first described in the 1970s (Jones, 1974; Rabechault and Martin, 1976). Jones (1995) gave a rather comprehensive and personal account of its development. These successful reports of oil palm cloning prompted the development of tissue culture laboratories to provide clonal oil palm planting material. Encouraging results from early field trials set the pace for more laboratories to follow suit. By the mid-1980's, there were already 10 clonal oil palm laboratories in Malaysia (Wooi, 1990) and others elsewhere (Le Guen et al., 1991).

However, when Corley et al. (1986) reported the mantling phenomenon for the first time, the whole clonal industry led by the pioneering Bakasawit/Unifield and Tropiclone commercial laboratories decided to cut back on production and reverted to research and development. The then, Palm Oil Research Institute of Malaysia (PORIM), now known as Malaysian Palm Oil Board (MPOB), as the custodian of the palm oil industry, was assigned the task of spearheading research in clonal abnormalities.

Through a concerted effort, by the early 1990's, the results obtained suggested that better tissue culture protocols needed to be established, which included subculturing procedures and the use of less devastating types of growth regulators. Alternative methods were also proposed such as suspension and protoplast cultures as a means to avoid subculturing. Cloning of dura and pisifera parents, followed by conventional crossing to circumvent the potential occurrence of somaclonal variants from clonal teneras, was amongst the different methods discussed (Ong-Abdullah, Viva 562/2011). Interestingly, up to 10% of abnormal palms spontaneously reverted to normal and remained normal for some time (Durand-Gasselin et al., 1990). Seedlings developed from Mantled fruits e.g., clone 115E, were normal; refuting the possibility that abnormality is due to a dominant gene effect or to maternally transmitted factors. Through conventional genetic crossings conducted by Rao and Donough (1990), this trait was also shown to behave in a non-Mendelian manner.

Earlier attempts that employed techniques such as flow cytometry, random amplified polymorphic DNA (RAPD) or the classical amplified fragment length polymorphisms (AFLP) analysis failed to yield any detectable differences between Mantled and normal palms (Rival et al. 1997, 1998; Matthes et al. 2001). However, when methylation sensitive or related technologies were utilized, the methylation level of the Mantled genome appeared to be altered (Jaligot et al. 2002, Matthes et al. 2001, Jaligot et al. 2004).

Subsequently, further research concentrated on understanding the underlying molecular cause(s) and epigenetic regulation of mantling. It was also known that in Mantled oil palms, staminodes and stamens of pistillate and functional flowers develop respectively as pseudocarpels (Morcillo et al., 2006). In severe cases, the flowers are sterile with abortive fruits leading to lower yields. It was postulated that since homeotic modifications had taken place, it was highly likely that the B-function homeotic MADS box genes of the ABCDE model for flower organ identity (Murai, 2013) are involved.

Following the MADS box hypothesis, MADS-box containing genes from the oil palm were isolated (Alwee et al., 2006; Auyong, 2006) using the MADS box-directed profiling technique (van der Linden et al. 2002). This method allows the visualization of DNA polymorphisms in restriction sites at the MADS box vicinity among normal, abnormal and reverted oil palms. Two markers, namely MM77 and MM78 (EP Patent Appl. No. 13162130.2) were identified and the latter was widely used for further validation although it was found not to fall in the class of MADS box genes. In the course of validating MM78 and from past experiences with other unrelated markers, it was confirmed that the functional use of these markers is genotype dependent. Therefore, they have little or no use when tested on clones from other genetic backgrounds. This has been the main point of contention in biomarker development for clonal fidelity of the oil palm.

Previous studies have found an overall decrease in DNA methylation in mantled palms relative to ortets and normal ramets (Jaligot et al. 2000; Matthes et al. 2001; Jaligot et al. 2002; Jaligot et al. 2004). These results are similar to observations in Arabidopsis and other plant cell cultures, in which transposable elements (TEs) are hypomethylated and expressed (Tanurdzic et al. 2008; Miguel et al. 2011; Castilho et al. 2000; Kubis et al. 2003). In addition to TEs, somaclonal regenerants in rice and maize undergo extensive gene and promoter hypomethylation (Stroud et al. 2013; Stelpflug et al. 2014), which might also contribute to somaclonal variation in oil palm and other crops. The homeotic transformations observed in mantled palms resemble defects in B-function MADS box genes, suggesting that retroelements within one or more MADS box genes, or the MADS box genes themselves are candidates for epigenetic modification (Adam et al. 2005). However, decades of research into DNA methylation changes in candidate retroelements (Castilho et al. 2000; Kubis et al. 2003; Jaligot et al. 2014) and candidate homeotic genes (Syed Alwee et al. 2006; Adam et al. 2007; Jaligot et al. 2014) have yet to identify epigenetic changes that are consistently found in somaclonal mantled palms. And indeed, recent studies of rice and Arabidopsis plants regenerated from tissue culture implicate genetic rather than epigenetic mechanisms as being responsible for somaclonal variation (Jiang et al. 2011; Miyao et al. 2012.

BRIEF SUMMARY OF THE INVENTION

Described herein are methods, compositions, and kits for predicting the presence or absence of a somaclonal abnormality (e.g., Mantled) in an oil palm plant, plant cell, or plant tissue. In some embodiments, the present invention provides a method for segregating an oil palm plant comprising: a) obtaining a biological sample from the plant; b) determining the methylation status of at least one cytosine within a differential methylation region (DMR) in the sample from the plant, wherein the DMR is within a sequence of DNA at least 70%, 80%, 90%, 95%, or 99% identical, or identical, to SEQ ID NO:1; c) correlating the methylation status of the at least one cytosine to the presence or absence of a somaclonal abnormality in the plant, wherein the correlation comprises predicting the presence or absence of somaclonal abnormality in the plant; and d) physically separating a plant predicted to have a somaclonal abnormality from one or more plants predicted to lack a somaclonal abnormality.

In some aspects, the DMR is within a DNA meta-region in the sample from the plant, where the DNA meta-region is at least 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the determining step comprises determining the methylation status of at least one cytosine in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects the method comprises predicting the presence of a somaclonal abnormality when the methylation status of the at least one cytosine is reduced relative to a control locus. In some cases, the presence of a somaclonal abnormality is predicted when the methylation status of the at least one cytosine in the DNA meta-region at least 70%, 80%, 90%, 95%, or 99% identical, or identical, to the sequence selected from the group consisting of SEQ ID NO:63, 64, 65, 66, 67, 69, and 70 (or selected from the group consisting of SEQ ID NO:63, 64, 65, 66, 67, 68, 69, and 70) is reduced relative to a control locus. In some cases, the presence of a somaclonal abnormality is predicted when the methylation status of the at least one cytosine in the DNA region is at least 70%, 80%, 90%, 95%, or 99% identical, or identical, to the sequence selected from the group consisting of SEQ ID NO:35, 36, 39, 40, 42, 43, 44, 45, 46, 48, 49, 51, 52, 57, 58, 59, 60, 61, and 73 is reduced relative to a control locus. In some cases, the presence of a somaclonal abnormality is predicted when the methylation status of the at least one cytosine in the biomarker at least 90%, 95%, or 99% identical, or identical to the sequence selected from the group consisting of SEQ ID NO:7, 8, 11, 12, 14, 15, 16, 17, 18, 20, 21, 23, 24, 29, 30, 31, 32, 33, and 71 is reduced relative to a control locus.

In some aspects, the method comprises predicting the presence of a somaclonal abnormality when the methylation status of the at least one cytosine is increased relative to a control locus. In some cases, the presence of a somaclonal abnormality is predicted when the methylation status of the at least one cytosine in the DNA meta-region at least 70%, 80%, 90%, 95%, or 99% identical, or identical, to the sequence selected from the group consisting of SEQ ID NO:63, 64, 65, 66, 67, 68, and 69 (or selected from the group consisting of SEQ ID NO:63, 64, 65, 66, 67, 68, 69, and 70) is increased relative to a control locus. In some cases, the presence of a somaclonal abnormality is predicted when the methylation status of the at least one cytosine in the DNA region at least 70%, 80%, 90%, 95%, or 99% identical, or identical, to the sequence selected from the group consisting of SEQ ID NO:35, 36, 37, 38, 41, 42, 47, 50, 52, 53, 54, 55, 56, 57, 62, and 74 is increased relative to a control locus. In some cases, the presence of a somaclonal abnormality is predicted when the methylation status of the at least one cytosine in the biomarker at least 90%, 95%, or 99% identical, or identical to the sequence selected from the group consisting of SEQ ID NO:7, 8, 9, 10, 13, 14, 19, 22, 24, 25, 26, 27, 28, 29, 34 and 72 is increased relative to a control locus.

In some aspects, the method comprises predicting the presence of a somaclonal abnormality when the methylation status of the at least one cytosine is either increased or decreased relative to a control locus. In some cases, the control locus is an endogenous control locus. In some cases, the control locus is an exogenous control locus.

In some aspects, the determining step comprises determining the methylation status of at least one cytosine in at least two, three or four different differential methylation regions (DMRs), wherein each DMR is independently within a sequence of DNA at least 70%, 80%, or 90%, 95%, or 99% identical, or identical, to SEQ ID NO:1. In some cases, each DMR is within a DNA meta-region in the sample from the plant, where each DNA meta-region is at least 70%, 80%, 90%, 95%, or 99% identical, or identical, to a sequence independently selected from the group consisting of SEQ ID NO:63, 64, 65, 66, 67, 68, 69, and 70. In some cases, each DMR is within a DNA region in the sample from the plant, where the DNA region is at least 70%, 80%, 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the determining step comprises determining the methylation status of at least one cytosine in a biomarker in each DMR, wherein each biomarker is at least 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In any of the foregoing embodiments, aspects, or cases, the somaclonal abnormality can comprise a reduction in fruit yield, oil yield, growth, or reproduction of the plant relative to a control plant. In some cases, the control plant is a parental plant. In some cases, the control plant is a wild-type plant of the same fruit form phenotype (dura, tenera, or pisifera) as the plant predicted to have a somaclonal abnormality. In some cases, the somaclonal abnormality exhibits a Mantled phenotype.

In any of the foregoing embodiments, aspects, or cases, the determining the methylation status can comprise bisulfite conversion; and/or the determining the methylation status can comprise digesting genomic DNA with a methylation-dependent endonuclease; and/or the determining the methylation status can comprise digesting genomic DNA with a methylation-sensitive endonuclease; and/or the determining of the methylation status can comprise measuring rates of methylated base incorporation during sequencing; and/or the determining of the methylation status can comprise measuring current as molecules including methylated bases pass through a nanopore. In any of the foregoing embodiments, aspects, or cases, the determining the methylation status can comprise methylated DNA immunoprecipitation, methylated DNA capture by affinity purification, or reduced representation bisulfite sequencing. In any of the foregoing embodiments, aspects, or cases, the determining the methylation status can comprise nucleic acid hybridization, e.g., microarray or bead array hybridization.

In any of the foregoing embodiments, aspects, or cases, the physically separating can comprise selecting plants predicted to have a somaclonal abnormality for destruction; and/or selecting plants predicted to lack a somaclonal abnormality for cultivation. In some cases, the plants selected for cultivation are germinated, planted, or transplanted. In some cases, the plants not selected for cultivation are discarded or destroyed.

In some embodiments, the present invention provides a computer program product for determining the presence or absence of a somaclonal abnormality in an oil palm plant, the computer program product comprising: a computer readable medium encoded with program code, the program code including: program code for receiving a methylation value representing a methylation status of at least one cytosine within a differential methylation region (DMR) in a sample from the oil palm plant, wherein the DMR is within a sequence of DNA at least 70%, 80%, 90%, 95%, or 99% identical, or identical, to SEQ ID NO:1; and program code for comparing the methylation value to a control value, wherein the control value distinguishes between plants with and without a somaclonal abnormality, wherein the comparison of the methylation value to the control value is predictive of the presence or absence of a somaclonal abnormality in the plant.

In some aspects, the DMR is within a DNA meta-region in the sample from the plant, where the DNA meta-region is at least 70%, 80%, 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some aspects, the at least one cytosine is in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects, the control value is a methylation value for a control locus exogenous to the plant. In some aspects, the control value is a methylation value for a control locus endogenous to the plant.

In some aspects, wherein the program code comprises program code for receiving the methylation status of at least one cytosine in at least two, three or four different DMRs, wherein each DMR is independently within a sequence of DNA at least 70%, 80%, 90%, 95%, or 99% identical, or identical, to SEQ ID NO:1. In some cases, each DMR is within a DNA meta-region in the sample from the plant, where each DNA meta-region is at least 70%, 80%, 90%, 95%, or 99% identical, or identical, to a sequence independently selected from the group consisting of SEQ ID NO:63, 64, 65, 66, 67, 68, 69, and 70. In some cases, each DMR is within a DNA region in the sample from the plant, where each DNA region is at least 70%, 80%, 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, each DMR is within a biomarker, wherein each biomarker is at least 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72.

In any of the foregoing computer program products, the computer program product can, in some cases, predict the presence or absence of a somaclonal abnormality in the plant. In some cases, the somaclonal abnormality exhibits a Mantled phenotype.

In some embodiments, the present invention provides a kit for determining the methylation status of at least one DMR in a biological sample from an oil palm plant, the kit comprising: (1) a polynucleotide (e.g., detectably labeled polynucleotide), or a pair of polynucleotides (e.g., wherein one or both polynucleotides of the pair are detectably labeled), capable of specifically amplifying at least a portion of a DMR, wherein the DMR is within a sequence of DNA at least 70%, 80%, 90%, 95%, or 99% identical, or identical, to SEQ ID NO:1; and a methylation-dependent, a methylation sensitive restriction enzyme, and/or sodium bisulfite; or (2) sodium bisulfite, primers, and adapters for whole genome amplification, and at least one polynucleotide to quantify the presence of the converted methylated and/or the converted unmethylated sequence of at least one cytosine from a DMR, wherein the DMR is within a sequence of DNA at least 70%, 80%, 90%, 95%, or 99% identical, or identical, to SEQ ID NO:1; or (3) methylation sensing restriction enzymes, primers and adapters for whole genome amplification, and at least one polynucleotide to quantify the number of copies of at least a portion of a DMR, wherein the DMR is within a sequence of DNA at least 70%, 80%, 90%, 95%, or 99% identical, or identical, to SEQ ID NO:1; or (4) a methylation sensing binding moiety and at least one polynucleotide to quantify the number of copies of at least a portion of a DMR, wherein the DMR is within a sequence of DNA at least 70%, 80%, 90%, 95%, or 99% identical, or identical, to SEQ ID NO:1.

In some aspects, the DMR is within a DNA meta-region in the sample from the plant, where the DNA meta-region is at least 70%, 80%, 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the DMR is within a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects, the kit comprises at least two, three, or four polynucleotides—or two, three, or four pairs of polynucleotides-capable of specifically amplifying at least a portion of two, three, or four different DMRs, wherein each DMR is independently within a sequence of DNA at least 70%, 80%, 90%, 95%, or 99% identical, or identical, to SEQ ID NO:1. In some cases, each DMR is within a DNA meta-region, where the DNA meta-region is at least 70%, 80%, 90%, 95%, or 99% identical, or identical, to a sequence independently selected from the group consisting of SEQ ID NO:63, 64, 65, 66, 67, 68, 69, and 70. In some cases, each DMR is within a sequence of DNA at least 70%, 80%, 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73 and 74. In some cases, each DMR is within a biomarker, wherein each biomarker is at least 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72.

In some aspects, the kit further comprises a detectably labeled polynucleotide probe that specifically detects an amplified DMR, or portion thereof. In some cases, the polynucleotide probe specifically detects an amplified DMR, or portion thereof, in a real-time amplification reaction.

In some embodiments, the present invention provides a method of predicting the presence or absence of somaclonal abnormality in an oil palm plant comprising: a) obtaining a biological sample from the plant; b) determining the methylation status of at least one cytosine within a differential methylation region (DMR) in the sample from the plant, wherein the DMR is within a sequence of DNA at least 70%, 80%, 90%, 95%, or 99% identical, or identical, to SEQ ID NO:1; and c) correlating the methylation status of the at least one cytosine to the presence or absence of a somaclonal abnormality in the plant, wherein the correlation comprises predicting the presence or absence of somaclonal abnormality in the plant.

In some aspects, the DMR is within a DNA meta-region in the sample from the plant, where the DNA meta-region is at least 70%, 80%, 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73 and 74. In some cases, the determining step comprises determining the methylation status of at least one cytosine in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72.

In some aspects, the method comprises predicting the presence of a somaclonal abnormality when the methylation status of the at least one cytosine is reduced relative to a control locus. In some cases, the presence of a somaclonal abnormality is predicted when the methylation status of the at least one cytosine in the DNA meta-region at least 70%, 80%, 90%, 95%, or 99% identical, or identical, to the sequence selected from the group consisting of SEQ ID NO:63, 64, 65, 66, 67, 69, and 70 (or selected from the group consisting of SEQ ID NO: 63, 64, 65, 66, 67, 68, 69, and 70) is reduced relative to a control locus. In some cases, the presence of a somaclonal abnormality is predicted when the methylation status of the at least one cytosine in the DNA region at least 70%, 80%, 90%, 95%, or 99% identical, or identical, to the sequence selected from the group consisting of SEQ ID NO:35, 36, 39, 40, 42, 43, 44, 45, 46, 48, 49, 51, 52, 57, 58, 59, 60, 61, and 73 is reduced relative to a control locus. In some cases, the presence of a somaclonal abnormality is predicted when the methylation status of the at least one cytosine in the biomarker at least 90%, 95%, or 99% identical, or identical to the sequence selected from the group consisting of SEQ ID NO:7, 8, 11, 12, 14, 15, 16, 17, 18, 20, 21, 23, 24, 29, 30, 31, 32, 33, and 71 is reduced relative to a control locus.

In some aspects, the method comprises predicting the presence of a somaclonal abnormality when the methylation status of the at least one cytosine is increased relative to a control locus. In some cases, the presence of a somaclonal abnormality is predicted when the methylation status of the at least one cytosine in the DNA meta-region at least 70%, 80%, 90%, 95%, or 99% identical, or identical, to the sequence selected from the group consisting of SEQ ID NO:63, 64, 65, 66, 67, 68, and 69 (or selected from the group consisting of SEQ ID NO:63, 64, 65, 66, 67, 68, 69, and 70) is increased relative to a control locus. In some cases, the presence of a somaclonal abnormality is predicted when the methylation status of the at least one cytosine in the DNA region at least 70%, 80%, 90%, 95%, or 99% identical, or identical, to the sequence selected from the group consisting of SEQ ID NO:35, 36, 37, 38, 41, 42, 47, 50, 52, 53, 54, 55, 56, 57, 62, and 74 is increased relative to a control locus. In some cases, the presence of a somaclonal abnormality is predicted when the methylation status of the at least one cytosine in the biomarker at least 90%, 95%, or 99% identical, or identical to the sequence selected from the group consisting of SEQ ID NO:7, 8, 9, 10, 13, 14, 19, 22, 24, 25, 26, 27, 28, 29, 34, and 72 is increased relative to a control locus.

In some aspects, the method comprises predicting the presence of a somaclonal abnormality when the methylation status of the at least one cytosine is either increased or decreased relative to a control locus. In some cases, the control locus is an endogenous control locus. In some cases, the control locus is an exogenous control locus.

In some aspects, the determining step comprises determining the methylation status of at least one cytosine in at least two, three or four different differential methylation regions (DMRs), wherein each DMR is independently within a sequence of DNA at least 70%, 80%, 90%, 95%, or 99% identical, or identical, to SEQ ID NO:1. In some cases, each DMR is within a DNA meta-region in the sample from the plant, where each DNA meta-region is at least 70%, 80%, 90%, 95%, or 99% identical, or identical, to a sequence independently selected from the group consisting of SEQ ID NO:63, 64, 65, 66, 67, 68, 69, and 70. In some cases, each DMR is within a DNA region in the sample from the plant, where each DNA region is at least 70%, 80%, 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the determining step comprises determining the methylation status of at least one cytosine in a biomarker in each DMR, wherein each biomarker is at least 90%, 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects, the somaclonal abnormality comprises a reduction in fruit yield, oil yield, growth, or reproduction of the plant relative to a control plant. In some cases, the control plant is a parental plant. In some cases, the control plant is a wild-type plant of the same fruit form phenotype (dura, tenera, or pisifera) as the plant predicted to have a somaclonal abnormality.

In some aspects, the somaclonal abnormality exhibits a Mantled phenotype.

In some aspects, the determining the methylation status comprises bisulfite conversion; and/or digesting genomic DNA with a methylation-dependent endonuclease; and/or digesting genomic DNA with a methylation-sensitive endonuclease.

In some embodiments, the present invention provides a method comprising: providing a prediction of a presence or absence of a somaclonal abnormality in a plurality of plants, wherein the presence or absence of a somaclonal abnormality is determined by a methylation status of at least one cytosine within a differential methylation region (DMR) in a sample from each plant, wherein the DMR is within a sequence of DNA at least 70%, 80%, 90%, 95%, or 99% identical, or identical, to SEQ ID NO:1; and physically separating a plant predicted to have a somaclonal abnormality from a plant predicted to lack a somaclonal abnormality.

In some aspects, the DMR is within a DNA meta-region in the sample from the plant, where the DNA region is at least 70%, 80%, 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the determining step comprises determining the methylation status of at least one cytosine in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects, the present invention provides a method for detecting or predicting a somaclonal abnormality for an oil palm plant, the method comprising: a) obtaining a biological sample from the plant; b) determining the methylation status of at least one cytosine within a differential methylation region (DMR) in the sample from the plant, wherein the DMR is within a sequence of DNA at least 90%, 95%, or 99% identical, or identical, to SEQ ID NO:1; and c) correlating the methylation status of the at least one cytosine to the presence or absence of the somaclonal abnormality in the plant. In some embodiments, the method further comprises physically separating a plant predicted to have the somaclonal abnormality from one or more plants predicted to lack a somaclonal abnormality. In some cases, the physically separating comprises selecting plants predicted to have a somaclonal abnormality for destruction.

In some cases, the physically separating comprises selecting plants predicted to lack a somaclonal abnormality for cultivation. In some cases, the plants selected for cultivation are germinated, planted, or transplanted. In some cases, the plants not selected for cultivation are discarded or destroyed. In some cases, the plants not selected for cultivation are treated to reduce the likelihood of a somaclonal abnormality. In some embodiments, the at least one cytosine is a first cytosine in a CHG sequence, wherein H is C, A, or T.

In some embodiments, the DMR is within a DNA meta-region in the sample from the plant, where the DNA meta-region is at least 90%, 95%, or 99% identical, or identical, to a sequence selected from the group consisting of SEQ ID NO:63, 64, 65, 66, 67, 68, 69, and 70. In some embodiments, the DMR is within a DNA region in the sample from the plant, where the DNA region is at least 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74.

In some cases, the determining step comprises determining the methylation status of at least one cytosine in a biomarker, wherein the biomarker is at least 90%, 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72. In some cases, the DMR is within a DNA region in the sample from the plant, where the DNA region is at least 90%, 95%, or 99% identical, or identical, to SEQ ID NO:84, 87, or 90.

In some cases the at least cytosine is in an AlwNI, BbvI, ScrFI, or RsaI restriction endonuclease recognition site. In some cases, the method comprises determining the methylation status of a first and a second cytosine, wherein the first cytosine is within a DMR within a DNA region in the sample from the plant, where the DNA region is at least 90%, 95%, or 99% identical, or identical, to SEQ ID NO:87, and wherein the second cytosine is within a DMR within a DNA region in the sample from the plant, where the DNA region is at least 90%, 95%, or 99% identical, or identical, to SEQ ID NO: 90. In some cases, the first cytosine is in a BbvI restriction endonuclease site, and the second cytosine is in a RsaI restriction endonuclease site.

In some cases, the method comprises predicting the presence of a somaclonal abnormality when the methylation status of the at least one cytosine is reduced relative to a control locus. In some cases, the method comprises predicting the presence of a somaclonal abnormality when the methylation status of the at least one cytosine is increased relative to a control locus. In some cases, the method comprises predicting the presence of a somaclonal abnormality when the methylation status of the at least one cytosine is either increased or decreased relative to a control locus. In some cases, the control locus is an endogenous control locus. In some cases, the control locus is an exogenous control locus.

In some cases, the determining step comprises determining the methylation status of at least one cytosine in at least two, three or four different differential methylation regions (DMRs), wherein each DMR is independently within a sequence of DNA at least 90%, 95%, or 99% identical, or identical, to SEQ ID NO:1.

In some cases, the somaclonal abnormality comprises a reduction in fruit yield, oil yield, growth, or reproduction of the plant relative to a control plant. In some cases, the control plant is a parental plant. In some cases, the control plant is a wild-type plant of the same fruit form phenotype (dura, tenera, or pisifera) as the plant predicted to have a somaclonal abnormality.

In some cases, the somaclonal abnormality is predicted to exhibit a Mantled phenotype.

In some cases, the determining the methylation status comprises bisulfite conversion. In some cases, the determining the methylation status comprises digesting genomic DNA with a methylation-dependent endonuclease. In some cases, the determining the methylation status comprises digesting genomic DNA with a methylation-sensitive endonuclease. In some cases, the genomic DNA is amplified after digesting.

In some cases, the determining the methylation status comprises bisulfite conversion; and/or the determining the methylation status comprises digesting genomic DNA with a methylation-dependent endonuclease; and/or the determining the methylation status comprises digesting genomic DNA with a methylation-sensitive endonuclease; and/or the determining of the methylation status comprising measuring rates of methylated base incorporation during sequencing; and/or the determining of the methylation status comprising measuring current as molecules including methylated bases pass through a nanopore. In some cases, the determining the methylation status can comprise methylated DNA immunoprecipitation, methylated DNA capture by affinity purification, or reduced representation bisulfite sequencing. In some cases, the determining the methylation status can comprise nucleic acid hybridization, e.g., microarray or bead array hybridization.

In some aspects, the present invention provides a method for detecting or predicting a somaclonal abnormality for an oil palm plant, the method comprising: a) obtaining a biological sample from the plant; b) determining the expression level of at least one small RNA in the sample from the plant, wherein the at least one small RNA is encoded by a sequence comprising a polynucleotide at least 90%, 95%, or 99% identical or identical to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161; and c) correlating the expression level of the at least one small RNA to the presence or absence of the somaclonal abnormality in the plant. In some embodiments, the expression level of the at least one small RNA is at least 2-fold increased or decreased relative to expression of the at least one small RNA in a normal control plant.

In some cases, the at least one small RNA in the sample from the plant is encoded by a sequence comprising a polynucleotide at least 90% (e.g., 91%, 92%, 93%, 94%, 95%, 96%, 97%, 98%, 99%, 99.5%, or 100%) identical to any one of SEQ ID NOs: 144-161. In some cases, the expression level of the at least one small RNA that is at least 90% identical to any one of SEQ ID NOs: 144-161 in a sample from a plant predicted to have a somaclonal abnormality is less than 50% of the expression level of the at least one small RNA in a normal control plant. In some cases, the at least one small RNA in the sample from the plant is encoded by a sequence comprising a polynucleotide at least 90% (e.g., 91%, 92%, 93%, 94%, 95%, 96%, 97%, 98%, 99%, 99.5%, or 100%) identical to SEQ ID NO:91. In some cases, the expression level of the at least one small RNA that is at least 90% identical to SEQ ID NO:91 in a sample from a plant predicted to have a somaclonal abnormality is less than 50%, 40%, 30%, or 10% of the expression level of the at least one small RNA in a normal control plant.

In some cases, the biological sample is derived from shoot apex tissue of the plant. In some cases, the biological sample is derived from <2 cm stage inflorescens tissue of the plant. In some cases, the biological sample is derived from at least 2 cm stage inflorescens tissue of the plant. In some cases, the biological sample is derived from an in vitro tissue cultured plant cell, a seed, or a seedling.

In some embodiments, the method further comprises physically separating a plant predicted to have the somaclonal abnormality from one or more plants predicted to lack a somaclonal abnormality. In some embodiments, the physically separating comprises selecting plants predicted to have a somaclonal abnormality for destruction. In some cases, the physically separating comprises selecting plants predicted to lack a somaclonal abnormality for cultivation. In some cases, the plants selected for cultivation are germinated, planted, or transplanted. In some cases, plants not selected for cultivation are discarded or destroyed. In some cases, the plants not selected for cultivation are treated to reduce the likelihood of a somaclonal abnormality. In some cases, the somaclonal abnormality is predicted to exhibit a Mantled phenotype.

In some aspects, the present invention provides, a method for detecting or predicting a somaclonal abnormality for an oil palm plant, the method comprising: a) obtaining a biological sample from the plant; b) determining the expression level of a transcript encoded by SEQ ID NO:5, 75, 78, or 80; and c) correlating the expression level to the presence or absence of the somaclonal abnormality in the plant. In some embodiments, the plant is predicted to have a somaclonal abnormality when the expression level of SEQ ID NO:5 is decreased relative to a wildtype control plant, or when the expression level of SEQ ID NO:75, or 78, or 80 is increased relative to a wildtype control plant. In some embodiments, the plant is predicted to have a somaclonal abnormality when the expression level of SEQ ID NO:75 or 78 or 80 is increased relative to an expression level of SEQ ID NO:5.

In some embodiments, the method further comprises physically separating a plant predicted to have the somaclonal abnormality from one or more plants predicted to lack a somaclonal abnormality. In some cases, the physically separating comprises selecting plants predicted to have a somaclonal abnormality for destruction. In some cases, the physically separating comprises selecting plants predicted to lack a somaclonal abnormality for cultivation. In some cases, the plants selected for cultivation are germinated, planted, or transplanted. In some cases, the plants not selected for cultivation are discarded or destroyed. In some cases, the plants not selected for cultivation are treated to reduce the likelihood of a somaclonal abnormality.

In some embodiments, the somaclonal abnormality is predicted to exhibit the Mantled phenotype.

In some aspects, the present invention provides a computer program product for predicting the presence or absence of a somaclonal abnormality in an oil palm plant, the computer program product comprising: a computer readable medium encoded with program code, the program code including: program code for receiving a methylation value representing the methylation status of at least one cytosine within a differential methylation region (DMR) in the sample from the oil palm plant, wherein the DMR is within a sequence of DNA at least 70%, 80%, 90%, 95%, or 99% identical, or identical, to SEQ ID NO:1; and program code for comparing the methylation value to a control value, wherein the control value distinguishes between plants with and without a somaclonal abnormality, wherein the comparison of the methylation value to the control value is predictive of the presence or absence of a somaclonal abnormality in the plant.

In some embodiments, the DMR is within a DNA meta-region in the sample from the plant, where the DNA meta-region is at least 90%, 95%, or 99% identical, or identical, to a sequence selected from the group consisting of SEQ ID NO:63, 64, 65, 66, 67, 68, 69, and 70. In some cases, the DMR is within a DNA region in the sample from the plant, where the DNA region is at least 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the at least one cytosine is in a biomarker, wherein the biomarker is at least 90% 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some cases, the control value is a methylation value for a control locus exogenous to the plant. In some cases, the control value is a methylation value for a control locus endogenous to the plant. In some cases, the program code comprises program code for receiving the methylation status of at least one cytosine in at least two, three or four different DMRs, wherein each DMR is independently within a sequence of DNA at least 90%, 95%, or 99% identical, or identical, to SEQ ID NO:1. In some cases, each DMR is within a DNA meta-region in the sample from the plant, where each DNA meta-region is at least 90%, 95%, or 99% identical, or identical, to a sequence independently selected from the group consisting of SEQ ID NO:63, 64, 65, 66, 67, 68, 69, and 70.

In some cases, each DMR is within a DNA region in the sample from the plant, wherein each DNA region is at least 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, each DMR is within a biomarker, wherein each biomarker is at least 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72. In some cases, the somaclonal abnormality is predicted to exhibit a Mantled phenotype.

In some aspects, the present invention provides a computer program product for determining the presence or absence of a somaclonal abnormality in an oil palm plant, the computer program product comprising: a computer readable medium encoded with program code, the program code including: program code for receiving a value representing i). an expression level of a small RNA (e.g., an expression level of a small RNA in a sample from a plant), wherein the small RNA is encoded by a sequence comprising a polynucleotide at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161; or ii). an expression level of a transcript at least 90%, 95%, or 99% identical, or identical, to SEQ ID NO:5, 75, 78, or 80; and program code for comparing the expression level value to a control value, wherein the control value distinguishes between plants with and without a somaclonal abnormality, wherein the comparison of the expression level value to the control value is predictive of the presence or absence of a somaclonal abnormality in the plant.

In some cases, the at least one small RNA in the sample from the plant is encoded by a sequence comprising a polynucleotide at least 90% (e.g., 91%, 92%, 93%, 94%, 95%, 96%, 97%, 98%, 99%, 99.5%, or 100%) identical to any one of SEQ ID NOs: 144-161. In some cases, the expression level of the at least one small RNA that is at least 90%, 95%, or 99% identical to any one of SEQ ID NOs: 144-161 in a sample from a plant predicted to have a somaclonal abnormality is less than 50% of the expression level of the at least one small RNA in a normal control plant. In some cases, the at least one small RNA in the sample from the plant is encoded by a sequence comprising a polynucleotide at least 90% (e.g., 91%, 92%, 93%, 94%, 95%, 96%, 97%, 98%, 99%, 99.5%, or 100%) identical to SEQ ID NO:91. In some cases, the expression level of the at least one small RNA that is at least 90%, 95%, or 99% identical to SEQ ID NO:91 in a sample from a plant predicted to have a somaclonal abnormality is less than 50%, 40%, 30%, or 10% of the expression level of the at least one small RNA in a normal control plant.

The computer program product can, in some cases, predict the presence or absence of a somaclonal abnormality in the plant. In some cases, the somaclonal abnormality exhibits a Mantled phenotype. In some cases, a plant predicted to have a somaclonal abnormality by application of the computer program product is physically separated from one or more plants predicted to lack a somaclonal abnormality.

In some aspects, the present invention provides a kit for determining the methylation status of at least one DMR in a biological sample from an oil palm plant, wherein the DMR is within a sequence of DNA at least 90%, 95%, or 99% identical, or identical, to SEQ ID NO:1, the kit comprising: (1) sodium bisulfite, oligonucleotide amplification primers, and at least one polynucleotide to quantify the presence of the unconverted methylated or the converted unmethylated sequence of at least one cytosine from the DMR; (2) a methylation-sensitive or dependent restriction enzyme, oligonucleotide amplification primers, and at least one polynucleotide to quantify the number of copies of at least a portion of the DMR; (3) a methylation sensing binding moiety and at least one polynucleotide to quantify the number of copies of at least a portion of the DMR, wherein the methylation status of the at least one cytosine is predictive of a somaclonal abnormality of the oil palm plant.

In some embodiments, the methylation-sensitive or dependent restriction enzyme is heterologous to the oil palm plant. In some embodiments, the methylation-sensitive or dependent restriction enzyme is selected from the group consisting of AlwNI, BbvI, RsaI, and ScrFI. In some embodiments, the kit comprises BbvI, and RsaI. In some embodiments, the at least one polynucleotide to quantify the presence of the unconverted methylated or the converted unmethylated sequence of at least one cytosine from the DMR comprises a sequence that specifically hybridizes to a sequence from the DMR containing a bisulfite converted cytosine. In some embodiments, the at least one polynucleotide to quantify the number of copies of at least a portion of the DMR comprises a sequence that specifically hybridizes to a sequence from the DMR containing a bisulfite converted cytosine.

In some embodiments, the methylation sensitive binding moiety is an antibody. In some embodiments, the DMR is within a DNA meta-region in the sample from the plant, where the DNA meta-region is at least 90%, 95%, or 99% identical, or identical, to a sequence selected from the group consisting of SEQ ID NO:63, 64, 65, 66, 67, 68, 69, and 70. In some embodiments, the DMR is within a DNA region in the sample from the plant, where the DNA region is at least 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the DMR is within a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some embodiments, the kit comprises at least two, three, or four polynucleotides—or two, three, or four pairs of polynucleotides-capable of specifically amplifying at least a portion of two, three, or four different DMRs, wherein each DMR is independently within a sequence of DNA at least 90%, 95%, or 99% identical, or identical, to SEQ ID NO:1. In some cases, each DMR is within a DNA meta-region, where the DNA meta-region is at least 90%, 95%, or 99% identical, or identical, to a sequence independently selected from the group consisting of SEQ ID NO:63, 64, 65, 66, 67, 68, 69, and 70.

In some cases, each DMR is within a sequence of DNA at least 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73 and 74. In some cases, each DMR is within a biomarker, wherein each biomarker is at least 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72. In some cases, the kit further comprises a detectably labeled polynucleotide probe that specifically detects an amplified DMR, or portion thereof. In some cases, the polynucleotide probe specifically detects an amplified DMR, or portion thereof, in a real-time amplification reaction.

In some aspects, the present invention provides a kit for detecting the expression level of an RNA in an oil palm plant, the kit comprising: a) an oligonucleotide primer capable of specifically hybridizing to a small RNA encoded by a sequence comprising a polynucleotide at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161; or b) an oligonucleotide primer capable of specifically hybridizing to a transcript encoded by SEQ ID NO:5, 75, 78, or 80, wherein the detected expression level is predictive of a somaclonal abnormality of the oil palm plant. In some cases, the kit further comprises a detectably labeled oligonucleotide probe; or wherein the oligonucleotide primer is detectably labeled. In some cases, the oligonucleotide primer of b) comprises SEQ ID NO:125, 126, 127, 128, or 129. In some cases, the oligonucleotide primer of a) is capable of is capable of specifically hybridizing to a small RNA encoded by a sequence comprising a polynucleotide at least 90% (e.g., 91%, 92%, 93%, 94%, 95%, 96%, 97%, 98%, 99%, 99.5%, or 100%) identical to one of SEQ ID NOs: 144-161.

In some aspects, the present invention provides a method of reducing somaclonal abnormalities an oil palm plant propagated by in vitro tissue culture comprising: exogenously applying to the plant an mRNA encoded by SEQ ID NO:5 or a sequence at least 90%, 95%, or 99% identical to SEQ ID NO:5; or exogenously applying to the plant a small RNA encoded by a sequence comprising a polynucleotide at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 123, 124, 130, 131, 132, 133, 134, 136, 137, 138, 139, 142, 143, 144, 145, 146, 147, 148, 149, 150, 151, 152, 153, 154, 155, 156, 157, 158, 159, 160 or 161. In some embodiments, the exogenously applying the mRNA or small RNA comprises contacting a cytoplasm or nucleus of the plant with the mRNA or small RNA. In some embodiments, the exogenously applying the mRNA or small RNA comprises contacting the plant with an expression cassette comprising a heterologous promoter operably linked to a polynucleotide at least 90%, 95%, or 99% identical, or identical, to SEQ ID NO:5.

In some embodiments, the exogenously applying the mRNA or small RNA comprises contacting the plant with an expression cassette comprising a heterologous promoter operably linked to a polynucleotide encoding a small RNA, wherein the polynucleotide comprises a sequence at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 123, 124, 130, 131, 132, 133, 134, 136, 137, 138, 139, 142, 143, 144, 145, 146, 147, 148, 149, 150, 151, 152, 153, 154, 155, 156, 157, 158, 159, 160 or 161. In some embodiments, the exogenously applying the mRNA or small RNA comprises contacting an in vitro tissue cultured plant cell with the mRNA or small RNA.

In some aspects, the present invention provides an expression cassette comprising a heterologous promoter operably linked to: i) a polynucleotide encoding a small RNA, wherein the polynucleotide comprises a sequence at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161; or ii) a polynucleotide encoding an mRNA, wherein the polynucleotide comprises a sequence at least 90%, 95%, or 99% identical, or identical, to SEQ ID NO:5. The expression cassette can be a heterologous expression cassette. In some aspects, the present invention provides a recombinant plant comprising any one of the foregoing expression cassettes.

In some embodiments, the present invention provides a method of predicting the presence or absence of somaclonal abnormality in an oil palm plant comprising: a) obtaining a biological sample from the plant; b) determining a methylation density of a differential methylation region (DMR), or sub-region, in the sample from the plant, wherein the DMR is within a sequence of DNA at least 70%, 80%, 90%, 95%, or 99% identical, or identical, to SEQ ID NO:1; and c) correlating the methylation density to the presence or absence of a somaclonal abnormality in the plant, wherein the correlation comprises predicting the presence or absence of somaclonal abnormality in the plant.

In some aspects, the DMR is within a DNA meta-region in the sample from the plant, where the DNA meta-region is at least 70%, 80%, 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73 and 74. In some cases, the determining step comprises determining the methylation density in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72.

In some aspects, the method comprises predicting the presence of a somaclonal abnormality when the methylation density is reduced relative to a control locus. In some cases, the presence of a somaclonal abnormality is predicted when the methylation density in a DNA meta-region at least 70%, 80%, 90%, 95%, or 99% identical, or identical, to the sequence selected from the group consisting of SEQ ID NO:63, 64, 65, 66, 67, 69, and 70 (or selected from the group consisting of SEQ ID NO:63, 64, 65, 66, 67, 68, 69, and 70) is reduced relative to a control locus. In some cases, the presence of a somaclonal abnormality is predicted when the methylation density in the DNA region at least 70%, 80%, 90%, 95%, or 99% identical, or identical, to the sequence selected from the group consisting of SEQ ID NO:35, 36, 39, 40, 42, 43, 44, 45, 46, 48, 49, 51, 52, 57, 58, 59, 60, 61, and 73 is reduced relative to a control locus. In some cases, the presence of a somaclonal abnormality is predicted when the methylation density in the biomarker at least 90%, 95%, or 99% identical, or identical to the sequence selected from the group consisting of SEQ ID NO:7, 8, 11, 12, 14, 15, 16, 17, 18, 20, 21, 23, 24, 29, 30, 31, 32, 33, and 71 is reduced relative to a control locus.

In some aspects, the determining step comprises determining the methylation density in at least two, three or four different differential methylation regions (DMRs), wherein each DMR is independently within a sequence of DNA at least 70%, 80%, 90%, 95%, or 99% identical, or identical, to SEQ ID NO:1. In some cases, each DMR is within a DNA meta-region in the sample from the plant, where each DNA meta-region is at least 70%, 80%, 90%, 95%, or 99% identical, or identical, to a sequence independently selected from the group consisting of SEQ ID NO:63, 64, 65, 66, 67, 68, 69, and 70. In some cases, each DMR is within a DNA region in the sample from the plant, where each DNA region is at least 70%, 80%, 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the determining step comprises determining the methylation density in a biomarker in each DMR, wherein each biomarker is at least 90%, 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects, the somaclonal abnormality comprises a reduction in fruit yield, oil yield, growth, or reproduction of the plant relative to a control plant. In some cases, the control plant is a parental plant. In some cases, the control plant is a wild-type plant of the same fruit form phenotype (dura, tenera, or pisifera) as the plant predicted to have a somaclonal abnormality.

In some aspects, the somaclonal abnormality exhibits a Mantled phenotype.

In some aspects, the determining the methylation density comprises bisulfite conversion; and/or digesting genomic DNA with a methylation-dependent endonuclease; and/or digesting genomic DNA with a methylation-sensitive endonuclease. In some cases, the methylation density is CHG methylation density.

In some embodiments, the present invention provides a method comprising: providing a prediction of a presence or absence of a somaclonal abnormality in a plurality of plants, wherein the presence or absence of a somaclonal abnormality is determined by a methylation density (e.g., CHG methylation density) within a differential methylation region (DMR) in a sample from each plant, wherein the DMR is within a sequence of DNA at least 70%, 80%, 90%, 95%, or 99% identical, or identical, to SEQ ID NO: 1; and physically separating a plant predicted to have a somaclonal abnormality from a plant predicted to lack a somaclonal abnormality.

Definitions

As used herein, "plant" refers to any cell, or group of cells, from an organism of the kingdom Plantae. "Oil palm plant" refers to any cell, or group of cells, of an organism of the species *E. guineensis*. Non-limiting examples include whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like), and progeny of same. Non-limiting examples further include a plant cell, or group of plant cells, from in vitro cell culture.

As used herein, "ortet" refers to source palm from which a clone is generated. "Clone" refers to a genetically identical, or substantially identical, copy of a palm from a specimen plant tissue or cell, obtained through asexual reproduction in sterile conditions. "Ramet" refers to plants derived through in vitro propagation. "Explant" refers to excised tissue of a palm for in vitro propagation. "Semiclone" refers to a progeny derived from a cross between a clonal parent and a seedling parent. "Biclone" refers to a progeny derived from a cross where both parents are clones.

As used herein, the term "somaclonal abnormality" refers to any phenotypic or genotypic (e.g., epigenetic) modification that arises from in vitro culture. For example, the Mantled phenotype can arise as a somaclonal abnormality that arises in oil palm plants subjected to in vitro culture.

"Methylation" refers to cytosine methylation and/or hydroxymethylation at positions C5 of cytosine, the N6 position of adenine or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was unmethylated or methylated, respectively.

A "methylation profile" refers to a set of data representing the methylation states of one or more loci within a molecule of DNA from e.g., the genome of a plant, e.g., cells or tissues from a plant. The profile can indicate the methylation state of every base in a plant, can comprise information regarding a subset of the base pairs (e.g., the methylation state of specific restriction enzyme recognition sequence) in a genome, or can comprise information regarding regional methylation density of each locus.

"Methylation status" refers to the presence, absence and/or quantity of methylation at a particular nucleotide, or nucleotides within a portion of DNA. The methylation status of a particular DNA sequence (e.g., a DNA biomarker or DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value." A methylation value can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of methylation status. This is of particular use when it is desirable to compare the methylation status of a sequence in a sample to a threshold value.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC (see, e.g., U.S. Pat. No. 5,405,760), McrA, MrrA, DpnI, MspJI, LpnPI, AspBHI, RlaI and SgrTI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., *Nucleic Acids Res.* 22(17):3640-59 (1994) and http://rebase.neb.com. Suitable methylation-sensitive restriction enzymes that do not cleave DNA at or near their recognition sequence when a cytosine within the recognition sequence is methylated at position $C^5$ include, e.g., Aat II, Aci I, Acl I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position $N^6$ include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

A "threshold value that distinguishes between plants with and without" a particular somaclonal abnormality refers to a value or range of values of a particular measurement that can be used to distinguish between samples from plants with the abnormality and samples without the abnormality. Ideally, there is a threshold value or values that absolutely distinguishes between the two groups (i.e., values from the abnormal group are always, or nearly always, on one side (e.g., higher) of the threshold value and values from the wild-type group are always, or nearly always, on the other side (e.g., lower) of the threshold value). However, in many instances, threshold values do not absolutely distinguish between abnormal and wild-type samples (for example, when there is some overlap of values generated from abnormal and wild-type samples).

The term "biomarker" refers to a subsequence of a DNA region, differentially methylated region (DMR), or DNA meta-region. In some cases, the biomarker is identical to a portion of the DNA region, DMR, or DNA meta-region. In some cases, the biomarker is substantially identical, or at least 90%, 95%, or 99% identical to a portion of the DNA region, DMR, or DNA meta-region. Sequence comparisons can be performed using any BLAST including BLAST 2.2 algorithm with default parameters, described in Altschul et al., *Nuc. Acids Res.* 25:3389 3402 (1997) and Altschul et al., *J. Mol. Biol.* 215:403 410 (1990), respectively. Thus for example, a DNA region or biomarker described herein can correspond to a DNA sequence in an oil palm plant genome even if there is slight variation between the biomarker or DNA region and the particular oil palm plant genome in question. Such difference can be the result of slight genetic variation between oil palm plants. Consequently, the DMRs, DNA regions, DNA meta-regions, and biomarkers described herein can be at least about 90%, 95%, 99%, 99.9% identical, substantially identical, or identical, to a subsequence of SEQ ID NO:1.

"Sensitivity" of a given biomarker refers to the percentage of somaclonally abnormal samples that report a DNA methylation value different from a threshold value that distinguishes between wild-type and abnormal samples. For example, in some cases, the presence of a somaclonal abnormality is predicted when methylation is increased relative to the threshold value. In such cases, the sensitivity is calculated as follows:

$$\text{Sensitivity} = \left[ \frac{\text{(the number of abnormal samples above the threshold)}}{\text{(the total number of abnormal samples tested)}} \right] \times 100$$

The equation may also be stated as follows:

$$\text{Sensitivity} = \left[ \frac{\text{(the number of true positive samples)}}{\text{(the number of true positive samples)} + \text{(the number of false negative samples)}} \right] \times 100$$

where true positive is defined as a sample from a plant confirmed to have a somaclonal abnormality (e.g., a Mantled plant) that reports a DNA methylation value above the threshold value (i.e. the range associated with the phenotype), and false negative is defined as a confirmed somaclonally abnormal sample that reports a DNA methylation value below the threshold value (i.e. the range associated with no somaclonal abnormality). One of skill in the art can readily modify the above equations in cases where somaclonal abnormality is predicted when methylation is below a threshold value. Similarly, where somaclonal abnormality is predicted by either increased or decreased methylation in a DNA region or within a biomarker, the above-equation and its modified version can be combined to obtain a sensitivity value.

The value of sensitivity, therefore, reflects the probability that a DNA methylation measurement for a given biomarker obtained from a known abnormal sample will be in the range of somaclonally abnormal-associated measurements. As defined here, the relevance of the calculated sensitivity value represents an estimation of the probability that a given biomarker would detect the presence of a somaclonal abnormality when applied to a plant with that condition.

"Specificity" of a given biomarker refers to the percentage of wild-type samples that report a DNA methylation value different from a threshold value that distinguishes between somaclonally abnormal and wild-type samples. For example, in some cases, the absence of a somaclonal abnormality is predicted when methylation is reduced relative to the threshold value. In such cases, the specificity is calculated as follows:

$$\text{Specificity} = \left[ \frac{\text{(the number of wild-type samples below the threshold)}}{\text{(the total number of wild-type samples tested)}} \right] \times 100$$

The equation may also be stated as follows:

$$\text{Specificity} = \left[ \frac{\text{(the number of true negative samples)}}{\text{(the number of true negative samples)} + \text{(the number of false positive samples)}} \right] \times 100$$

where true negative is defined as a sample from a plant confirmed to be somaclonally normal that reports a DNA methylation value below the threshold value (i.e. the range associated with no abnormality), and false positive is defined as a sample from a plant confirmed to be somaclonally normal that reports DNA methylation value above the threshold value (i.e. the range associated with abnormality). The value of specificity, therefore, reflects the probability that a DNA methylation measurement for a given biomarker obtained from a known non-abnormal sample will be in the range of wild-type associated measurements. One of skill in the art can readily modify the above equations in cases where somaclonal abnormality is predicted when methylation is below a threshold value. Similarly, where somaclonal abnormality is predicted by either increased or decreased methylation in a DNA region or within a biomarker, the above-equation and its modified version can be combined to obtain a specificity value. As defined here, the relevance of the calculated specificity value represents an estimation of the probability that a given biomarker would predict the absence of a somaclonal abnormality when applied to a plant without that condition.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

As used herein, the terms "nucleic acid," "polynucleotide" and "oligonucleotide" refer to nucleic acid regions, nucleic acid segments, primers, probes, amplicons and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA.

A nucleic acid, polynucleotide or oligonucleotide can comprise, for example, phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. For example, a polynucleotide of the invention can contain one or more modified, non-standard, or derivatized base moieties or one or more modified sugar moieties.

"Percentage of sequence identity," or "identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polypeptide sequences means that a polypeptide comprises a sequence that has at least 75% sequence identity. Alternatively, percent identity can be any integer from 75% to 100%. Exemplary embodiments include at least: 75%, 80%, 85%, 90%, 95%, or 99% compared to a reference sequence using the programs described herein; preferably BLAST using standard parameters, as described below. One of skill will recognize that these values can be appropriately adjusted to determine identity of proteins encoded by two nucleotide sequences by taking into account codon degeneracy, amino acid similarity, reading frame positioning and the like. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

As used herein, the term "specifically hybridizes," in the context of an oligonucleotide, refers to an oligonucleotide that hybridizes under suitable conditions to a sequence, but does not hybridize to other related or unrelated sequences. In some cases, the suitable conditions are stringent hybridization conditions. In some cases, the suitable conditions are nucleic acid amplification conditions, such as PCR amplification conditions. In some cases, oligonucleotides that specifically hybridize to a nucleic acid can hybridize to a bisulfite converted nucleic acid but not to a nucleic acid of the same sequence that is resistant to bisulfite conversion (e.g., a methylated nucleic acid) or has not been subjected to bisulfite conversion. In some cases, oligonucleotides that specifically hybridize to a nucleic acid can hybridize to a nucleic acid sequence but not to a nucleic acid of the same sequence that has been subjected to bisulfite conversion.

The term heterologous, in the context of a heterologous promoter refers to a promoter operably linked to a polynucleotide sequence encoding an RNA or protein, wherein the promoter is not found operably linked to that polynucleotide in a wild-type organism. Similarly, the term "heterologous" in the context of a heterologous expression cassette refers to an expression cassette that differs from any of the expression cassettes found in a wild-type organism. Thus, the term heterologous expression cassette can contain endogenous promoters and endogenous coding sequences, so long as the expression cassette as a whole is not naturally found in the wild-type organism.

DETAILED DESCRIPTION OF THE INVENTION

I. Introduction

Figure 1:
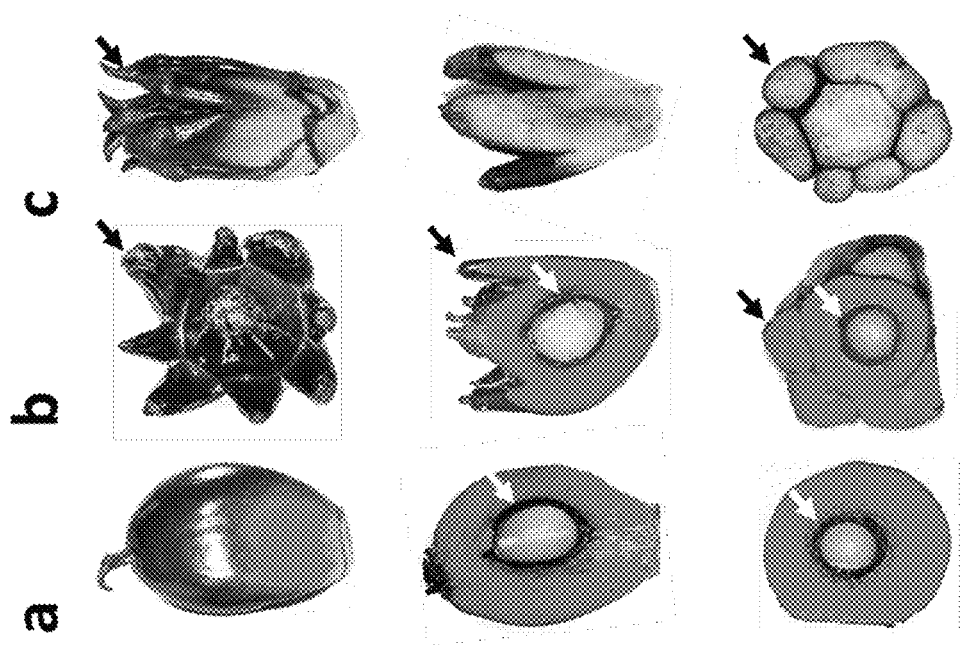
FIG. 1. Normal and mantled fruit forms. a-c, Fruit forms of (a) normal, (b) fertile mantled and (c) parthenocarpic mantled fruit. Images are displayed as whole fruit (top), longitudinal sectioned fruit (middle) and cross sectioned fruit (bottom). Whole fruits are shown as side views of normal and parthenocarpic mantled, and as a top view of fertile mantled so that multiple pseudocarpels are visible. Black arrows indicate one of several pseudocarpels per abnormal fruit. White arrows indicate the lignified shell and kernel of normal and fertile mantled fruit which are absent in parthenocarpic mantled fruit.

The development of oil palm planting material that consistently exhibits high oil yields has been hindered by the emergence of somaclonal abnormalities in plants that have been in vitro cultured. Oil palm plants exhibiting somaclonal abnormality as a result of in vitro culture include, for example, those exhibiting a Mantled phenotype. The present inventors have identified a molecular mechanism underlying somaclonal abnormality in oil palm plants: differential methylation within the oil palm locus corresponding to SEQ ID NO:1. The inventors have also identified DNA regions, meta-regions, and biomarkers within SEQ ID NO:1, where the methylation status is predictive of the presence or absence of a somaclonal abnormality. Methods, compositions, kits, and computer program products, including those described herein, can therefore be utilized to determine the methylation status of one or more DMRs, DNA regions, meta-regions, biomarkers, or cytosine nucleotides (e.g., cytosines in a CHG motif) therein to predict the presence or absence of a somaclonal abnormality in a plant and/or separate plants based on the predicted presence or absence of somaclonal abnormality each plant. For example, a culture of plant cells can be assayed to predict the presence or absence of a somaclonal abnormality (e.g., the Mantled phenotype).

II. DNA Regions

Differential methylation can be detected in a DNA region. A DNA region comprises a nucleic acid having one or more methylation sites of interest (e.g., a cytosine, a "microarray feature," or an amplicon amplified from a select primer or primer pair) and flanking nucleic acid sequences (i.e., "wingspan") of up to 4 kilobases (kb) in either or both of the 3' or 5' direction from the amplicon. This range roughly corresponds to the lengths of DNA fragments obtained by randomly fragmenting the DNA before screening for differential methylation between DNA in two or more samples (e.g., carrying out methods used to initially identify differentially methylated sequences as described in Example 1, below). In some embodiments, the wingspan of the one or more DNA regions is about 0.5 kb, 0.75 kb, 1.0 kb, 1.5 kb, 2.0 kb, 2.5 kb, 3.0 kb, 3.5 kb or 4.0 kb in both 3' and 5' directions relative to the sequence represented by the microarray feature. In some embodiments, the wingspan of the one or more DNA regions is about 2 kb, or 2 kb, in both the 3' and 5' directions relative to centermost nucleotide in the sequence represented by a microarray feature.

The methylation sites in a DNA region can reside in non-coding transcriptional control sequences (e.g., promoters, enhancers, etc.) or in coding sequences, including introns, exons, and retrotransposon elements of the oil palm genome locus corresponding to SEQ ID NO:1. In some embodiments, the methods comprise detecting the methylation status within, at, or near one or more transposable elements (e.g., comprising a nucleic acid sequence that is in, or within about 1.0 kb, 1.5 kb, 2.0 kb, 2.5 kb, 3.0 kb, 3.5 kb or 4.0 kb 3' or 5' of, a transposable element in SEQ ID NO:1).

The DNA regions of the invention also include naturally occurring variants, including for example, variants occurring in different subject populations and variants arising from single nucleotide polymorphisms (SNPs). SNPs encompass insertions and deletions of varying size and simple sequence repeats, such as dinucleotides and trinucleotide repeats. Variants include nucleic acid sequences sharing at least 90%, 95%, 98%, 99% sequence identity, i.e., having one or more deletions, additions, substitutions, inverted sequences, etc., relative to a DNA region described herein. Where the nucleic acid is an siRNA having a length of 21 or 24 nucleotides, variants include nucleic acid sequences sharing at least 15, 16, 17, 18, 19, 20, 21, 22, 23, or 24 identical nucleotides, e.g., having 1, 2, 3, 4, 5, 6, 7, 8, 9 or more deletions, additions, substitutions, inverted sequences, etc., relative to a DNA region described herein.

III. Methods

In some embodiments, the presence or absence of somaclonal abnormalities (e.g., the Mantled phenotype) can be predicted by determining the methylation status of one or more cytosines within a genomic region of an oil palm plant corresponding to SEQ ID NO:1. SEQ ID NO:1 contains three different retrotransposons (SEQ ID NO:2, Element 1 (Rider); SEQ ID NO:3, Element 2 (Karma); SEQ ID NO:4, Element 3 (Koala)) and the EgDEF1 gene, which is transcribed in at least four different forms (cDEF1, encoded by SEQ ID NO:5; tDEF1, encoded by SEQ ID NO:75; kDEF1, encoded by SEQ ID NO:78; and gDEF1, encoded by SEQ ID NO:80).

The methylation status of one or more cytosines (e.g., cytosines in a CHG motif) of SEQ ID NO:1 can, e.g., be determined and compared to a control, or a threshold value, and the presence or absence of somaclonal abnormalties can thereby be predicted. In some cases, a somaclonal abnormality is predicted when the methylation is increased at one or more specific cytosines (e.g., relative to a control or threshold value). In some cases, a somaclonal abnormality is predicted when the methylation is reduced at one or more specific cytosines (e.g., relative to a control or threshold value). In some cases, a somaclonal abnormality is predicted when the methylation is either increased or reduced at one or more specific cytosines (e.g., relative to a control or threshold value).

In some embodiments, the presence or absence of somaclonal abnormalities (e.g., the Mantled phenotype) can be predicted by determining the expression level of one or more transcripts that are differentially expressed in normal versus mantled plants, plant cells, or tissues. In some cases, a somaclonal abnormality is predicted when expression of one or more transcripts is reduced (e.g., relative to a control or threshold value). In some cases, the transcript is encoded by a sequence within SEQ ID NO:1. In some cases, the transcript is encoded by SEQ ID NO:77. In some cases, the transcript is encoded by a sequence within one or more of SEQ ID NOs: 130-134, 136-139, 142-143, or 144-161. In some cases, the transcript is encoded by a sequence within one or more of SEQ ID NO:144-161. In some cases, the transcript is an siRNA transcript (e.g., a 24mer siRNA). In some cases, a somaclonal abnormality is predicted when expression of one or more transcripts is increased (e.g., relative to a control or threshold value). In some cases, the transcript is encoded by a sequence within one or more of SEQ ID NO: 135, 140, or 141. In some cases, the transcript is an siRNA transcript (e.g., a 24mer siRNA).

A. Methods for Determining Methylation

Any method for detecting DNA methylation can be used in the methods of the present invention.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 8,361,719; 7,901,880; and 8,163,485. In some embodiments, amplification can be performed using a primer, or pair of primers, that is gene specific. Alternatively, adaptors can be added to the ends of the randomly fragmented DNA, the DNA can be digested with a methylation-dependent or methylation-sensitive restriction enzyme, intact DNA can be amplified using a primer or primers that hybridize to the adaptor sequences. In this case, a second step can be performed to determine the presence, absence or quantity of a particular gene in an amplified pool of DNA. In some embodiments, the DNA is amplified using real-time, quantitative DNA amplification (e.g., PCR).

In some embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact (e.g., uncut by the methylation-sensitive or methylation-dependent restriction enzyme) DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, wild-type) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved due to the presence of methylation at the cleavage site, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved due to the lack of methylation at the cleavage site, then the remaining intact DNA will be inversely proportional to the methylation density, and thus may be compared to a control to determine the relative methylation density of the locus in the sample. Such assays are disclosed in, e.g., U.S. Pat. No. 7,910,296.

Kits for the above methods can include, e.g., one or more of methylation-dependent restriction enzymes, methylation-sensitive restriction enzymes, amplification (e.g., PCR) reagents, and one or more probes and/or primers. In some cases, the one or more probes and/or primers are specific for, e.g., specifically hybridize to, SEQ ID NO:1, or a portion thereof. In some cases, the one or more probes and/or primers are specific for, e.g., specifically hybridize to, bisulfite converted SEQ ID NO:1, or a portion thereof.

Quantitative amplification methods (e.g., quantitative PCR or quantitative linear amplification) can be used to quantify the amount of intact DNA within a locus selected by one or more amplification primers following restriction digestion. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002). Amplifications can be monitored in "real time."

Additional methods for detecting DNA methylation can involve genomic sequencing before and after treatment of the DNA with bisulfite. See, e.g., Frommer et al., *Proc. Natl. Acad. Sci. USA* 89:1827-1831 (1992). When sodium bisulfite is contacted to DNA, unmethylated cytosine is converted to uracil, while methylated cytosine is not modified.

In some embodiments, restriction enzyme digestion of PCR products amplified from bisulfite-converted DNA is used to detect DNA methylation. See, e.g., Sadri & Hornsby, *Nucl. Acids Res.* 24:5058-5059 (1996); Xiong & Laird, *Nucleic Acids Res.* 25:2532-2534 (1997).

In some embodiments, a MethyLight assay is used alone or in combination with other methods to detect DNA methylation (see, Eads et al., *Cancer Res.* 59:2302-2306 (1999)). Briefly, in the MethyLight process genomic DNA is converted in a sodium bisulfite reaction (the bisulfite process converts unmethylated cytosine residues to uracil). Amplification of a DNA sequence of interest is then performed using, e.g., PCR primers that hybridize to CpG dinucleotides. By using one or more primers that hybridize only to sequences resulting from bisulfite conversion of unmethylated DNA, (or alternatively to methylated sequences that are not converted) amplification can indicate methylation status of sequences where the one or more primers hybridize. Similarly, the amplification product can be detected with a probe that specifically binds to a sequence resulting from bisulfite treatment of unmethylated (or methylated) DNA. If desired, both primer(s) and probe(s) can be used to detect methylation status. Thus, kits for use with MethyLight can include sodium bisulfite as well as primer(s) or detectably-labeled probe(s) (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In some embodiments, a Ms-SNuPE (Methylation-sensitive Single Nucleotide Primer Extension) reaction is used alone or in combination with other methods to detect DNA methylation (see, Gonzalgo & Jones, *Nucleic Acids Res.* 25:2529-2531 (1997)). The Ms-SNuPE technique is a quantitative method for assessing methylation differences at specific CpG sites based on bisulfite treatment of DNA, followed by single-nucleotide primer extension (Gonzalgo & Jones, supra). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In some embodiments, a methylation-specific PCR ("MSP") reaction is used alone or in combination with other methods to detect DNA methylation. An MSP assay entails initial modification of DNA by sodium bisulfite, converting all unmethylated, but not methylated, cytosines to uracil, and subsequent amplification with primers specific for methylated versus unmethylated DNA. See, Herman et al., *Proc. Natl. Acad. Sci. USA* 93:9821-9826, (1996); U.S. Pat. No. 5,786,146.

Additional methylation detection methods include, but are not limited to, methylated CpG island amplification (see, Toyota et al., Cancer Res. 59:2307-12 (1999)) and those described in, e.g., U.S. Patent Publication 2005/0069879; Rein, et al. *Nucleic Acids Res.* 26 (10): 2255-64 (1998); Olek, et al. *Nat Genet.* 17(3): 275-6 (1997); and PCT Publication No. WO 00/70090.

In some embodiments, the methods include: obtaining a biological sample from a plant; determining the methylation status of at least one cytosine (e.g., cytosine in a CHG motif) within a differential methylation region (DMR) in the sample from the plant, wherein the DMR is within a sequence of DNA at least 70%, 80%, 90%, 95%, or 99% identical, or identical, to SEQ ID NO:1; and correlating the methylation status of the at least one cytosine to the presence or absence of a somaclonal abnormality in the plant, wherein the correlation comprises predicting the presence or absence of somaclonal abnormality in the plant.

A biological sample can be obtained by any method known in the art. In general, the biological sample is obtained in a manner that preserves the nucleic acid of the sample. In some cases, the biological sample is obtained and treated to preserve the methylation status of genomic DNA therein. In some cases, the biological sample is obtained and treated to preserve RNA integrity.

Alternatively, in some cases, the methods include providing a prediction of a presence or absence of a somaclonal abnormality in a plurality of plants, wherein the presence or absence of a somaclonal abnormality is determined by a methylation status of at least one cytosine within a differential methylation region (DMR) in a sample from each plant, wherein the DMR is within a sequence of DNA at least 70%, 80%, 90%, 95%, or 99% identical, or identical, to SEQ ID NO: 1; and physically separating a plant predicted to have a somaclonal abnormality from a plant predicted to lack a somaclonal abnormality.

In some cases, the method further includes physically separating a plant predicted to have a somaclonal abnormality from one or more plants predicted to lack a somaclonal abnormality. In some cases, the plants can be physically separated, e.g., by selecting plants predicted to have a somaclonal abnormality and destroying or discarding them. In some cases, the plants are physically separated by selecting plants predicted to lack a somaclonal abnormality for cultivation. In some cases, plants selected for cultivation are germinated, transplanted, or planted. In some cases, plants not selected for cultivation are discarded or destroyed. In some cases, physically separated plants are treated to reduce, mitigate, eliminate, or prevent the somaclonal abnormality. For example, the physically separated plants can be contacted with an expression cassette containing a promoter operably linked to a polynucleotide encoding a transcript that is reduced in expression in a plant predicted to have a somaclonal abnormality.

In some cases, the DMR is within a DNA meta-region in the sample from the plant. The meta-region contains two or more overlapping DNA regions that exhibit differential methylation. Exemplary DNA meta-regions include overlapping 4 kb wingspan regions (2 kb 5' and 3') centered on biomarkers corresponding (e.g., at least 90%, 95%, or 99% identical, or identical) to SEQ ID NOS: 7, 8, 9, 10, 11, 12, 13, 14, 15, 16, 17, 18, 19, 20, 21, 22, 23, 24, 25, 26, 27, 28, 29, 30, 31, 32, 33, 34, 71, and 72. In some cases, the DNA meta-regions are in SEQ ID NO:1, or are in the locus corresponding to (e.g., at least 70%, 80%, 90%, 95%, or 99% identical, or identical, to) SEQ ID NO:1 in the oil palm genome. Exemplary DNA meta-regions include those at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the DMR is within a DNA region in the sample from the plant. The DNA region can, e.g., be a 4 kb, wherein the DNA region is at least about 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the cytosine is in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some embodiments, the presence of a somaclonal abnormality is predicted when the methylation status of at least one cytosine is reduced relative to a control locus. In some embodiments, the presence of a somaclonal abnormality is predicted when the methylation status of at least one cytosine is increased relative to a control locus. In some cases, either an increase or a decrease in methylation of at least one cytosine predicts the presence of a somaclonal abnormality. In some cases, the at least one cytosine is in a locus, retrotransposon, DNA meta-region, DNA region, or biomarker corresponding (e.g., at least 70%, 80%, 90%, 95%, or 99% identical, or identical) to a sequence selected from SEQ ID NOS: 1-5, and 7-75, 78, or 80.

The methylation status of the at least one cytosine can be compared to a control locus to determine a relative change in methylation. For example, if the methylation status of the cytosine at the test locus indicates a higher degree of methylation as compared to the methylation status of at the control locus, then the methylation status of the test locus is increased. As another example, if the methylation status of the cytosine at the test locus indicates a lower degree of methylation as compared to the methylation status of at the control locus, then the methylation status of the test locus is decreased. Typically, the control locus will have a known, relatively constant, methylation status. For example, the control locus can be previously determined to have no, some, or a high amount of methylation, thereby providing a relative constant value to control for error in detection methods, etc., unrelated to the presence or absence of a somaclonal abnormality. In some embodiments, the control locus is endogenous, i.e., is part of the genome of the individual sampled. Alternatively, the control locus can be an exogenous locus, e.g., a DNA sequence spiked into the sample in a known quantity and having a known methylation status.

In some embodiments, the methylation status of at least one cytosine in 2, 3, 4, 5, 6, 7, 8, 9, 10, 11, 12, 13, 14, 15, 16, 17, 18, 19, 20, 21, 22, 23, 24, 25, 26, 27, or 28 different differential methylation regions (DMRs) are determined to predict the presence or absence of a somaclonal abnormality. In some cases, the DMRs are in a locus, retrotransposon, DNA meta-region, DNA region, or biomarker corresponding (e.g., at least 70%, 80%, 90%, 95%, or 99% identical, or identical) to a sequence independently selected from SEQ ID NOS: 1-5, and 7-75.

In some embodiments, the predicted somaclonal abnormality is an abnormality that reduces fruit yield, oil yield, growth, or reproduction of an oil palm plant. In some cases, the reduction is relative to a control plant, such as a parent plant, or a wild-type plant of the same fruit color (nigrescens or virescens) or shell thickness (dura, tenera, or pisifera) phenotype. In some cases, the somaclonal abnormality exhibits a Mantled phenotype.

B. Predicting Abnormality by Gene Expression Analysis

Methylation of genomic DNA can affect expression (transcription and/or translation) of nearby gene sequences. Therefore, in some embodiments, the methods include the step of correlating the methylation status of at least one cytosine in a DNA region with the expression of nearby coding sequences, such as one or more transcripts of cDEF1 (SEQ ID NO:5), tDEF1 (SEQ ID NO:75), kDEF1 (SEQ ID NO:78), or gDEF1 (SEQ ID NO:80), and/or one or more transcripts of a retrotransposon near the EgDEF1 locus (SEQ ID NO:2, 3, or 4). For example, expression of gene sequences within about 1.0 kb, 1.5 kb, 2.0 kb, 2.5 kb, 3.0 kb, 3.5 kb or 4.0 kb, or more, in either the 3' or 5' direction from the cytosine of interest in the DNA region can be detected. In some embodiments, the methods include the step of detecting or quantifying the expression of nearby coding sequences, such as one or more transcripts of cDEF1 (SEQ ID NO:5), tDEF1 (SEQ ID NO:75), kDEF1 (SEQ ID NO:78), or gDEF1 (SEQ ID NO:80), and/or one or more transcripts of a retrotransposon near the EgDEF1 locus (SEQ ID NO:2, 3, or 4), and correlating the expression with a presence or absence or prediction of a somaclonal abnormality.

In some cases, expression of cDEF1 is correlated with a normal phenotype. For example, in some cases, cDEF1 expression is higher in plants with a normal phenotype, and thus a Mantled phenotype is predicted when a low level (e.g., relative to a threshold or control) of cDEF1 expression is detected. In some cases, expression of tDEF1 is correlated with a Mantled phenotype. For example, in some cases, tDEF1 expression is higher in plants with a Mantled phenotype, and thus a Mantled phenotype is predicted when a high level (e.g., relative to a threshold or control) of tDEF1 expression is detected. In some cases, expression of kDEF1 is correlated with a Mantled phenotype. For example, in some cases, kDEF1 expression is higher in plants with a Mantled phenotype, and thus a Mantled phenotype is predicted when a high level (e.g., relative to a threshold or control) of kDEF1 expression is detected. In some cases, expression of gDEF1 is correlated with a Mantled phenotype. For example, in some cases, gDEF1 expression is higher in plants with a Mantled phenotype, and thus a Mantled phenotype is predicted when a high level (e.g., relative to a threshold or control) of gDEF1 expression is detected. In some cases, the threshold or control is a sample from a normal plant or an expression value for a normal plant. In some cases, the threshold or control is a sample from an abnormal (e.g., Mantled) plant or an expression value for an abnormal (e.g., Mantled) plant.

In some cases, expression of an siRNA encoded within SEQ ID NO:1 is correlated with a normal phenotype, and thus a Mantled phenotype is predicted when a low level (e.g., relative to a threshold or control) of siRNA expression is detected. For example, in some cases, a Mantled phenotype is predicted when a low level (e.g., relative to a threshold or control) of expression of one or more siRNAs encoded by one or more of SEQ ID NOs:144-161 is detected. In some cases, a Mantled phenotype is predicted when expression of one or more siRNAs encoded by one or more of SEQ ID NOs:144-161 is reduced by at least 50% relative to a control or threshold value. As another example, in some cases, a Mantled phenotype is predicted when a low level (e.g., relative to a threshold or control) of expression of an siRNA encoded by SEQ ID NO:91 is detected. In some cases, a Mantled phenotype is predicted when expression of an siRNA encoded by SEQ ID NO:91 is reduced by at least 50%, 60%, 70%, 80%, or 90% relative to a control or threshold value.

Methods for measuring transcription and/or translation of a particular gene sequence are well known in the art. See, for example, Ausubel, *Current Protocols in Molecular Biology*, 1987-2006, John Wiley & Sons; and Sambrook and Russell, *Molecular Cloning: A Laboratory Manual*, 3rd Edition, 2000, Cold Spring Harbor Laboratory Press. In some embodiments, the gene or protein expression of a gene encoded in SEQ ID NO:1, 2, 3, 4, 5, 75, 78, or 80 is compared to a control, for example the expression of a nearby gene sequence from a sample from plant known to be negative for somaclonal abnormality or known to be positive for somaclonal abnormality, or to an expression level that distinguishes between somaclonally abnormal and wild-type states. Such methods involving detection of expression, like the methods of detecting methylation described herein, are useful in predicting the presence or absence of somaclonal abnormality (e.g., useful in predicting the presence or absence of the Mantled phenotype) in a plant.

In some cases, the expression of a regulatory RNA is detected. For example, a regulatory RNA that modulates the expression of cDEF1 (SEQ ID NO:5), tDEF1 (SEQ ID NO:75) can be detected. Exemplary regulatory RNAs include, but are not limited to, microRNAs. In some cases, the expression of one or more regulatory RNAs that are at least partially encoded within a retrotransposon located in the genomic locus corresponding to SEQ ID NO:1 is detected. Differential DNA methylation can result in changes in regulatory RNA expression (e.g., microRNAs, small interfering RNAs and antisense RNAs) which can then result in changes of gene expression in cis or in trans. Likewise, regulatory RNAs themselves can direct the establishment and/or maintenance of DNA methylation state in plants via the RNA-directed DNA methylation (RdDM) system. See Vu, et al. 2013 Development 140: 2953-60, Regulski, et al. 2013 Genome Res 23: 1651. Therefore, in some cases, mechanisms involving regulatory RNAs may be involved in either the establishment of differential DNA methylation associated with the Mantled phenotype, or in the mechanism by which differential DNA methylation regulates the function of genes involved in the Mantled phenotype.

In some embodiments, the methods further comprise the step of correlating the methylation status of one or more cytosines in SEQ ID NO:1, or DNA region, DNA metaregion, or biomarker therein, to expression of one or more of the gene regions identified in SEQ ID NO:1, 2, 3, 4, 5, 75, 78, or 80. In some embodiments, the methods further comprise the step of correlating the methylation status and/or expression level to the Mantled phenotype.

In some embodiments, the expression of a small RNA is detected. Small RNAs are a small non-coding expressed RNA molecules. Small RNAs can be involved in gene regulation and other biological processes. Exemplary small RNAs detected or quantified by the methods of the present invention include one or more small RNAs encoded by a polynucleotide sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161. Exemplary small RNAs detected or quantified by the methods of the present invention include one or more small RNAs at least partially encoded by a polynucleotide sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161.

In some cases, small RNAs are differentially expressed in normal versus abnormal (e.g., Mantled) plants. Such differential expression can be detected in a plant sample and correlated with a predicted normal or abnormal (e.g., Mantled) phenotype for the plant corresponding to the sample. Such differentially expressed small RNAs include, but are not limited to those encoded by, or at least partially encoded by, a polynucleotide at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161.

In some cases, an abnormal (e.g., Mantled) phenotype is predicted when expression of a small RNA encoded by, or at least partially encoded by, a polynucleotide sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, or 143 is increased (e.g., relative to a threshold or control). In some cases, an abnormal (e.g., Mantled) phenotype is predicted when expression of a small RNA encoded by, or at least partially encoded by, a polynucleotide sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 135 140, or 141 is increased (e.g., relative to a threshold or control). In some cases, the threshold or control is a sample from a normal plant or an expression value for a normal plant. In some cases, the threshold or control is a sample from an abnormal (e.g., Mantled) plant or an expression value for an abnormal (e.g., Mantled) plant.

In some cases, an abnormal (e.g., Mantled) phenotype is predicted when expression of a small RNA encoded by, or at least partially encoded by, a polynucleotide sequence at least 75%, 80%, 85%, 90%, 95%, or 99% identical, or identical, to SEQ ID NO:135, 140, or 141 is detected, or when an increased expression level (e.g., relative to a threshold or control) is detected. In some cases, a normal phenotype is predicted when expression of a small RNA encoded by, or at least partially encoded by, a polynucleotide sequence at least 75%, 80%, 85%, 90%, 95%, or 99% identical, or identical, to SEQ ID NO: 130, 131, 132, 133, 134, 136, 137, 138, 139, 142, or 143 is detected, or when an increased expression level (e.g., relative to a threshold or control) is detected. In some cases, the threshold or control is a sample from a normal plant or an expression value for a normal plant. In some cases, the threshold or control is a sample from an abnormal (e.g., Mantled) plant or an expression value for an abnormal (e.g., Mantled) plant.

In some cases, an abnormal (e.g., Mantled) phenotype is predicted when expression of a small RNA encoded by, or at least partially encoded by, a polynucleotide sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161 is decreased (e.g., relative to a threshold or control). In some cases, an abnormal (e.g., Mantled) phenotype is predicted when expression of a small RNA encoded by, or at least partially encoded by, a polynucleotide sequence at least 75%, 80%, 85%, 90%, 95%, or 99% identical, or identical, to SEQ ID NO:97, 115, 118, 119, 120, 121, 122, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161 is decreased (e.g., relative to a threshold or control).

In some embodiments, the methods include: obtaining a biological sample from a plant; detecting or quantifying expression of one or more of SEQ ID NO:2, 3, 4, 5, 75, 78, 80, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161; and correlating the expression or expression level to the presence or absence of a somaclonal abnormality in the plant, wherein the correlation comprises predicting the presence or absence of somaclonal abnormality in the plant.

A biological sample can be obtained by any methods known in the art. In general, the biological sample is obtained in a manner that preserves the nucleic acid of the sample. In some cases, the biological sample is obtained and treated to preserve the RNA therein. In some cases, the biological sample is obtained and treated to preserve RNA integrity.

Alternatively, in some cases, the methods include providing a prediction of a presence or absence of a somaclonal abnormality in a plurality of plants, wherein the presence or absence of a somaclonal abnormality is determined by gene expression analysis; and physically separating a plant predicted to have a somaclonal abnormality from a plant predicted to lack a somaclonal abnormality.

In some cases, the method further includes physically separating a plant predicted to have a somaclonal abnormality from one or more plants predicted to lack a somaclonal abnormality. In some cases, the plants can be physically separated, e.g., by selecting plants predicted to have a somaclonal abnormality and destroying or discarding them. In some cases, the plants are physically separated by selecting plants predicted to lack a somaclonal abnormality for cultivation. In some cases, plants selected for cultivation are germinated, transplanted, or planted. In some cases, plants not selected for cultivation are discarded or destroyed. In some cases, physically separated plants are treated to reduce, mitigate, eliminate, or prevent the somaclonal abnormality.

In some embodiments, the predicted somaclonal abnormality is an abnormality that reduces fruit yield, oil yield, growth, or reproduction of an oil palm plant. In some cases, the reduction is relative to a control plant, such as a parent plant, or a wild-type plant of the same fruit color (nigrescens or virescens) or shell thickness (dura, tenera, or pisifera) phenotype. In some cases, the somaclonal abnormality exhibits a Mantled phenotype.

C. Sampling and/or Sorting

Oil palm nucleic acid can be obtained from any suitable cell or tissue of an oil palm plant. For example, oil palm nucleic acid can be obtained from a leaf, a stem, a root, a seed, or a plant cell or group of plant cells in, or obtained from, in vitro culture. In some cases, the oil palm nucleic acid is obtained from endosperm tissue of a seed. In some embodiments, nucleic acid is extracted from a plant cell (e.g., a plant cell in, or obtained from, in vitro culture), a seedling, an immature (e.g., non fruit bearing) plant, or a mature plant. In some cases, the oil palm nucleic acid is obtained in such a manner that the oil palm plant is not reduced in viability or is not substantially reduced in viability. For example, in some cases, sample extraction can reduce the number of viable plants or seeds in a population by less than about 20%, 15%, 10%, 5%, 2.5%, 1%, or less. In some cases, nucleic acid is obtained from a population of plant cells, wherein the population of plant cells is of a uniform or substantially uniform genotype and/or epigenotype at one or all genomic loci. For example, a sample of nucleic acid from a portion of plant cells in an in vitro culture can be extracted, assayed, and the results used to sort the in vitro culture. Exemplary tissue types for obtaining a suitable sample include leaf from in vitro plantlets and nursery ramets. Alternatively, tissues such as roots, inflorescence and zygotic embryos can also be used. Tissues from potential ortets can also be screened prior to tissue culture. Seeds from semiclones and biclones can be tested as well.

Sampling can be automated. For example, a machine can be used to pick plant cell colonies or clumps, or portions thereof, in an in vitro culture for analysis. Similarly, a machine can take samples from a plant or seed, or to take samples from a plurality of plant cell colonies, clumps, plants, or seeds. Sampling can also be performed manually. Further sampling methodologies are described herein.

In some embodiments, the sampling is controlled to deter contamination of the sample. For example, washing steps can be employed between sample processing steps. Alternatively, disposable or removable sample handling elements can be utilized, e.g., disposable pipetting tips, disposable receptacles or containers, or disposable blades or grinders.

In some cases, samples are purified prior to detection of the methylation status of one or more cytosines within a DMR of an oil palm plant. For example, samples can be centrifuged, extracted, precipitated (e.g., alcohol precipitated), or purified using a solid support (e.g., using nucleic acid binding beads or membranes). Additional methods for purification of plant nucleic acids are known by those of skill in the art.

In some embodiments, the presence or absence of a somaclonal abnormality (e.g., the Mantled phenotype) is predicted, and the plant is sorted based on the predicted phenotype. The somaclonal abnormality (e.g., the Mantled phenotype) can be predicted, e.g., based on the methylation status of one or more cytosines in SEQ ID NO:1, or one or more DNA regions, DNA meta-regions, or biomarkers therein, and the plant is sorted based on the predicted phenotype. In some cases, the somaclonal abnormality (e.g., the Mantled phenotype) can be predicted, e.g., based on methylation status or gene expression, and the plant is sorted based on the predicted phenotype.

For example, a plurality of plants can be sorted (e.g., physically separated) into Mantled or non-Mantled (e.g., wild-type) plants based on their predicted phenotype (e.g., based on their methylation or expression as described herein). Wild-type plants can be sorted and stored or utilized and planted or otherwise separated from plant propagation material used for the clonal generation of plants lacking one or more somaclonal abnormalities. In some cases plants having one or more somaclonal abnormalities, e.g., Mantled plants, can be discarded or destroyed (e.g., autoclaved) or not cultivated in commercial oil palm production.

In some cases, the plant is a plant cell, a clump of plant cells, or a colony of plant cells from in vitro culture and the in vitro culture is discarded or destroyed when one or more plants from the culture are predicted to have a somaclonal abnormality (e.g., one or more plants are predicted to exhibit a Mantled phenotype). In some cases, the plant is a young ramet and nucleic acid from the plant is assayed to predict the presence or absence of a somaclonal abnormality. In some cases, the young ramet is then sorted before it is planted in the field. For example, young ramet predicted to have a somaclonal abnormality (e.g., the Mantled phenotype) can be discarded. Ramets predicted to lack a somaclonal abnormality can be further cultivated and/or planted in the field. As yet another alternative, oil palm plants that have been planted in the field for optimal palm oil yield, but are not mature enough to verify the absence of a somaclonal abnormality (e.g., a Mantled phenotype) can be assayed and plants predicted to have a somaclonal abnormality can be removed from the field.

In some embodiments, the presence or absence of a somaclonal abnormality and plant fruit color and/or shell thickness phenotype is predicted. Methods for predicting fruit color and/or shell thickness phenotype, and/or sorting based on such predicted phenotypes, are disclosed in, e.g., U.S. patent application Ser. No. 14/226,508, filed on Mar. 26, 2014; and Ser. No. 13/800,652, filed on Mar. 13, 2013. In some cases, fruit color can be predicted and/or sorted based on the genotype of the VIR gene. In some cases, shell thickness can be predicted and/or sorted based on the genotype of the SHELL gene.

In some cases, the fruit color and/or shell thickness prediction is combined with a methylation status or gene expression information to predict the presence or absence of a somaclonal abnormality (e.g., the Mantled phenotype). In some cases, the plant is sorted based on one, two, or all three predicted phenotypes. For example, the plant can be sorted into nigrescens or virescens seeds or plants and dura, tenera, or pisifera seeds or plants based on their predicted phenotypes. The plants can then be verified as predicted to lack a somaclonal abnormality (e.g., the Mantled phenotype). In some cases, the plants can be predicted to lack a somaclonal abnormality (e.g., the Mantled phenotype), and then such plants can be sorted and/or stored based on their predicted, or expected, nigrescens, virescens, dura, tenera, and/or pisifera phenotypes.

In some cases, the prediction of one or more phenotypes is performed in young plants before cultivation in the field. Therefore, in some cases, the samples are young ramets during hardening in the pre-nursery or acclimatization in the nursery. In some embodiments, the samples are obtained from a semiclonal or biclonal plant that has been germinated and then cultivated less than 1, 2, 4, 6, months or less than 1, 2, 3, 4, or 5 years. In some embodiments, the samples are obtained before the plant has been germinated (e.g., from a seed) or shortly thereafter (e.g., less than about 1, 2, 3, 4, or 5 weeks after germination).

In some embodiments, the methylation status of at least one cytosine is determined an combined with DNA fingerprinting methods to aid in cataloging, selecting, maintaining, organizing, identifying, or tracking of clonal material, stocks, strains, or cultures. For example, in vitro cultures can be confirmed to derive from a specified source or lineage suing DNA fingerprinting and methylation status or gene expression used to predict the presence or absence of a somaclonal abnormality. Similarly, the presence or absence of a strain, stock, or varietal protected under a Plant Variety Protection Act (e.g., the Plant Variety Protection Act of Malaysia or Indonesia) can be ascertained and the presence or absence of a somaclonal abnormality predicted. In some embodiments, palms can be identified and/or confirmed using DNA fingerprinting as having, or likely having, one or more desirable phenotypes (e.g., fruit color, shell thickness, pest resistance, etc.) and the presence or absence of a somaclonal abnormality predicted. Methods for DNA fingerprinting are known in the art and include, e.g., those described in Lim & Rao, J Oil Palm Research, 17:136-144 (December 2005); Billotte, et al., Genome, 44(3): 413-425 (2001); Jack & Mayes, Oleagineux, 48(1): 1-8 (1993); Jack, et al., Theor Appl Genet, 90:543-649 (1995); Cheah, et al., Advances in Oil Palm Research p. 332-70 (2000); and Corley, J. Oil Palm Research, 17:64-69 (2005).

Machines can be utilized to carry out one or more methods described herein, prepare plant samples for one or more methods described herein, or facilitate high throughput sorting of oil palm plants.

In some cases, a machine can sort and orient seeds such that the seed are all oriented in a similar manner. The seeds for example, can be oriented such that embryo region of the seed is down and the embryo free region is oriented up. In some cases, the seeds can be placed into an ordered array or into a single line.

In some embodiments, the seed is held in pre-determined orientation to facilitate efficient and accurate sampling. For example, the machine can orient the seeds by seed shape or visual appearance. In some cases, the seed is oriented to facilitate sampling from the 'Crown' of each respective seed, containing the cotyledon and/or endosperm tissue of the seed, so that the germination viability of each seed is preserved.

In some cases, a machine can separately store plants and corresponding extracted samples. For example, a sample may be obtained from an in vitro culture, and the culture stored. In some cases, the extracted samples and stored plants are organized, labeled, or catalogued in such a way that the sample and the plant (e.g., culture) from which it is derived can be determined. In some cases, the extracted samples and stored plants are tracked so that each can be accessed after data is collected. For example, a sample can be extracted from a culture and the presence or absence of a somaclonal abnormality (e.g., the Mantled phenotype) predicted for the sample, and thus the seed. The plant can then be accessed, germinated, planted, stored, or destroyed based on the prediction.

In some cases, the extraction and storing are performed automatically by the machine, but the methylation analysis and/or treatment of analyzed plants performed manually or performed by another machine. As such, in some embodiments, a system is provided consisting of two or more machines for extraction of samples, sorting and storing, and prediction of the presence or absence of a somaclonal abnormality (e.g., the Mantled phenotype).

In some cases, the plants are stored in an array by the machine, such as individually in an array of tubes or wells. The plants can be sampled and/or interrogated in or from each well. The results of the sampling or interrogating can be correlated with the position of the plant in the array.

Sampling can include extraction and/or analysis of nucleic acid (e.g., DNA or RNA). Sampling can further include magnetic resonance imaging, optical dispersion, optical absorption, ELISA, enzymatic assay, or the like.

Systems, machines, methods and compositions for plant culturing, sampling, and/or sorting are further described in, e.g., U.S. Pat. Nos. 4,910,146; 6,307,123; 6,646,264; 6,673,595; 7,367,155; 8,312,672; 7,685,768; 7,673,572; 8,443,545; 7,998,669; 8,114,669; 8,362,317; 8,076,076; 7,402,731; 7,600,642; 8,237,016; 8,401,271; 8,281,935; 8,241,914; 6,880,771; 7,909,276; 8,221,968; and 7,454,989. Systems, machines, methods and compositions for plant culturing, sampling, and/or sorting are also further described in, e.g., U.S. Patent Application Publication NOs: 2012/180386; 2009/070891; 2013/104454, 2012/117865, 2008/289061; 2008/000815; 2011/132721; 2011/195866; 2011/0079544; 2010/0143906; and 2013/079917. Additional systems, machines, methods, and compositions for plant culturing, sampling, and/or sorting are further described in international patent application publications WO2011/119390; and WO2011/119394.

Also provided herein are methods for using the systems, machines, methods, and compositions described herein for plant (e.g., a seed, a seedling, a plant, a plant cell, a plant cell colony, or a clump of plant cells) sampling or sorting. For example, a plant or set of plants can be loaded into a sampler, and a sample obtained. In some cases, the plant can be stored, e.g., in an array. In some cases, the storage is performed by the machine that samples the plant. In other cases, the plant is stored by another machine, or stored manually. In some cases, DNA can be extracted from the sample. In some cases, sample can be obtained and DNA extracted by the same machine. In other cases, the DNA is extracted by another machine, or manually. The extracted DNA can be analyzed and the presence or absence of a somaclonal abnormality (e.g., the Mantled phenotype) predicted. In some cases, the extracted DNA is analyzed by the same machine, by another machine, or manually. In some cases, the presence or absence of a somaclonal abnormality (e.g., the Mantled phenotype) is predicted by the machine, a different machine, or manually. In some cases, stored plants can be disposed of (e.g., cultivated, treated, or destroyed) based on the prediction of the presence or absence of a somaclonal abnormality (e.g., the Mantled phenotype). In some cases, stored plants can be disposed of based on the VIR genotype or predicted fruit color phenotype, based on their predicted shell thickness phenotype, and/or based on the prediction of the presence or absence of a somaclonal abnormality (e.g., the Mantled phenotype). For examples, plants predicted to have a somaclonal abnormality can be discarded or destroyed, or treated. As another example, plants predicted to be pisifera and/or Mantled, or dura and/or Mantled, can be removed from (e.g., separated from) the population of plants that are selected for planting and cultivation in the field for oil production. Similarly, e.g., plants predicted to be tenera and having an absence of somaclonal abnormality (e.g., lacking the Mantled phenotype), can be separated from other plants and/or selected for field cultivation. In some cases, the plant is disposed of by the machine, a different machine, or manually.

In some cases, the plant (e.g., a seed, a seedling, a plant, a plant cell, a plant cell colony, or a clump of plant cells) or plants are shipped from a customer to a service provider, analyzed, and returned. In some cases, only plants with a predicted phenotype or phenotypes are returned. For example, only plants predicted to lack a somaclonal abnormality, or a combination thereof are returned. In other cases, plants are sampled, and the samples are shipped from a customer to a service provider for analysis. The customer can then utilize information provided by the analysis to dispose of the plants.

In some cases, reagents, such as the compositions described herein are provided for sampling of plants manually or automatically. For example, endonucleases, oligonucleotide primers or probes, or a combination thereof as described herein can be provided. As another example, reaction mixtures or kits containing reagents necessary for analysis of nucleic acid from an oil palm plant can be provided, as described herein.

C. Screening Culture Conditions

In vitro culture can produce somaclonal abnormalities in oil palm lines. For example, in vitro culture can give rise to oil palm plants having the Mantled phenotype. In some cases, culture conditions or protocols can screened to identify conditions or protocols that reduce or eliminate the generation of somaclonal variants. Such conditions or protocols can then be used to develop clonally propagated oil palm plant lines having reduced, or no, somaclonal abnormalities. For example, an in vitro culture can be subjected to standard culture conditions as a control. A similar, or identical culture can then be subjected to a test condition. The presence or absence, proportion, or likelihood of a somaclonal abnormality can be determined in the control and test cultures. Test conditions that reduce or eliminate somaclonal abnormalities can then be identified and utilized. In some cases, the experiment can be repeated iteratively to further improve culture conditions. Exemplary culture conditions include, but are not limited to, physiological state of palm during sampling, type of explant, number of subcultures, number of ramets per embryogenic line, auxin hormone level and type, cytokinin hormone level and type, salt concentration, osmolarity, pH, temperature, photoperiod, presence and/or type of feeder cells, media composition, etc.

In some cases, in vitro plant cultures can be screened to identify cultures that have developed somaclonal abnormalities. For example, an in vitro oil palm plant culture, or a set of in vitro oil palm plant cultures can be assayed, the presence or absence of somaclonal abnormalities can be predicted, and then cultures predicted to have a somaclonal abnormality, or a high percentage or likelihood of somaclonal abnormalities, can be separated, discarded or destroyed. In some cases, cultures predicted to have a somaclonal abnormality can be treated to reduce the likelihood of, prevent, or revert the somaclonal abnormality.

IV. Reducing Somaclonal Abnormalities

In some embodiments, plants (e.g., plant cell in vitro tissue cultures) are treated to reduce, prevent, mitigate, eliminate, or revert a somaclonal abnormality or a predicted somaclonal abnormality. In some cases, somaclonal abnormalities are reduced, prevented, mitigated, eliminated, or reverted by exogenously applying to the plant an mRNA encoded by SEQ ID NO:5 or a sequence at least 90%, 95%, or 99% identical to SEQ ID NO:5; or exogenously applying to the plant a small RNA encoded by a sequence comprising a polynucleotide at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 123, 124, 130, 131, 132, 133, 134, 136, 137, 138, 139, 142, 143, 144, 145, 146, 147, 148, 149, 150, 151, 152, 153, 154, 155, 156, 157, 158, 159, 160 or 161.

In some cases, the exogenously applying the mRNA or small RNA comprises contacting a cytoplasm or nucleus of the plant with the mRNA or small RNA. In some cases, the mRNA or small RNA is produced in an in vitro transcription reaction. In some cases, the exogenously applying the mRNA or small RNA comprises contacting the plant with an expression cassette comprising a heterologous promoter operably linked to a polynucleotide at least 75%, 80%, 85%, 90%, 95%, or 99% identical, or identical, to SEQ ID NO:5. In some cases, the exogenously applying the mRNA or small RNA comprises contacting the plant with an expression cassette comprising a heterologous promoter operably linked to a polynucleotide encoding a small RNA, wherein the polynucleotide comprises a sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 123, 124, 130, 131, 132, 133, 134, 136, 137, 138, 139, 142, 143, 144, 145, 146, 147, 148, 149, 150, 151, 152, 153, 154, 155, 156, 157, 158, 159, 160 or 161.

In some cases, the exogenously applying the mRNA or small RNA comprises generating a transgenic plant with a heterologous promoter operably linked to one or more of the foregoing polynucleotides and generating an in vitro tissue culture from the transgenic plant. In some cases, such a tissue culture system can reduce or eliminate the generation of somaclonal abnormalities. Thus, oil palm plants having one or more desirable properties such as high oil yield, or a desired dura, tenera, pisifera, virescens, or nigrescens, phenotype, can be generated indefinitely via in vitro tissue culture propagation techniques without, or with less, risk of generating plants with a somaclonal abnormality.

V. Kits

This invention also provides kits for the detection and/or quantification of methylation within the DMRs, DNA regions, DNA meta-regions, or biomarkers of the invention using the methods described herein.

The kits of the invention can comprise at least one polynucleotide that hybridizes to at least one of the diagnostic biomarker sequences of the invention and at least one reagent for detection of methylation. Reagents for detection of methylation can include, e.g., sodium bisulfite, polynucleotides designed to specifically hybridize to sequence that is a produce (e.g., an amplification product) of a biomarker sequence of the invention if the biomarker sequence is not methylated (e.g., containing at least one C→U conversion) or to specifically hybridize if the biomarker sequence is methylated, and/or a methylation-sensitive or methylation-dependent restriction enzyme. The kits can provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, a kit for determining the methylation status of at least one DMR in a biological sample from an oil palm plant is provided, the kit including: (1) a polynucleotide, or a pair of polynucleotides, capable of specifically amplifying at least a portion of a DMR, wherein the DMR is within a sequence of DNA at least 70%, 80%, 90%, 95%, or 99% identical, or identical, to SEQ ID NO:1; and a methylation-dependent, a methylation sensitive restriction enzyme, and/or sodium bisulfite; or (2) sodium bisulfite, primers, and adapters for whole genome amplification, and at least one polynucleotide to quantify the presence of the converted methylated and/or the converted unmethylated sequence of at least one cytosine from a DMR, wherein the DMR is within a sequence of DNA at least 70%, 80%, 90%, 95%, or 99% identical, or identical, to SEQ ID NO:1; or (3) methylation sensing restriction enzymes, primers and adapters for whole genome amplification, and at least one polynucleotide to quantify the number of copies of at least a portion of a DMR, wherein the DMR is within a sequence of DNA at least 70%, 80%, 90%, 95%, or 99% identical, or identical, to SEQ ID NO:1; or (4) a methylation sensing binding moiety and at least one polynucleotide to quantify the number of copies of at least a portion of a DMR, wherein the DMR is within a sequence of DNA at least 70%, 80%, 90%, 95%, or 99% identical, or identical, to SEQ ID NO:1.

In some cases, the DMR is within a DNA meta-region in the sample from the plant. The meta-region contains two or more overlapping DNA regions that exhibit differential methylation. Exemplary DNA meta-regions include overlapping 4 kb wingspan regions (2 kb 5' and 3') centered on biomarkers corresponding (e.g., at least 90%, 95%, or 99% identical, or identical) to SEQ ID NOS: 7, 8, 9, 10, 11, 12, 13, 14, 15, 16, 17, 18, 19, 20, 21, 22, 23, 24, 25, 26, 27, 28, 29, 30, 31, 32, 33, 34, 71, and 72. In some cases, the DNA meta-regions are in SEQ ID NO:1, or are in the locus corresponding to (e.g., at least 70%, 80%, 90%, 95%, or 99% identical, or identical, to) SEQ ID NO:1 in the oil palm genome. Exemplary DNA meta-regions include those at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the DMR is within a DNA region in the sample from the plant. The DNA region can, e.g., be a 4 kb, wherein the DNA region is at least about 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the cytosine is in a biomarker, wherein the biomarker is at least 90%, 95%, or 95% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some embodiments, the kit determines the methylation status of at least one cytosine in 2, 3, 4, 5, 6, 7, 8, 9, 10, 11, 12, 13, 14, 15, 16, 17, 18, 19, 20, 21, 22, 23, 24, 25, 26, 27, or 28 different differential methylation regions (DMRs) are determined to predict the presence or absence of a somaclonal abnormality. In some cases, the DMRs are in a locus, retrotransposon, DNA meta-region, DNA region, or biomarker corresponding (e.g., at least 70%, 80%, 90%, 95%, or 99% identical, or identical) to a sequence independently selected from SEQ ID NOS: 1-5, and 7-75.

In some embodiments, the kit contains a detectably labeled polynucleotide probe that specifically detects an amplified DMR, or a portion thereof.

VI. Computer Program Product

The calculations for the methods described herein can involve computer-based calculations and tools to predict the presence or absence of somaclonal abnormalities (e.g., predict the Mantled phenotype) in a plant or plant cells. For example, a methylation value for a DNA region, DNA meta-region, biomarker, a portion thereof, or one or more cytosines therein, can be compared by a computer to a threshold or control value, as described herein. The tools are advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

In some embodiments, the computer program product contains a computer readable medium encoded with program code, the program code including:

program code for receiving a methylation value representing the methylation status of at least one cytosine within a differential methylation region (DMR) in the sample from the oil palm plant, wherein the DMR is within a sequence of DNA at least 70%, 80%, 90%, 95%, or 99% identical, or identical, to SEQ ID NO:1;

program code for comparing the methylation value to a control value, wherein the control value distinguishes between plants with and without a somaclonal abnormality, wherein the comparison of the methylation value to the control value is predictive of the presence or absence of a somaclonal abnormality in the plant.

In some cases, the DMR is within a DNA meta-region in the sample from the plant. The meta-region contains two or more overlapping DNA regions that exhibit differential methylation. Exemplary DNA meta-regions include overlapping 4 kb wingspan regions (2 kb 5' and 3') centered on biomarkers corresponding (e.g., at least 90%, 95%, or 99% identical, or identical) to SEQ ID NOS: 7, 8, 9, 10, 11, 12, 13, 14, 15, 16, 17, 18, 19, 20, 21, 22, 23, 24, 25, 26, 27, 28, 29, 30, 31, 32, 33, 34, 71, and 72. In some cases, the DNA meta-regions are in SEQ ID NO:1, or are in the locus corresponding to (e.g., at least 70%, 80%, 90%, 95%, or 99% identical, or identical, to) SEQ ID NO:1 in the oil palm genome. Exemplary DNA meta-regions include those at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the DMR is within a DNA region in the sample from the plant. The DNA region can, e.g., be a 4 kb, wherein the DNA region is at least about 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the cytosine is in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

The methylation status of the at least one cytosine can be compared to a control value, wherein the control value is a methylation value for a control locus to determine a relative change in methylation. For example, if the methylation status of the cytosine at the test locus indicates a higher degree of methylation as compared to the methylation status of at the control locus, then the methylation status of the test locus is increased. As another example, if the methylation status of the cytosine at the test locus indicates a lower degree of methylation as compared to the methylation status of at the control locus, then the methylation status of the test locus is decreased. Typically, the control locus will have a known, relatively constant, methylation status. For example, the control locus can be previously determined to have no, some, or a high amount of methylation, thereby providing a relative constant value to control for error in detection methods, etc., unrelated to the presence or absence of a somaclonal abnormality. In some embodiments, the control locus is endogenous, i.e., is part of the genome of the individual sampled. Alternatively, the control locus can be an exogenous locus, e.g., a DNA sequence spiked into the sample in a known quantity and having a known methylation status.

In some embodiments, the methylation status of at least one cytosine in 2, 3, 4, 5, 6, 7, 8, 9, 10, 11, 12, 13, 14, 15, 16, 17, 18, 19, 20, 21, 22, 23, 24, 25, 26, 27, or 28 different differential methylation regions (DMRs) are determined to predict the presence or absence of a somaclonal abnormality. In some cases, the DMRs are in a locus, retrotransposon, DNA meta-region, DNA region, or biomarker corresponding (e.g., at least 70%, 80%, 90%, 95%, or 99% identical, or identical) to a sequence independently selected from SEQ ID NOS: 1-5, and 7-75.

In some embodiments, the predicted somaclonal abnormality is an abnormality that reduces fruit yield, oil yield, growth, or reproduction of an oil palm plant. In some cases, the reduction is relative to a control plant, such as a parent plant, or a wild-type plant of the same fruit color (nigrescens or viriscens) or shell thickness (dura, tenera, or pisifera) phenotype. In some cases, the somaclonal abnormality exhibits a Mantled phenotype.

In some cases, the computer program product predicts the presence or absence of a somaclonal abnormality (e.g., the Mantled phenotype) in the plant. In some cases, the computer program product provides the data for another computer program product, or a person of skill in the art, to predict the presence or absence of a somaclonal abnormality in the plant. In some cases, the computer program product calculates a statistical confidence (e.g., a p-value, t-statistic, etc.) for a prediction of the presence or absence of a somaclonal abnormality in the plant.

EXAMPLES

The following examples are offered to illustrate, but not to limit the claimed invention.

Example 1: Global DNA Methylation Profiling Reveals Differential DNA Methylation in Mantled Clonally Propagated Materials Microarray features were designed based on a genome build of the pisifera oil palm genome (Singh et al. 2013, *Nature* 500, 340-344). Over 1 million features were designed to unique 61 base sequences across the unique sequence of the oil palm genome. Although repetitive sequences make up approximately 57% of the oil palm genome, unique sequence features could be designed to sequences flanking distinct repetitive elements, as well as unique sequences embedded within specific repetitive elements. Loci that are differentially methylated in Mantled clonal materials relative to phenotypically normal clonal material were identified using a DNA microarray-based technology platform that utilizes the methylation-dependent restriction enzyme McrBC (Ordway et al. 2006 *Carcinogenesis* 27: 2409-2423; Ordway et al. 2007 *PLoS ONE* 2: e1314). See, e.g., U.S. Pat. No. 7,186,512. The genomic region in which a given microarray feature can report DNA methylation status is dependent upon the molecular size of the DNA fragments that were labeled for the microarray hybridizations. In the microarray experiments, DNA in the size range of 1 to 4 kb was purified by agarose gel extraction and used as template for cyanogen dye labeling. Therefore, the genomic region interrogated by each microarray feature is 8 kb (i.e., 4 kb upstream and 4 kp downstream of the sequence represented by the microarray feature).

The fruit form phenotypes associated with the mantled abnormality are shown in FIG. 1. DNA was extracted from spear leaf of 78 clonally propagated palms (ramets), including 37 parthenocarpic mantled ramets, 41 normal ramets and 10 ortets from which clonal ramets are derived. These samples were derived from four industry sources and represented 11 independent clonal propagation events as described in FIG. 2, and each clonal propagation event gave rise to 3 to 5 normal trees and 2 to 5 mantled trees. Genome wide DNA methylation maps were generated from four independent microarray hybridizations representing two technical replicates with a dye-swap reversal hybridization per replicate.

Figure 3:
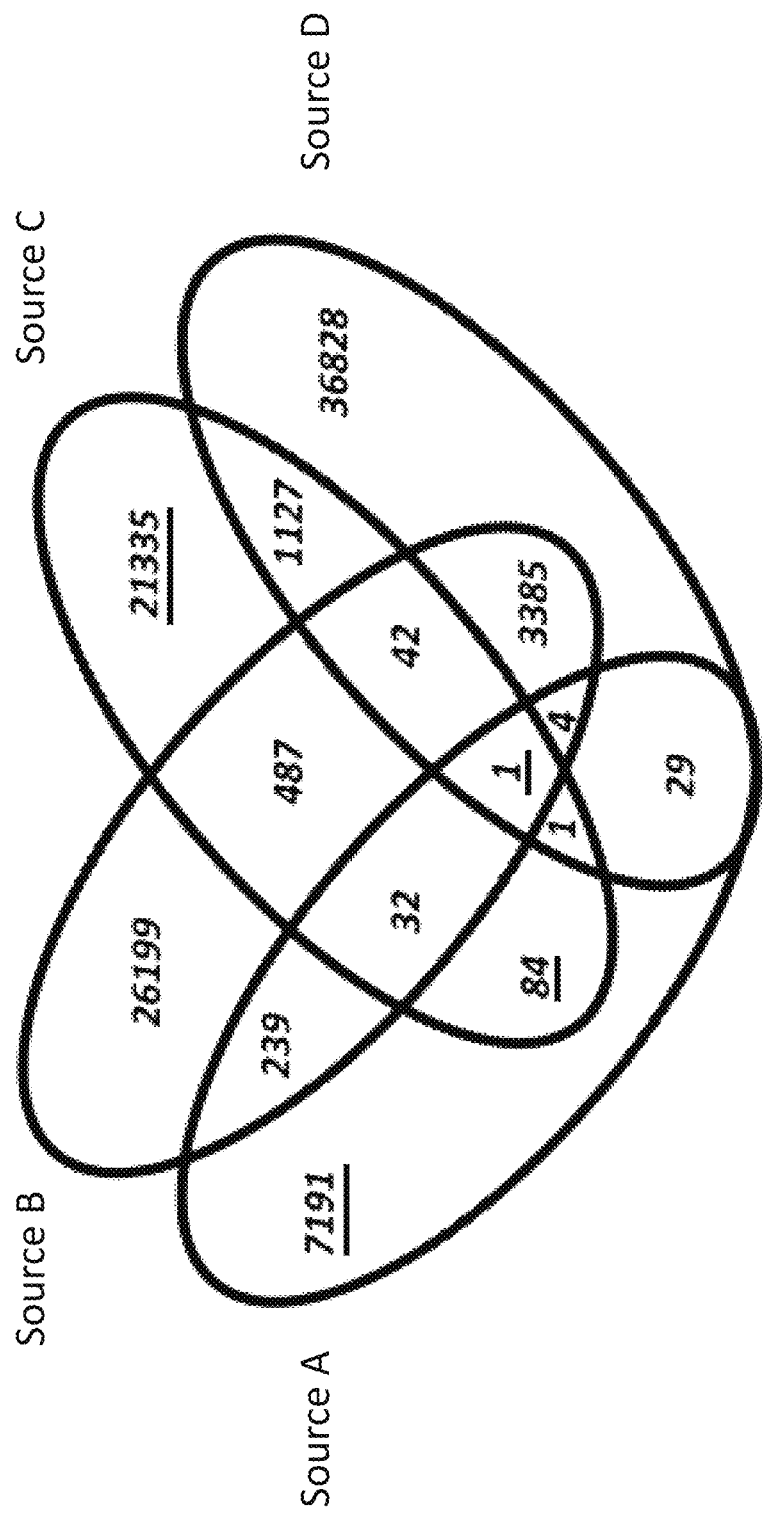
FIG. 3. Venn diagram of microarray features reporting significantly differential methylation between mantled and normal ramet leaf (p<0.05, two-sided Student t-test, Methods). Each oval represents clonal lineages obtained from one source (genotype): Source A (5 mantled and 9 normal ramets), Source B (14 mantled and 15 normal ramets), Source C (10 mantled and 10 normal ramets), and Source D (8 mantled and 7 normal ramets). Relatively few features are shared between genotypes, and only one feature detects hypomethylation in mantled palms from all 4 sources. Underlined numbers indicate subsets that include one of the four microarray features mapping to the Karma LINE element (element 2 as diagrammed in FIG. 2).

Thousands of loci were differentially methylated between genetically identical ortet, parthenocarpic mantled and normal ramet samples, most of which (~90%) were hypomethylated in mantled, consistent with previously reported reductions in total 5 mC levels (Matthes et al. 2001; Jaligot et al. 2002; Jaligot et al. 2004). Interestingly, most of these hypomethylated loci (~75%) mapped to transposons and repeats, while less frequent hypermethylated loci mapped to both genic and repetitive sequences. These results were consistent with similar maps of cell cultures of Arabidopsis (Vaughn et al. 2007), but differed from epigenomic maps of somaclonal regenerants in rice, in which loss of DNA methylation is largely confined to genes (Stroud et al. 2013), despite the activation of some TEs (Miyao et al. 2012; Cui et al. 2013).). To identify epigenetic differences between mantled and normal clones from multiple clonal lineages, significant differentially methylated regions (DMRs) between normal and fully mantled samples were first identified within each source population independently, based on microarray feature hybridization. Hybridization results were then compared between source populations on a feature by feature basis (FIG. 3). Although tens-of-thousands of significant features were detected between mantled and normal clones in each population, 99.9% of these were exclusive to either one (94.4%) or 2 (5.5%) of the 4 populations, indicating significant genotypic variation in epigenetic response to tissue culture. Only 79 differentially methylated features were common to 3 of the 4 populations (67% of which were associated with a repetitive element), and only a single microarray feature detected differential methylation between normal and mantled clones in all 4 populations (FIG. 3).

Figure 4:
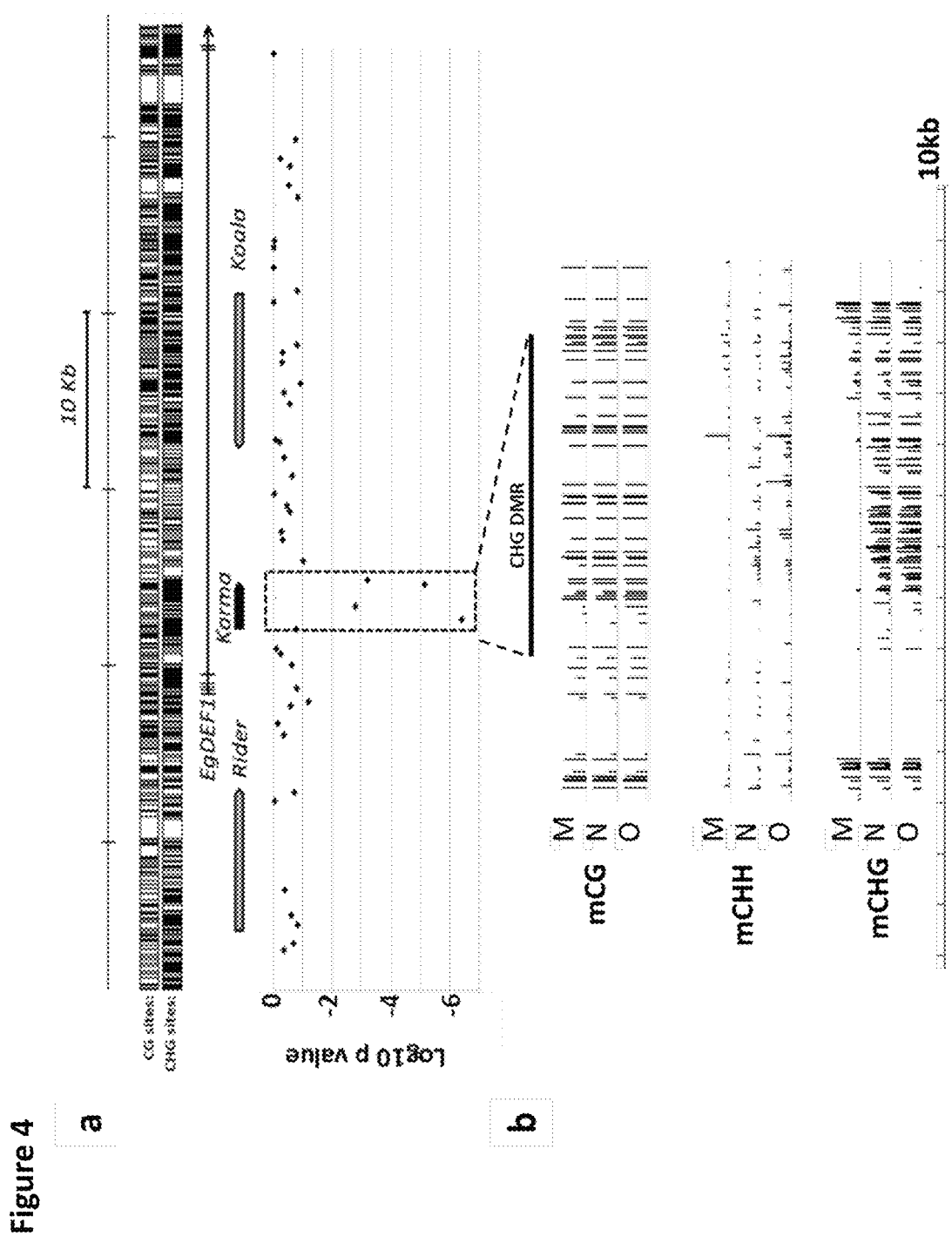
FIG. 4. Epigenetic profile of the EgDEF1/MANTLED gene on chromosome 12. a, Microarray feature data are plotted on a schematic map of the EgDEF1/MANTLED gene including Rider, Karma and Koala retrotransposons. CG and CHG sites are shown above. $\text{Log}_{10}$ p values for differential DNA methylation density measurements between normal (n=41) and parthenocarpic mantled (n=37) clonal ramets are plotted on the y-axis (two-sided Student's t-test). b, Genome-wide bisulphite sequencing of ortet (O), normal (N) and parthenocarpic mantled clonal ramet (M) leaf samples. DNA methylation densities of individual cytosines across Karma (boxed in a) are plotted on a 0 to 100% scale and represent the mean of ortet (n=5), normal ramets (n=5) or mantled ramets (n=5). CG, CHG and CHH methylation are plotted separately, as indicated to the left of the histograms. The location of the differentially CHG methylated region (CHG DMR) corresponding to the Karma retrotransposon is highlighted by a horizontal bar.

The single feature that distinguishes mantled from normal clones in all 4 populations lies within the ~35 kb intron 5 of EgDEF1 (FIG. 4a), the oil palm ortholog of the *Antirrhinum majus* DEFICIENS gene, which encodes a floral homeotic MADS box transcription factor similar to *Arabidopsis* APETALA3 (AP3) (Adam et al. 2005). def mutants in *Antirrhinum*, and ap3 mutants in *Arabidopsis*, result in stamen to carpel (B class) homeotic transformations, strongly reminiscent of the mantled phenotype in oil palm (Jaligot et al. 2011). EgDEF1 spans ~40 kb on *E. guineensis* chromosome 12 and includes 7 exons (FIG. 4a). A Ty1/copia retrotransposon lies upstream of the EgDEF1 promoter in the sense orientation, and shares similarity with the Rider element of tomato (*Solanum lycopersicum*), while a Ty3/gypsy retrotransposon, Koala, is located near the center of intron 5 in the antisense orientation. Consistent with a previous report (Jaligot et al. 2014), no DNA methylation difference within either of these retrotransposons was consistently detected in mantled clones across multiple populations (FIG. 4a).

A third, previously unreported, repetitive element lies within intron 5, in the sense orientation, and has homology to rice Karma family LINE elements. Karma elements, along with Tos17 copia-like elements, are activated in rice embryogenic tissue culture, although unlike Tos17, Karma elements only transpose in regenerated plants, in which transgenerational DNA hypomethylation of the element persists (Komatsu et al. 2003). The 3.2 kb oil palm Karma element is flanked by a 13 bp target site duplication (TTCAAAATGATGA) and encodes a reverse transcriptase open reading frame homologous to rice Karma ORF2. As in mammalian LINE elements, ORF2 is preceded by a splice acceptor sequence (GAACAGAATGC) immediately adjacent to the target site duplication, and is followed by a polyadenylation signal, resembling 5'truncated Karma elements in rice (Komatsu et al. 2003; Cui et al. 2013). The unique 60 nucleotide microarray feature, which consistently detected hypomethylation in mantled clones, not only maps to the Karma element, but serendipitously includes the predicted splice acceptor site. All three additional microarray features mapping within the Karma element also detected significant hypomethylation in mantled clones, albeit in fewer clonal lineages (FIGS. 3 and 4a).

The identified differentially methylated region of the genome maps to coordinates 58360 to 61400 of scaffold 13008 of the published *E. guineensis* genome build (FIG. 1 of Singh et al. 2014, Nature 500, 340-344). The sequences of the four features reporting these differential DNA methylation measurements are provided in SEQ ID NO: 15, 16, 17 and 18. The sequences of 4,061 bp regions spanning the 61mer feature sequence (+/−2 Kb from the 61mer feature sequence) are provided in SEQ ID NO: 43, 44, 45 and 46. A merged sequence from 2 Kb upstream of significant feature 57600 to 2 Kb downstream of significant feature 62840 is provided in SEQ ID NO: 66.

Figure 2:
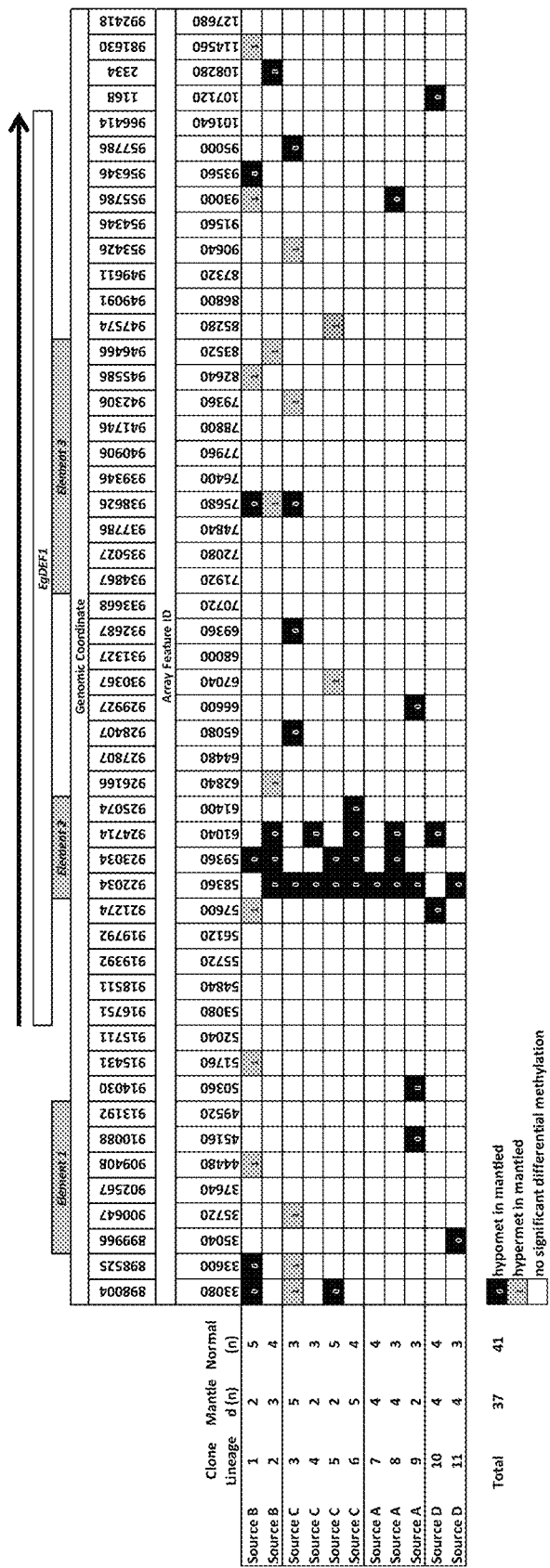
FIG. 2. Summary of significant mantled vs. normal DNA methylation changes. The "EgDEF" box indicates the region from the 5' of exon 1 through the 3' end of the transcript. Element 1 (Rider), 2 (Karma), and 3 (Koala) retrotransposons are indicated by grey boxes, as labeled. Array feature ID numbers are indicated. Genomic coordinates indicate the coordinate of the 5'-most base of each array feature relative to Scaffold p5_sc00322 of the published E. guineensis genome (Singh et al., 2013), with the exception of Array feature IDs 107120 and 108280. These two features mapped to Scaffold p5_sc25957 of the published E. guineensis genome (Singh et al., 2013) and genomic coordinates are relative to p5_sc25957, as published. This small scaffold has subsequently been mapped to the EgDEF1 interval, as diagrammed. Clonal lineages are indicated in the left-most column and the number of mantled and normal samples within each lineage is indicated. Black boxes represent statistically significant hypomethylation events in mantled relative to normal samples. Grey boxes represent statistically significant hypermethylation events in mantled relative to normal samples (p<0.05, two-tailed Student's t-test). White boxes represent measurements reporting no significant differential DNA methylation. There are statistically significant differentially methylated regions (DMRs) across the entire locus, one of which spans the Karma retrotransposon.

To further analyze DNA methylation across an approximately 95 Kb region spanning the EgDEF1 gene, data generated by microarray features representing from coordinate 33080 to 127680 of scaffold 13008 were analyzed to compare mantled vs. normal clonal material from each clonal propagation event independently (FIG. 2). Within Element 2 (Karma), mantled samples displayed hypomethylation relative to normal samples in samples derived from all 11 clonal propagation lineages. However, as summarized in FIG. 2, other distinct regions displayed differential DNA methylation events in a more lineage-specific manner. For example, lineages 1, 2, 3 and 5 displayed hypermethylation of sequences associated with the 5' end of Element 3 (Koala) in mantled samples. The sequences of the four features reporting these differential DNA methylation measurements are provided in SEQ ID NO: 25, 26 27 and 72. The sequences of 4,061 bp regions spanning the 61mer feature sequence (+/−2 Kb from the 61mer feature sequence) are provided in SEQ ID NO: 53, 54, 55 and 74. A merged sequence from 2 Kb upstream of feature 79360 to 2 Kb downstream of 83520 is provided in SEQ ID NO: 68. Furthermore, regions associated with Element 1 (Rider) displayed differential DNA methylation in mantled samples derived from lineages 1, 3, 5, 9 and 11. The sequences of the eight features reporting these differential DNA methylation measurements are provided in SEQ ID NO: 7, 8, 9, 10, 11, 12, 13 and 71. The sequences of 4,061 bp regions spanning the 61mer feature sequence (+/−2 Kb from the 61mer feature sequence) are provided in SEQ ID NO: 35, 36, 37, 38, 39, 40, 41 and 73. Merged sequence from 2 Kb upstream of feature 33080 to 2 Kb downstream of 35720 is provided in SEQ ID NO: 63. Merged sequence from 2 Kb upstream of feature 44480 to 2 Kb downstream of feature 45160 is provided in SEQ ID NO: 64. Merged sequence from 2 Kb upstream of feature 50360 to 2 Kb downstream of feature 51760 is provided in SEQ ID NO: 65. As shown in FIG. 2, other regions within EgDEF1 intron 5 or downstream of the 3' end of the EgDEF1 gene were occasionally differentially methylated in various clonal lineages. The sequences of all 30 features reporting these differential DNA methylation measurements are provided in SEQ ID NO: 7 to 34, 71 and 72. The sequences of 4,061 bp regions spanning the 61mer feature sequence (+/−2 Kb from the 61mer feature sequence) are provided in SEQ ID NO: 35-62, 73 and 74.

Example 2: Verification and Validation of Differential DNA Methylation in Normal and Abnormal Cloned Trees To verify Karma hypomethylation in mantled clones, sample trios comprising genetically identical ortet, parthenocarpic mantled and normal ramets, from 5 independent clonal lineages (15 samples) were subjected to whole genome bisulfite sequencing. The density of CG methylation was strikingly similar in ortet, normal and mantled samples across the entire EgDEF1 locus, including the Karma element (FIG. 4b), and was higher in introns and flanking regions than in exons. In contrast, the density of CHG methylation was dramatically reduced in mantled clones, revealing a DMR covering ~170 CHG sites throughout the length of the Karma element (FIG. 4b). The density of CHH methylation was much lower than CG and CHG and was only subtly reduced in mantled clones (FIG. 4b).

Figure 5:
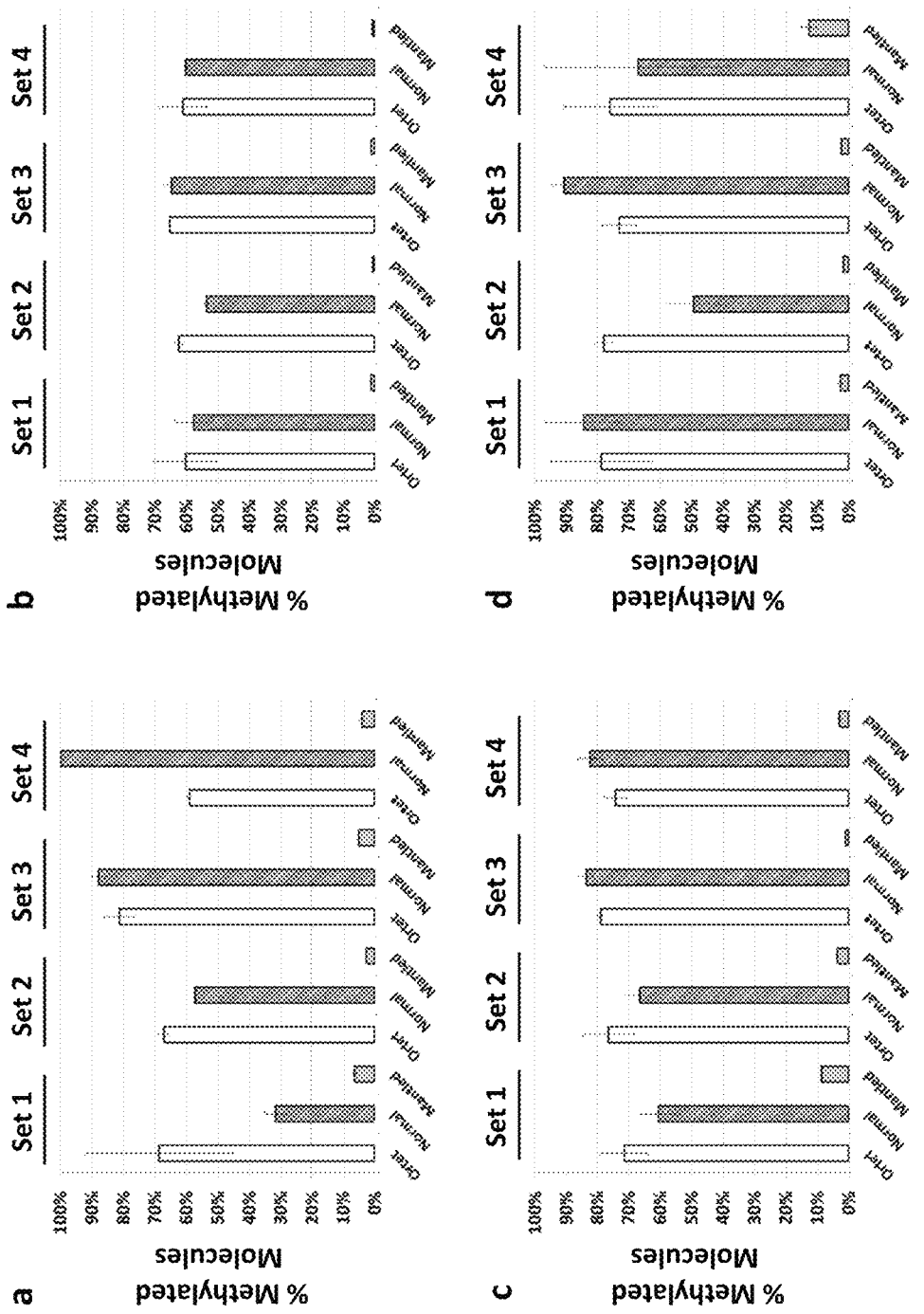
FIG. 5. Differential CHG methylation as measured by four independent MethylScreen assays. Assays were designed as described in Example 2. Each assay monitors methylation of a specific CHG cytosine within the differentially methylated region (CHG DMR). Sets 1, 2, 3 and 4 indicate independent sets of an ortet sample, plus 1 normal and 1 mantled sample from trees derived from the ortet of the same set. The percent densely methylated molecules was calculated as described in Example 2. CHG methylation sensitive restriction enzymes used were AlwNI (a), BbvI (b), ScrFI (c) and RsaI (d). Error bars represent standard deviations for duplicated assays.

To further validate the differential CHG methylation in Element 2, four independent MethylScreen assays (See, e.g., U.S. Pat. Nos. 7,910,296; 8,361,719; 7,901,880; and 8,163, 485) were designed to monitor CHG sites within methylation sensitive restriction enzyme target sequences that are blocked by CHG methylation but are not sensitive to either CHH or CG methylation. A first amplicon was designed to amplify a 576 bp region within Karma that contains a site for the methylation sensitive enzyme, AlwNI. Forward and reverse primer sequences are provided in SEQ ID NO: 82 and 83, respectively. The sequence of the amplicon is provided in SEQ ID NO: 84. The restriction site includes two CHG sites, and methylation of these cytosines blocks digestion by the enzyme. A second amplicon was designed to amplify a 633 bp region within Karma that contains sites for the methylation sensitive enzymes, BbvI and ScrFI. Forward and reverse primer sequences are provided in SEQ ID NO: 85 and 86, respectively. The sequence of the amplicon is provided in SEQ ID NO: 87. Each of these enzyme sites includes a CHG site, and methylation the site blocks digestion by the enzyme. The same amplicon (SEQ ID NO: 87) was used for each of the two enzyme assays separately. Finally, a third amplicon was designed to amplify a 632 bp region within Karma that contains a site for the methylation sensitive restriction enzyme, RsaI. Forward and reverse primer sequences are provided in SEQ ID NO: 88 and 89, respectively. The sequence of the amplicon is provided in SEQ ID NO: 90. The site includes a CHG site, and methylation of the site blocks digestion by the enzyme. Each of the four MethylScreen assays was performed on genomic DNA from four independent sets of ortet, normal and mantled samples that had been whole genome bisulfite sequenced, as described above. Genomic DNA was split into two equal portions. The first portion was mock treated (excluding the restriction enzyme). The second portion was digested with each of the four methylation sensitive restriction enzymes in separate reactions. Quantitative PCR amplification was performed on each portion in duplicate (alternatively, results can be analyzed by gel electrophoresis, without the use of real-time quantitative PCR). The delta Ct of the enzyme digested portion Ct minus the mock treated portion Ct was calculated for each of the two replicated assays. The % densely methylated was calculated as $2^{-dCt}$. The average % densely methylated, and the standard deviation between the duplicated assays, are provided in FIG. 5. These results demonstrate that each of the four MethylScreen assays are capable of detecting the hypomethylation of Mantled clone DNA relative to both ortet DNA and Normal clone DNA.

Figure 6:
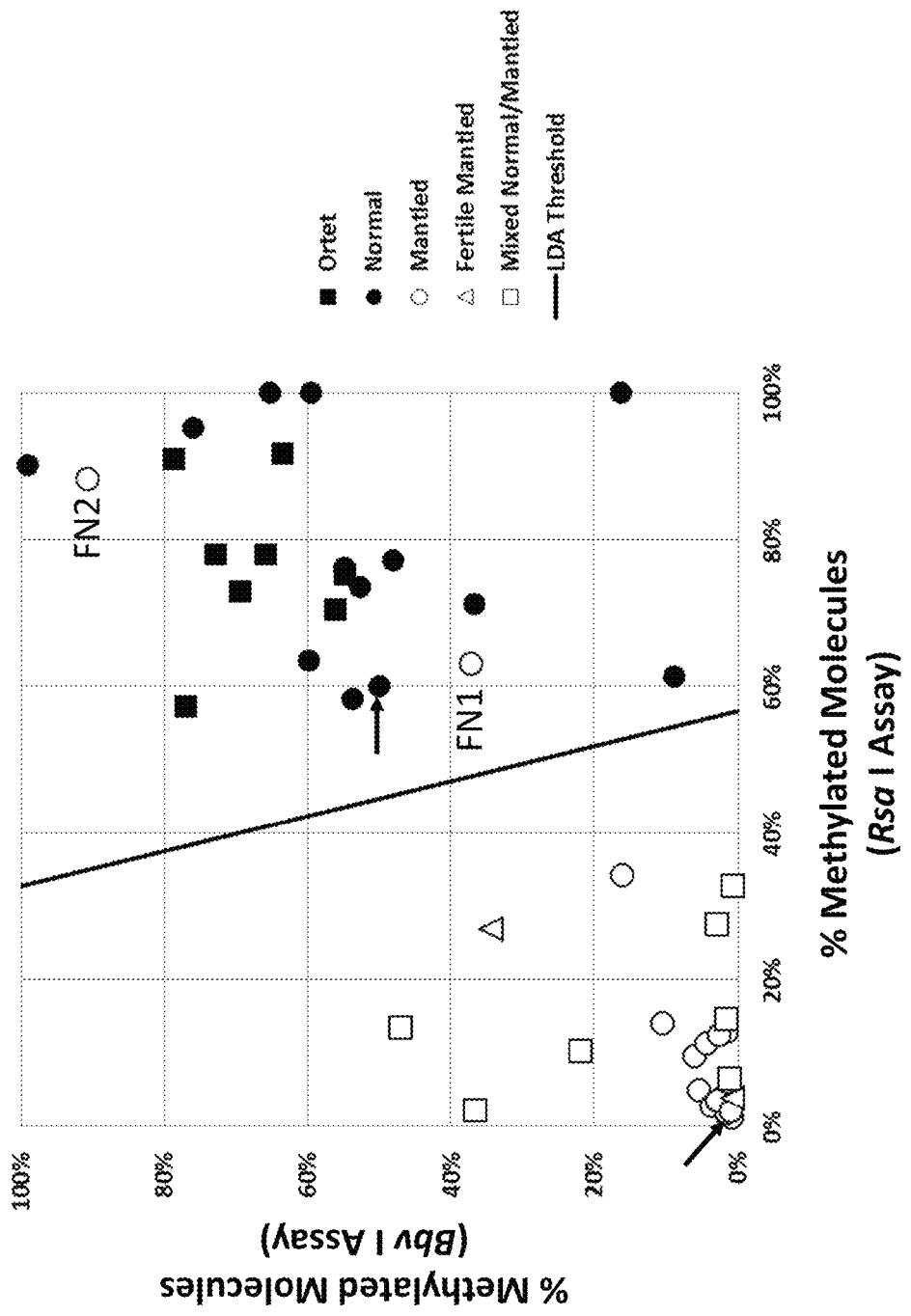
FIG. 6. Linear discriminate analysis (LDA) of CHG methylation in leaf DNA samples from ortet, mantled and normal clones from ramets independent of those represented in FIGS. 2-5. CHG methylation was monitored by digestion with the methylation sensitive restriction enzymes Bbv I or Rsa I, followed by quantitative PCR, as described in Example 2. The diagonal line represents the LDA-determined threshold between normal (ortets (n=8) and normal ramets (n=13)) and mantled (parthenocarpic mantled ramets (n=19), fertile mantled ramets (n=2) and mixed ramets yielding both normal and fertile mantled fruit (n=7)) CHG methylation density predictions. Two false negative parthenocarpic mantled samples are indicated (FN1 and FN2). Arrows indicate normal and mantled control samples further analyzed in FIGS. 7b and 7c, respectively.

To validate differential CHG methylation in unrelated clonal palms, the Bbv I and the Rsa I qPCR assays were performed on mature leaf samples from a panel of 49 palms. These samples represented 21 clonal lineages from 4 independent industry sources and included 8 ortets and 13 normal clones, 19 parthenocarpic mantled clones, 2 fertile mantled clones and 7 partially revertant clones yielding bunches with both mantled and normal fruits. Although the restriction site assays monitored only 2 of ~170 CHG sites in the DMR, a threshold value determined by linear discriminant analysis provided 93% sensitivity and 100% specificity for detection of mantling, reflecting the strong association of Karma hypomethylation with the mantled phenotype (FIG. 6). Fronds taken from all 7 of the revertant palms were scored as mantled, consistent with the observation that normal bunches on mixed palms arise late in development and revert to the normal phenotype (Corely, 1986).

Figure 7:
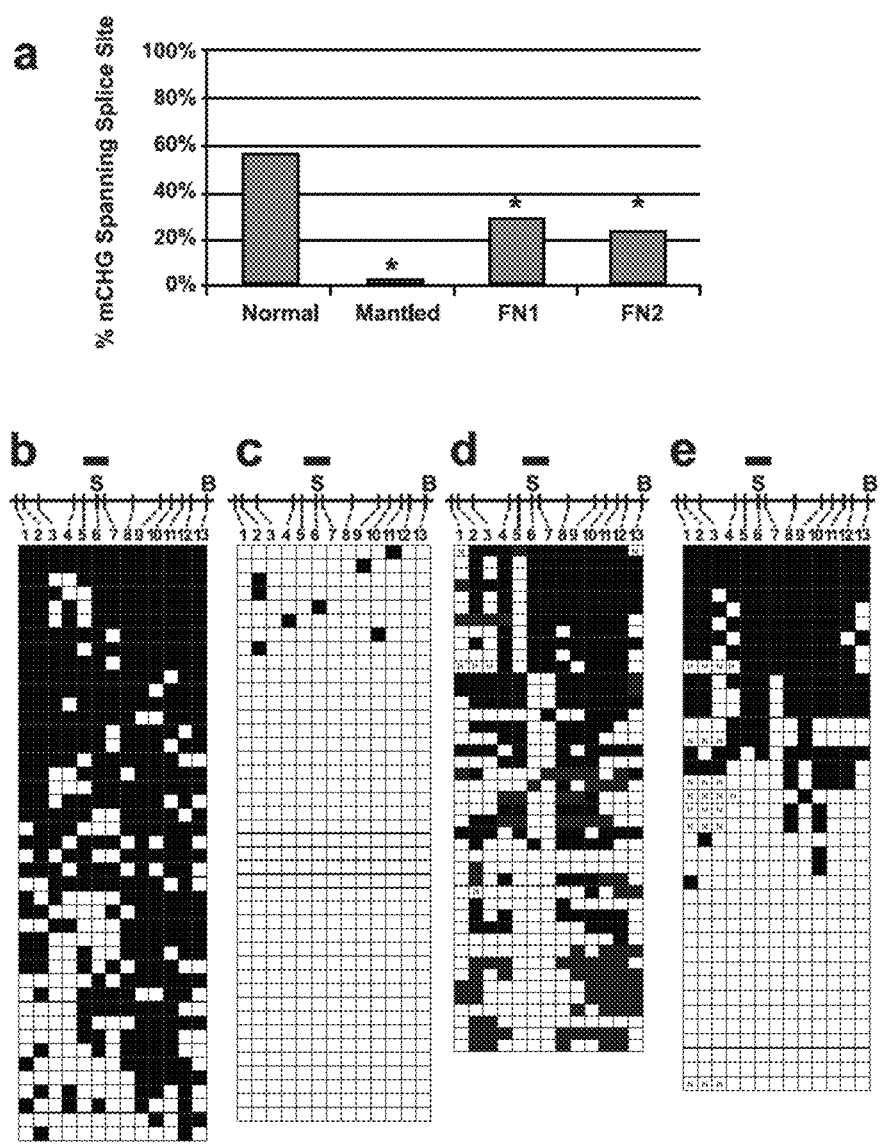
FIG. 7. a, Bisulfite sequencing analyses of the Karma element in leaf samples from normal and mantled clones (ramets), as well as two false negative mantled samples. CHG methylation density (unconverted CHG cytosine base calls/total cytosine base calls) was calculated at the Karma splice acceptor site (site 6 in b-e), plus the two additional CHG positions 27 bp upstream (site 5) and 16 bp downstream of the splice site (site 7), all of which were covered by the unique common microarray feature that detected hypomethylation in mantled palms from all 4 sources in FIG. 3. The mantled control sample and both false negative mantled samples were significantly hypomethylated relative to the normal control, as indicated by asterisks (p<0.0001, two-tailed Fisher's exact test). b-e, Individual bisulphite sequencing reads from the antisense strand of the Karma element in (b) the normal control, (c) mantled control and (d) FN1 and (e) FN2 false negative mantled samples. 13 antisense CHG sites across the sequencing amplicon are shown to scale. "S" indicates the cytosine at the Karma splice acceptor site (CAG/CTG). "B" indicates the Bbv I site. The common microarray feature reported in FIG. 3 is indicated by a bar surrounding the splice site. Methylated and unmethylated CHG sites are indicated by black and white boxes, respectively. Boxes including "N" indicate CHG positions within specific reads that were not high quality DNA sequencing base calls and so the DNA methylation state of those bases was undetermined.

Although CHG methylation density at the two restriction sites was highly predictive, it did not correlate perfectly with the mantled phenotype. The two false negative mantled palms (FN1 an FN2 in FIG. 6), and 2 control palms (arrows in FIG. 6), were further analyzed by bisulfite sequencing of a region spanning the Karma splice acceptor site (FIG. 7). As predicted by qPCR, this region was densely CHG methylated in the normal control sample, while the mantled control sample had lost CHG methylation (FIGS. 7b-c). The false negative mantled samples (predicted to have normal methylation by the restriction site assays) retained substantial CHG methylation in surrounding regions, however CHG methylation near the splice acceptor site was significantly reduced, by 50%, relative to the normal control sample (FIGS. 7a-b and d-e), suggesting that hypomethylation at or adjacent to the splice acceptor CHG site is sufficient to predict the mantled phenotype. Because of their strong predictive properties, we named the MANTLED hyper- and hypo-methylated epialleles Good Karma and Bad Karma, respectively.

Example 3: Phenotype Reversion in Epigenetic Mosaics

Figure 8:
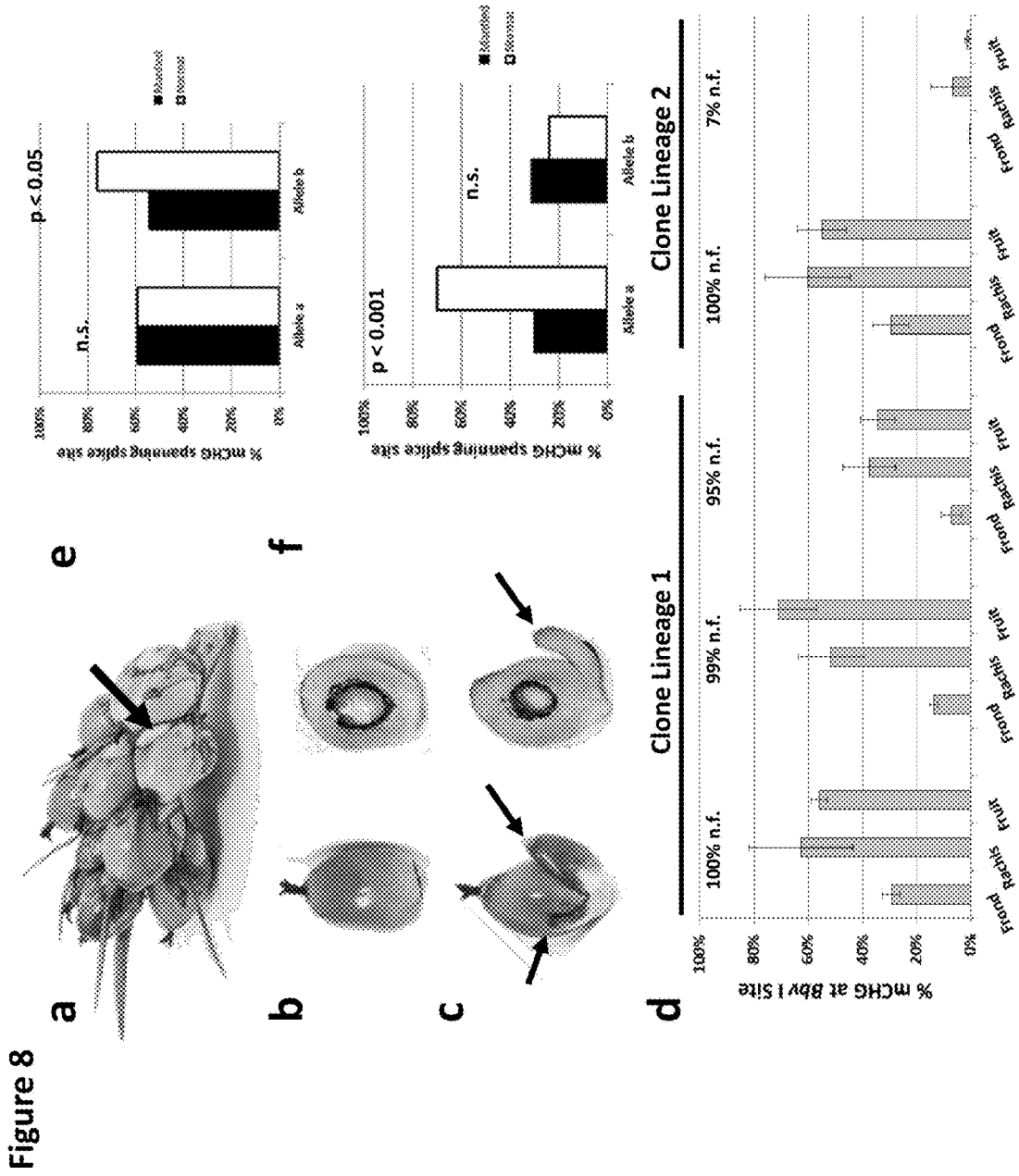
FIG. 8. Karma CHG methylation in revertant palms. a, spikelet from a revertant ramet giving rise to mixed bunches including both normal and fertile mantled fruit with only one or two pseudocarpels per fruit (arrows). b-c, whole (left) and longitudinal sectioned (right) normal (b) and subtly mantled (c) fruit from the bunch represented in (a). d, CHG methylation density at the Bbv I site. Normal ramets yielding 100% normal fruit from each of two independent clonal lineages (1 and 2) are shown, as well as revertant ramets yielding mixed bunches with 99%, 95% or 7% normal fruits (n.f.) per bunch. Error bars indicate standard deviations across biological replicates of fronds (n=4), rachis sections (n=8) or fruits (n=2). e-f, Methylation density at the Karma splice acceptor site, plus the two additional CHG positions 27 bp upstream and 16 bp downstream of the splice site (determined as in FIG. 7) in normal (white bars) and subtly mantled (black bars) fruits from the two revertant ramets in clonal lineage 1 yielding 99% (e) or 95% (f) normal fruit (two-tailed Fisher's exact test, n.s. indicates not significant). For each ramet, normal and subtly mantled fruits were collected from the same bunch. Alleles were analyzed separately by detecting a heterozygous SNP within the bisulfite sequencing amplicon that did not affect a CHG site.

Mantled palms sometimes revert, giving rise to bunches including both normal and mantled fruit (Rao & Donough, 1990). We hypothesized that DNA methylation might sometimes be restored in revertant and mosaic palms, resembling epialleles in maize that are also regulated by transposons (McClintock, 1965; Martienssen et al., 1990; Martienssen & Baron, 1994). Although rare, we identified two clonal lineages giving rise to palms with bunches of both normal and (fertile) mantled fruits. Clone lineage 1 included two revertant clones with 99% and 95% normal fruit per bunch, respectively, in which abnormal fruits had only one or two small pseudocarpels (FIGS. 8a-c). A second lineage (clone lineage 2) included a mosaic clone with a only 7% normal fruits. Relative to normal control clones, CHG methylation at the Bbv I site (FIGS. 5-6) nearest the Karma splice site (FIG. 8d) was low in fronds from revertant and mosaic clones. However, methylation was restored in fruit from the two revertant clones, but not from the mantled mosaic clone (FIGS. 8d-f).

As with similar epialleles in maize, Linnaria, Arabidopsis and tomato (Martienssen et al., 1990; Cubas et al., 1999; Manning et al., 2006; Kinoshita et al., 2007), reversion of the abnormal phenotype during development accompanied by restoration of DNA methylation suggests that methylation of the Karma element is the cause of the mantled phenotype. Differential methylation between individual mantled and normal fruits was not observed, however, likely reflecting non-cell autonomy of the weak mantled phenotype (FIG. 8d). Non-cell autonomy of the DEF and AP3 genes leads to similar reversion in mosaic chimeras of Antirrhinum and Arabidopsis (Furner et al., 2008; Perbal et al., 1996; Jenik & Irish, 2001). Interestingly, bisulfite sequencing of the region spanning the Karma splice acceptor site in normal and mantled fruits from mosaic clones revealed that CHG methylation at the splice acceptor site was significantly different depending on the phenotype, suggesting that revertant fruits were indeed mosaic for hyper- and hypo-methylated cells (FIGS. 8e-f).

Figure 9:
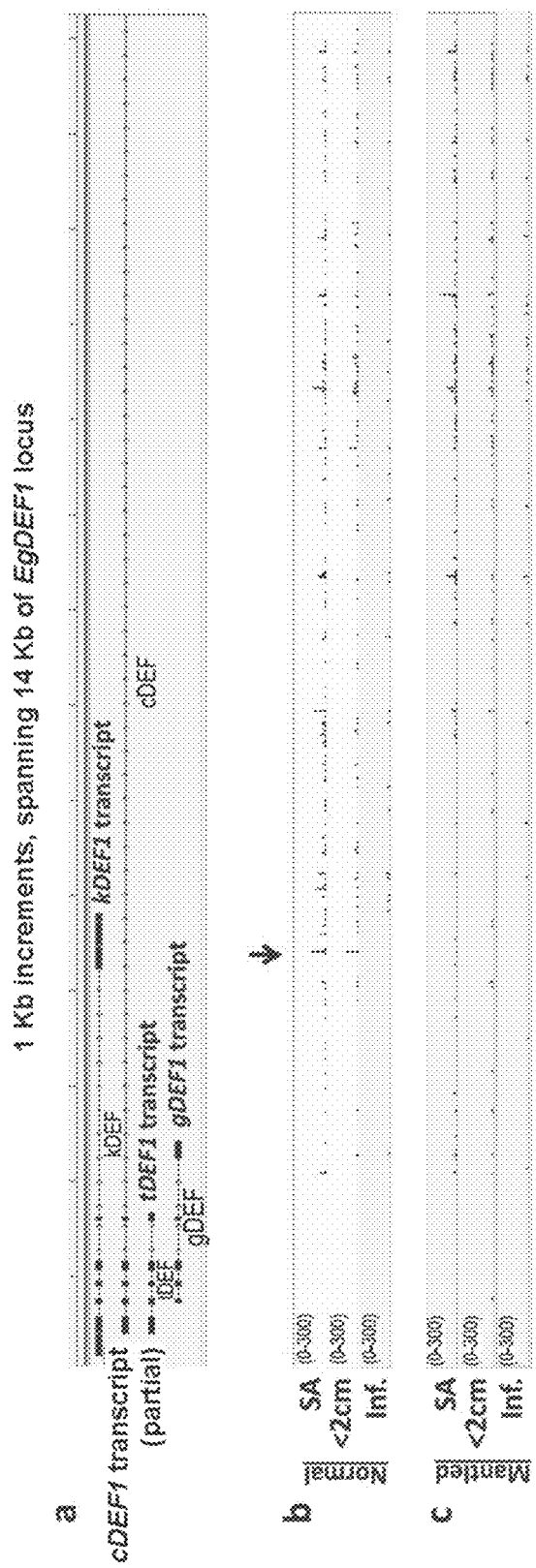
FIG. 9. Differential expression of small non-coding regulatory RNAs in Mantled tissues. a, Transcript models as described in Example 5. b, Distinct 24mer siRNA counts as determined by whole transcriptome small RNA sequencing of Normal shoot apex (SA), <2 cm stage inflorescence tissues (<2 cm) and later stage inflorescence tissues (Inf.). The x-axis is genomic position in scale with the transcript models shown in A. The y-axis is fragments per kilobase per million fragments mapped (FPKM) normalized read counts on a scale of 0 to 3.0. Vertical bars indicate the FPKM normalized read count for distinct 24mers derived from positions across the EgDEF1 locus. Data represent three independent samples per tissue type. c, Distinct 24mer siRNA counts as determined by whole transcriptome small RNA sequencing of mantled shoot apex (SA), <2 cm stage inflorescence tissues (<2 cm) and later stage inflorescence tissues (Inf.). Plots are generated as described in B. The vertical arrow indicates a specific 24mer siRNA (SEQ ID NO: 91) that is expressed 11-fold higher in normal shoot apex relative to mantled shoot apex.

Example 4: The Mantled Phenotype is Correlated with Changes in Non-Coding Regulatory RNA Expression In plants, small noncoding regulatory RNAs can impact DNA methylation and gene expression. To determine the correlation between the Mantled phenotype and expression of small noncoding regulatory RNAs, whole transcriptome small RNA sequencing was performed on shoot apex tissues derived from 3 Normal clonal trees and 3 Mantled clonal trees, <2 cm stage inflorescence tissues derived from 3 Normal clonal trees and 3 Mantled clonal trees, and later stage inflorescence tissues derived from 3 Normal clonal trees and 3 Mantled clonal trees. Small RNA sequencing libraries were generated by standard Illumina technology and each library sample was uniquely barcoded so that the transcriptome of each sample could be analyzed individually. Libraries were sequenced in pools of four libraries per HiSeq 2500 lane. 24 nucleotide sequencing reads (representing the 24mer class of small RNA) were mapped back to the reference oil palm genome (Singh et al. 2013). Reads that had an exact match to the sequence within the EgDEF1 gene interval were identified and mapped to their corresponding sequences of the EgDEF1 reference sequence. The number of mapped reads for each distinct 24mer sequence was calculated for each sample, and the read counts were FPKM normalized within each sample by the calculation: (# exact mapped 24mer reads of a distinct 24 mapped to the EgDEF1 locus)/(# of total 24mer reads mapped to the reference oil palm genome)*1,000,000. FIG. 9 shows plots of 24mer siRNA reads relative to the EgDEF1 genomic locus (FIG. 9A). Individual tracks are shown for normalized counts for shoot apex (SA), <2 cm inflorescence (<2 cm) and later stage inflorescence (Inf.) from Normal (FIG. 8B) and from Mantled (FIG. 8C) cloned trees. As can be seen by comparing tracks for SA and <2 cm tissues between Normal and Mantled phenotypes, there are numerous 24mer siRNAs detected in Normal samples that are either less abundant or not detected in Mantled samples. Substantially fewer distinct 24mer siRNAs are detected in the later stage inflorescences regardless of phenotype, consistent with an important role of small noncoding regulatory RNAs in early floral development. One strong peak (corresponding to the 24mer siRNA provided in SEQ ID NO: 99) in Normal SA and <2 cm that is significantly reduced in Mantled SA and <2 cm maps to a genomic region 152 bp downstream of the splice site of EgDEF1 exon 5 into the Karma element to produce the kDEF1 transcript (see Example 5).

To further address differential 24mer siRNA expression, 24mer siRNAs that displayed at least a 2-fold difference in expression in one phenotype relative to the other were identified for each tissue type: shoot apex, <2 cm stage inflorescences and later stage inflorescences. As predicted by the analysis shown in FIG. 9, shoot apex tissue has the largest number of distinct 24mer siRNAs differentially expressed in Normal relative to Mantled tissues (Table 1).

TABLE 1

24mer siRNAs Differentially Expressed in Shoot Apex

| SEQ ID NO. | Genomic Coordinate | Sequence | Fold Change (Normal/ Abnormal) |
|---|---|---|---|
| 91 | 922424 | CTCTAGCAAGGCGATCAGAAGATT | 11.0 |
| 92 | 954273 | TCAGGTGTTATGTCAGTTTGGACT | 5.9 |
| 93 | 935533 | AAGTCTCCACTCTATCTATCCCGA | 5.0 |
| 94 | 948570 | GGGTCAACAAGGTCTGAGAACACT | 4.1 |
| 95 | 933745 | CGCAATCAGAATCAACTGGCCAAT | 3.8 |
| 96 | 926352 | ATGATACACGGTTGCATGCCCTGC | 3.4 |
| 97 | 924957 | GATCTATGGTGCAAGGAGTTAATT | 3.2 |
| 98 | 927895 | AGAGAGAGGGTTAAAGGACAATGC | 2.9 |
| 99 | 933648 | ATAGGGAGAATAGCTTGGCTTCGA | 2.9 |
| 100 | 939466 | TCGGGTTCTTTTATTCGTGGATTT | 2.9 |
| 101 | 932689 | AGGGGAGATTGTTGGCTTAGCTTG | 2.8 |
| 102 | 928308 | AGTAGACTCGATGATGATAAGACT | 2.7 |
| 103 | 928688 | ACCAGCACGGTCAAGGATAGGCAT | 2.7 |
| 104 | 928306 | ATAGTAGACTCGATGATGATAAGA | 2.7 |
| 105 | 937978 | CCTCCAACATCGGCCAAGTTAGTT | 2.7 |
| 106 | 927714 | AAATCCTACTTGTTTCTCTGACCT | 2.5 |
| 107 | 926387 | CATGAGGCATGCAAGGTATTGAAT | 2.4 |
| 108 | 937739 | AAGGCTGGCTAACTCAAAGAAGAG | 2.4 |
| 109 | 932932 | AATGATCGAGAAGGGCTGGAGACA | 2.3 |
| 110 | 933604 | TGACCCACCATCGAGAAGGACCGA | 2.3 |
| 111 | 936422 | ATAACTGACAAGTGGCATTGATCT | 2.3 |
| 112 | 945502 | AGAAGGATGAGAAGAGAGATTGTC | 2.3 |
| 113 | 924825 | AAAGATGTTAGCTCCTGTTCGAGA | 2.0 |
| 114 | 937738 | AAAGGCTGGCTAACTCAAAGAAGA | 2.0 |
| 115 | 935465 | AGAGATTGTGAACAAATGGAGAGA | 0.4 |

The 24mer siRNA (SEQ ID NO: 91) that maps 152 bp downstream of the splice site of EgDEF1 exon 5 into the Karma element is the most differentially expressed and is expressed at 11-fold higher levels in Normal shoot apex tissue relative to Mantled shoot apex tissue. An additional 23 siRNAs (SEQ ID NO: 92-115) also have higher expression in Normal relative to Mantled shoot apex, with fold differences ranging from 2 to 5.9-fold. A single 24mer siRNA was detected as expressed 2.5-fold higher in Mantled relative to Normal shoot apex tissue (SEQ ID NO: 115). Of the 25 siRNAs differentially expressed in Normal relative to Mantled shoot apex tissue, two (SEQ ID NO: 91 and SEQ ID NO: 97) map within the differentially methylated region. These siRNAs may affect DNA methylation and/or differential splicing of the EgDEF1 gene. Furthermore, the other 23 siRNAs may play roles in aspects of EgDEF1 gene expression.

Consistent with the analyses shown in FIG. 9, the later developmental stages (<2 cm stage inflorescence and later stage inflorescence) display progressively fewer 24 siRNA expression differences between Normal and Mantled. In <2 cm stage inflorescence, 10 distinct siRNAs were found to be differentially expressed by at least 2-fold (Table 2).

TABLE 2

24mer siRNAs Differentially Expressed in <2 cm Inflorescens

| SEQ ID NO. | Genomic Coordinate | Sequence | Fold Change (Normal/Abnormal) |
|---|---|---|---|
| 116 | 932666 | ATATTGTCTGCTCTTCACCAAAGA | 4.2 |
| 117 | 951091 | CTCGTAAGGCCCAAGGGTAGTCAT | 3.1 |
| 104 | 928306 | ATAGTAGACTCGATGATGATAAGA | 2.8 |
| 97 | 924957 | GATCTATGGTGCAAGGAGTTAATT | 0.5 |
| 118 | 933595 | AAAATAGCTTGACCCACCATCGAG | 0.5 |
| 119 | 933643 | ATAGAATAGGGAGAATAGCTTGGC | 0.4 |
| 115 | 935465 | AGAGATTGTGAACAAATGGAGAGA | 0.4 |
| 120 | 927834 | TCCTGTCCAGATATTTGCGCCTCT | 0.4 |
| 121 | 932922 | ACAACTAGCCAATGATCGAGAAGG | 0.4 |
| 122 | 933686 | AACACACTGCTGAAAAGGACTAGG | 0.2 |

These include siRNAs represented by SEQ ID NO: 97, 104 and 115 that were also differentially expressed in shoot apex. The siRNA represented by SEQ ID NO: 104 is overexpressed in Normal relative to Mantled shoot apex (2.7-fold) and <2 cm stage inflorescence (2.8-fold). The siRNA represented by SEQ ID NO: 115 is overexpressed in Mantled relative to Normal shoot apex (2.5-fold) and <2 cm stage inflorescence (2.5-fold). The siRNA represented by SEQ ID NO: 97 is overexpressed in Normal relative to Mantled shoot apex (3.2-fold), but is overexpressed in Mantled relative to Normal<2 cm stage inflorescence (2-fold). An additional 7 siRNAs were detected as differentially expressed in <2 cm stage inflorescence (SEQ ID NO: 116-122), as indicated in Table 2. Finally, two siRNAs were detected as overexpressed in Normal relative to Mantled later stage inflorescence (Table 3, SEQ ID NO: 123 and SEQ ID NO: 124).

TABLE 3

24mer siRNAs Differentially Expressed in later stage Inflorescens

| SEQ ID NO. | Genomic Coordinate | Sequence | Fold Change (Normal/Abnormal) |
|---|---|---|---|
| 123 | 951590 | AAACTCATGGTGTCAAGGGACGTG | 3.5 |
| 124 | 951656 | GCTACACAGGCACAATCTCGATTT | 2.3 |

Figure 10:
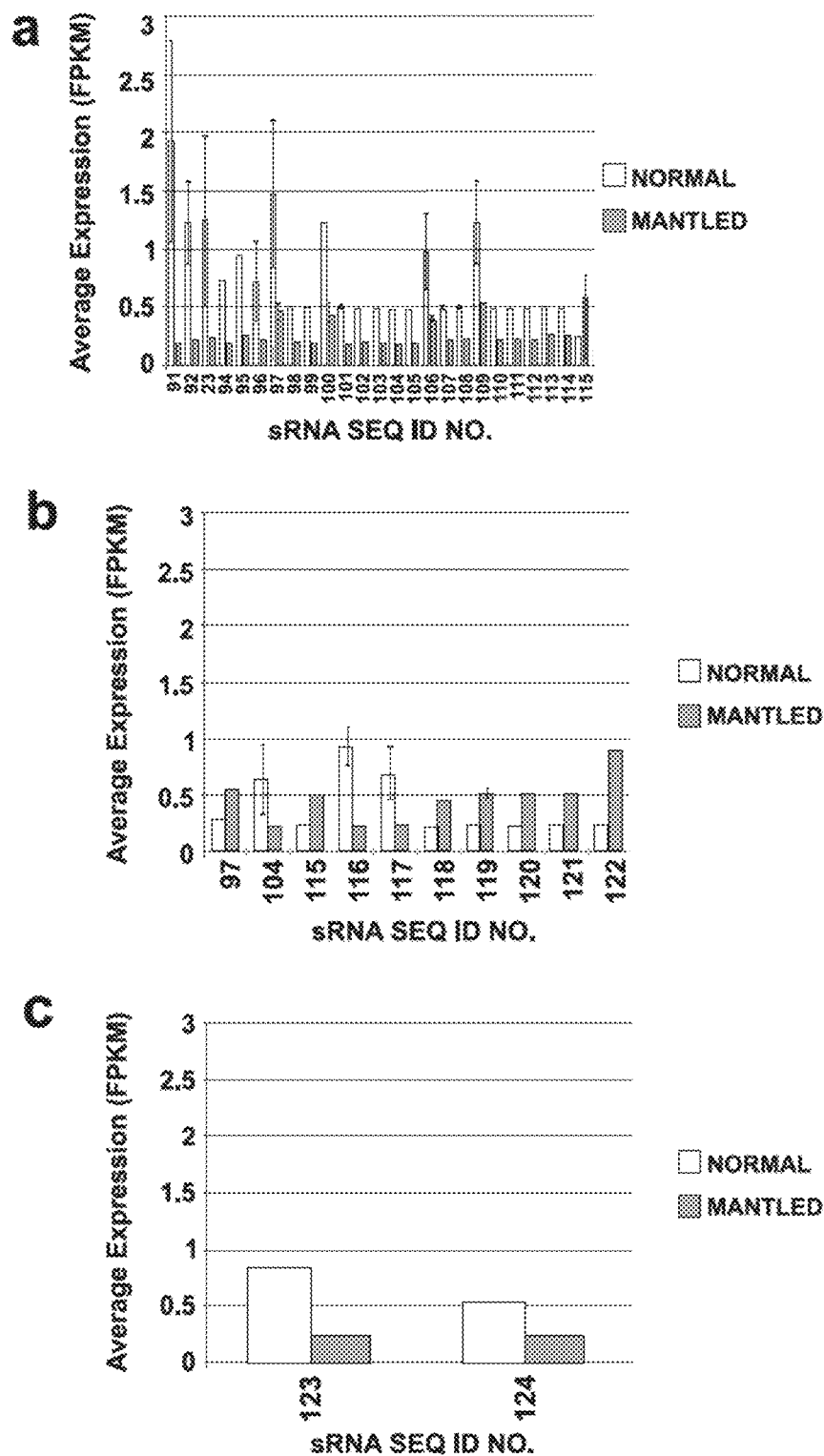
FIG. 10. Differential expression of siRNAs in mantled tissues. a, Average FPKM normalized 24mer siRNA read counts in normal (open bars) and mantled (gray bars) shoot apex samples. Error bars represent standard deviations for three replicates. X-axis labels indicate the SEQ ID NO: for each distinct siRNA. b, Average FPKM normalized 24mer siRNA read counts in normal (open bars) and mantled (gray bars) <2 cm stage inflorescence samples. Error bars represent standard deviations for three replicates. X-axis labels indicate the provided SEQ ID NO for each distinct siRNA. c, Average FPKM normalized 24mer siRNA read counts in normal (open bars) and mantled (gray bars) later stage inflorescence samples. Error bars represent standard deviations for three replicates. X-axis labels indicate the SEQ ID NO for each distinct siRNA.

Normalized siRNA expression levels (FPKM method) of these siRNAs in Normal and Mantled tissues, along with standard deviations across the three replicates per tissue state per phenotype, are shown graphically in FIG. 10. In addition to 24mer siRNAs expressed at quantitatively different levels in Normal relative to Mantled tissues, 24mer siRNAs were identified that are expressed in tissue types of one phenotype but not the other. Table 4 lists 24mer siRNAs that were detected in an average of at least 3 reads for tissue types of one phenotype and no reads were detected in the same tissue of the other phenotype.

TABLE 4

24mer siRNAs expresses only in tissues of one phenotype and not the other phenotype

| SEQ ID NO. | Genomic Coordinate | Sequence | Tissue type | Phenotype expressing 24mer siRNA |
|---|---|---|---|---|
| 130 | 667783 | AAATTCTTACTTCTGAGCATACTT | Shoot apex | Normal |
| 131 | 923085 | CGAGGTGGTGTCAATGGATAGAAT | Shoot apex | Normal |
| 132 | 346343 | CTCTTTGTTATACAATCACGGTGT | Shoot apex | Normal |
| 133 | 922431 | CAAGGCGATCAGAAGATTATCGAA | Shoot apex | Normal |
| 134 | 314456 | GTGCCATATGTCATAGTCAACTGT | Shoot apex | Normal |
| 135 | 923490 | AATCTGATATTGGCATCCACATGA | <2 cm Inflorescence | Mantled |
| 136 | 1065423 | CCTGACTTTCGGTTGGCTGTCTCT | <2 cm Inflorescence | Normal |
| 137 | 1065863 | AATCCTACTTGTTTCTCTGACCTT | <2 cm Inflorescence | Normal |
| 138 | 1066135 | CTCTAGCAAGGCGATCAGAAGATT | <2 cm Inflorescence | Normal |
| 139 | 1066138 | AAATGGCATACTCTGGCAATTCGA | <2 cm Inflorescence | Normal |
| 140 | 314911 | TCTATCTCATCCCTCTCAACCAAT | later stage Inflorescence | Mantled |
| 141 | 314191 | GTAGCCCATGTCTTTGTTTTCCCT | later stage Inflorescence | Mantled |
| 142 | 334759 | TGTGGATGGCTAACGATATGGACT | later stage Inflorescence | Normal |
| 143 | 314753 | ACTAGCACCATGTGTCGTTATGGG | later stage Inflorescence | Normal |

Five distinct siRNAs (SEQ ID NO: 130-134) were detected in Normal shoot apex, but not in Mantled shoot apex. One siRNA (SEQ ID NO: 135) was detected in Mantled<2 cm stage inflorescence, but not in Normal<2 cm stage inflorescence. Four siRNAs (SEQ ID NO:136-139) were detected in Normal<2 cm stage inflorescence, but not in Mantled<2 cm stage inflorescence. Two siRNAs (SEQ ID NO: 140 and 141) were detected in Mantled later stage inflorescence, but not in Normal later stage inflorescence. Finally, 2 siRNAs (SEQ ID NO: 142 and 143) were detected in Normal later stage inflorescence, but not in Mantled later stage inflorescence. Therefore, quantitative detection of expression of one or more of these siRNAs (SEQ ID NO: 82-124) may be useful for the prediction of the Mantled phenotype in somaclonal materials, long before field planting and the development of the Mantled abnormal fruit phenotype. Furthermore, ectopic expression of one or more siRNAs (e.g. SEQ ID NO: 91 and SEQ ID NO: 97) during cell culture stages of somaclonal propagation may be useful to maintain or reset the DNA methylation state of the differentially methylated region within the Karma element and/or the appropriate splicing of mRNAs derived from the EgDEF1 locus, thus inhibiting development of the abnormal Mantled fruit phenotype in clonal derived palms.

Figure 11:
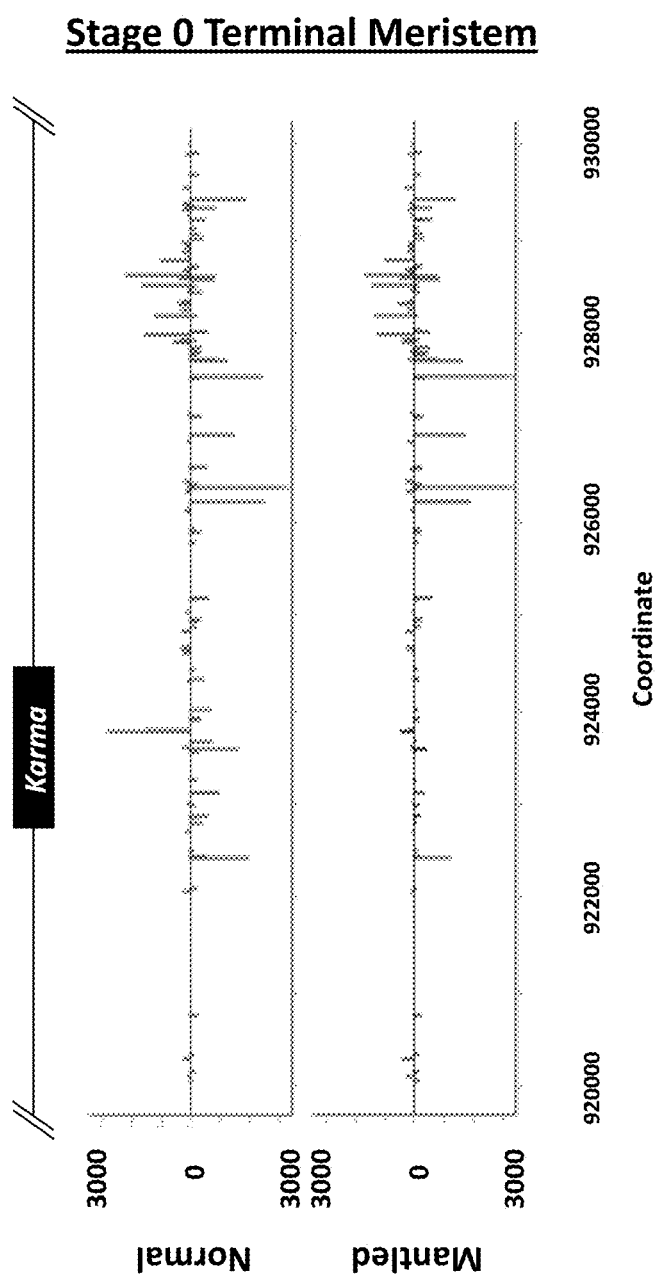
FIG. 11. Repressed 24nt siRNA expression in mantled inflorescences map to Karma. Small RNA sequencing in normal (n=5 biological replicates) and parthenocarpic mantled (n=7 biological replicates) stage 0 Terminal Meristem. Fragments per kilobase per million mapped reads (FPKM) normalized expression values for each 24nt siRNA are plotted on a region of intron 5 including Karma (black box). Bars above and below the zero line represent sense and antisense siRNAs, respectively, and are plotted on the same scale. A cluster of 24nt siRNAs expressed from the Karma region are repressed in mantled relative to normal stage 0 inflorescence tissues.
Figure 12:
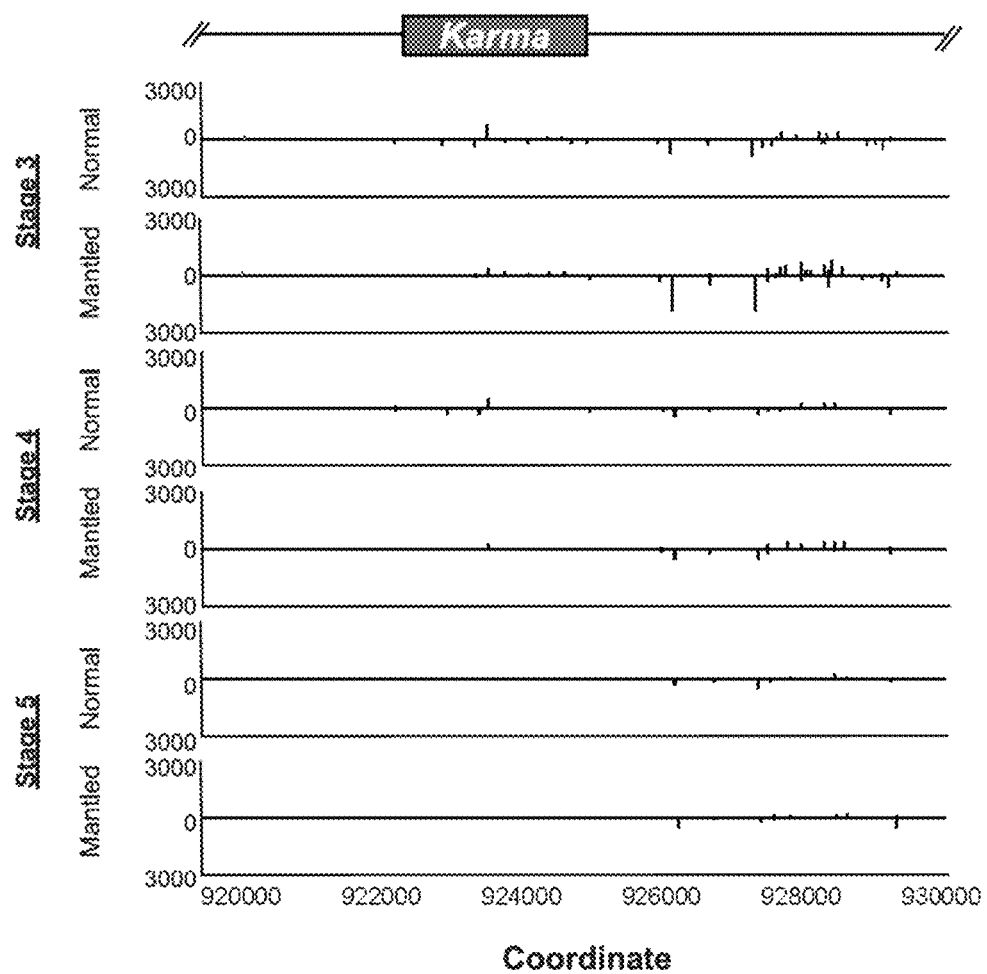
FIG. 12. 24nt small RNA analysis of inflorescence development stages 3-5. FPKM normalized expression values for each measured 24nt siRNA are plotted in scale with the genomic elements diagrammed at the top of the figure. Bars above and below the zero line represent sense and antisense siRNAs, respectively, and are plotted on the same scale in both directions.

Because in *Arabidopsis* and maize, 24nt small interfering (si)RNAs guide CHH and CHG methylation, and DNA methylation in turn is often required for the biosynthesis of 24nt siRNA by RNA polymerase IV (Regulski et al., 2013; Zhong et al., 2012; Hollick 2012), we further analyzed siRNA expression in a time course of inflorescence development in both normal and mantled female flowers. Small RNA sequencing was performed on female inflorescence tissues at stages 0, 2, 3, 4 and 5 (7 mantled and 5 normal biological replicates at stage 0, 6 mantled and 8 normal biological replicates each at stages 2 and 3, 7 mantled and 5 normal biological replicates at stage 4, and 5 mantled and 4 normal biological replicates at stage 5). Stages were histologically classified as stage 0 (terminal meristem); stage 2 (initiation of perianth organs); stage 3 (development of perianth organs and initiation of reproductive organs); stage 4 (development of reproductive organs); stage 5 (fully formed reproductive organs), as previously defined (Adam et al., 2007). siRNA reads mapping to the genomic scaffold including EgDEF1 were identified and normalized as fragments per 1,000 mapped reads (FPKM) to the entire oil palm reference genome (Singh et al. 2013). FPKM values for each 24mer were compared between biological replicates of normal and mantled samples by Student's t-test, two-tailed assuming equal variance. The analysis identified a cluster of 24nt Karma siRNAs in normal inflorescence at stage 0, which were reduced or absent in mantled inflorescence, while other siRNAs matching the EgDEF1 intron, but outside of Karma, were not significantly differentially expressed (FIG. 11). In summary, several 24nt siRNAs derived from Karma were repressed or silenced in mantled relative to normal stage 0 inflorescence tissues (SEQ ID NO: 144-147, 150-158 and 160-161) (Table 5). Several of these 24nt siRNAs were also repressed or silenced in mantled relative to normal stage 2 inflorescence (SEQ ID NO: 145, 151, 154 and 157), and two 24nt siRNAs were significantly repressed at stage 2 (SEQ ID NO: 148, 149 and 159) (Table 5). Finally, at stage 3, one 24nt siRNA repressed at stage 2 remained repressed in mantled relative to normal (SEQ ID NO: 149). The decrease in the number of differentially expressed siRNAs at later stages of inflorescence development is the consequence of the overall decrease in expression of siRNAs in later development stages, even in normal tissues (FIG. 12). siRNAs derived from near the Karma splice acceptor site were mostly in the antisense orientation (Table 5), raising the interesting possibility that 24nt siRNAs complementary to the alternatively spliced exon cooperate with aberrant DNA methylation in an epigenetic mechanism giving rise to the mantled phenotype. Therefore, quantitative detection of expression of one or more of these siRNAs (SEQ ID NO: 82-124 and 144-161) may be useful for the prediction of the mantled phenotype in somaclonal materials, long before field planting and the development of the mantled abnormal fruit phenotype. Furthermore, ectopic expression of one or more siRNAs (e.g. SEQ ID NO: 144-161) during cell culture stages of somaclonal propagation may be useful to maintain or reset the DNA methylation state of the differentially methylated region within the Karma element and/or the appropriate splicing of mRNAs derived from the EgDEF1 locus, thus inhibiting development of the abnormal mantled fruit phenotype in clonal derived palms.

TABLE 5

24mer siRNAs downregulated in mantled female inflorescence development

| SEQ ID NO: | Genomic Coordinate[a] | Orientation[b] | Sequence | Mantled Avg.[c] | Normal Avg.[d] | t-test[e] | Stage[f] |
|---|---|---|---|---|---|---|---|
| 144 | 922791 | ANTISENSE | TTCAGTCAGAGACTTCAGGCCAAT | 27.16 | 367.54 | 0.0269 | 0 |
| 145 | 922864 | ANTISENSE | AGGCTCTCACAGAAAATGAATTTG | 159.12 | 565.42 | 0.0362 | 0 |
| 145 | 922864 | ANTISENSE | AGGCTCTCACAGAAAATGAATTTG | 23.29 | 233.70 | 0.0457 | 2 |
| 146 | 923116 | ANTISENSE | TTATACAGCTAAATTCTCAGTCCT | 23.96 | 282.73 | 0.0012 | 0 |
| 147 | 923117 | ANTISENSE | TATACAGCTAAATTCTCAGTCCTT | 13.97 | 442.34 | 0.0000 | 0 |
| 148 | 923120 | ANTISENSE | ACAGCTAAATTCTCAGTCCTTATT | 23.29 | 290.03 | 0.0066 | 2 |
| 149 | 923123 | ANTISENSE | GCTAAATTCTCAGTCCTTATTAAT | 0.00 | 332.96 | 0.0067 | 2 |
| 149 | 923123 | ANTISENSE | GCTAAATTCTCAGTCCTTATTAAT | 67.53 | 257.59 | 0.0295 | 3 |
| 150 | 923545 | ANTISENSE | CATTCTAAACTGAGGAAAACTTAT | 23.96 | 236.90 | 0.0013 | 0 |
| 151 | 923588 | ANTISENSE | AGGTTCAGAAGAAATTGATCGGGT | 397.31 | 1588.90 | 0.0128 | 0 |
| 151 | 923588 | ANTISENSE | AGGTTCAGAAGAAATTGATCGGGT | 41.13 | 278.10 | 0.0138 | 2 |

TABLE 5-continued

24mer siRNAs downregulated in mantled female inflorescence development

| SEQ ID NO: | Genomic Coordinate[a] | Orientation[b] | Sequence | Mantled Avg.[c] | Normal Avg.[d] | t-test[e] | Stage[f] |
|---|---|---|---|---|---|---|---|
| 152 | 923601 | SENSE | ATTGATCGGGTAGAAAGGTAAACT | 114.41 | 300.01 | 0.0273 | 0 |
| 153 | 923658 | ANTISENSE | TGCAGTGCTTACAGGGATCCCACT | 22.16 | 719.92 | 0.0000 | 0 |
| 154 | 923765 | SENSE | ACGAGGAGTATAACTAAGGGCACT | 499.49 | 2836.15 | 0.0009 | 0 |
| 154 | 923765 | SENSE | ACGAGGAGTATAACTAAGGGCACT | 130.63 | 647.59 | 0.0301 | 2 |
| 155 | 923780 | SENSE | AAGGGCACTCTAGAATATGTTGGT | 110.50 | 1008.90 | 0.0017 | 0 |
| 156 | 923780 | SENSE | AAGGGCACTTTAGAATATGTTGGT | 88.46 | 517.53 | 0.0005 | 0 |
| 157 | 924004 | ANTISENSE | TGGTTTACAGCACACATGAAATAT | 81.33 | 673.52 | 0.0066 | 0 |
| 157 | 924004 | ANTISENSE | TGGTTTACAGCACACATGAAATAT | 0.00 | 191.09 | 0.0115 | 2 |
| 158 | 924322 | ANTISENSE | GGCATGAAGGATCTACTATTTTCT | 110.20 | 419.35 | 0.0059 | 0 |
| 159 | 924322 | ANTISENSE | GGCATGAAGGATCTACTATTTTCT | 0.00 | 192.51 | 0.0500 | 2 |
| 160 | 924604 | SENSE | ACTTTTATGCATGCTTAACACCCT | 73.33 | 257.62 | 0.0235 | 0 |
| 161 | 924610 | SENSE | ATGCATGCTTAACACCCTATGGGA | 30.35 | 240.33 | 0.0018 | 0 |

[a]Genomic coordinate indicates the nucleotide position relative to the reference *pisifera* oil palm genome build (Singh et al. 2013) corresponding to the 5'-most base of the 24mer siRNA.
[b]Indicates whether the siRNA is expressed from the sense or antisense strand relative to EgDEF1 expression.
[c]The average FPKM normalized expression value for biological replicates of mantled inflorescense tissues at the indicated stage.
[d]The average FPKM normalized expression value for biological replicates of normal inflorescense tissues at the indicated stage.
[e]Significance of differential expression determined by Student's t-test, 2 sided, assuming equal variance.
[f]Indicates the inflorescence development stage at which repressed expression in mantled tissues was detected.

Figure 13:
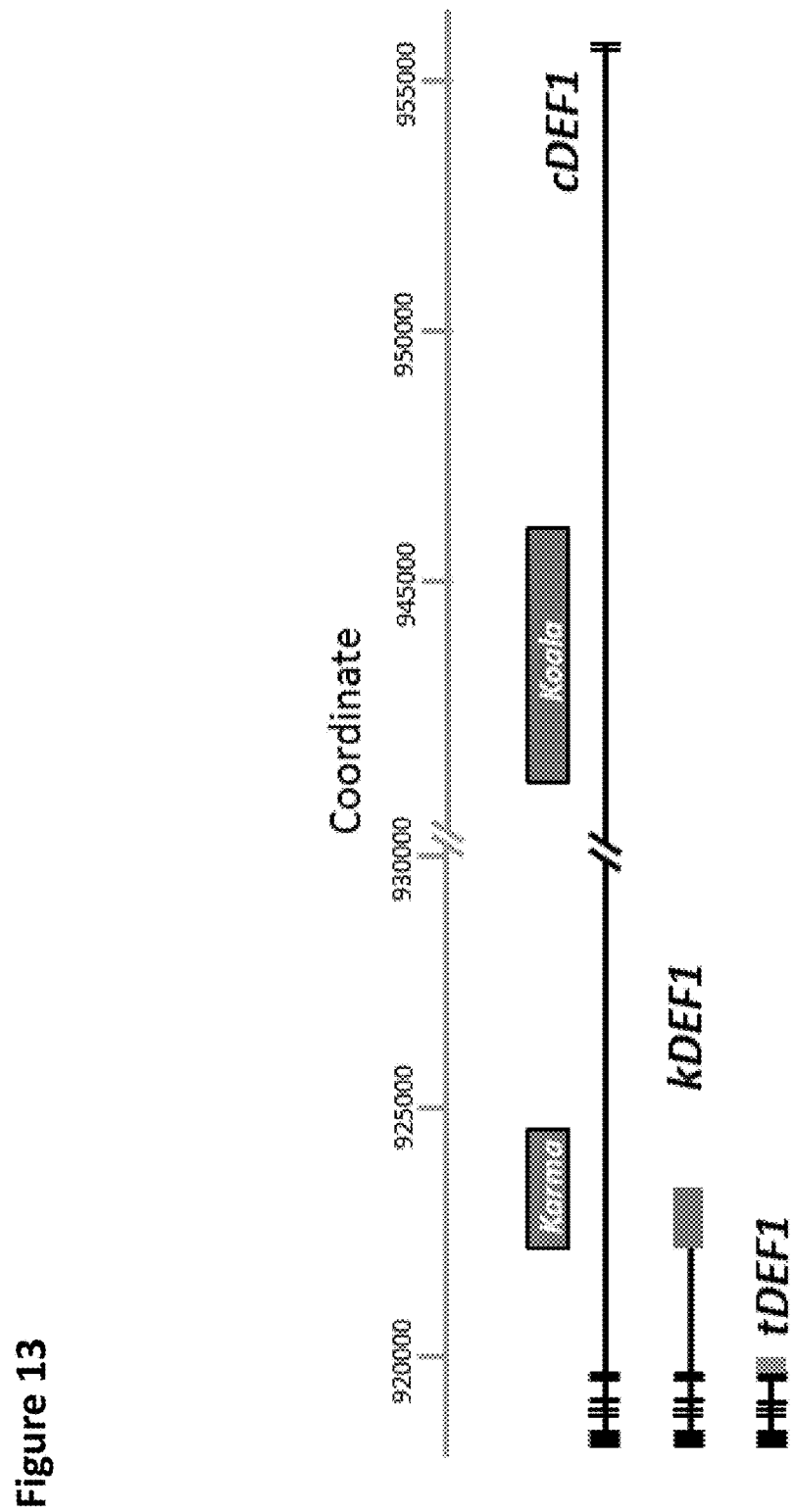
FIG. 13. Alternatively spliced transcripts. EgDEF1/MANTLED transcripts were assembled from transcriptome sequencing of female inflorescences from normal and parthenocarpic mantled palms (3 biological replicates each of shoot apex, <2 cm inflorescence and late stage inflorescence for each phenotype). Black boxes represent exons, Karma and Koala elements are labeled and represented in scale above the transcript model diagrams. Alternative splicing of exon 5 to the splice acceptor site at the beginning of Karma resulted in kDEF1 transcripts in mantled but not normal inflorescence. A third transcript (tDEF1) that does not utilize the exon 5 splice donor site was detected in both normal and mantled inflorescence. Coordinates are relative to the reference pisifera oil palm genome build (Singh et al. 2013).

Example 5: The Mantled Phenotype is Correlated with Changes in Alternatively Spliced Transcript Expression Gene expression in normal and mantled tissues throughout stages of inflorescence development was analyzed by whole transcriptome next-generation sequencing of female inflorescences from normal and parthenocarpic mantled palms (3 biological replicates each of shoot apex, <2 cm inflorescence and late stage inflorescence for each phenotype). Four differentially spliced mRNA transcripts derived from the EgDEF1 locus were detected (FIGS. 9 and 13). First, cDEF1 transcripts (SEQ ID NO: 5) were detected in both normal and mantled tissues. These full-length transcripts include splicing of all EgDEF1 introns so that the mature mRNA includes complete exons 1 through 7 of the EgDEF1 gene and encode the full length EgDEF1 MADS box transcription factor (SEQ ID NO: 6). Second, a shorter transcript, tDEF1 (SEQ ID NO: 75) was detected in both normal and mantled tissues. This transcript includes EgDEF1 exons 1-5, however exon 5 does not splice to exon 6. Instead, the tDEF1 mRNA extends from exon 5 into intron 5 and terminates shortly thereafter. The tDEF1 mRNA encodes a truncated protein due to a frameshift and early translation termination within the predicted K Domain of the MADS box protein (SEQ ID NO: 76). Next, an alternatively spliced transcript was detected exclusively in mantled tissues. This transcript, kDEF1 (SEQ ID NO: 78), splices from EgDEF1 exon 5 to the splice acceptor site of the Karma element within intron 5. The location of this alternative splicing site falls within the differentially methylated region (FIG. 4-8). The alternative splicing event leads to a frame shift following exon 5 coding sequencing and early translation termination with the predicted K Domain of the MADS box protein (SEQ ID NO: 79). Finally, an additional alternatively spliced transcript, gDEF1 (SEQ ID NO: 80) was detected at very low levels in a small number of mantled tissue samples. This transcript splices from EgDEF1 exon 5 into a region of intron 5 that is upstream of Karma and the differentially methylated region. This splicing even also leads to a frameshift following the exon 5 coding sequence and early translational termination within the K Domain of the MADS box transcription factor (SEQ ID NO: 81). It is noted that such expression of truncated MADS box transcription factor proteins (kDEF1, tDEF1 and/or gDEF1), which include the MADS box domain required for protein heterodimerization and DNA binding but lack the C-terminal domains of the protein required for transcriptional activation can have a dominant negative impact on the function of the full length MADS box protein and, thus, lead to homeotic transformation phenotypes such as that displayed in clonal palms with the Mantled fruit abnormality.

Figure 14:
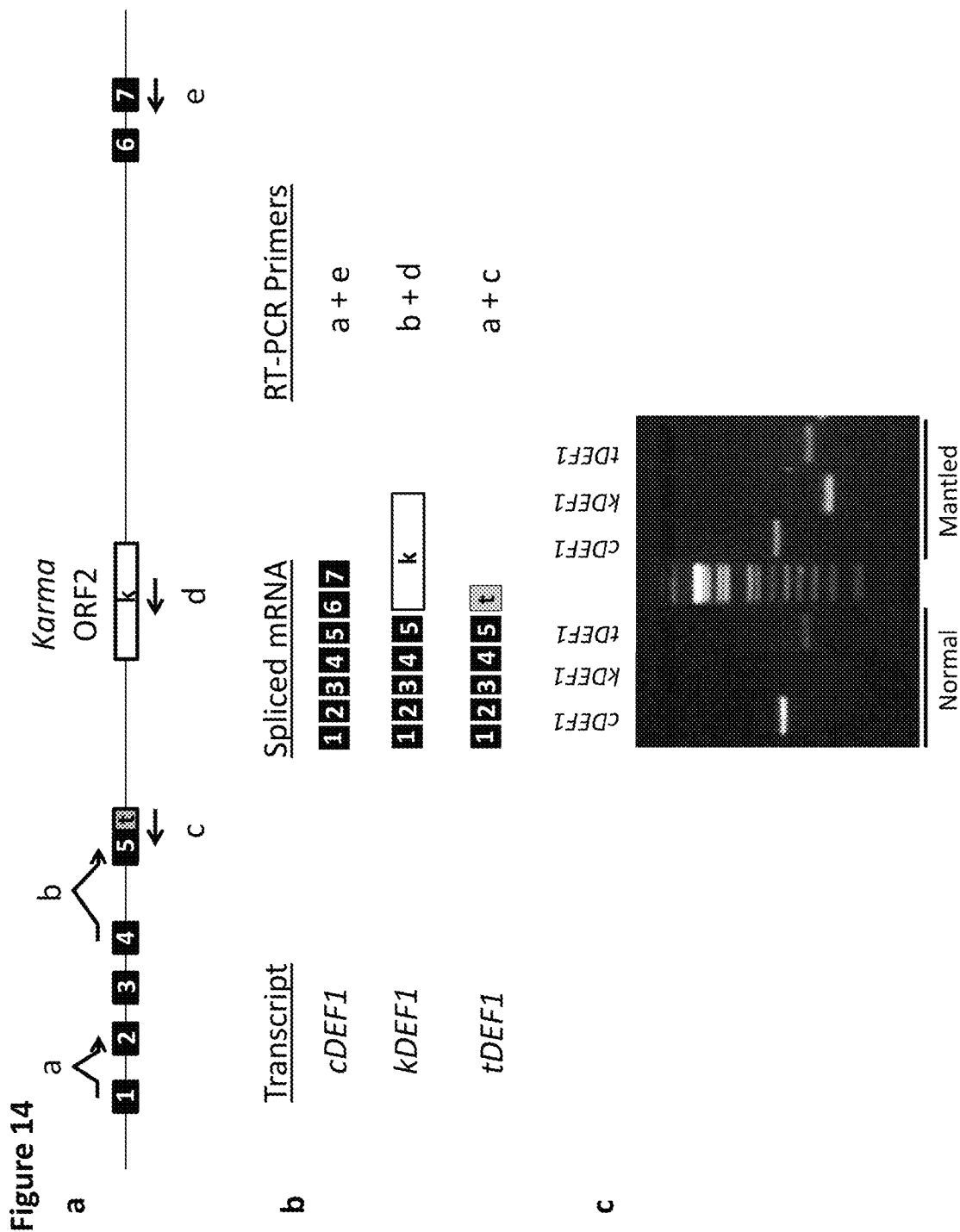
FIG. 14. Design of qRT-PCR assays for cDEF1, kDEF1 and tDEF1. A. Gene model of EgDEF1 indicating relative positions of transcript-specific qRT-PCR primers, as described in Example 5. Black boxes represent EgDEF1 exons. Gray box ('t') represents intron 5 sequence included in the tDEF1 transcript. Open box ('k') represents Karma ORF2 sequence. Arrows indicate qRT-PCR primers. B. Summary of alternatively spliced transcripts and qRT-PCR primers used to specifically detect each transcripts. C. End point RT-PCR results for each assay using normal or mantled total RNA as template.

To quantitatively measure expression of cDEF1, tDEF1 and kDEF1, qRT-PCR assays specific to each transcript were designed and optimized (FIG. 14). To specifically measure cDEF1 expression, a forward PCR primer was designed to span the splice junction of EgDEF1 exons 1 and 2 (a in FIG. 14a, SEQ ID NO: 125), and a reverse primer was designed within EgDEF1 exon 7 (e in FIG. 14a, SEQ ID NO: 126). To specifically measure kDEF1 expression, a forward PCR primer was designed to span the splice junction of EgDEF1 exons 4 and 5 (b in FIG. 14a, SEQ ID NO: 127), and a reverse primer was designed within the Karma element (d in FIG. 14a, SEQ ID NO: 128). To specifically measure tDEF1 expression, a forward PCR primer was designed to span the splice junction of EgDEF1 exons 1 and 2 (a in FIG. 14a, SEQ ID NO: 125), and a reverse primer was designed to span the 3' sequences of exon 5 and the 5' sequences of intron 5 included in the tDEF1 transcript (c in FIG. 14a, SEQ ID NO: 129). Multiple locus-specific reverse oriented primers were designed and pooled for use as RT primers so that all possible transcripts could be amplified as cDNA products from a common reverse transcriptase reaction using stage 4 normal and stage 5 mantled total RNA samples as template. A summary of exon splicing for each analyzed transcript, and the qRT-PCR primers used is provided in FIG. 14b. End-point PCR reactions using these RT products as templates and each primer pair separately are shown in FIG. 14c. cDEF1 primers amplify a band of the predicted size from both normal and mantled RNA templates, although qualitatively more product is amplified from the normal sample relative to the mantled sample. kDEF1 primers amplify a band of the predicted size from mantled, but not normal RNA. tDEF1 primers amplify a band of the predicted size from both normal and mantled RNA, although qualitatively more product is amplified from the mantled sample relative to the normal sample. Quantitative efficiencies of the PCR primers, along with primers for an endogenous housekeeping gene reference qRT-PCR assay, PD00380, for oil palm (Chan et al. (2014) PLoS ONE 9: e99774) were determined by amplifying a dilution series of cDNA templates in real-time PCR assays using SYBR green quantification methods.

Figure 15:
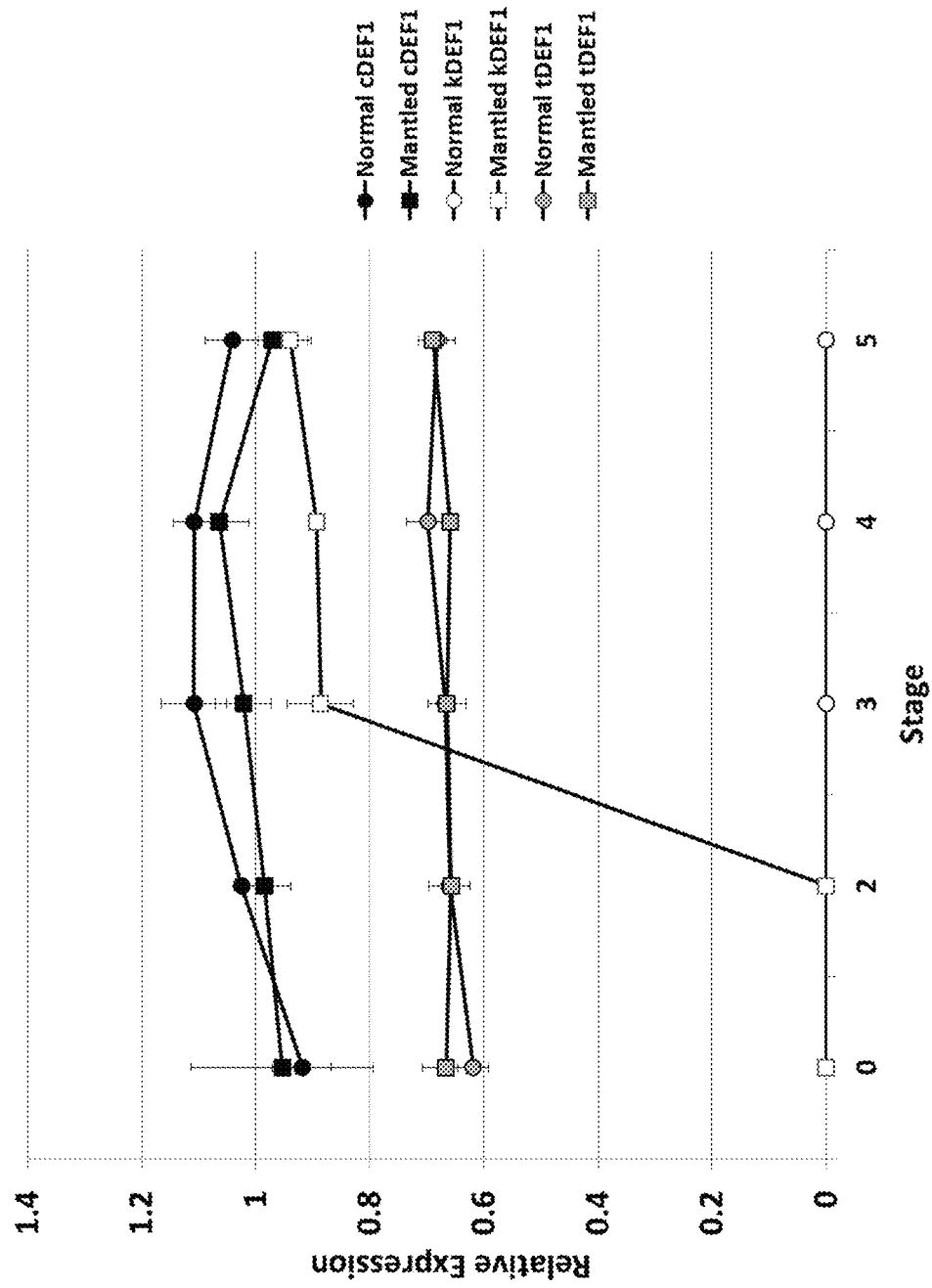
FIG. 15. Quantitative reverse transcriptase PCR (qRT-PCR) analysis of cDEF1, tDEF1 and kDEF1 expression throughout normal and parthenocarpic mantled female inflorescence development. Error bars represent standard deviations between three technical replicate assays of 3 biological replicate tissue samples per phenotype, per stage. Expression relative to an endogenous reference gene is shown.

The qRT-PCR assays were used to quantitatively measure cDEF1, tDEF1 and kDEF expression throughout the female inflorescence time course (FIG. 15). Gene expression was quantified in developing inflorescence stages 0, 2, 3, 4 and 5. All first strand cDNA reverse transcription reactions were performed from 1 µg total RNA using a cocktail of reverse primers specific EgDEF1 exons 6 and 7, as well as 3' regions of Karma. For each stage, three technical replicates were performed for three biological replicates per phenotype, per stage. qRT-PCR reactions were performed using 1 µL first strand cDNA in 1× Roche SYBR Master Mix on a Roche LC480 instrument. Cycle thresholds above 33 cycles were not included in calculations, and detectable expression was calculated only for samples in which expression was detected in at least 2 of 3 technical replicates. Expression levels were quantified by extrapolation from the standard curve for each assay, and expression levels relative to an oil palm gene expression reference gene (Chan et al. 2014) were calculated. In both normal and mantled tissues, cDEF1 expression levels rise subtly from stage 0 through late inflorescence (FIG. 15), while tDEF1 is expressed at a constant, lower level. However, in these results kDEF1 expression is restricted to inflorescence stages 3 to 5, exclusively in mantled tissues. Therefore, unlike tDEF1 expression, the expression of kDEF1 in female inflorescence is, in some cases, only found in mantled, and is predicted to encode a severely truncated form of the EgDEF1 MADS box transcription factor.

In conclusion, the mantled fruit abnormality phenotype of oil palm, which arises as a consequence of somaclonal propagation, is correlated with multiple molecular abnormalities at the EgDEF1 locus. Tissues from mantled palms have significant CHG hypomethylation of a differentially methylated region that covers a Karma family LINE retrotransposon element embedded within intron 5 of the EgDEF1 gene. Hypomethylation of this region is sensitively and specifically diagnostic of the Mantled phenotype, and assays quantitatively measuring methylation content at any of multiple CHG sites within this region have strong diagnostic power for predicting the abnormality. Four alternatively spliced transcripts derived from the EgDEF1 gene have been detected, one of which (cDEFJ) encodes a full-length MIKC family MADS box transcription factor and three of which (kDEF1, tDEF1 and gDEF1) encode truncated proteins that include the MADS box, I and partial K domains, but lack the C-terminal transcription activation domain. In normal tissue, the predominantly expressed transcript encodes the full length cDEF1 protein. However, in Mantled tissue, expression is predominantly derived from the alternatively spliced kDEF1 transcript, and to a lesser extent, the alternatively spliced tDEF1 transcript. These findings support a mechanism by which epigenetic deregulation of the EgDEF1 locus leads to expression of truncated dominant negative proteins that interfere with the normal homeotic floral organ specification pathway, thus leading to the mantled fruit phenotype. Moreover, the expression of small non-coding regulatory RNAs from the EgDEF1 locus are significantly altered in tissues from mantled relative to normal palms, especially at early developmental stages.

Figure 16:
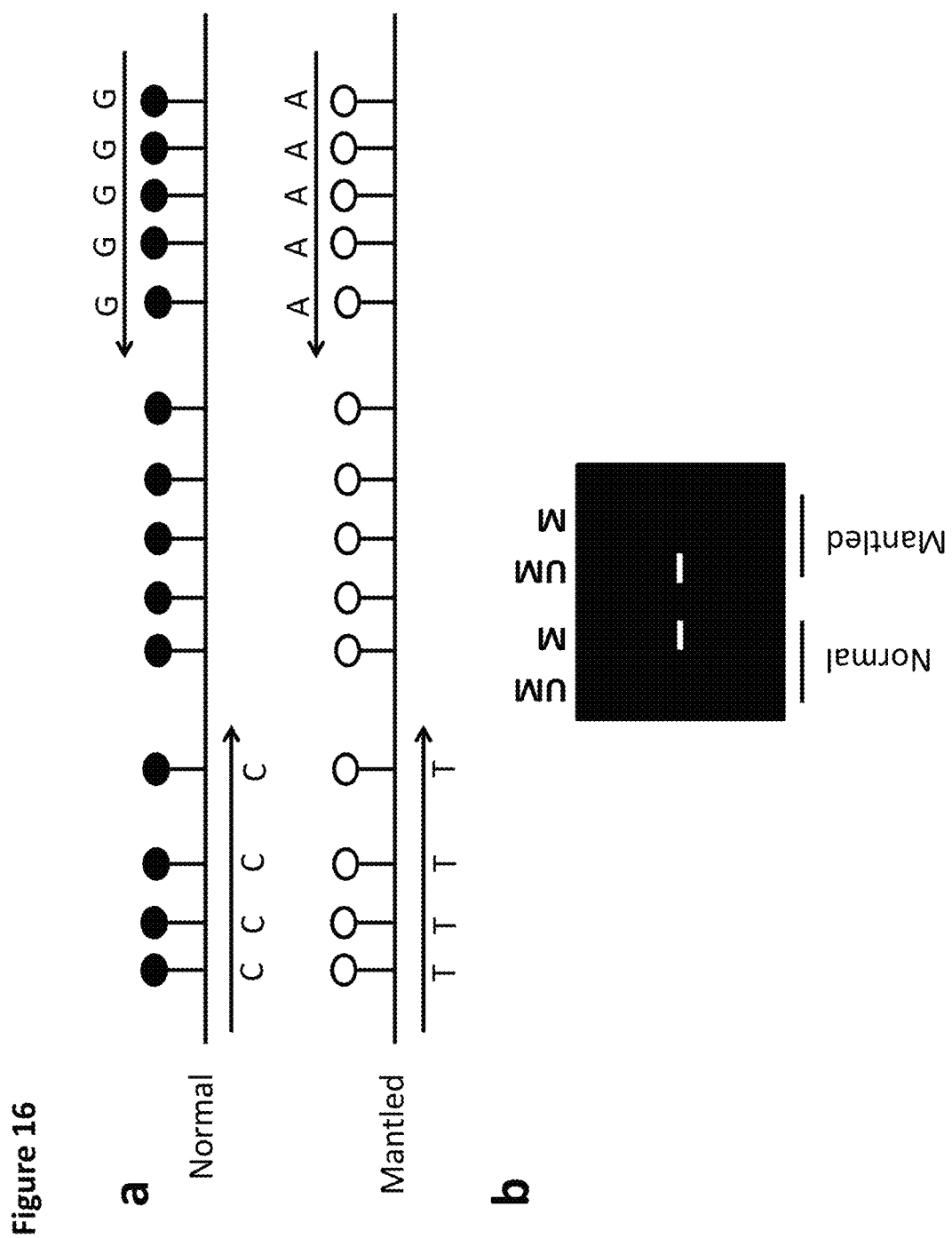
FIG. 16. Example of Methylation Specific PCR assay for detecting differential DNA methylation in DMRs disclosed herein. Details of the assay are described in Example 6.

Example 6: Detection of Differential DNA Methylation by Methylation Specific PCR DNA methylation can be quantified by methylation specific PCR (MSP) methods. Using this method, DNA samples are treated with bisulfite to convert unmethylated cytosines (but not methylated cytosines) to uracil. Primers are designed to cover potential methylated cytosine sites, and different primers are designed for methylated vs. unmethylated configurations. An example of analyzing a DMR identified herein in mantled and normal samples using MSP is shown in FIG. 16. It is noted that such an assay can be performed on clonal material prior to planting in the field, at a time in which the eventual mantled phenotype would be otherwise unknown. For simplicity, all potential DNA methylation sites are indicated as methylated (filled circles) in normal DNA and unmethylated (open circles) in mantled DNA (FIG. 16a). It is noted, however, that a given DNA molecule may include a mixture of methylated and unmethylated cytosines. Primers intended to amplify molecules that are methylated at sites within the primer sequence are designed so that primers have cytosines at potential methylation sites in the primer for one strand and guanines at potential methylation sites in the primer for the other strand. Primers intended to amplify molecules that are unmethylated at sites within the primer sequence are designed so that primers have thymines at potential methylation sites in the primer for one strand and adenines at potential methylation sites in the primer for the other strand. Bases within primers that correspond to cytosines that are not potential methylation sites are designed to base pair with the converted sequence since all unmethylated cytosines are converted to uracil. Normal and mantled DNA samples are treated with bisulfite to convert unmethylated cytosines to uracil, and the converted DNA is used as template for PCR amplification with each primer pair (UM for unmethylated primer pair and M for methylated primer pair) separately. Normal samples, in which the cytosines are predicted to be methylated, amplify with the M primer pair, but not the UM primer pair. Mantled samples, in which the cytosines are predicted to be unmethylated, amplify with the UM primer pair, but not the M primer pair (FIG. 16b). Differential intensities of bands may also be diagnostic of the phenotype, rather than presence or absence of a band.

A modified approach can be applied in which one of the two PCR primers includes only one, two or three potential methylation sites. Following bisulfite conversion, a site behaves similar to a single nucleotide polymorphism in unconverted DNA. For example, following bisulfite conversion, a methylated cytosine remains cytosine and will base pair with guanine. However, an unmethylated cytosine is converted to uracil and will base pair with adenine. Therefore, a method suitable for detection of a single nucleotide polymorphism is also suitable for monitoring the methylation status of a cytosine within the mantled DMR. These methods may provide quantitative or qualitative measurements.

Figure 17:
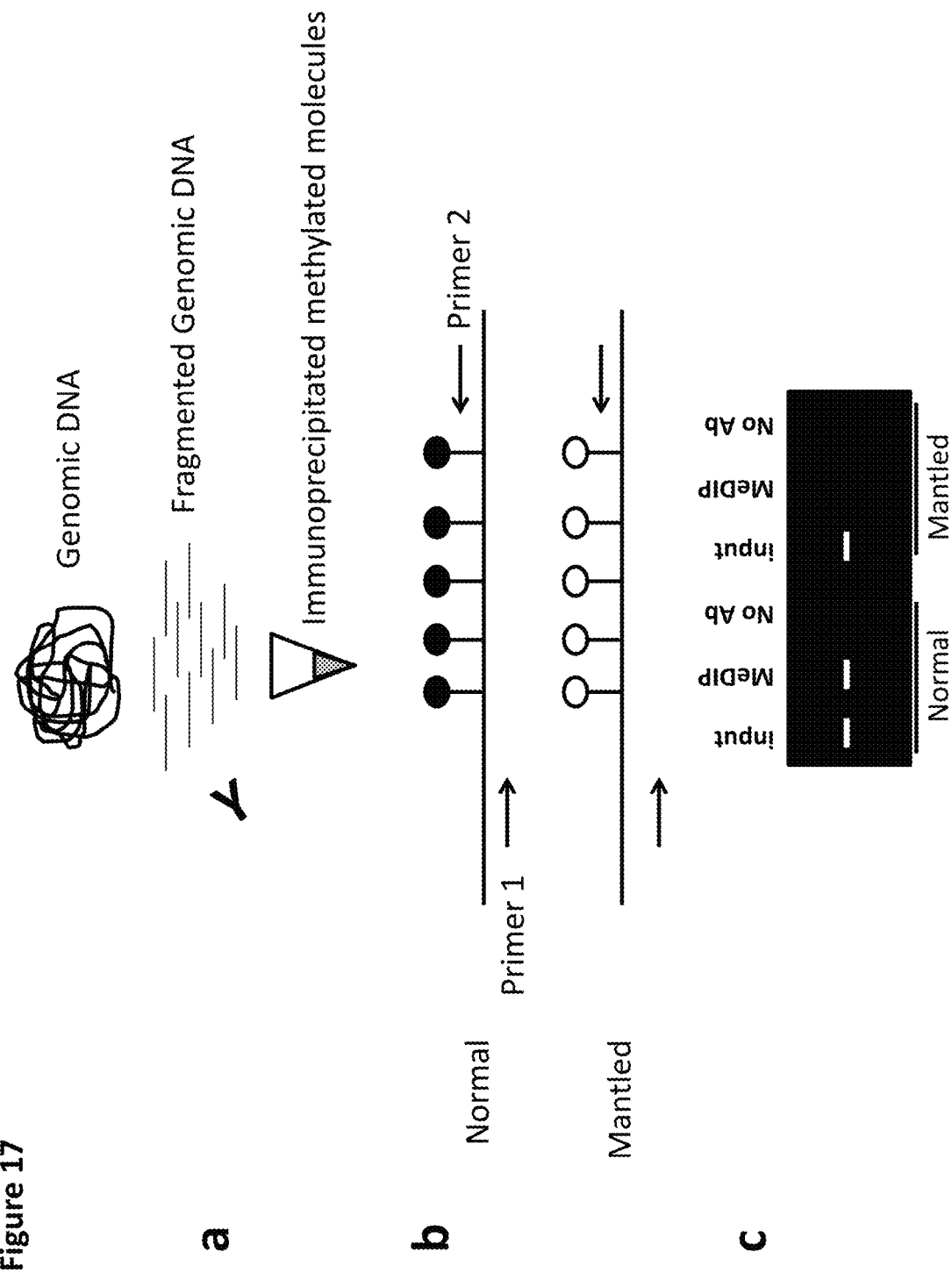
FIG. 17. Prophetic example of Methylation DNA Immunoprecipitation assay for detecting differential DNA methylation in DMRs disclosed herein. Details of the assay are described in Example 7.

Example 7: Detection of Differential DNA Methylation by Methylation Dependent Immunoprecipitation DNA methylation can be quantified by methylation dependent immunoprecipitation (MeDIP) methods. In this method, an antibody specific to methylcytosine is used to immunoprecipitate cytosine methylated DNA molecules, followed by amplification of specific DNA sequences. An example of analyzing a DMR identified herein in Mantled and normal samples using MeDIP is shown in FIG. 17. It is noted that such an assay could be performed on clonal material prior to planting in the field, at a time in which the eventual Mantled phenotype would be otherwise unknown. For simplicity, all potential DNA methylation sites are indicated as methylated (filled circles) in normal DNA and unmethylated (open circles) in Mantled DNA (FIG. 17b). It is noted, however, that a given DNA molecule may include a mixture of methylated and unmethylated cytosines. DNA from normal and Mantled samples is fragmented by restriction enzymes or by sonication or by mechanical shearing (FIG. 17a). An antibody specific to methylcytosine is added, and complexes of antibody and methylated DNA molecules are immunoprecipitated using standard methods (FIG. 17a). Immunoprecipitated fractions are then PCR amplified with primers designed to flank the DMR (FIG. 17b). PCR amplification reactions can be analyzed by agarose gel electrophoresis (FIG. 17c). As a positive control, input DNA (without immunoprecipitation) is amplified. As a negative control, mock immunoprecipitated fractions without antibody is amplified. The 5-methylcytosine specific antibody immunoprecipitated fraction shows amplification of the DMR region in normal samples, but not in Mantled samples. Differential intensities of bands may also be diagnostic of the phenotype, rather than presence or absence of a band.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for detecting or predicting Mantle phenotype in an oil palm plant, the method comprising:
   a) obtaining a biological sample from the plant;
   b) detecting an increase or decrease in the methylation status of at least one cytosine within a differential methylation region (DMR) in the sample from the plant relative to a control locus, wherein the DMR is within a sequence of DNA at least 95% identical to SEQ ID NO:66; and
   c) physically separating a plant predicted to have the Mantle phenotype from one or more plants predicted to lack the Mantle phenotype based on the detected methylation status.

2. The method of claim 1, wherein the physically separating comprises selecting plants predicted to have Mantle phenotype for destruction.

3. The method of claim 1, wherein the physically separating comprises selecting plants predicted to lack Mantle phenotype for cultivation.

4. The method of claim 3, wherein the plants selected for cultivation are planted or transplanted.

5. The method of claim 3, wherein the plants not selected for cultivation are discarded or destroyed.

6. The method of claim 3, wherein the plants not selected for cultivation are treated to reduce the likelihood of Mantle phenotype.

7. The method of claim 1, wherein the at least one cytosine is a first cytosine in a CHG sequence, wherein H is C, A, or T.

8. The method of claim 1, wherein the DMR is within a DNA region in the sample from the plant, and wherein the DNA region is at least 95% identical to SEQ ID NO: 43, SEQ ID NO: 44, SEQ ID NO: 45, or SEQ ID NO: 46.

9. The method of claim 1, wherein the method comprises predicting the presence of Mantle phenotype when the methylation status of the at least one cytosine is reduced relative to a control locus.

10. The method of claim 9, wherein the control locus is an endogenous control locus.

11. The method of claim 9, wherein the control locus is an exogenous control locus.

12. The method of claim 1, wherein the detecting an increase or decrease in the methylation status comprises bisulfite conversion.

13. The method of claim 1, wherein the detecting an increase or decrease in the methylation status comprises digesting genomic DNA with a methylation-dependent endonuclease.

14. The method of claim 1, wherein the detecting an increase or decrease in the methylation status comprises digesting genomic DNA with a methylation-sensitive endonuclease.

* * * * *

SEQUENCE LISTING

```
<160> NUMBER OF SEQ ID NOS: 161

<210> SEQ ID NO 1
<211> LENGTH: 78321
<212> TYPE: DNA
<213> ORGANISM: Elaeis guineensis
<220> FEATURE:
<221> NAME/KEY: misc_feature
<222> LOCATION: (14421)..(15355)
<223> OTHER INFORMATION: n is a, c, g, or t
<220> FEATURE:
<221> NAME/KEY: misc_feature
<222> LOCATION: (55950)..(57363)
<223> OTHER INFORMATION: n is a, c, g, or t
<220> FEATURE:
<221> NAME/KEY: misc_feature
<222> LOCATION: (64044)..(65002)
<223> OTHER INFORMATION: n is a, c, g, or t
<220> FEATURE:
<221> NAME/KEY: misc_feature
<222> LOCATION: (65951)..(66637)
<223> OTHER INFORMATION: n is a, c, g, or t

<400> SEQUENCE: 1
aatctattag tatctgacaa aagttaaatt agagtcgaaa cactaaatga caattaggga      60
tcaacttgat caagtagata gagaatatta gaaaagagag aaattaacaa gatagaacat     120
gattaattag gtgacatagc ccgacaatcc aattggtcta agcaagttga tttaatcaaa     180
```

```
tcacggttga actaatatat agatagctca ataaaaatca tacataattg aatctaatga    240
tatttggatc tgaccaagat ggaatttgac atgctgtccg atgatcgtga atcaagactc    300
tctttgctaa ttaagatcaa attagaatca ttgaaagaga atcttttact ggatcaagag    360
agagaaatat ataagagag tgaaatagtc tatagaaaaa aaatttagag agagaaatta     420
agaagaaaaa ataaattttt ttagagaaag aaagtgggta tacaagctca gagaagggag    480
agaggaaaga gagagaaatg ctctcttatt ttcttttttt tctttttttct tcttttcttt   540 ttttttttcca ttcttctttc cctttttctgc ttaatggaat aggggacctc ccattcccct  600
tctatttcta gagttggggg ctcaaaattg atgatagcta tcattgggga tgtaggctat    660
ggtgatgcag tagaggatca ccgaccgatg atcgatggtg atgttgcaat caaaaaatca    720
agaaagatag atggaaaata aaggaaaata aggagaaata gatctcaact tgtttggatg    780
ctaacccact cactgacgac tccacttcaa ctatggccgg agcttgctat ggaaaagaag    840
ccaaggcctt caaggatgaa caccaatggt gaggaagatg gtcgaaaata aagaatggc    900 tggcttttct aatcgacaaa atagggtatc gcccttctta gcaaatattc ggcaataaat    960
atctagaatc caggatccta ggactatgga agagggagag gagggcaagt caaaggatgc   1020
cagattctta tctagcttcc gacaatgatg gggccctatt ttcgataaac acaatcgagg   1080
atgttcggaa aagggttttt tcgatgatga ttctagtgac caactatgag atttcaaagg   1140
gggtgagggg ggtttaaata agatgggagg gaagtttgaa tcctccttaa atctgaacct   1200
ttttcgacaa agccaagagc gtgaaggaga ctccttcgtg aagtcaaaga tggaatagac   1260
tcccttcggg agtttggttc atcacccaac ttccctagca tgtgcggagt atgtgctagc   1320
cttttctctc tttttttttt cattttttt catcctttaa gatccatgca gtttctaggt    1380
tgagggattg gggtatcaca ttctctctcc taaaaaaaaa ttattttcaa aattttttta   1440
cctatatttt caaaagttgg gattcatggt ccaaatctca tccttgaatt tttttgatat   1500
tctaattctc gaaaaaattt catcgttaaa tcatttcata agagaaaagt caatacctca   1560
agagttgatc tgaatcaaaa ttattatctc tagtaatcga aatcaatatc ttaatttcaa   1620
ataagaatat ccagtttatt gtcaaaatta ttaactactc ttgacttaat tgatctatta   1680
cataatcgta aataaattct aacatactct tgaagtgtag aatataagat tgataaacaa   1740
tcctatatcc gttctaatag atataaaagc ataaacttta aatattttaa atccaagatt   1800
aagaatcaat gatccactta tcctagactc aagatattag aaatttttt ttgtacaata    1860 gatagaggat gtactggtga aaatcatgta gcgatatcca aaataatttt taattaaaaa   1920
tattatcctt ttcattatca atgaattta tctataagaa agatcaaatc atatgatcca    1980
tcttaaattt ttaactcaaa aaattaatat tgcaaactag ctcaaaataa ttttgatcac   2040
tacatttctg ctgtgcattc taatttaaac cgttcacatt tttagattc atgaaataat    2100 tttgaccaaa gtattactcc atactatagt caaaaaagat taaaatatta gattctaatt   2160
aaagccaaag ataaactttt gattctcatc cttaattttg cctaaagtat aattatttg    2220 attaacccctt aagcgcaata acacattcaa aaccaacaga taggtttact ataatccaaa  2280
tgaattaaat cttaattctt ttatcaattc atttagacaa tttcaaatca aaattctata   2340
agtaatatca ataaaaaaa attttgatgc tccaataagt tagaacttaa atcaaaatat    2400
ataagtaaaa ttgatttaat catctcttct aaagtttctt ctattaagat ctttaatatc   2460
tatcaaatac attccacaat aatcatgcaa acctttaaa aattaaattc tcaatgcctt    2520
tactacattt taacaccaag ctcgataata gtgataaaga aacatctaga tcagctttat   2580
```

```
aatcaaaaat tttgacttac aattttacgt gtgtctcaaa atcttgaata aatataaata    2640
agatctttta tcttgatcca aaaatagtaa tcaaggattt cattagtaac ttcaacaaca    2700
atggtaaaaa aattttctat ccattgataa acccaaattt tgaattgaag tttcatgcat    2760
accatatagc ctttaataag atctattatt tggatctaaa gatagtaatt aaaattgtta    2820
atgattccac taagatgaat actttacaat ctcataatta atttcttcaa taaaaataga    2880
cttcttgata atgtctccaa ttgtatattt tttttttattt ctacaagaaa acttcataca    2940
tttttttacgt tccaatataa atcttaaaaa gttattccaa tcaaatatca taaaagatct    3000
tcttagtcca accttaaata acttttatga atgaatcttt atcttgccac taaataatga    3060
attttaaaat caagagcaac atcacagcat tctgtcatgt caaatttgtg ttagatgtat    3120
gtcctagaaa tcaattagat tgacaatgta aattttttaa ggatataatt tatatatttt    3180
gatttattaa taaaataaaa tttaaattaa ttttttattca tatttttttta tctatgaatc    3240
atctaaagaa ttaataagat gatgatacat attcttaaga gttcaaaatt tgaaatatat    3300
gtcattgatg attaatttct gaatactttt gaattcttaa gagtttagaa gatcttgacc    3360
caagtagtgt gaatagtgaa aaaaagtttt cacatacttc acatcaaaaa tttaagttga    3420
ataaattgta catatgacag gtattatagt ttgacgagta atctataacc tctatcttat    3480
caaaattctg atagaaagat tgtattgtat gataactgta cttagaggtt cacctttat    3540
tttactggat taccactaca tgttgctaga tgtcactggt ggattgtgag atctacgaag    3600
attatcttga tgatcgataa ttctcattga aaagattgaa actattttaa tgatgttgtg    3660
atagagatca taatatatct tattatcaga cagaatagaa ttctatggga tcatacacaa    3720
taggagatta agactgatca aatagttgaa tgatgattaa gaatcattac ggagttcaga    3780
ttatcaatat aattgataat tagactaact tataattgtt acaagtagca aggacttaac    3840
tgctaaaggt taataggttc aaaaagaact tatgtataaa tgttgtgcat cttaatttga    3900
ttggatcaaa ttagttatgg ctgaattcaa gatgaatcaa ataggaattt ggttcaattg    3960
aatttgggtc aagctttagg cttaggtcac atatacccaa aatcatttgg atgcatcagg    4020
tgtgtgacac ctgaatcagg cctttctaaa ctatttttgag taagtttgat caagtcaaaa    4080
ggatccacac cctaaggttt cttgaataaa accttaggca ccacattgag gacctatagg    4140
aaactttgac cctctctcat atggggtggc acactgaggt tttataaaaa ccttaggcac    4200
ccatttttagc cataaaaaaa aagctccaag ggatggggca gtagccatga agaatccttg    4260
gctgtcagga ctctattcaa aagagttctc aaggttttgg actcttatgg agccctagga    4320
tttgtttgcc tataaataga tggccacccc aaggctttag ataatgttag agacttgtga    4380
agctctcccc tttctcttgg ttgccggccc acctctctc ctctctcttc catgccccaa    4440
gacttctttc ttgtctccat catcttgctg aaatttagat ttcagcaaga aaagtcaagt    4500
agaagtcaaa gttctaatgt agctcacaag atgttgagaa cttcctccat ctggcaaagg    4560
ttctgcaaga gagctagcat cctgagaaac aaaaagattg ctgatcagcc ctcatctcca    4620
tatggatatt tgtagagatc agatgcatgc atagctagaa gagaatctta tcacgatcat    4680
cactcgtgaa gatcatctac ctgtgcaaag gtatgagata agaaaaatat ttttttttatc    4740
ataattcatg aatcctttgc ttatattata ctgagattct tggaatggat ttttttctcta    4800
gtaaaactct agagatcaga tctcgaagtc ttcttcatat aaaggttttg aaagttcttt    4860
atattttcgc tgctttgatt caaaataaat tgatctatt ttgcctttca accttttctca    4920
tatttattga catataaagc tttaattaat gagattaatg aaaagcatgt gcgaaatact    4980
```

```
gagaaaatcc taacagtgat atcagagcta cttttgtaca taagaaaagg attcaagtta    5040
aataaaatct gtttgattta agtaaatgaa tcaatcaaaa tttatcctaa cataagtttg    5100
tcctggtata atggtcaaga ccattatgtt gaaaggttat cctaggacaa aaagtctaag    5160
taaaatctat tttatttaag taaatgaatc aattaaagtt tattctaata taagattgcc    5220
ttagcataat ggtgaagacc cttatgttga aaggttgtcc taggatggaa agtgattgat    5280
gagacaaata tatcatgaaa gtattttca cagatggaat aaaatatata tattttgttt    5340
gtgaaaatga gatttcatga atgtgtttgt cattcaatat gtgtggtgat catcttgaat    5400
tgccacaaat cctttttgga ttagggttgt atcatgactc acaaatcctg atggtttgca    5460
aaattttgca ttctgtagtg atagaaacca aaagttaatc cagttttgga ataagattga    5520
tcaattggta tctaaggcaa gtattttata atggtggtta cttaattagt tataaaagta    5580
cgaagagtct cctaccaatc ttacacttat ctagccaatt tggttgattg aattctgaat    5640
ttgggttgct taagtgttaa gttcactaca aatatattgc aaccatgatt ccgacttagt    5700
caaccaagcc tagatctctt gaatagattc atgttaatta tggatttaca taggatataa    5760
ataaataatt aaaacttgaa gagatctaaa tgaaaccttc tcgtacatat taaatcgaat    5820
gatcttccat cattgtagat atacggatac tctactgatg ttgatgattt tcgactagat    5880
atagtacttt ggttgcatcg aaaaagtaca accactttat aacatgagat gttgcagggt    5940
agagatgggg ttgggcccaa taattgttag gtgaggatcc aaatgatggc tgcacttgcg    6000
tgtgaatggc gagtctgact taattaagaa atagagctaa taactattag atgaggcttc    6060
aggacttaga gacttatgac cactacaact tacttgagaa gcaatggata aagagtcgtc    6120
tatttatcaa ctgacgcatc accaataact atcagatgga gtgatgtata attagtggga    6180
ctatagtatc cacttgaaat cttaatcgta aaaattttg tttctccacc tgaagagcat    6240
gggagattcg aaaaaatagt gggggtagtt tattttaaa ataaagctcc taaaataaac    6300
taaaataagt taaatacaaa gtctaactag aatcttcttc tctctgtaga aaatatctgc    6360
ttccaacctc tatttcatat ccttaagact aattgtttga ctagacccag ttataaagat    6420
tgactctaaa acttaaagat agtcttgagt tttgaaaaga tgagctatgt cctggatcaa    6480
gatatcctct ctctaccagc ttgtcccacc cctaatcaag gggcatccta tgaaaagtgg    6540
ttaaacgatg ataacaaggc ttggtgctgt gtgctgacat ctatgtccat tgaactccaa    6600
tgccagcata agggtacaaa ctgtccaagg tatattgact catctacaag agttatatag    6660
tgagtagagc catgtatctc actaggaagt atttaagaga ctcttcaaga tgaagaagta    6720
tgatggatag tctgttaatg atcattgtct gataatgatc aagaacttga aagaacttga    6780
gaagctcgat atgtctatca ataagaaatt gcagattgat ttgatcctac aattccttac    6840
tgattcatat gtgtagttta ttataaacta ccatatgaat aaaatacagt gcaccaaggt    6900
tgagttgtta aatatactga taactactga agggacctcg aagagttcaa gaggcactgt    6960
tcttattatg gagcagacct catctttcaa gaaaaagtct actgaaaaga agaaaaagtt    7020
tgtgaagaag cagaagttag agaataggcc aaagaaagaa gttttcaaga agaaggccac    7080
aaaaaaggaa aagtattttc actgcaactc tgatgaccat tggaagagaa actattctga    7140
ttatgtggca agcttgaaga acaaaaaaga tagcataacct tctgaagata tgtctgatct    7200
tctcgttatt gaaactaatc ttacaatttc ttttacttc agttaggtta tagactctag    7260
ctctagtgct catctatgca cttctataca ggatctggag gaaagtagaa ggctgaggaa    7320
```

```
agaagaaata atccaacaag ttgaaaatga tgcaagagtt gttactatgg ctgtggagat    7380
ctatcctcta cgactaccat ctgatcttag tttaattctt agagactgtt attttatacc    7440
tactgctagc aaaaaattga tctctatttc atctctagca taggataatt atgtattaaa    7500
ttttaataaa gattattata ccatttattt gaaaaataaa atggttggac gtaattttt     7560
aattgacagt ctctatcatt tacatgttga tgtatctatg aatgtaacca agcagaaagt    7620
gaatgccata ggatctaaaa gatctaaaga tgaaataaat tatatgtggc acattaggct    7680
agatcatata agagaagaaa ggattaacag attggagaaa gatgggctct tgggcttatt    7740
gactactgag ttatatccga tctgtgaatt ctgccttcaa gaaaaaatga tcaagctgcc    7800
ctttatgaaa caaggagaaa agaccattaa gatatttgcc ctggtacata ttgatatatg    7860
tggcccatta attcgatgcg ctggtcaaag aaggttgtct ctatttcatc atctttatcg    7920
ataattattc acagtatgga tatgtgtatc ttatgagata caaatatgaa gtctttgaaa    7980
aatttaaaaa atttagaaat gaagtaaaaa aataaactaa aatttttta aagatttttc     8040
aatcagattg aaaagttgaa taccttaatg gagaatttct aaattatctc aaaaaaaata    8100
gcatagtctt ataatggact ccatttggaa tgtcttaact caatagagtt tcgaaataga    8160
gaaatcaaac tttattagat atggttcggt ccatgattag tttcattgac cttctcttat    8220
ttctttggag atatagttta cttaccacta attatctatt gaatagggtt tcctctaaaa    8280
tcatttctac cacattgtat gagatatggt attgtagaaa atcaagtctt gatcatatca    8340
agatttaagg atatccgacc catatcaaaa tatttcagac ggacaagtta gaggtcagat    8400
ctatgaaagc tcggttcaaa agtatcttaa ggagtctta ggatattatt tctacttttc       8460
agaggatcac aatatgatta taagccaaca tgctctcttc cttaaaaaat agttcatgca    8520
agatggaagt agtaggaggc agattgagct tgaagagagt ctctgaagag caatgagtct    8580
cagaacttac gtaaaaccta tttaagttga gccaatacac acacctcttc ctccatctcg    8640
tagatccagt aaaattttc attctcctga gagatactta ggtatcatca tagagaatgt     8700
agagaaaata tttctcgtga aaaatgagac atatgaaaat gaccccaaaa cctatagcga    8760
ggcaatatca aatatcgact ataagaaatg gttagaggct atgaagttag aaattaactc    8820
aatacactta aaccaagtct gaacctttat ggatccgtca gaaggtatgg tacctattat    8880
gtataaatag atctacaaaa gaaagattgg ttttgatgga aaggtagaga cctttaaggt    8940
aaagcctgtg actaaaggtt atagctgaca cgaaagcatt gactatcaat atattttttc    9000
actagtagtt atgctaagtc catttgaaca ttacttgcga ttgcagcata ttatgattat    9060
aagatatgac agatagatgt gaaaactatt tttctaaatg aatatcttta ggaagttatc    9120
tatatagagt agactttgtg tttcacttcc agtgatggcg atcacaaagt ttacaaattg    9180
taaagatcta tttatgcact caaacaagca tcttggagct ggaatactta tttcaatgat    9240
gtaatcaaat catttagttt catcaaaaat gagaaagaat cgtgtgtgtt taagaaaatc    9300
agtgggagta ctgttacttt tcttgtattg tacgtggatg acatcctcct gatcgaaaat    9360
gatattttta tgttaatttt agtcaaaata tagttgtcta agaaattctc catgaaggat    9420
cttggggaag catcctatat tttggagata atgtctata gtgataaatc tatgaggatg      9480
ccaggccttt cacagaagat gtacattaag gaagtgctga agaagttcag catgaaaaac    9540
tccaagtgga gacttctatc cttcaggtat gggattcatc tctccaagaa ggtgtgcctc    9600
aacacatctt aagagataca gtacatgagc aaaatcccctt atactgcggc tataggaagt   9660
ctcatgtatg tcatgttatg tacatgacct gatatagctt atgttgtgag tgtcacaagt    9720
```

```
agatatcagt tgaatgcagg tgaaaaacac tggacatcta tgaaatgtat ccttaagtac    9780
ttgagaagga ttaaggatat gttcttgatc tttagaggag gagaattaag ggtgcaagaa    9840
tataccgact taaattttat gtttgatatt gatgatcgaa aattgacatc agattatatt    9900
tttttatgca acggtggtac tgtgagttag aaaagtttca agttgcctat catagcagac    9960
tccattatag aagatgagtt tataatcaca ttggaagcta ccaaagaggc attctggttt   10020
aaaaaattta ttacagagct ggatataatg ccatcagatg tcataccact ctactgcgac   10080
aacaatagtg ccataactct agctaaggag ctgaggtctc accaaaagtc taagcacata   10140
gagcaatgat ttaatctcat tcgcaattat ctcgaaaaaa atatatcaag gtatagaaag   10200
tagatactat ggataatatg acagacccac taactaagta gctgagtcaa taaaaaatcg   10260
aagtccatct tgagaagatg ggacttagat tgtggccaa ttgattttag tgcaaatagg    10320
agattgttag atgtatactc taaaagtcaa ttagactgac aaatataaat tttctaagga   10380
cataatttat atattttgac ttattaataa aataaaattt ggattaattt tttattcata   10440
ttttagtatc catgaattat ccaagagatt aatatgataa tgatatatat tctcaagagt   10500
tgaaaatttg aaacatacgt cattgatgat taattttga atgctttcga ttaatggatg    10560
atcataagga tagtaattaa tccgatcaat gtacaaatca cttcttttt gatagacgag     10620 tctcgagtct atactatgga gacactggag caagagtgca ggtatttgtt agagaacaaa   10680
ggtatcgagc gtgactaata cgagaagtca attggatggc tatccactcg ttaatgactt   10740
atttgatact acagtagtat gtctagtcct tagatctgca atgcctcagg tgttcataat   10800
gagactgtta gagtttgact gtacataaac ttgatttcta gccatatgga tctttatagt   10860
gcatgttggc tacagtaggt tcgttgtagg aataggatgt gcacatagat agaatctatc   10920
atccttgata gacaaaaaaa atgatcctat ataatttatg agactgagtt caaaaaatct   10980
tgactaagac agtgtgaata atgaaaagaa gtttccacat atatacttca catcagcaat   11040
tccagttaaa taaatcctac atataatagg tattgtagtt tgatgaataa tctataaacct   11100 ccatcttatt gaaactctga tagaaggact gtatcatatg gtaactgtat caagagattc   11160
atctactatt ttgctgaatt gtcactacaa actgctagat gtcactgata gattgtggga   11220
cctatgaaga ttatcttgat gatcgatgat tctcatggag aagattgaaa ctatttcaat   11280
gatgttgtgg tagaaatcac aatatatctt actactagat agaatagaac ctatgaggtc   11340
acacataata aaaatttgag attgatcaga ttgttgaatg atgattaaga attgttacag   11400
gattcagatt atcaatataa ttgataattg gactaacttg taattattat aagtagcaaa   11460
gatttaattg ctaaaggtta gcagattcaa ggaggactta tgtgtaaata atgtacatct   11520
taatttgatt ggatcaactt agttatggct aaatttaaga tgaatcaaac agggatttag   11580
tttaatcgaa tttgggtcaa gctttgggct taggtcacat gcactcaaaa gggtttggat   11640
gcatcaagtg tgtgacaccc aaaccaagcc tccctaaact attttgagtt ggttttgacc   11700
aagtcaaaag ggtccacacc ctagggtttc ttgaataaaa ccctaggtgc cacattgagg   11760
accaattagg aaactttgac attctttcac acggagcagc acactagggt ttcatgaaaa   11820
ccctaggcac ccatttttagc cataaaagga aagctccaag ggatgggatg gtgccatgaa   11880
gaatccctgg ccattgggac tccattcaaa agttctctag gttttgggct cttatagagc   11940
cctagggttt gtttgcctat aaataggtcg ctaccccaag gctttagata atgctagagg   12000
cttgtgaagc tctctccttt ctcttgtttg ccatcccacc ttctctcctc tctcctccat   12060
```

```
gcctcaagac ttctttcttc tctccatcat cttgttgaaa tttagatttc aatgagaagg   12120
atcaagtaga gtcagagttc tactgcagtt ctcaaggtgt tgagaacttt cttcatcagg   12180
caaagattct gcaaaggagt tagcacctca aagaaccaag aaagttgcta atctgccctc   12240
atctccatgt ggatacttat agaggccaag catgacgaga agagccttat cacgatcatc   12300
actcgtggag atcatctacc cgcgcaaagg tatgagataa gaaaaaaata ttttcttat    12360 catgattcat gaatcctttg cttatgttac attgagactc ttggattaga ttttttctct   12420
aataaaattt caaagattag atctcgaagt cttcttcacc taaaggtatt gaaagttctt   12480
tatattttcg ctactttgat tcaaaataga ttagatttgt tttgcctttc aattttttctc  12540 atatttattg agatatgaag ctttaattaa tgagattaat aaaaagcata tgtgaaatac   12600
tgagaacatc ctaacaattt gagcttacaa ttcacttaaa caactaatga tcaaattaat   12660
aatcacaatg cacaataaaa attcatgata aatcttttg ttgttacttt agatcaaaat    12720
ccaactaatc ataacatgat ccacggattg cctatcatat atcaaaccct ctgaattatt   12780
aatcttaaac gatcttttca ttcatgatca taagattag ttaaaaatca tgaagacaac    12840
ttatattgta atcatcatag atctgtatct taacatcctt agtgtttacc tacctatact   12900
catcctatgt ttgattctat atatcataat ttattcacta atactttgat atcatataaa   12960
ttatcgcatc cccaatctaa gatcatattg gtactttaat atttcattag tgggggttat   13020
gcattagtac tttgatacct tatcagttga atggttaaac actggtactt tgatatccta   13080
tcagtggagg ttatacgctg gtactttaat atcctatcag taagatggtt aaatactgat   13140
actttgataa cctcccagtg ggtgttgtat gctagtactt tattatccta ccaatggggc   13200
agttaaatgc tactactttg atacgctacc aatgggatag ttaaacgcta gtaatctaat   13260
cttagcttga cataaagtaa cgtcgactcg agtttagggt cgactcgaga gaatgttagg   13320
gttagcttga tatgaaagag ggtcgctcgt caatattttg gagtcaactc ttgtttatgg   13380
atgatctaga aagtgtcaga gtgagctcga gtactgcata tttctgatac attgtctatg   13440
ctagaatgtg ctagaactga ttatcttctt tatcaaagtt gattttgag taacttgatg    13500 atcaatttt ctaggctaga cttgctttgt caaaatgagc acttgttagt ttagagaatc    13560
ttcacctaca catgatctca agcattcatt agtaccaaaa atacttaagt attttgatat   13620
catcaaaatc aattcttggg ttaacacaat acttttcaaa taataagcat acagatataa   13680
tcctataaca atttaaattt tgttcatata tcaatttctt taaaaatatt atattcatct   13740
tgatagctat gaactaaatc aaaatacata ctagtataca acttttactg ggagagtatt   13800
agattaccag catttaacca tcccactggc aaggtatcaa attaccaata cacaaccctt   13860
atttataaag tatcaaagta ccagtgttca actgcctcac tggcaggata tcatagtact   13920
agtatttaac taccacattg acaggatatg gaattatcag tatttaacca tcattagtag   13980
aattttgatg catagtcagg ctgcgagtca aaatctatct caaatcaaaa tattgatcac   14040
atgtctaatt ctgtatcata attcattccc ttatgctcta atattatatt aattgtcata   14100
cttctagctc gagatcatga gccaaggatt gcagtaacta ccgcatactt atagagaact   14160 cttctataa gcatacaaga tattctaaat atactatcaa tatatcatag agaaattaat    14220
ttaaataact aaaagttaat attcaattaa taaattcaac tggcaaatgt atttaaaaat   14280 tttcatcaa ataaatcttg attaataaat attaattaat aacaatagat ttaaatcgaa    14340
acaaggttga tattgttaga atttgatgcc tcaagattca gcccacattg agtccacagt   14400
gaggttcgcg acgaaaaatg nnnnnnnnnn nnnnnnnnnn nnnnnnnnnn nnnnnnnnnn   14460
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 14520 |
| nnnnnnnnnn | nnnnnnnnnn | nnnnnnnnnn | nnnnnnnnnn | nnnnnnnnnn | nnnnnnnnnn | 14580 |
| nnnnnnnnnn | nnnnnnnnnn | nnnnnnnnnn | nnnnnnnnnn | nnnnnnnnnn | nnnnnnnnnn | 14640 |
| nnnnnnnnnn | nnnnnnnnnn | nnnnnnnnnn | nnnnnnnnnn | nnnnnnnnnn | nnnnnnnnnn | 14700 |
| nnnnnnnnnn | nnnnnnnnnn | nnnnnnnnnn | nnnnnnnnnn | nnnnnnnnnn | nnnnnnnnnn | 14760 |
| nnnnnnnnnn | nnnnnnnnnn | nnnnnnnnnn | nnnnnnnnnn | nnnnnnnnnn | nnnnnnnnnn | 14820 |
| nnnnnnnnnn | nnnnnnnnnn | nnnnnnnnnn | nnnnnnnnnn | nnnnnnnnnn | nnnnnnnnnn | 14880 |
| nnnnnnnnnn | nnnnnnnnnn | nnnnnnnnnn | nnnnnnnnnn | nnnnnnnnnn | nnnnnnnnnn | 14940 |
| nnnnnnnnnn | nnnnnnnnnn | nnnnnnnnnn | nnnnnnnnnn | nnnnnnnnnn | nnnnnnnnnn | 15000 |
| nnnnnnnnnn | nnnnnnnnnn | nnnnnnnnnn | nnnnnnnnnn | nnnnnnnnnn | nnnnnnnnnn | 15060 |
| nnnnnnnnnn | nnnnnnnnnn | nnnnnnnnnn | nnnnnnnnnn | nnnnnnnnnn | nnnnnnnnnn | 15120 |
| nnnnnnnnnn | nnnnnnnnnn | nnnnnnnnnn | nnnnnnnnnn | nnnnnnnnnn | nnnnnnnnnn | 15180 |
| nnnnnnnnnn | nnnnnnnnnn | nnnnnnnnnn | nnnnnnnnnn | nnnnnnnnnn | nnnnnnnnnn | 15240 |
| nnnnnnnnnn | nnnnnnnnnn | nnnnnnnnnn | nnnnnnnnnn | nnnnnnnnnn | nnnnnnnnnn | 15300 |
| nnnnnnnnnn | nnnnnnnnnn | nnnnnnnnnn | nnnnnnnnnn | nnnnnnnnnn | nnnnnaagat | 15360 |
| attactaaat | tttgcttcta | atctcactct | taaatagtac | ttacctttga | aactaggcat | 15420 |
| ttgaatctga | aaagaaaga | ggagattatg | agcttgatag | ttcagtaaat | catgaataaa | 15480 |
| ttagctaaat | aaatctatga | ataatagtat | attaaaaata | aatatgtaag | atacaataat | 15540 |
| tcaaaatga | attcatatat | ataatacttt | ccaataata | agtatgtggc | tgcaatcctt | 15600 |
| tcgtaattca | aattttgttc | attaattatt | tttttcaaaa | catcacatgg | atagtcatga | 15660 |
| actaaatcaa | agtaccagtg | cataacccct | attgataaag | aatcaaataa | caagtgtttg | 15720 |
| actgcctcat | tatcaggata | tcaaattatt | aatgcataac | ctccactgct | agggtatcaa | 15780 |
| agtagcaacc | tcaatcacct | cactggaagg | gcatctagtt | tcagtattta | actactccac | 15840 |
| tggcaaggtg | ttaaattatc | aatatttaac | ctccactgat | aggatttttga | tatatagtca | 15900 |
| gactgcgagc | caaaattcat | ttcaaaccaa | aatattttc | tcaaagacat | attttatgtt | 15960 |
| tcacattgaa | aaattcacaa | aaattatgcg | atattgaaat | caattggata | aaatccacgt | 16020 |
| caaatttagt | atattcaatc | ataaatcatt | tactattcta | gaaaaggtat | attaaaagta | 16080 |
| taatgcatca | atttcataaa | tcataaatat | ctcaatataa | aaaatatttt | attatttatt | 16140 |
| aataaatcta | ggagaagtga | agcattactt | atcttgtaag | taaaactaac | caactgatca | 16200 |
| aattaattct | gagaatcttt | ctcaaaactc | atcaccacta | tatcaaaaac | ttgtgcttct | 16260 |
| tgctatgtaa | gagcatagac | cctttcttcg | atctggggtt | ccaagtttct | attttatttt | 16320 |
| gttcaactat | caaattagac | tgactttca | ttttttgtg | gatattcagc | tattttatgg | 16380 |
| cctttctaac | aataaccaaa | gtatgtacca | atattccaac | aataatcatt | tattgcatga | 16440 |
| ttttcaccgc | atcgaaatat | ttgatattat | caatcaatcc | aaacttgtta | ttcactgacc | 16500 |
| tcttattcaa | acccttagta | tatttaatat | tctacctttg | tgattcattc | aatcgatttc | 16560 |
| tttttttta | ttttctttcc | ctttctatat | gctcttcatt | aacttttctt | tcaattatca | 16620 |
| atgctttatt | caatacatct | gtataagtag | ttaactcata | tagtaccatt | tatttctaa | 16680 |
| tttctatcct | caattccaac | tcaaatttat | ctactcagtc | acattcatct | tcaaccaatc | 16740 |
| tcgaagcaaa | cttgacaagc | tccataaatt | tagcttcata | ttctacaact | attatatttc | 16800 |

```
tttatttcag ataaataaat ttttattctt tctgaatcct catactctaa gaaaaatatt    16860
tttatcataa aatatctttt gaaatcactc ccaagcgagt tgttctccat cttgttcata    16920
tttaggtttc attctctatt atcaattaaa tgtctcatct ttcaacatgt atgatgcata    16980
taagattttt tcatcatcat ggtatctctt aacaataaat gctttctcca tctccataag    17040 ctaatttta gctcctattt catagttttc ttaaaagtca atggagacaa cttcttaaat     17100
tctatgatat tactttattg ctcctattgc tcttatgtcc ttgtggtgac aatatttatt    17160
gttgcacttg ctgtagaggc agttactgtt actgcaattg ctattacgat tccatcaagc    17220
cgactagtgt ctgcattatt tggataatag ttgattttg ctactttatt tagatgttgg     17280
tggcaaaatc aatgacttct ttttgctgag agatgccacc aacctactaa gtatcatcat    17340
cttattggtt gatacctta gcagcacctc gagtggttct ttttatctga tatggaacca    17400
tcttaatctt gcatgaaaaa caaacttcgc aaaattttct tttaaaatct aatatctaat    17460
attatacttt tattaaaatt taattatgat tatttaaga ataaaaaatt taaattttga     17520
aatcctcaca aggctggcca agagataatg accatcatcc tagtcggttt gacgtaggac    17580
atccaaagat caactataat tcaagcatca tattgagatg ctaggatata atcgatggtg    17640
aaatttaatg atgctcgact gatcaagatg ggggccggcc cgatggcctg ttcaacaatc    17700
attgatcaaa attttttaac caaggtctat caagatcatt aaaaagtctt tctaagatct    17760
ataaattgta ataagagac acaatctaga gagacacact ttttacataa agaaagtaga    17820
aattttaggg agagaaatta gagagaaagg ggaaagagag aggaagctga gaggaagaaa    17880
gaaaagagaa agactctctc tcttttctt ttctttcttt tctctctttt cttttctctt    17940 tcttttttt cttccttttc tttctttctt tctttggctc attagaaaaa taggggacct    18000
attgatcccc ttgtttccta aataggggag gaatctcatc ttggtagcta tggccggcga    18060
tgtgagccaa agtggcaaaa tcatgaatct cccaacctgc agccgacatt gacttttggc    18120
actggaaaat caagagaatt tgacaaaaaa tgggaaaaaa ttgaaaccaa aatagggacc    18180
aaaatccggt aatagctagc aaaaatcctt gatctttgct catggaggat aggaaaaaag    18240
attattcaag agattaaggg aatcttatct cattttttg ctgtgcttag gccatggtgg     18300
ttgcagaaat cgtttgtgaa agctcgacaa actctgcaat ttcttcgggc ttgggcctcg    18360
atctttaata ggagaagaga gaagtcctct ttcttttaaa tagagtcgga gggaaggagt    18420
ttgattccct ccttatggtg gtttcaaact ctgatcggaa gtccattgga aaagaagact    18480
cccattagtt ttaaaatcta ataagattta ttgattagaa aattgataaa aaatgattat    18540
taaaaaagta gcataattat ttaaatcaat gatgcttaga ttgttggagg taaatagtaa    18600
taaaatcaaa aaattaaaat tcatgggacc aaaaaataat gaacaagatt tgaaagaaat    18660
gtctataaat aagaatttat gaaacagggg aacattgatc aaaggtgtgt taaatagtgt    18720
ccttaaagtg ttattgtccc tctcacgtag actttgtgtg ttgggagaga acatagtaat    18780
tctctcaacc tatgcaacct aaatcttttg aaaagaaatt taaaattata gaaaaattgg    18840
caaactagaa ttttggtcat tttctttatt agtaaaaaat atactaagtt atatgtcttt    18900
atttatacta gtgaggtcta tctttgcaca attcagacca aatttatatt ctagttaaaa    18960
gaggtataga ttttttaaaa tagatataac tagtggaaat agtcatagaa aagttaaaaa    19020
tcaatgaaag gtagattca cttctatatt ggctttattt gtggtcactt tatctaattc      19080
ttttttttga tggagcaata taccctgtta aaatcttctc gattttttt tcactttaag     19140 caacctattt cgatgcctaa acaatggaat ttagtttaac cacttaatat gctacacttt    19200
```

```
taaaaggagc accatattgt agggcttgaa aagttacttg atttaaaaaa agagcatctt    19260
aattggacat catacaagta agttatgacc tccgaaaatt tgatacatga tttatcatct    19320
tgatatggta aatcttgtta agatttcctc atggtgtcta aagtggccgg ttcatactga    19380
gtttggtgat tcttctggtc aatggttaat tgctcgaata tttttaagat ataactaatc    19440
tccaactctg ccgactcctt agtagtatga gcacatggaa agcttgacct aattgatttc    19500
ttaaattgct tgaaatcagt acttagaaaa tatgcaaaat ggatgaaatg tttattgcag    19560
cgagagcttt ctgatctgta cgaccgagag cttactagtt ttttatgagc tatacgtttt    19620
gcacttaagc ctaattttaaa tagtgaaata gttttgcaac aattcaaaac aattaaaatc    19680
aaaagacaag ctgctatgca tgttcaactg actcggcttt caatcgcaat atgtcacata    19740
ggctggccta gaatgcagat gcgtgcgtgg tgagcatcct aaaaacctac atatccaata    19800
aattcccact agttggtgaa gtattaaatg taactcgtat taacttttta atgtaggact    19860
aaagtttatt cgactaatta agaactaaat actttaataa ttgaactttt ccaaccagaa    19920
atcagaaaat atttaagtaa ttaaatatta cataataact agatcaaaat atcatggttc    19980
ctctctcgct cgagatcaat tgggatgttg gtttatcttg gtcatccatc gagatgactc    20040
tatcttagcc tttcaaaacg gcgcggtacc acgggtctca ccgcttcgtt acatcgaatg    20100
ccaccatccc tttttttttt tttttttat ttatttatgc tttcttgctc ctagattggt    20160
gcggcctcat tacaactcca ctgctacttg atgcttccct ctagcatctc ctttgcagct    20220
ctctcacttc caccactctt cggcctaatg ttgggaaacg acgaaggggc cttacaaaaa    20280
tgtcatccat gatggcagtg gagaagaaaa catcgctggg gctttccttc gatatccttc    20340
gcagccaaag ctcttatagg gttatatggg agaacgctgc attatttggg tgatcttttt    20400
ggatggtgtt gttgactgat gctagttttg cttcatgaat tgaatattta cacaagatga    20460
gaatacaatc tagtacaatt ggtaccaatt acctgggttt gactcctgct cgcatctgat    20520
tgaagcttgg ttaatgtgca tctcaattaa ttcagaaaga tcatcggact tcatgtgaat    20580
tattttgact agcatgaata gggctaaata aggctgaaat atgtgttaaa tttttaaaat    20640
tataacttga tcatatgatg tccaattgag atgttttcaa atcaaaattt ttttcgagat    20700
ttatcactta atgttaaact cttagaaggt cgaaacagac tgaaagtttt cttttcaaga    20760
tgtattttga ccgagtatat aacttgatga tcatatgatg cccaattgag atgttttcaa    20820
atgaaaattt ttttttgagat ttatgactta atgttaaact cttaaaaggt cgaaacagac    20880
tgaaagtttt cttttcaaga tgtattttga ccaaatatat ctcataatct ataagaata    20940 tatttcataa tctatgaata attagataga gcgacagaag ataatgctaa tgtaaaaatc    21000
acgatctatt ttttataaaa tttaatattt ttatataatc acttttacta tagtcatatt    21060 tattttttaaa aatttagtta tatttaaaat atcaaaaaaa tttgacttga attatataag    21120
aaaggatctt cctactatta tagatagaag ctttatatca tagtttacag tgtatggatc    21180
atcaatgaaa gaaagaggga tgtaaacctt acttttgaaa ttttctatt tgtttctaaa    21240 tttttttaaag gatccaagtt gagaattgag agaattcttt cttctgcaa atcaaatcat    21300 tagtataatc cacatggaga cgttgtaata gaaagtagaa actatatttt atgaataata    21360
gaaagggagt tgatttacgc caagcctttt gtttgcttga ttaattattt attttatgg    21420 tgttagctgg accccatgaa tagcaaccat cgttgggtca gggtcgtgta tttgttttgg    21480
ggtcttcatt aatatacacg gtggtaaatt gttgggggcg cgtcagatgg aaccaatcct    21540
```

```
ggttccttac ggtactgtag tgctctatat gtggacggct gtcattctat ccgtgaaata    21600
agaggtgttg ttttttcttta aaaagcagca ctctcctcag caaaaacctc agaatccacc    21660
atgtaatatt actcatcctt ggtcttaaag ctgtagcaat acattacttc caaatgccaa    21720
gcaattaaat aaactacata catcgaacct ctttagtacg tacgtctttt caaaaatatt    21780
tttttcgaag atccgacaaa tgtgaaatgc ttattaactt ctttaatgtc tgttttttgct   21840 tgcatattta cacagacata ccatcaactc catcagttgt tgtttgataa ttcgcttgcc    21900
gagcagagaa gagagagagc aagagagaaa ggaggcatag agagcgtgag atgggaaaag    21960
cgaccgattc ttaaactggc gagacatcac acgttacccg gtacacccaa agctttcacg    22020
aatttggaaa gtgaagccat tatggaagcg ctagcttttt gctctccctt gccggaatgg    22080
aaaggccccc gaccttcttt accccttcct ccacgccacc cacccaccac tcttctatac    22140
acctttatag ctcccttctc ctttggcttt cttttaagca gagctcagag gaaaagagac    22200
cttcctgggt gcttgagaaa tagagaagag agaaaagaga gttggagatg ggaggggga    22260 agatagagat caagaagata gagaatccta caaacaggca ggtgacctac tccaaggagga   22320 ggacggggat catgaagaag gctaaggaac tgacggtgct ttgcgatgct gaggtctcgc    22380
ttatcatgtt ctccagcacc ggcaagttct ccgagtattg cagcccccctt tccgagtgtg   22440 tacacgatat tatccctcct cgtcccccctt ttttttttt ttgataaaaa tgaaactcat    22500
atagtcttct tttatgatta tgtgtttgta atgatggatg attgatggct ggatggcagc    22560
accaagacca tatttgatcg ctaccagcag gtgtcaggga tcaacctgtg gagcgcccaa    22620
tacgaggcag aaactcttct tcttcttctt ctcctctctc tctacaaata tgctttttt    22680 ctaattttc ttttcaaaga aaaagaaaa aaatgatttt ctaatattga tgtatttct     22740 tgtgggagta gaaaatgcaa aacactttga accatctgag ggagatcaac cagaacctcc    22800
gcagagaaat aaggtggagg gccaaaagag aatattgtaa tattagtact ttctggtaaa    22860
aataagcatg tagtttctttt ttgcctttaa attttgttgt gctggttctg atgagcaggc   22920
agcggatggg tgaagatctc gacagtttgg gcatccatga actgcgcggt cttgagcaaa    22980
atttagatga ggctttgaag gttgttcgtc acagaaaagt aagatcccc atttattcac    23040 tgcacctatt ttaattcctt attctccatg ttttgagagc ttttgagata aatgatgaga    23100
agcgcatcga gatcgagttg tctatattct ggaatgatta atttttttaat tctcaattaa    23160 tgctgtttca ttgctaaata ttcagccata tattttgtct ctgcatggga tttctatgct    23220
aaaattcctc agattcagc atacagaatc catgagactt gccttggctt taccacaagt    23280
actccagaat caaaattgtg aaagaaaaat aggataaatc tggttaagct gtaatttatt    23340
tacttacttt ctatctatat taaaattatt cagattattt tgcaaattta tggatatgct   23400
tgaatcacgt atctgatact ttctcttcat ctggatggca gtaccatgtg atcaccacgc    23460
agacggatac ctacaagaaa aaggcaaggc taacatgctt tcttaccatc attctttacg    23520
gtctttgatc cggttttgcg tgtccacttc ttacgtagtc tttttcaaac attcctatct    23580
aagactgaag gtaatgattt gcaaaggaat agctttactg ttttcctcta agtagatgaa    23640
atattactca cgtagaaagg agccatcata attgcagaaa gaataaaact gaatggaata    23700
tgagtagaat tgtcaaaatc ttggtttaag ggttttaata gccagatgag aaagcaacct    23760
acttttcttg aacaacttgt ttgtgactgt cttgttgctc ccatcttgca tctatgatta   23820
gcaaaatata tgataaatag atattcagat ttgatcgaaa agaaggaaga ttttctttaa    23880
tccatttaat ttgaatctca caaaaaaaaa gtagaagatt tggacacgat cgctgggggc   23940
```

```
agcacgctct taatagaatg gtgtcacgtt gcagatctcg aaaaattatt caattttttt    24000
taaaaaaaaa agagtcattg aaattagacg ttgtatgacc atgttatgat ctctgaaagt    24060
ttgacttctg actcaacttc ccaatatagc agattttact cctgaaccat gtttaacctc    24120
ctgactcata gtggccaaag tatctacatc gagttcactg gtcttcttgg atcacattca    24180
taagaatact tcccataatt ttgctcaacg ttgttttttct catcaaccaa aggtatatgc    24240
tttttaaaat tgaaatgccc atgaatatta tggcattctt ttatttgaca ttttggttga    24300
tcctatattg tttgtttggc attcaacact tcttcatggg aacctttgaa atgaggtagg    24360
tgctaggatt tttcttttta cctatccata tcatatttcc aatgtcttct tttacattag    24420
gttctttagt gacaataggg gaaacgaccc aatataatac ccttgaaaat ttgggcaata    24480
tctactaaaa ctaacttgaa taaaatatta acataaaaag ggatttagta acataaaagc    24540
ataactcaaa atcactcacc ttgtgtgcca cgttctcatt gcccttatta ttttttgcatt    24600 gtgaattgtg tcccccaata aagcaacgtg aatggtggaa gagagttgaa tggctttgtt    24660
gagtaattgt tttgagttac tatagcattg ctctactaaa attgaaatct tgctgtgagg    24720
ctatgtatga gaagcaagtt catgctttt gactgttggg atggaagtat gagcaatctt    24780
tttaatagaa aatggacgaa tcatgaagtt tttccttttt attgaaaaag atgatcgaaa    24840
aatatgtgca agatagaaaa acactgaaaa gataaaatga gaagtaaaag tggaagtcta    24900
ggagaagaaa atttaagaga aatatcttca atgagaggat gtgtgcacca acaaagccaa    24960 cttttcactaa agaatgtaat gactcacctc tactttcttc gaataagggg ttccagttgt    25020
ggaaagtata tagaatcttc tgaaagactg agtaaatgga gcaattcctt ctaagaaata    25080
ttatggcatt tctctcccac gaaatttcaa agcaaagagc agctagtagt tgatcctcta    25140
atctcttaat tgaagtttgg aatttctctt gcctctattt ggcccaaagg tcatgaagat    25200
ctaccggcca acctcttaag ttgaattaga tcttaataga agtccaaatg cttcttgtag    25260
aagaacatct aataaataaa tgagtgatag attctaatcc agagacaaag agcacacctc    25320
gaattcactt gccatccttt tctagctaga acttctctag catgaaactt gttccttaag    25380
gcaagccaaa taaatactca cattttagga atgactgcct tccaaataat tttataatat    25440
ggacaaatta gaccaccatt attgataaac ttgcaatgaa caattataaa tgagttttca    25500
ggttggcaca ttagcaatat aggatggttt gattattaaa aggatgatat gaagggtttc    25560
aaggtggttt gcctcgttca aatcaaagga ttttgaagat taatattcca agataaggtt    25620
ctccaactcc attaggaaag tgtcttcatg tcatcttaga gaagcagctc gtaccaaact    25680
tgacagatgt tttatttatt tagagtgaca cagatacect ttggcaatac tctccatcct    25740
tgtccgaaca acttctaatc acacctcact tatcttgcat ctaactcaga ggctacaagt    25800
tacacctttc aacaaacctt ttcggtttga aaatttgtga tttcattatt tagagttcga    25860
agagcatatc aagtattggt cggagttggc acccaaagca aacgaaacag ttactgacat    25920
ggtccaaaag ctgagatttc taagatccca acttaagcac tgaataaagc cattatggga    25980
aatatcattt taacgaaaga ggaatttaga gtaagaattg attctcttga taccgaagaa    26040
gaactaatac agctttcatc acttcaaaat gatgaacaga tgcatctcaa gtcagcacta    26100
gaccatcttc taaaatagga agatctatgg aagcaacact cccaaatgca gtggcttcaa    26160 aatgggggatt gcaatacgaa gtttatccat gtttgggcaa gtaacaggaa aaaaagaata    26220
ctatcactga actctagcaa ggcgatcaga agattatcga atagcagcaa atccaatcca    26280
```

```
cattctacaa cttttttct accctactag gctcgactga ggaatgactc atccaagctg    26340
attagaagat tctttatcca gaaggacctc tggatcttgc tgacattgag tatccattta    26400
tggagaaaga aatccatgat acagtgtatg acttggcttt ggaaaagtca cccggatgat    26460
attttcccat tctccttcta tatgcacttc tagtgtatca tcaaacatga cctgatgaac    26520
ctactgtaaa atcagctaat gtagaccatc tgaactactt gttcatcacc cttatcccaa    26580
aaaaaaattg gtgtgtattc agttagagac ttcaggccaa taagcctgat taatggagta    26640
ataaaaaata tttcaaaaac tctatcgaaa aggctctcac agaaaatgaa tttgttaatt    26700
ttatccacag agcttgcttt caacaaagga agaaatatct ctgaatattt tgtaatgact    26760
atggaaacta tacacttctg caaagctgaa gtacacaagg atctcaatta taaagtcgac    26820
ttcgagaaag cttttgacaa tgtggattgg agctttctat tgaaattgct atccagcacg    26880
gggctttgat tcgaggtggt gtcaatggat agaatatctg atttatacag ctaaattctc    26940
agtccttatt aatggtgata aaggtaaact ttttaaattg aggaaagatc tcaggcaagg    27000
agatcctcta ttcgcctagc tctttctctt agttgttgat atagaatgat caagggagca    27060
agtaggttca atcttttgt tggaattgga tcatataata tcatgggata acttcaaagc    27120
ttttagttca ctgatgacac acttatattt tgcagatatg atctaaaata catcaaaact    27180
cttaaatttt tactctatag ttatgagcta ctgatgggtc tcaaaattaa cttttgaaaaa    27240 ttccaatttt ttggcttgag aattgcaaag atgtcagtac agcaagttgc atctatccta    27300
gaaagcaagg tggctacatt ttccattact tatttgggtc tcccactcca tcattctaaa    27360
ctgaggaaaa cttattggaa tccactcctt gagaaggttc agaagaaatt gatcgggtag    27420
aaaggtaaac ttcttaacct ctagggtagg cttatactaa ctaatgcagt gcttacaggg    27480
atcccactac tctggaggga tacattcctt ctccctcaat tcattatcaa ataaattgat    27540
aaaatccatc gatcattcat ttggagagga aacgaggagt ataactaagg gcactctaga    27600
atatgttggt cgaatatttg tcgatcaaaa aaatttggag gactgggggt tcctcaatct    27660
aaaaattttc aatacaattc ttctttgtaa atggtggtgg aagctctact ctaatgctgg    27720
tgacccgtgg tgtagtttta ttgccactat ccacccaact tcacactaga gatctaaagg    27780
tatacacaaa tcaacctctt cattttggaa tggtttacag cacacatgaa atatttctac    27840
tcctaatcca ctttcaagtt agcaactagt attatttgg aaagatagtt ggttacataa    27900
tcatccactg aaggatcgat ttcctcacct ttacacaata gcattgaagt gcaacaactc    27960
agtggcaaag gtattaagca atctacttga taatagctct tttagtactc ctcttcctca    28020
aagataccaa gaagattttc agagtctata ggaaagcatt gaacaaatta cattaacgga    28080
acgacctgat actatacaat ggaaatggtt tagtagcaat attttttgg catgaaggat    28140 ctactatttt ctgcaagatg gaggagtttg gcctctactg agtaatatta tataaaaact    28200
cctaatacca aagaaagcca agttatttgc ttggctaagt gctcacaaca aaatcccaat    28260
gaaagctaat cttcttaata gaggaataat tggaactgat tactgtacac tttgcgatga    28320
cttatcagaa actaatgatc atctaatgct catctatact ttttcaaaag caatttggaa    28380
tcaagtactt tcagacctgc aattgtcgaa acttttatgc atgcttaaca ccctatggga    28440
tacttggaga ctcatcaata tgcaacacga tagaagacct aaactagctg ctctattcgt    28500
aattggtcaa tggtgtcttt ggaaggaaag aaataaaaga ttattcgact tctatacttt    28560
ttatccacga tcgattgctg aaactgtgtc acttttctt tcttgggcat cacacctaac    28620
aacggagcaa ctaaagatgt tagctcctgt tcgagaagtt ctcttatcta agaatgaaaa    28680
```

```
cacacaatct ttagtgagaa ttacagatgc taacaggcgc agatgaatgt tttatgagca    28740
tttttatagc tgcagcttat atgtgatcta tggtgcaagg agttaattat aaccatggat    28800
attagttagg ttgactatca gaaatcatct ccaatacatt ctatgtaacc actgatcaat    28860
tccatgttca actagatagg aacctgccta tatacaggta tgtccctgat gtaactatag    28920
tatactatta ttcataaata aataacgaag gttttacctt cttctcataa aaaaaagta    28980 tcttcatgtc atcctatatg tcatgcatct cctttgctac ttcttttatt tacttcttaa    29040
acttggttct accatatatt atcagcccct tttaaatttg cttttggata ttgcatattc    29100
cactcttcaa tcacctcatg ccaagcaaaa catttattca cacttgaaaa ccaatataag    29160
aataccaaag aatttatcca tgaaattcta gaaactttgg ttttactcct ttctccatca    29220
ttcaaaaagg ttcaaaatga tgataactct atatagctta tttatcaaat ttacgaggtt    29280
ggtgttcaat gttttgtga aaaaaatatc ttgctatcca catagtttga atccatactt    29340
ttgctatctt gagtttcaaa aatttttaatt tgctacaatt tgttgctatt agcatatgac    29400
tacttttaag aagataagcc aatatactat tttcctaaga atttaaaaaa tcaaaaataa    29460 aaattttat ttaagatttt ttaagggttg ttttccaaat gtgcaatggg gcttaatctt    29520
ggcatcattt tctaacttgt agaattttga cccaagtaac atttgtccaa tcacttagaa    29580
cttctataac ttcgtacaat catttgttaa tgttgttcat ctatttatct atattatcta    29640
tctggaatat agttgctctt aattattttt atatatcgcc tattatccac cctaagcttt    29700
catgttcatc ctcatgttgt tggaggtgca tgtcttattc caaactatt accattgctg    29760 tagattttaa aaaatttgct agtttaggac tttttaatct tttgatatca tgttgatgta    29820
agctaaccct ctaaggctag tcataataca ttttaaggat ttatgttata tgagaccaaa    29880 atttaacaa aatgaagtgt tggaaattgg tagaatggaa gtgtaaagat gcttagagac    29940
atagaactag ccctgggcca tgtaaatctt ccaaaagaag aagaaaataa taaaattaag    30000
atcatattca atctctacag aaaagttggt ctttgttgta taataagcca tcttaacata    30060
tgatggacaa taaatatat aaacttatga gttttaatac ttagatggaa gaaaagggac    30120
agatatgtca caccccatcc tactagcatg agtaggcaca tgatacacgg ttgcatgccc    30180
tgcagagttt gactcatgag gcatgcaagg tattgaatag tagtctaggt aaaattaaaa    30240
aacttggagc attctaaaaa taaatcaagt tcatttata aaatcaatat ttattatgga    30300
ctccatcaaa tattatgcgc ataacatttt atttgcaaat agaagaagat aagtcctaga    30360
tcctaagtct cctactctta gtctcataat tcatccaagc tatccaccaa atatctaaaa    30420
cgaaaaagaa aaacgatagt atgctaatag ctttgtaagt caccttttat ctctaattag    30480
atcaagcata ttagatataa aacaataatt ttcaaagtat atgatttgca attaggaata    30540
aatatttgat aaatacagaa taaatttttca taaagcatat ttactaacat tatttataaa    30600
atatataatg cttatatcaa taaatcaatt tctaaatcaa tatatataaa ctatccattc    30660
tgtcttagcc ttacaactat tgctaccatt ccctgtagca tggttaggaa gagactagct    30720
cttgaatact catgtcattt atcaacatat gcgaatgatc attcgactaa tatagtcaaa    30780
aaaaaattac tctgatttat ataaattaaa aattagtaaa taatatatgc tagtaatcac    30840
cttaccagct aagctctaaa gaaaattagc ttttgaatat acatcatgct attgattatt    30900
atatgtcagt gcttgtctca ttttgtggca tgcaagaaga ctagatccta aacttatatg    30960
catagtcaga ttaaagagca aatgttgcat ctgattatat gaacatctat tatgatgtag    31020
```

```
agtttgtatc atgtatattt aatttaaaca caaatataat tatacataaa taatattcat    31080
attttaaatt ttaaatattt agataattat tctagtgcag gtataaaaat aagcaatata    31140
aaattttaaa tcgatttata taacatgcat aataaaaaaa attaaggata gaggtactta    31200
ctgctcaact cataaaacat aagaaatctc tttaactaac tttagtgcaa cctagataga    31260
acatattaat gattaagttt tcatctaaaa taaacataga tatcatttta aaatcttagg    31320
catttaaatg gtctcatgat tgtgaggct ttcttcagat tctacaattt tgaaattttt     31380
tcaaattata atttttttac cttgattgat aacaaagcca ataatacacc tcaaatccaa    31440
atgtattcct aatagttttc aataaatcta atatcaataa atcataatta agatatcaat    31500
ccattctatg aatttgacca taaatcctac ttgtttctct gaccttcact ataaattaat    31560
catcaaacta ataagtgag gggatcataa ttcttttacg acaatccaag aattcaagtc     31620
tagcatccac attagatggc ttcctgtcca gatatttgcg cctctccaaa attgagatta    31680
tcagattaag aaaaataaaa taagagagag ggttaaagga caatgccttc taggtagtga    31740
tgtccgacat cataattttg atcaaatcta tggggcaacc aataatatta gggaaagagg    31800
attggatttg agcaagaata gcaaagtcat tgtcatcaat ggcctgattc attgagttca    31860
atgaaggatt ggtggttgag tggtggaggt ggcatctagg aaggagagag aaagaaaaag    31920
atagagagaa agagataaga aaaatagaga gaaggtggca gttaagatcc cttttgtga     31980 ttaatatata gcggtaagat actcaaagat ctcaccttat cgacctcaaa cactaaggga    32040
ggtggaagga gggactacta cccatgaagc tagagaaagg gatgatgatg attggaggaa    32100
ggaagaagga aaaatagtag actcgatgat gataagacta aaagaaaagg gtttgactta    32160
gccacttggt atataatgag gtttggtatg gagtcaatag cttgagtaat agcatggaaa    32220
gagagaagga gctgaagaga gtactaagtc ttattagaat aaagaaagat agaatcttag    32280
cgaaaaatag ggcctcaaat ctttcaggta gaggaaaaag agggatcaac gaatgaaaga    32340
ctaaggaaaa ggtgtggagt aggatatact ctcgattagt ctctcaatca tggattctag    32400
tagggcttcg tcagctgctc aatcatggat tctgatagct caaatggtgg taagtagaaa    32460
gagagagatc taaagagatt gatagtggcc ttaaaaccag cacggtcaag gataggcatg    32520
ccttagagag aggaaaagag agagagatta atggaaataa gcgagaaaaa tatattctta    32580
gagaatagat tggcgataag aagaggaggt ggttggggca tgcttaaaga aataaagaaa    32640
attgagtagg cggaaagtgg tgatgcttgg cgatgagaag atttgagaga gagagcaaaa    32700
aaatgtggat gatggtcata ggataggaa aggaaagaac aaagaagggg gtgctaagct     32760
aactctttct accttcctca caccctgaag caaaggattt ggccaaggat ggacaaatgg    32820
gcgagggctt tggtggatcc atgcctaccc tttctccctc tcacgatgat tctagtcaag    32880
ctatctatct ttgatagctt gagccaagcc aattgacttg atccaatctc tctaaatcca    32940
tacaaactta agagagtgta ttgattcact tattctcttc taagttgata agaaacataa    33000
ttaagtggag ctcattaagt atttcaggta gttgctaact tggcaaaatg gaagcaataa    33060
taaattttaa aagactatag cttggtataa tctcaaccat ccatgattta gaaagatctt    33120
cagactcaat atagaattact ttggctacta caggtaagag ctaaatagga tccaaaagta    33180
agatccatca cattagtaag tcaaattata tgtcaaatct tagtaggtat acttagtcct    33240
acgatgccta attaaaatga tcatcatttg aaccttaaaa tggactagtc aactaaaatt    33300 tttcttttg aagaagattt agaccataaa atatcttcta atctgtgaag aattagatag     33360
agcgaggaat ataaaattga tgtagaaatc aagatctatc atatatacaa ttttaatatt    33420
```

```
ttttcataa ttttaaata tttatcttct tttttatag gtctagtcct atttaaacta    33480
ggaagaggag tccaacttga cttatgcaat aggggatgtc cttctagaag ataagaataa    33540
tttgatcaga attatataag agcaaacctc attattataa atagggcta tatacatcaa    33600
tttatgagat agagaatcaa tgaaacaaaa gtagacttaa gttttatttt cataattctt    33660
ctatcttcta cttttttct aggagattca agttgagtgg attgaagaaa atctttcatc    33720
ttctcgatcg gatcatattg gtattagagc gttggtcttc tatatttatg gagagcttta    33780
atgtattgtt taaatacgtg aacaatacaa acaatcaaga gaagtgctat ccatgcttca    33840
aatacatcga aatataaaag caaatatggc tactaattct ttttcaatgg acaatgagat    33900
aaaaggatgt cttacacaac tcaaggagaa gattgtgcaa ctcatgaaga ttgtctccag    33960
attgaagata atttcaatac aagcacaaac accagcaact catgttgtga aactgtttcc    34020
tatgtttgga gatgaagatc ttctatctag tgaggagatt gaattaccta aaagtatgaa    34080
aaatctttct tcaatcattg aaagttaaag cttgaattga gatccccata tataatggaa    34140
ccattgatga aaaaagcta gataattggc taaactaatt acaaacctat tttattatct    34200
atagatatta tggcatctag aagatagctt ttacttatct caagctttct agccatgctc    34260
ttatctgatg aaattcatat atgagaaata ataatatttt taatatggtg cagagccaat    34320
tcaaaggttt aatcaagaag taattttatc taattggcca taaggaagat cggtggatca    34380
aatgataata cttatgatag aaacataatc aatccactta ggactatacc accaagttcc    34440
acaaacaggc aatctgcctt ggaatcttta tcaacaatta tacaattttt ataaagtatg    34500
ttgaaagtct tcatgagagc atctaaaaaa agatgaaact ctttaaggtt gatgatatca    34560
gtaaagctaa catgaaagtc atagagattg aggagaaaaa tcaaattaga gaagataagg    34620
aaggcaaaaa gcatatcaac ataactcaaa aaaaaaaat tatgatcatt gaaatctttg    34680
aaaatacatc aaggagaagt attgaaagtt tcatcctgaa ttggagctaa agtagaagaa    34740
gcccaaggat gataattta agaaaaataa aaagtggtcc tcaattctat agagattgag    34800
gagctatctg aacttgagta agcaaacttc aaattgagct tgatggtgag aaaacctaat    34860
acaacaatta aaacggatct agaggtacat gacaactcac ccactaaag attcaagtga    34920
agcagagtat cattaaggct attataaatc tttgaagcta gaagaacctc attttccaat    34980
atttggttca gaaatcgagg ttgtagatca agcctcatcc atatccttat cctcttagtt    35040
ggattcagaa ggatgtcaag ttaaaaatta tgagatagtg taccttcaag ttagccatca    35100
ctgagaggtt tatttgtgag gtaactttg aaatagtttc tttggatatt tgtcaagtta    35160
tccttagaaa tgtgtacctt tagaatcaag atgcaatttt ctatagacga tagagaaagt    35220
atcatcttat aagggatgag aaaaagttca tgatcaacac ctcaagaaca taaggtaact    35280
ttgaccttgc aactgttgcc caagtgaagt gatttgttaa tgtttgtgat gagtgcatga    35340
tgatggtata aagaaccgat atcactcatg agaggtcaag gccttgtcct ttggttccat    35400
caatcgatca atagagattg agattaagga ggagtcacta tagtccttgt cgatgaggaa    35460
ggatgacaac aagcattcct accatgaagt ctagatttga gagcaaatga aagtaatcca    35520
ctgagacctg agagcaaaaa aaggcgagac caaaaatcat cttcaagtaa agtcaaatgg    35580
ttcaaccatg agatggggaa gtaagtattt tcccaccttc aattctaact ttgtagaaac    35640
taaatccctt aaacagggga gccctaattt aagaggatcc tcagattcat gtgtgactac    35700
tttggctatt acaataagag ctggatagga atcgaaagca aaattcacca cattaggaag    35760
```

```
ccaaattgta tggcaaactt caagagacca taacttgatc acatgaaatc caattaagat    35820
gattttattt ttgaatttga atatttttt gagatctata actttagatc taaatcaagc     35880
taaaatttta ttgcttacgc cttcaaaata ggctagtcaa atcaaaactt ttcttttcaa    35940
aaaagacttt gactgaaaga tatctttcaa tctatgaaga atcaagtaga gtgatgaaag    36000
ataaagttga tataaaaatt gagatctatc tcttataaaa ttttagtaat tttatttttt    36060
ttaatattta tctttattta gagatctatt cctatttaaa ctagaaagaa ttgtccaacc    36120
taacttgttc aatgatcaac atcctcctaa aagataaaaa gaagaatctg actcaaatta    36180
taaaagggcg gacctttttt tttgatgaaa agggaggaaa aaaatccatc aaaatttatt    36240
aagaaaaaaa gagtacaaga aaagaaggat atgaaagagt aagagaagcc ccacaacatc    36300
catcaatatt taaaatttaa atttaaatct cccccatcat tctatcaata tttgatattc    36360
aaatttaaat tcttcgcagc atcccaccaa catttgaaat tcaaatcctt tcatacaaac    36420
aaaataatat ttttcaaatt ctcaactttg agtttcaaaa ttgagaagcc tacatattgt    36480
ctgctcttca ccaaagaggg gagattgttg gcttagcttg gcccaagaga agagaagaag    36540
gccaaggccc aatctgtagc ctagagaagg agggtttggt agctacttaa taatcggatc    36600
taaccgataa agacactatc tctattagaa gaaaaggtag agagaaaaag aggcaattgg    36660
ttaacttcag agggggagga ggtaagctgt tgaggagatt aatctgacgc aaggaaaaaa    36720
gaagagctga caactagcca atgatcgaga agggctggac acaatccaag cccagcacca    36780
agaagcaaga gaaagaattt ggaggtcaaa ggaggagtcc aggaagagag agcgaaacac    36840
aatgttcgga tctagccgac aacgatacca attatactag gaaagaaggt aaaaagggaa    36900
agagcaatcg atcatcttca gcaaagaaaa ataaagagg cacccgacag tcaagcccat     36960
ggccaaatca gtcagcaaga ggacctcaca agatctagac gatgctaagg ggaagggagg    37020
aagaaaagag atccagtaac tgtccaacac caggaaaagg aggagataag aggaagggag    37080
aagtcatttt tctatcttgg gccgaaggag ggagaaggaa gaaagaggaa agaacatcct    37140
caaagtcgaa ggaaggaagg aaagagaggg gggaagggt cacagtcaga tataccagaa    37200
gggatagatc cagtgtcaaa gagagaaaag agagaggaga tcagaaaata aaatttgatg    37260
actgactaat tgtcatgaaa ggctaatgac aactcataaa aaaagtatag tagtaaagag    37320
aggggggatag gcttggttag ggaagagatt ccgacaacaa agagaaagaa agagagagag    37380
agagagaacc ggctcccagc caaaaatagc ttgacccacc atcgagaagg accgacaaag    37440
agagagaaag atagaatagg gagaatagct tggcttcgaa tcaaaaatga tctaacacac    37500
tgctgaaaag gactaggaag agagagagag ggggtagggg agtatctcgg ctcgcaatca    37560
gaatcaactg gccaatgcca gaaaagagag gaagagagag atagagaaga tatagcaaaa    37620
gagaagagat ggacaaaagg agagaggaag ggagggagag agagaaaaaa taggagagag    37680
aggggcttgg tggctgactg tcagaagaag cctcgatgct cgaagattag atggaagaaa    37740
aaaaaatttc tcaaaacttc tcttttctat aagagcaaac ctcactatta taaatagggt    37800
tatgtatctc agtttatgat gtgaagaatt aatgaaaaat tggactttag ctctattttt    37860
gtaattcttt catcttctat ttttatgaaa ttcaagttga gccgattaaa agaaataatc    37920
tttctttccg attggatcaa tccattaact agatacttca aaaatcaaaa tgacctatct    37980
aaaatcctaa atcaaataca aaaccaaaat aactaaatta agatagaaca aactacaatt    38040
acaaaaaact ggctaaagtg tttaaatgct tttactccta agtttcttct tgctcaccat    38100
taatgcttga tctttagctg ggatcatatc agccttatga ccactataag accaacataa    38160
```

```
caactcactt gtattgctcc tttaaaatta tacaaaacta gtgtctaata tgtaccatgc   38220
gaatgtctgt ttctcaccag aaaatggatg ggcttcttgt gcaagcacct tcttcctaca   38280
aataataaaa tatgcatccc ttctctcatc ttactaaata aaataattaa aggctttact   38340
atcaggaaat ctggctttat ccatataatt ttggaagttt tatttgaaca taacattacg   38400
agtactagat tacatcagga ggtggttcct cttatttcta ttaagagaaa atcaatttt    38460 cttttaagaa agatcatttc attttcatca ggtagcgtac tctactaata tacttccaca   38520
acaatatata gggattagat tataggatgg actttaaggc ttcttttcga gagccctgat   38580
ttctcaatca cattcccttt tctttctcat gtaatggcat ttaagagtgc atccagggcc   38640
caacaattag tcacaagtgt tcttttata catggtacat atttgctatt ttttagctta    38700
ttttaacttg attgtgaaga tatcatgaga aaattagatt taaagcctag caatcttgaa   38760
cccataattt caagttaaca ggtggaagag tccattatta tgtgagacca acttagactg   38820
caaaactatc tgatattgga ctatttacta cacccttttt tcatgtgcaa tgtttgtaaa   38880
gagaagatat atgatgtagc gagataggat agtttggctc taatattgtg ttaatattca   38940
aaccaaaatc ctaagctaat agatggaaga gaaatgactt atatacatgt gcattattgg   39000
atatatcttt atgggagaaa taatcacatg gatgtttata tcacacatct catatgtgca   39060
tgttgttgta aggcttcaaa agacagacga tgagattggt cttggatcaa attggaatgt   39120
ttcttagttg aatttggaga agtctgcaac aaatcctata aagaagtcc cgaaattggt    39180 ggggcacctt tcgatccaag acccttcgat ggataagtca aataaagcct tgagaacaga   39240
ttgtggaaat ggaagaatag aaggatgaga aaagagattg tgaacaaatg gagagaggac   39300
tcttgtttcc ttcagtggag gagttgaaaa tgattcaaca aagtctccac tctatctatc   39360
ccgacttacc ttatggaggg tatgttaccc tcctttatat agaggggtga ggaggcttgc   39420
tcaagttgtt aggccgttaa tttattataa tagaatggtc agctatataa agatcatggg   39480
atgtttatcc atgtgatgat tagctatagg atagctagaa aatatctaat gcttaattag   39540
atgatagctg tcagataacc gtctgcattc ttatagtaca tcgatatttt atcgacgtga   39600
ctagcttaaa tcagcaactg actgaactga atattatgat tcttttagtt aacaatcata   39660
ttggttagag accgatgtaa ttcatagtag atcgatcaca agctgagatg agtatcatat   39720
tttaagaaca atactagcaa gttagatcga tcaaatgtca gatgaaaaag tagatcagta   39780
aacgttcgat ggaacctgaa agaatattta tgatttagat aataatctat catcacgtat   39840
ccagataatg agatcatata acatgtacca atatatgccc tccatttttc acaccgaagt   39900
gaagttcttc acatcgggtg tggaaagtct cttcagaaga tctcacctga cctgtattgt   39960
catcataaat gctccatacc acgatggttg gaagtattaa ttttttaatc actcaaagtc   40020
atacacaatt tcttgaaaat gatttgttga acttagtaat gatgagcgct tagaaaatcg   40080
ggagctcaca attatttggg tggctagtcc ctaatgtgta tgtgctaggt gtcatactgt   40140
aattggccac ttcagctatc acatggatcc tgcttgcatg gcttaatcaa gaagaggtgc   40200
gtcgcaacaa ctctctgcag aaccatcgga taactgacaa gtggcattga tctaatggca   40260
tatcaaatgg attgagactg ttagtaaatt ttataaatag gtctatactc tgttcaaaaa   40320
ttactttact attttttttca catgacagtc ttgctgaaat ttttcagag ccctaacat    40380 cattggtatc ggagtagaga ccccccaaag tcattggagc cggagaagaa agaagtaaag   40440
aagtctttta aaagcttcct caaattcctc tttacatatt aggcagactc tttcatcttc   40500
```

```
aacttctttt ccatgaacat ctgagatttt aggttttaca atctttattt tttttttttgg   40560
atagttattc cctttttctct cttttttttt ctgtttctct tttcccattc acctttactt   40620
tcttctttcc tttcaaaaat atcttttgat aggactaatg agataagtca ggaccaatgg   40680
atatctcggt caacccaacc actgctcaag tttgagatgg aaaatctatc tcggacaaca   40740
gctgaagtta gtacctcagg ttaggatgat ctagaatctc ctataagaga ttttttagat   40800
tatttcggcc caagtactga acaatctgtc ctgaccaatc tcgatcttta ggaacttaag   40860
aaaaaatatt cgattcagct tataactcca agttgggatg gtaggattat tgaacctcca   40920
gaaggttatg tcgtatttta tgatgaggca cttcgatctg gactttaatt tctcttacat   40980
cctttcttca gtaatgtttt agacttctat aaactccatc caatctaggt tactcccaat   41040
gccattagga tgatcatagt tttcattatc tatcgtaaat tttttgctat agaactaaga   41100
atttctctct ttaggatgct ggtcatccta agaaaacatc cttatgaaaa agactgatgg   41160
tatttcttac cttggcctca atataaaattc ggtcccactc ttcctttttc aatacataat   41220
tgaaaaaatc atttttcttt tatttcttct aatgtttcgt agggttttat ttgtaaatag   41280
tctaagccta aaccaaaatg gaactcaaat aacaaaatat tatctgagga tgaggagact   41340
tttgtagagc ttttagatat gaaagtatcc aagttgagcc tactggtgtc caatcagtcc   41400
ttgtttgaca ccgacatcag tcagatctct ccttaagata agtctgatgt taattcttttt   41460
tctttattgc tttatcattt ttcatcattt ttcttttcta acaatctttt tccttatata   41520
gtagcaataa tgaagttcaa cctacaaagg ctggctaact caaagaagag gaagaaggat   41580
ctaaccgatt gctctcaaga agagtaagga gactgctcct ctaagatcga ttggcccccg   41640
atcatcacct gggccaatat taattgacat agatgctaca tcgatctcca ctataccacc   41700
agcaaaatca actcatcaac ctactaaggt ggcttgtcca cctcctaaag agtctgcaca   41760
tccaaagtag gcatcttccc caacacctcc aacatcggcc aagttagttt ggctgagcaa   41820
tcagcatctg aggtcacaga ctcctgatgt caacccacca actttctcat caaaaaaaaa   41880
ttgacttggc gaaggtatca cttttggaga cacccagact aggcaaggac ttgctctgta   41940
caatgatgcc tcaaaaggac ctagatgctg ataggaggga tctttctttg gagcaaataa   42000
taaattatgg attcaacagt atcatgaacg tgagtcttca ttctcttcca ctctcttctt   42060
tcttttttctt tttttttttt acattggcta tttgttgatc tgaatatatc tttctttttg   42120
cagtcggttg tgtatttcaa gttgctcaat gagcacttga catggttctt caaaaataaa   42180
aatttttttg aaagagaggc tcaaggccaa gaaagaggcc aaaaaagcag ttgaggaggt   42240
caagaaggca gtaaagaaga aggctgtcaa agaaagcaaa atgatggagg ggctgaagaa   42300
acagctccaa gaaaaaatag attccattaa ggagactgga caaccaatga cagatgaatg   42360
ataaagatga caagttgtaa aaacagcctg aaaaaaatct caagttggaa ggccaagctg   42420
aaggaggtcg agtcaataat tgaaaagcat gatgaagctc ttgtcccata ttagagacaa   42480
cttgataaag acaaagagtg gatgtcaagg attattgaag attataagaa ttccgacact   42540
tttcaagatg acgttactga ggcctcaaaa ggagctttca attatggctt tttgagctac   42600
aggagtttaa ttatcaagct ctttcctaac cttgatctca gcaaggtcat aatagaagca   42660
gctctagaag tagtagccga agtgacttct gcaacaacta ctgagcttgc ttccacttct   42720
atcattggag tttctccgat cgaagtccca aacagtccaa tcgaggcctc catcatcgaa   42780
gctatttcga aggaatcagt cggcaaagac cttacctcaa ctcctccaac aaataactcc   42840
caagctaagg cctgaattat cttcttcttt ttttttctaaa catttgtatt agcccgatgt   42900
```

```
gggcttctat aaatactttt tacattaatg aatgagtttt tcaatgtcaa tattttttct    42960
ttttaactaa tactaatctt ggatgatccg atctgggttg gatgtctcaa aaaatatcat    43020
tcacgataga tagttatttt ctgacttcgg ttagatgatt atgagtatat gtaattcaac    43080
cttggttagg taagtaatca aatattaact attctcaaac caagtagata acgaagtcaa    43140
tgtgattaac tttaacaagt aagattgtta tggaatgaaa ttgaatcaga tcaactaact    43200
atagataact taatctctca taattcactg taaaggttct aaaagtacct ttatctaagt    43260
tcgaagtgac aagtcgggtt cttttattcg tggatttatg acccatgctg tcttttttgtg   43320 atcttcatta ttaatcacct taaatcgata tagcaaaatc cagtttatag atctgagtgc    43380
tttcttgtca gattgagtct atcctattat ctgtgaaacc tgatctagag atcaagtatt    43440
ttaggttttt tatttaaggt ccaattcgaa gattgagtat ccaatgtcat attgttaggt    43500
ccaatttgga gattggatgt ctcactatca tctcgtgagg tccaatccaa agatcgaata    43560
tctcactatc atctcatgag gtccaatcca gagattggat gtctcacatc atcttgtgag    43620
atccaattcg aagattggat gtctcacatc atctcatcct attgtggttg gaattttttgt   43680 agccttagtt tgactttttc tgacctcatt tggacaccta aatcttatta tcatcgtttg    43740
atcgattttt actaatctac tttggatgaa aaagaattct tcaatggaac ttttgattag    43800
aactttatct tcattgggat agaaatcgaa tgctttattg aaagatttta ttgataatac    43860
attctgagat ttttaatatt tcatgttctc gaaatgatcg taccatctaa attttaatt    43920 cgataagctc ttggatggat cacctcagta atctgataag gtccttccca attcgggatg    43980 agttttctt actccattgg ttttgagact tcagctcatt ggagaaccaa atctccttat    44040
aaaaaatttt aggctttacc tgagagttgt aatatctggc tacttttgt ttataaacta    44100 ccatatgaat ctgggctttt tctcgagttt tctcaaataa attgagatca gtcctcagtt    44160
gatctgaatt attttcttca tgaaaatttt ctattctggt tgtaggtaaa ctgatctcga    44220
ctagtattat agcctctgtt ccgaaagtaa gtttaaaaga tatttctcta gttggtctct    44280
gaggtgtagt tctgtatacc cataaaaatat tataaaatta ttctaccccg agactttag    44340 cctcaatgag ttttattttt aggccttgaa agatagttct ataaataaat ttagcttctc    44400
catttgattg tagatgtcca atcgaagtaa atatatgatc tatgtagagc tcagaataaa    44460 ttttttaaa atttttgatta tcaaattatt gctcattatt agtaattata actcaaggca    44520
aaccaaaatg gtaaataatt attttttcaca taaaatctca tatttttttct cagtgattta    44580 tgtcagaggt tcaatttcta tccattgggt aaaataatca atagtcacaa ctaaaaattt    44640
tctttgctcc atggccatta gaaaggatcc cagaatatcc attctccata tagcaaaagg    44700
ccacagcact gtaatagaaa taagttcagt tgtaggctga tgttatatat tggcgtacct    44760
ttgacactga tcgcagtact tattaataaa gtcggttgaa tcttttttgaa tagtaggcca    44820 ataataatct tactgaatta tttcataagc taaaattta ccccccaaat ggttactaga    44880
gattccttta tgaacttctc gaaggatgta atcagcttcc gatggcctta ggcataggag    44940
cagtgggagt gaatataacc tctgatataa ttgattatct tgaacaacat accatggggc    45000 ctgtcttta attcttgttc cttcgactgg atcaaccggt agaggttctt tagtaatata    45060
ctccattaat gggtcaatgg aacttagctc atattaaatt tggacaatta gtaaggcctc    45120
gatactagac ttttttaagaa tatcaataag aacaccttga tttagtttga aaaaatctga    45180
tgtggctaaa tgagataggg catcagctca gacatttttgt ccttggtatt tgcatgatct    45240
```

```
tcagattttc aaagttttt  aataattctt  tcatattata  taaatattga  aacatcataa   45300
aatctttagc  ttcaaattaa  tctcatacct  gactgacgat  aaattgagaa  tcaataaaaa   45360
tttaattt    tttaacatta  agctccttag  ccattttgag  tcctacaatt  agcgtttcat   45420
attctactcc  attgtttgag  tgttaaaatt  aaatctcaaa  gcacgctcac  taacaatgcc   45480
ttctagactc  gttagaatta  aactagttct  actttcttc   gaatttgagg  ctccatcaat   45540
gtacagtatc  aaataagaat  ctttgatatt  tttcaattct  tttaagattg  gttcttcatt   45600
aggaatagag  cattcaataa  taaaatcagc  taatacttaa  actttcaatg  aagatcgagg   45660
cccatattga  tatcaaattc  atttaattca  atagcctatt  tgaatatcct  tcttaaagta   45720
tcaagctact  gtaaaattaa  ttttaaaggt  tgatcgatca  gaattataat  agaatgagcc   45780
taaaaatacg  atcaaagtca  tcttgctaat  gcaatgaggg  tataaattat  cttctcaatt   45840
ttagaatatc  gagtttcaac  atctctaaat  aatttatttg  tataataaat  ggatctttgt   45900
atccctgcat  catttcaagc  taaatcgaa   ctaacagcat  ttgctgaaat  agatagatac   45960
atgaataatt  tttgacctt   gatcggcttt  gatagtaatg  gagctgtgcc  gagatatttc   46020
ttgagatcat  cgaaggctgc  ttgacattca  tcttatcaat  cgaagtcttt  gatctgcctt   46080
agaatttaa   agaaaggaag  atatttatca  gctgatctga  aataaaatta  actaagcaat   46140
gctactcatc  cagtaagttg  gtgtacttct  ttgatggagc  tcggatgctt  catttcacat   46200
agagcttgaa  ttttcttaag  attgacttta  attcctcttt  gagttacaaa  aaaatctaaa   46260
aaaattttg   aagttacttc  aaaagcatat  ttgttgggat  tgagcttcat  ttgatatttt   46320
cgtagtctct  aaaggcttct  tccagattgg  caatatactg  atctgactca  gtatttttta   46380
ctaatatatc  atcaacataa  actttgatat  taatttcaat  ttgttactta  aaaatcttat   46440
taatcaagta  ttagtatgta  gcacctacat  ttttaagatc  aaaagacatc  attttataac   46500
aatgcaaatc  ttttcagtg   atgaaggcca  tattttcttc  atcctcaagt  gccattttga   46560
tctgatataa  ccagaaaaag  tatccataaa  gcttagtaat  ttgtgtcttg  aagtagcatc   46620
aacaagctga  tcaatttttg  agagagaaaa  actatctttt  aggcaagctt  tattgagatc   46680
ggtataatca  acatagatcc  ttcattttc   attagccttt  ttaaccatga  caacatttac   46740
aatccacttt  ggatattatg  cttctctgat  gaatttgtct  ttcaagagtt  tgtcgacttc   46800
ctcatctatt  attttttatc  ttttcggggt  gaaacttctt  ttcttctgtt  gcattggttt   46860
atgctttgga  tcaacattca  gcttatgtac  aataagatca  gttaaaatct  caggcatatt   46920
agagactgac  taaacaaaga  catcggcatt  catccgaaga  aaagatatta  atttctccct   46980
cagatcaggc  ttcaatagag  atccaatttg  gacagttttt  tttggatcat  cacacaaaag   47040
aacagtaata  agtttctcga  ctggttctcc  tcgattttg   atgatatcaa  ctttacttc    47100
ttgatcaagt  attttaattg  gtagagcttc  cacagacctt  ttcatttta   cagctatcag   47160
aaaatactac  ttagcaagta  tctgatttcc  tcatatttct  ccaactccat  acttagtttg   47220
gaattggatt  agtaaatgat  aagtgaagac  tatagcctta  agggcgttga  gcctaggtcg   47280
gtcaagaata  gcattataag  ctgatggtat  tttgacaata  aaaaagtga   gtcttacagt   47340
tgactggcat  ggttctatcc  ctgcagtgac  ggacaaagtg  acctctcctt  ccacagctac   47400
aggatttcta  gaaaatccaa  ttacgggggt  accaacctat  ttagctaatt  tatcatattc   47460
attctttgga  atgtatcata  gaacaatata  ttagcagagc  tttcattatc  aataagtatt   47520
cttttatat   catatttggc  tattgccata  agatgacaa   cagcatcatt  acgaggagtt   47580
tgaactctaa  catcatcatc  gaaaaatgaa  attatgtgat  ccatgcactg  atgctttgga   47640
```

```
aggctttcag taatctcagc cacctcctca gttccgtcga gatctgagat catattgatg    47700
actgcagcag tagacttgtt gtgatcattc tcattgttgg gcttctatca ttggtcagta    47760
gcttgacttg cccgatctcg aacatattta ctaaagtaac attagtggat caatacttca    47820
atttatctt ttaattatcg atgctcctca gtatcatggc catagtctcg atggaaatga    47880
cagtattttc tcttatctct ctttgctgga ggggctttca taggattagg ttggcgaata    47940
tatcctaaat cctcgatttc tatcagtatc tgagctcgag gagtagatag tgaggtatag    48000
atgtcgaatc accgaggtgg gcttttgaac ttcagattct tctgaggtcg ttcagagtta    48060
tcctgttggt ttttatgatc ttcttcctag ggccactttt ttccatctct tttttcttc     48120
acctaacgaa gtatgcatgc tctctttctt ttcagcttga gcatacttac aaacctagat    48180
caatatttgt tcataattgt ttgggtagtt cttattaaga gagaagatca ggcgattact    48240
cttgagtcct tgcttcaaag ctgccattgc aatggactca ttgaagttct tcactttcag    48300
tatgcggca ttaaagcatg ccacatattc ttgaagagat tcaccttcct actatttgat     48360
agtaaaaaga ttgctagtat ttttcaaatg aatccattta ttatcaaaat acgtgatgaa    48420
tatttgctaa ctgtgtgaaa gatgaaatag atcatgtctg gaggtcagag aactagattc    48480
ttgcagatgt tttgagagtg attggaaaag tgatgcaaaa tagggcatta gatacccctt    48540
gtagtcttat aatggctctg aagccttcaa gatgatttaa gggattgatg gagccatcga    48600
atgtttccac tgtaggtatc ttgaatcgag gaggaactga tttaccaaga attttttgag    48660
aaaaaagaga tcgtaagttg aaatctcttc taccttgaga atggcttcca atctatatct    48720
ccatcatttt cttctcaaga ttttgaatct tttgtccaag accctcctcc atacatggct    48780
tcttatgtgg agcagatttc acttcccaag agtgatcagt atggtcaaga agatgatcat    48840
gatgaagatc ttgaggagtt ggttgctaag tgtgatgtga ttggactact tgggggggcta    48900
cttttttgcta ccgttctgtc gtatactaca gcagtaagag cttggacctg ctgaaccaag    48960
agactaaact attgtggatc aataataatt gaaggttagg tattctcctg aacatcttca    49020
ggagaagatg aagtaggtaa aggatgattt ggtgccttct tgttcaccat ttctactaaa    49080
atattttaag tgcccttcct ctaacactaa tctattactg caaggcttca aaagacaggc    49140
aacgagatgg gtcttgaatc gaactagaat gtttcttggt tgaatttggc gaagtctgta    49200
acaaatcttg caaagaaaat ctcgaaacct acgggtacct tctggttcaa gatcctctga    49260
tggataagtt aggtaaagtc ttgagaatag gttgtgaaaa tagaagaata gaaggatgag    49320
aagagagatt gtcggtaaat ggagagatga ctcttatttc tttcaatggg ggagctgaaa    49380
ataattcagc agagtttcca ctctatcaat cctgacttat tttgtggagg gtaccttggc    49440
cccttcatat atagggatg aagaggcctg gtaaggttgt tagactatta ggagagtttg    49500
ttagatcgtt aatttattat aatagaatga ccagctatat aaaaatcatg gagtatttac    49560
ccacatggtg attgactgta gtataactga aagatagcta atgcttagct ggatgactgc    49620
tgttagataa ctgtctgcat tcttacggta cattgatatt ttaccaatgt gacatagctt    49680
aaatcggcaa ctggctgaac taaatattat gtatcccttt agttaacaat catgtcggtt    49740
agagatcaat gtaattcgca gcagatcgat cataagctga gatgagtatc atattttaag    49800
aacaacgctg ggcgagttag gccgatcaaa tgtcagactg aaaaagcaga tcaataaacc    49860
tctgatgtga tctgaaagaa tatttatgat ttaaataata atctatcacc acgtatccag    49920
ataatgaggt catataacat gtaccaacag tgcatttttc catctagtta agaggttggt    49980
```

```
tagtggcatt tgtcttcgat atgtaatgtt cacataacta atgtgcttag tagcattctt    50040
ttgtaaggtt aaatcttcaa tgatcttaag ttcacataat tgcctttgtg ccctattagt    50100
ttatagttga cctttttaatt caagagacag tcaccttagc aatcgatgtc tgcttagatt   50160
gggccaatta ggtactcaca ttaatatatt gaatcatgtt tgaatataaa ggattagatt    50220
gatttataag tttccttttta ttgtttacat actgatactt agattgactt actacattat   50280
ttgatatgtt atgttctaat ttttggatta aaattgttgt ttctgatttc tccttacatc    50340
taatactttg tataatttat tattttttag catgattgag tgtagaggat tagattgatt    50400
tttaagttta ttttgattat ttacatgccg atacttaaat tgacttacta cattattcaa    50460
tatgttatgt ttcaattatt gagttaaaat ttttatttct gatttctact gatgtccagt    50520
gtgtgtgtgt gtacgtatgt gtgtatatat ttatttacat atatatgtat gtatgtatac    50580
agacatacat acatacatac atacatacgt acacacacac acacacacac acacacacac    50640
acacacacac atatatatat atatatatct gtgtgtgtgt gtgtctctct ctctatatat    50700
gtataagtat gtatgtatgt atgtgtatat atatatatat atatatatat atatctatat    50760
gtgtgtatgc atgtatgtat atgtatgtat gtatatacat atatgtatat atatgtatat    50820
atatgtgtat atatgtatat atatgtgtgt gtgtgtatac atatgtatac atacatatct    50880
atacatacat atgtatacat acatacatat atatgtatat atacatatac atgtatacat    50940
acatgtatac acatacatgt atacatatac atgtatacat atatgtatac atatacatat    51000
atacatatat atatatatat gtatatacgt gtgtgtgtgt gtgtaagtaa ttaagtatgt    51060
agtgtgtgtg tgtgtgtgta tatatattta tatctgtgtg tgtgtgtata tatgtatgta    51120
tgtatgtatg tatatatata taaatacata catacatatt tatacacaca tatctataca    51180
caaatatgta tacatataga cacacacaca cgcgtgcgcg cgcgcgcgca cacacacaca    51240
tatatatata tatatataga tagatagata tatgtatgta tgtatatata tatgtatata    51300
tatgtataca tatgtgtata tatgtatata tatatgtgtg tgtgtgtgtg tgtgtgtaca    51360
tatgtataca tacatatcta tacatatata tatatataca tatatatata catatacata    51420
tatatatata tacataaata tatatacata tacatacata catatatata tatatatata    51480
tatatatata tatatatata tacacataca tacatacata tacatatata catacacaca    51540
cacacataca cacatgtata cgtacatgta tgcatataca tgtatacgta catgtataca    51600
tatacatgta tacatacata tatagatata tatatacaca tatgtatata tatatatata    51660
tatatacaca tatataggtt atttggaacc taagaaactt gcaaagttac tagatgcaat    51720
gttcggaaac catggaccgt aacaactgga gtagtatttg ggtcatgaat tcatggctag    51780
atcatgaatt gagtgggagt caaccgaagt agggccagct cagacacttg tatttaggtc    51840
ccatgcttgc gtgcattctc ttccctgata tcctttggct ttgctgcctc aaatcctcga    51900
gctatcttat catcatcgca ttgagctcca taccttgctc tttcctaact gtcactgtcc    51960
ccatcaaacc tccggagatc ctctttcttc tccaatgttg agatttgttg gagtcttccc    52020
accttctcac ttcaatgggt ggcaatttca agtgccagtt cccttatttg tcccagctat    52080
attgacaatg gggcttattc tagggtttct catggacata gtgataataa taatcaaggg    52140
accaagagag aaaaatcttt ctagtctgtg ttctttaagt ttgagagata ggcagcacat    52200
ttttttaata agccttttttc actcatcgga tcctgatttt cagttgttcg acctgaacag    52260
ttcaagcaat tgaactgctt gggtcactat tttggacgat tttcagccat ttttaagtat    52320
tgtttgactg gatccacgct gcgtagtggg cattgcgttg atcaagtaga cctgtaaggg    52380
```

```
tcaacaaggt ctgagaacac tgaatggatg ctccataatc ctcttgttat ctgtcaacca    52440
tttggaatct tttaaaacaa catgtggtga taatatatat gataaactgt gatagattca    52500
tgtatagatt atacatatga aaatgtagag tgcttagtaa aagtgatgaa gagcaatgcg    52560
ttagaatgtg ctagcctttg acctaaaaat tggaatgccc aatgatgagt tatgataaaa    52620
ttgtgacgtg atttatgaag tctaatgttt agttggcttg cagtttcaga tgcgataaag    52680
aattttatga tttagctctt tggtttttta acatgcaaac atttaattgt actgaaaaac    52740
atttatttcg aaacatgtag gagactattg gatattgaaa ttaaaattga cttttggtg     52800 tttcacaata tttcttaata aacactacga ctatgtaaat aggtggtgga tcaaagggaa    52860
agaaatgttt ggtgattatt tttagaaaag acaagaagta tttgataaat ggttattttt    52920
caaccgatta atgagagaat gactatgaac ctatgaggtg cacctcttat gatgttgcat    52980
ggatgaagca tctaatccat gggtacaatt tactaaaata taggcccaat tctgagacag    53040
gaacatttac aactcatgta caaagaagaa acttaaagta tcatggatgc cgggatattt    53100
ccttcttcaa atctttcaaa agctgtagtt ttcattataa ggaaaaatga ttataactaa    53160
catcttctat aggtgatgag tggacactag aaggctttcc tataataaca gtagagagag    53220
tagaaaagcc tgtcagcatg cggtccataa gtatatatac atattttcag cgcttaaagt    53280
aaattttctt gtaccaaaaa aagataaatt ttcaaaataa gaactaaaat caactgaaat    53340
gtttgaaatc tgattcgtag gtacatggag aagagtgtaa gacagcaaat atcataaagg    53400
cagaataaga gctggtaatc ttgtaacctg gcgcaactat gttatgcatg tctatatgtg    53460
tgcatgttta tgtataacaa gtaatatttc ttttcttatt tactcacttc agttaggaag    53520
tcaatccaat ctcccctttgc ttgggtgtgt tcagattatc aagggccata acagtagtgc    53580
tggtaagcac ctgtttaatg gataaatggc gacaaattct ctccccttct gctcactcta    53640
ttatcatacc ttccgtctta cccatctgct atatcttata aggaacataa ggatcgacat    53700
agcttcatgc tatcacatta caagctaaga tcggaataat acctaatctt ttcgatctac    53760
tattaggtat tactataggg ttgtaaattg ggtttaggtt ttgaactata ttatattttg    53820
gtgtaagaat atagtgccac actatcttga accagactag ctgttgcact tttttgcagg    53880
catcaatatt ttgttcatcc aaaaaaaaat attgcacatg cacagatgaa gtatgagggc    53940
tgtaatcatg tgagaggaaa cacagatggt tgtgatccta taatgcttga agaatgtgat    54000
ccctctttta gttagtatac cttctcttgtt tttctccctg ataggaaata tgaaatgaag    54060
gtatatcttt atgaaaaaga tggatgcata gaatatacaa atataaattt atacaggata    54120
agagaaaggc ctccagcaat ttgcacaata atagtgaaaa aagattaaat aaattcccaa    54180
caatggcgcc aatatgtgat atgcaactat gagtaggctt tcctgttgca acaatcaata    54240
aatatgtcat gcgaggcttt taaggtagag cactaacatt ctaatctgaa ggcctaggta    54300
caattttgaa tttaggactt gtttggatga ctgagtacaa aatcccataa gaatcattga    54360
tttgggccaa cacaactacc tacatgaggc ttaacctagt ctaattttat aaataccaag    54420
ggaactatta tagtaggcca gcccaaatgc catagggaat aaaagatgaa gtatggaggt    54480 ttttttttatt ccttatggga tttggactag tccactgcaa tgattcttta aatatttcta    54540
aataagtcta acctaacctc atttggacag ttgtattagt ccaaatccgt aatttccata    54600
gaattttggc tacagtcatc ccaggccctt aaatttaaaa gatcatattt aaacatgct     54660 tgaattctag attttaatct gggcccttta acttccatag ttggtcttga aatagacagc    54720
```

```
ccagccccaa gctcatggcc ctactgtatc ttcgtttggc tgtgcccttt agtaggatgt    54780
cttaggtgtg tgaaaagcac ctgaatattt cccacacaat gtgttttttt ttcagtacaa    54840
accggctatc acaccattct aatatgagta cagtccagag aatcagaata caaaatatct    54900
cgtaaggccc aagggtagtc atcgccttca caccaagtcc agtctccgat atgcttcgca    54960
acaaaagagg cagcccaatc catggtgcta ttcgcctccc ggaatacatg ttggacaaac    55020
gacatattgg cgtgatgaag ggacttctag atatcataga acagtgaata ggttttttagg    55080 tgtttcacct tgtcctgaat ccaactaatg accatggccg agtcatcctc gataaagatc    55140
ctctccgctc gtagctcata tcttatgcag atgatgtccg cccaaacaac gtggagctct    55200
gccccatgaa cggatgggtc gaagatcttc tagcaaccaa aagcttgaca tctggatctc    55260
aaataatata gcccgcacca cccctaccat ctctgacact actatcaaag ttgaccttga    55320
caaactccaa ggatggagct tctcaagaaa tgaaaagagt cctcggagtc actgcaggca    55380
tagcaaggga gtcccagaaa ctcatggtgt caagggacgt ggtggcagta ctcctcagct    55440
aagcaacaag ctctccacca ctcgctacac aggcacaatc tcgattttaa aaatcaagct    55500
gtttctgtac agccaaatct gataggcggt gtacgccatc ctaataccccc aaggcaaccc    55560 ctcaaccata ttctgatgga ccgcatcccg aaaaggcaaa agccatgggc cactatcaac    55620
cttctagatt tggccccccg ccatcctcca aatcagatat gccctcgagc aatggagtaa    55680
ggcatactct attgactcat cctctagttc atagatcaag caagcagtag gaagctccgt    55740
gcttctgtct ttgagaagtg tctgagtagg tagtcgatcc caggcaacct tctagaggaa    55800
aagtctgatc ctagagtgga ctagccatgt gtatatatat atatatatat atgtatgtat    55860
gtatgtatgt atgtatgtat gtatgtacgt acatacatac atacacacac atacatacat    55920
atacatacat acatatacat acatacatan nnnnnnnnnn nnnnnnnnnn nnnnnnnnnn    55980
nnnnnnnnnn nnnnnnnnnn nnnnnnnnnn nnnnnnnnnn nnnnnnnnnn nnnnnnnnnn    56040
nnnnnnnnnn nnnnnnnnnn nnnnnnnnnn nnnnnnnnnn nnnnnnnnnn nnnnnnnnnn    56100
nnnnnnnnnn nnnnnnnnnn nnnnnnnnnn nnnnnnnnnn nnnnnnnnnn nnnnnnnnnn    56160
nnnnnnnnnn nnnnnnnnnn nnnnnnnnnn nnnnnnnnnn nnnnnnnnnn nnnnnnnnnn    56220
nnnnnnnnnn nnnnnnnnnn nnnnnnnnnn nnnnnnnnnn nnnnnnnnnn nnnnnnnnnn    56280
nnnnnnnnnn nnnnnnnnnn nnnnnnnnnn nnnnnnnnnn nnnnnnnnnn nnnnnnnnnn    56340
nnnnnnnnnn nnnnnnnnnn nnnnnnnnnn nnnnnnnnnn nnnnnnnnnn nnnnnnnnnn    56400
nnnnnnnnnn nnnnnnnnnn nnnnnnnnnn nnnnnnnnnn nnnnnnnnnn nnnnnnnnnn    56460
nnnnnnnnnn nnnnnnnnnn nnnnnnnnnn nnnnnnnnnn nnnnnnnnnn nnnnnnnnnn    56520
nnnnnnnnnn nnnnnnnnnn nnnnnnnnnn nnnnnnnnnn nnnnnnnnnn nnnnnnnnnn    56580
nnnnnnnnnn nnnnnnnnnn nnnnnnnnnn nnnnnnnnnn nnnnnnnnnn nnnnnnnnnn    56640
nnnnnnnnnn nnnnnnnnnn nnnnnnnnnn nnnnnnnnnn nnnnnnnnnn nnnnnnnnnn    56700
nnnnnnnnnn nnnnnnnnnn nnnnnnnnnn nnnnnnnnnn nnnnnnnnnn nnnnnnnnnn    56760
nnnnnnnnnn nnnnnnnnnn nnnnnnnnnn nnnnnnnnnn nnnnnnnnnn nnnnnnnnnn    56820
nnnnnnnnnn nnnnnnnnnn nnnnnnnnnn nnnnnnnnnn nnnnnnnnnn nnnnnnnnnn    56880
nnnnnnnnnn nnnnnnnnnn nnnnnnnnnn nnnnnnnnnn nnnnnnnnnn nnnnnnnnnn    56940
nnnnnnnnnn nnnnnnnnnn nnnnnnnnnn nnnnnnnnnn nnnnnnnnnn nnnnnnnnnn    57000
nnnnnnnnnn nnnnnnnnnn nnnnnnnnnn nnnnnnnnnn nnnnnnnnnn nnnnnnnnnn    57060
nnnnnnnnnn nnnnnnnnnn nnnnnnnnnn nnnnnnnnnn nnnnnnnnnn nnnnnnnnnn    57120
```

```
nnnnnnnnnn nnnnnnnnnn nnnnnnnnnn nnnnnnnnnn nnnnnnnnnn nnnnnnnnnn    57180
nnnnnnnnnn nnnnnnnnnn nnnnnnnnnn nnnnnnnnnn nnnnnnnnnn nnnnnnnnnn    57240
nnnnnnnnnn nnnnnnnnnn nnnnnnnnnn nnnnnnnnnn nnnnnnnnnn nnnnnnnnnn    57300
nnnnnnnnnn nnnnnnnnnn nnnnnnnnnn nnnnnnnnnn nnnnnnnnnn nnnnnnnnnn    57360
nnntatatat atatagtata ctatatagta tatatatagt atatatagta tatatatata    57420
tatatatata tagtatatat atatatatat atatatatat gtgtgtgtgt gtgtgtgcgc    57480
gtgcgcgcac gcacgtgtgt atctcgatct gtgtgtgtgt ggtccatctt cacacttttc    57540
cctcaaaaaa accccccttg agattttgtt cagctgaaag gggttcataa aacttgccct    57600
tgcttggtcc tagggtttaa gatttatatg caatattcat taagacgtct aaatgtcata    57660
atattttgag gttacaaata ttaacaaaca gccttggata caaaccttt tctcaaagaa     57720 tcttgtatct gttcttcctc agatgacatg tgatttatgc tacggcctag ttctaaggac    57780
ttttctctgt cattaacata aaaaaaaaac agaaatatat tccttagtaa ggaaatagtt    57840
gtgcactatg attgctatgt ctctcaaaat tataccaaac tttttatgat atagagtgaa    57900
aatcaaatca gcatgtatgg tctatttgcc aaatagggtt gagcataggt cgggttcggt    57960
cgagttgaga gaaaaatttc atccgatcaa attcaatcgg attgaagaaa attcaatcca    58020
ctgccaatca ttcattatgc ataaactatc taaaactgaa atgaatagtt tgtagcagga    58080
tcaggtgtta tgtcagtttg gacttcaatg ttaacccaat attgatttta aatccaacat    58140
tggtccactt agacttattt atttatttt atcaatttaa tataaaaag atctaaacct      58200 cataagtcat aaattttgga tttatttttg aacatgtaca aaataaaaca gaaaaaagaa    58260
aaaattactt atctaaaagt aactatatct gaaaactttc actttagaat tgtcttaaat    58320
taatgtactt ccatcaacaa ttcaatgtta atatttttat gaatccaaat ggatgataga    58380
gtatttttta gaatgaagta ttgaagtcta aatgacatcg tcccaaaata aaagtgaatt    58440
tatgaaatac tacatctgtc ggattcggtt tcatacggat taaaagtgta ggaatagaat    58500
ccgattataa ataattattt ttttataaat tctaattcaa ttttattcga tttatatttt    58560
ttaaccggtc aaaattaata tttattaagt aggattggat ggatttattc gtatctcgat    58620
tatttgctca gcccattgcc aaatctaaac tcttttcaga taggttccat gtgaacatga    58680
tacatgagat gcagtgtgat agtacacacc attgctaaga aaactttgga gtttgcgtaa    58740
caatatctgt ttaccattta aaaaatggca gttttgaatt ttaacacgct ctcctccaga    58800
ttcagcttat gaacttttcg aataaaaata cccctggact attttttccaa aaagtaccag    58860 catcttttga acttgaatgg aaattcggcc aataaaatgt tttcatttat tgaagaaata    58920
aacagggtaa cgcagtagct ctatttcctc tgcttttctt ttctatatta ataacatgat    58980
tattcatctc tctcggatca caaaaaaatt aagctattca agctttattt atatttcatt    59040
tttaaatttt ttacttaaat acaaaatctc ccatcccact actacggcag catgtttcct     59100
atgtatgatt atttcattc aaatgatatc atttttata atttatattg tatgtaatta      59160
attcatttat agttcttaca ttttcctgtt tctagtagat acaataaagc ggttttggac    59220
tagtagcttg ttctctgtat cgaagtttaa ctaaagcttt gacaataata tatgaatcca    59280
tatcactggg taggagagga atatgttggg tataaaggat ttaaggaatt agatattttc    59340
atacaattgt attgcattgc agacagtaat tagattacta tgcaattatt ctctctctcc    59400
atgtttgttg cagttgaaga actctaatga agctcacaaa aatttactgc atgaacttgt    59460
```

```
aagtggaatt agacgactcc gttgtcctcc attttctttt attttcttta aaatcatctg    59520
ccattcaaat agacagaaaa aaaaggattg attagctatt ggatgcctct tgaattcagg    59580
aaatgaagga cgagcaccca gtttatggtt ttgtggatga tgaccctagc aactacgcag    59640
gtgcactggc tcttgccaat ggggcttccc acatgtatgc tttccgtgtt cagccgagcc    59700
agccgaatct ccatcgaatg gggtttggct cccatgacct gcgccttgct tgattttatt    59760
gtagcttaaa gaccttacaa cttccagagt ggtgttatat attagtatct taagctatat    59820
gacagtggta agcctctcta tccgctactt gttatccttt aggtactttg catgtggtgc    59880
aaggttataa ttgccttgtg tttctattgt cttcctcatg gtacttactg gactgatgat    59940
gtcaagtgaa atggagttgt tgaatcctg actgaaattt ctcttggtcc atcaagtgca    60000
agagtaagtt tagacatcac ttgcaagctt tgctaggaa ataagtagtt tcattgcact    60060
aatgatttcg aattttttgtt ttcgggttag agaaacctag attaatgctg ttattggatg    60120
ctggcagtca gatgaagatt atgtttgatt gtacctcgtt ggacagatgc tcatgcgtag    60180
atccataact ctatttcatt tcatttccct gtacacaatt gaaacagggc atatatgaat    60240
aggtatagaa cagatgattc ctgcaatatt ggaggtggct agctcagctt agactaaagt    60300
tggtctagct gggatattct gaacacctga gatgttcaaa taatgtggga taacttggcc    60360
caactcaact aaacattggc tcaaagcata gtcaaggtaa agcttgagca agctcttttg    60420
agcttggttc gagtccgagc tgagcccggg ccgcttgttt agctgatgaa ctgaattcaa    60480
atagccggta ctcagcttgg ctccactcga ttcatgagtt cgaatcccct caagttcaac    60540
ctcgaacttg acggtgtagt cccacaacca tggccacctc ataatgtggg acggccatta    60600
tgcattcctc tagtgcctgc tccatatgac ttttgttctc attataccat gcacctaaat    60660
gagtgctcat agtgacaatg tttagcctcc acgtataatg tgtgccagct aactagaagc    60720
ctaaactttg gtgaaatttc tgcaatgttg tggttgtaaa acgctcctac gttgagacat    60780
gatggtatct aagattatag acaaactatc atgctgaatc aacccaaatc caaggtgaat    60840
aaaacttgat acaaagccga gctccattgc aatagtacaa tggattctgc acttgaagaa    60900
cattacaaaa tcattttttc ccaaaaagaa acattgcgaa cagaccaaag cgtaaagaaa    60960
ttacatgatt caactaattc aagctttcca tgatgtaggc actcgctaga tgtagtaggg    61020
tgataacttg ctttgtgagg gtggatcata agcttaacct caatctatcc caatctatcc    61080
tttcccttga cctatccatg ccaatctagg ccatttctgc ataaatataa cttaatccca    61140
gtggatccgg cctagtttca ctcactccaa cacattccta ctcaatggta gccaatcctt    61200
tctttagccc tcaaatataa tcctaatcta gcatagccaa ccatcaatca tgcctaataa    61260
agcccgacta caccaacccg atcattcctg atcgtacaca atcaagactt atcctaattg    61320
atcctagctt tttttaggcc tctcttatag aacctgtgcc aattctggac aagctaatcc    61380
aatcttagca gccaaaaata ttacatgttt aattagccaa atcgaaccta tcataaaccc    61440
aatatataat cggaccatac caagatcatc atcctatatt tccttctctt gttataacta    61500
cacctaaaaa ggaatttctt catacttatg aggggtatat tatgataaaa attccttcat    61560
tttagccctc catccttgtc tattttggg accactagcc aagtaacacc ttaagagccc    61620
tccatcttaa tattccctct aactagctcg atttcttctt cattctttct tgcgatgtg    61680 tcccctccaa tttaattctt acatgttggg atttgagtac tgaaaaataa tagataaaga    61740
gaaagtaaaa actatgctaa tgataatacc aaaggcataa agaaatcaca gcagtcgcaa    61800
aaacatcaaa tttttttatg gttcggccta agcctatatc tacataggga cgagagtaag    61860
```

```
aagaagcttc cactataata atagtttaga gtacaaaaac ttctctgaca ccatgtaggg   61920
aacatcgctt ctaatacaag aaagaagaaa tccaagatta aacaaacctc tagaaaaatt   61980
cttctcgatg gaataactct aatctgagat tgaacaatct tctccaatcg atgatctcca   62040
atcttctttt cttaaatgaa gcacccttca agcctctctt cttttctctc ttcctatcct   62100
cttttgtggc tcacaacctc ctctcctttt tatgttctat gttcctcaca tcacatccac   62160
agactcattt ttatagataa aaaattagag tctatttcgg actccttttc cacacacaag   62220
atggcttccc acgccattgg ttccgtgcgc atgactttt tcatgccaca aaggattccg   62280
tgctgcaaaa gttttccata tccatgcagt ttccacacac cacaaaaact ttcgcacact   62340
tctcgaaggc ttttcatgct cgaccctttt tggttttcaa ttaaattgat ggatcccata   62400
tgaggaggga ccacaccaat aaatctcctc cttctaactc atatggtagg ttccatcaag   62460
cctgtagcac ctttgcattt tatcagtttt gttcctgaag ccggcttcat caatatatta   62520
gaactatttt cttcagtgtc aacttttta agcttgaacc acttcatctc tagcatattg   62580
acatgctttt ggaaagtatg tcaaattgct caaaattaat cttacggttc tcttttcgt   62640
tagattctag tgcatattac gcactttaac ataagatcta aggaaggaag aggactgagg   62700
taaggtgaag tgattttttt ttgagttggt aatggtacaa aagttatact agaccgtggg   62760
tacctaatct cggagattac catttagatt tggttcttga tcatttgtat agtgatgcat   62820
ttaaaaaatt atttgagcaa aacagtgaat gccattgggt ctgagagatc caaaatcaaa   62880
taacctaaag tatatagatg gttcctttag ctaggtcatg tatgagaaaa aatgatctgc   62940
cgactggaga aaatagatct ttgagctcat tgactgttaa gtcatatcta gtctgtgaat   63000
catctctttg aggattaatg atcaagctat cctttatggg ttaaaagaat aggatcactg   63060
aaatacttat cctagtatac atataatgtg catggcctat ttgatgagtc agactagaag   63120
gttatcacta cttcatcacc tttactgatg agcaatcatg atatggatat gtatgtgaga   63180
tacaaatcta aaagattttg aatggttcaa agaattcaga tatgaagtag aaaagataaa   63240
tcaaaaaatt tttaaaggta cttgatcgga tctagaatgc aataccaaat aaaaaatttg   63300
ttgattatct aaaaaaagtg atatagtttc atgatggaat tcttcttgta cacctcagct   63360
caacggtata tatatgagga gcaatagcac tatatgagat atggtccggt ccatcatgaa   63420
tatcactaat ttaattatta tttatttaag agcaagattt aatttttaaa atttaaatta   63480
gattttttct aaaattggtt tcaccgcacc atatgagata tgatttggtg gataagttag   63540
aggatagatc tgtgagaact catttatagg gtatcccaaa aggtatttaa aatattactt   63600
tttcttccca gtagttgaca atatgattgt gagcaatcat actgttttct taaaaatagt   63660
ggaaggatga actcaaaaag aaagtctcta agaacaacg agtcacaaga cctatacaac   63720
ctatttaaga tgagccagta tatgtagtac ttccttcacc tcatcaattt agtaggatct   63780
cctatctttt agaaagatac tcggtattct tacaaaggat ttagaaaag tgtttccttga   63840
gggagattga gaatataggg atgatctcaa aacctacaat gacataatat aaggaatcat   63900
gtagttacat gaaggtcagt gggagggttc catactgaca tcgattatga tgtggttaca   63960
tatagaattt ttttttcaaa gatctagatc aaacattctg aaaataaaag gtctatagag   64020
ataaatccga aaaggatgtt tgannnnnnn nnnnnnnnnn nnnnnnnnnn nnnnnnnnnn   64080
nnnnnnnnnn nnnnnnnnnn nnnnnnnnnn nnnnnnnnnn nnnnnnnnnn nnnnnnnnnn   64140
nnnnnnnnnn nnnnnnnnnn nnnnnnnnnn nnnnnnnnnn nnnnnnnnnn nnnnnnnnnn   64200
```

| | |
|---|---|
| nnnnnnnnnn nnnnnnnnnn nnnnnnnnnn nnnnnnnnnn nnnnnnnnnn nnnnnnnnnn | 64260 |
| nnnnnnnnnn nnnnnnnnnn nnnnnnnnnn nnnnnnnnnn nnnnnnnnnn nnnnnnnnnn | 64320 |
| nnnnnnnnnn nnnnnnnnnn nnnnnnnnnn nnnnnnnnnn nnnnnnnnnn nnnnnnnnnn | 64380 |
| nnnnnnnnnn nnnnnnnnnn nnnnnnnnnn nnnnnnnnnn nnnnnnnnnn nnnnnnnnnn | 64440 |
| nnnnnnnnnn nnnnnnnnnn nnnnnnnnnn nnnnnnnnnn nnnnnnnnnn nnnnnnnnnn | 64500 |
| nnnnnnnnnn nnnnnnnnnn nnnnnnnnnn nnnnnnnnnn nnnnnnnnnn nnnnnnnnnn | 64560 |
| nnnnnnnnnn nnnnnnnnnn nnnnnnnnnn nnnnnnnnnn nnnnnnnnnn nnnnnnnnnn | 64620 |
| nnnnnnnnnn nnnnnnnnnn nnnnnnnnnn nnnnnnnnnn nnnnnnnnnn nnnnnnnnnn | 64680 |
| nnnnnnnnnn nnnnnnnnnn nnnnnnnnnn nnnnnnnnnn nnnnnnnnnn nnnnnnnnnn | 64740 |
| nnnnnnnnnn nnnnnnnnnn nnnnnnnnnn nnnnnnnnnn nnnnnnnnnn nnnnnnnnnn | 64800 |
| nnnnnnnnnn nnnnnnnnnn nnnnnnnnnn nnnnnnnnnn nnnnnnnnnn nnnnnnnnnn | 64860 |
| nnnnnnnnnn nnnnnnnnnn nnnnnnnnnn nnnnnnnnnn nnnnnnnnnn nnnnnnnnnn | 64920 |
| nnnnnnnnnn nnnnnnnnnn nnnnnnnnnn nnnnnnnnnn nnnnnnnnnn nnnnnnnnnn | 64980 |
| nnnnnnnnnn nnnnnnnnnn nnactatgta tgttggctat gtaggttccg attcgctgtt | 65040 |
| tggaatatga tatacctaga tgaaatctat cgatcttgat agaaaaagag aagtcctatg | 65100 |
| tgattcgtaa gactgagttc agaaaaatct ctgaccagag taagtgtgaa tattgaaaaa | 65160 |
| ttttttttac gaaattcaca aatgaactcg agtcgagcca atgtagcata tgactgatga | 65220 |
| tagagtttga cgagttctca atgacctccg tcaaattggg actctcgata gagggattgt | 65280 |
| atcacacgat aactgcacct agggattcac ttttctattt tgctagcttg ccactatatg | 65340 |
| ttgctagacg tcactggtgg atcgtgagaa ctcactaaaa tcattttcgg atcaacgatc | 65400 |
| tttgctgagg taagttggaa tcgtttcagt ccatcgaaaa gagtttcgat gatactgtga | 65460 |
| tggagatcac gatatgtctc actatcaaac agaatagaac ctgaggagtc acatacaaaa | 65520 |
| agagcttaac ctgatcaatg gcttggatta tatttgaatt atcaattaga ttgatagttt | 65580 |
| gaatattaga aactgctaat ttgtaaccgt tacagttttg acaactacta attgttagcg | 65640 |
| caaggactta attgcaagta ttataatttt tttgaggctg attaaattat aaattaaatt | 65700 |
| ttaattaatt taattcagat ttaatttaat tagacttaat ttaatttaat attaattgga | 65760 |
| ttcaattatc caaatcagat ttggatttca agcctgattg gatcaggctt gacagccttt | 65820 |
| tcgaatttgg ctcattttag actcgatttg aatccgtttg aggttctatt tggatcagat | 65880 |
| aaaccatgac ttagagagct caagtttttt gggactctct ttagaaatca tgtcaaaagg | 65940 |
| agaagtagag cnnnnnnnnn nnnnnnnnnn nnnnnnnnnn nnnnnnnnnn nnnnnnnnnn | 66000 |
| nnnnnnnnnn nnnnnnnnnn nnnnnnnnnn nnnnnnnnnn nnnnnnnnnn nnnnnnnnnn | 66060 |
| nnnnnnnnnn nnnnnnnnnn nnnnnnnnnn nnnnnnnnnn nnnnnnnnnn nnnnnnnnnn | 66120 |
| nnnnnnnnnn nnnnnnnnnn nnnnnnnnnn nnnnnnnnnn nnnnnnnnnn nnnnnnnnnn | 66180 |
| nnnnnnnnnn nnnnnnnnnn nnnnnnnnnn nnnnnnnnnn nnnnnnnnnn nnnnnnnnnn | 66240 |
| nnnnnnnnnn nnnnnnnnnn nnnnnnnnnn nnnnnnnnnn nnnnnnnnnn nnnnnnnnnn | 66300 |
| nnnnnnnnnn nnnnnnnnnn nnnnnnnnnn nnnnnnnnnn nnnnnnnnnn nnnnnnnnnn | 66360 |
| nnnnnnnnnn nnnnnnnnnn nnnnnnnnnn nnnnnnnnnn nnnnnnnnnn nnnnnnnnnn | 66420 |
| nnnnnnnnnn nnnnnnnnnn nnnnnnnnnn nnnnnnnnnn nnnnnnnnnn nnnnnnnnnn | 66480 |
| nnnnnnnnnn nnnnnnnnnn nnnnnnnnnn nnnnnnnnnn nnnnnnnnnn nnnnnnnnnn | 66540 |
| nnnnnnnnnn nnnnnnnnnn nnnnnnnnnn nnnnnnnnnn nnnnnnnnnn nnnnnnnnnn | 66600 |

```
nnnnnnnnnn nnnnnnnnnn nnnnnnnccc catcgaaaag agtttcgatg atactgtgat   66660
ggagatcacg atatgtctca ctatcaaaca gaatagaacc tgaggagtca tatacaaaag   66720
gagcttaacc tgatcaatgg cttggattat atttgaatta tcaattagat tgatagtttg   66780
aatattagaa actgctaatt tgtaaccgtt acagttttga caactactaa ttgttagcgc   66840
aaggacttaa ttgcaagtat tgtattttt ttgaggctga ttaaattata aattaaattt   66900
taattaattt aattcagatt taatttaatt agacttaatt taatttaata ttaattaggt   66960
tcaattatcc aaatcagatt tggatttcaa gcctgattgg atcaggcttg acagtctttt   67020
cgaatttggc tcattttaga ctcgatttga atccgtttga ggttctattt ggatcagatg   67080
aaccatgact tagagagctc aagtttttg ggactctctc tagaaatcat gtcaaaagga   67140
gaagtagagt attatttttt tcatccttct ttcttcacac gcatgaaagg agaggggca   67200
ccaatagttg gtgccctgcc ttatctggat gtcttttca tccaatttttt tttttaattg   67260
aatttgattt aaaatagaat agaaatatct tagattaagg tatagaagta ctttttttat   67320
gtgataaaaa aatagagaa agaggacgtg cgctaattat tggcgtgaga catctttcct   67380
tctttcttcc cttatctcaa cgcacatcta tcctttgatt tgttttgaa caccttggat   67440
taaagagat gagatctctt gggcattaag aaggagttgt gcgtgggatt tgagatgtgg   67500
tgcgacaaaa aattaaaaga ggatgcatga agggaggtgg cgtgcgttag atgcgagagg   67560
cttctttctt acatctttct ctcctcccca atgcctcttc cttccttctc cacttcacgt   67620
ccatgcccag attcaataaa gatcagatct aagaaaagaa aagagagaga aaagagaag   67680
aagaagggtt cttcttttct tcatggtgat ctggtataga tcctgttgga tttgtgcgaa   67740
agagtttgag caacgatctg cttctttaag atctgaaaga aaagatcaag atccatggat   67800
gaagagtgag atctgcaagg tgctagcaca ccagtgatct cggtgctccg atcaaatggc   67860
tccgtgtgga tatcagctga ggtcgaacgc gtgcatggct acgatcagaa tctgcgatat   67920
ctgcaggatc cgagatatgg agattcgatc tccattttat ttttctaaca gtttattttt   67980
ctatttcaga tatcagatcg tgggtacata tttgtatcaa gatctttact atggttttca   68040
gatctgattt gatacgtaaa taaattaaaa ttatttaat ttatttattt tcactgtgta   68100
gatgtctaga aaaattta aactacacgt acgaaatcga agcatttct aacaactctg   68160
actatcacca tagcgacgt atatctcttg cttcccacca aacttcttta ataagttctt   68220
tagccatagc atttctttat cgacctttgt tatggtgatg tattcaacct ccatcgacga   68280
taatgtgaca cttttatgac tttgattgcc acaacaccgc tccctctgag aatatcatca   68340
gataatctga cgtggatttc tgtatgtcca catcatcgat catgtccgta tctgtgtaag   68400
cctgtagcat aggatctcca ctatcatggc ataaatatat cctggatatc tatttaagat   68460
atcttattt ccacttcatt gctttccggt gctccttcc aaagtttgaa agaaaccgat   68520
tgaccatacc atccacttga gcaatattag acctggtgta caccatagca tacataagac   68580
tccccaccac ttagtccttc tcactctttc tgctttgctc tttaatcaat gtaaagtgtc   68640
ctacaagcag acaccaccgg cttcactcta ctcatgttga atcaatccag caccttctca   68700
acataggcct cctatgacaa ccataggacc tggatctcct atctctagca attcttatcc   68760
ttaatatcat tttgacctat cccaagtctt ccgtcataaa tgttcgatcc aactttacct   68820
tcaaatcatt gattttggta atgtggcatc ccacaatcag catgtcatca acatatagca   68880
aaaatttgat aaaattattg tcaaaatatt ttttcatgaa catgcaatgg tcagaactta   68940
```

```
ctttcttata tccattctcc attatgatgg aatcaaactt cttgtactac tatcatggtg    69000
cctgcttcag ttcataaaga tttttcttca agcaacacac tatgttctca ttaacctttc    69060
atttcaaact cttctagtta ctctatatat tctcctcctc caagtcgcca tgaaggaatg    69120
ccatcttcac atcaaattgt tccacctcaa catctaaaca gccagcgaga tcgaggataa    69180
ctcgagtaga cgtgagcttt acaacgattg agaaaatctc ttcaaaatcg atacttttc    69240 tctgaccaaa atcttttcaca actaatctca tcttgtacct tggttataaa ctattctcct   69300
atggcttcaa tctgaacatc tatttatttt tgagtgcttg cttttctta ggtatattca    69360 ccaactcata tgtattattt ttctataaag aattcatctc ctctttcatt gccttcatcc    69420
actcctcact atgctggagc tctatggctt cagagtagga ctcaagctct tccacatctg    69480
ttaatagcac ataatcctat ggtggatatc ttatggatgg cgtccactct cttgtgaatc    69540
tctggacctc ttatgcaggt ggttcaacat gcaactcaat ttgaacacca tccgcactct    69600
cctcagcctc atgactatca tatgtaccgt catctagt tgctctcctg ttatcaagac     69660
ttctcgaaga ggtatctggg cataagtcta tagggctgct cggggttgac ttcggcttct    69720
taggcttctt aaaatcatcg atcgtctgat cctccaaaaa aataatgtca tagttgcaca    69780
cgatcttcca ctccatagaa tcccacaatc gatagttgaa ctctccgtcc tcactatagc    69840
tcaggaatat gcactgcttc accttgacat ctagtttgga tctctcatct ttaggaatat    69900
gcacgaatgt cctgcatcca aagattttca aataatcata agaatatct ttctccaaca    69960 atattctcta tagtgtatca cacttaagag tataagaaaa aaaaagatta atgctatgga    70020
tcacagtcat caatgcctcc ctccagaatg ccttcgatag tttagcataa gagcgcatgc    70080
tcccgatcct ctcgcaaatc atcctgttca ccctctcaac aatctcattt tgttgtggca    70140
tcttaggcac tgtcttctct agtctgatgc catttcattg atagtatttt ttgaaagaac    70200
ccctgtattc accctgttg tccgtccaaa tatacttcag ctttttgccca gtctttcttt    70260 caacagagat gtcaaattac ttgaatatta tcgagcactt gatccttcat ttttaaaata    70320
tatgtccaaa ttttttagaa gtgatcatca ataaaagtca tgaagtaaga acatccataa    70380 aaaatttat cactcagaga acaaacatca ctgtgaataa gatctaatgc accaattttt    70440
cttttagaaa aaaattctaa aaagaaactt ggatttgctt acccatcaag caactttcat    70500
atatcttcaa tccaaaacta tgaataggaa gagcattctt cttagtcaaa attgacattc    70560
ctttttggct tatatgtccc agtcgtcaat gccataattc taaggtagaa gattcttcca    70620
ctacattcac ctcccctta ccgagcttgg cttgtatgaa gtagagaaag ccttgcttga     70680
tacttttggc tactactagc gattttttgg ttagcttcta tttgctgtct ccaaatatat    70740
tgtagtagtc ctcctcatct aatacccta tcgataacaa gttcagatga atatctagta    70800
catgtcgaat attttcaaa aatagcctgt accccaagct cgtgatcagc ataatatctc    70860
caatatcaag gatttttaat tctccatcat tctccatctt tattgtccca aagttactga    70920
aatgacaaga tgagaataat tttcacctca ctgtaacatg atacgaagtg gccaaatcga    70980
tcacccagat agagtctcaa ccaatagtac ttgcaagatc atcatttgtt gtgccacaag    71040
caacgatcat ctctccatcc gtagctactg ctatcatctt attgttcgag ctggagtcat    71100
cacttgatta ttttttgact tctcctttt tagtaatcgg tagtctttct taaagtgatc    71160
ctttttgccg tagttgtaat atctatcact tcgagacttg gatctcttcc gtaatttagt    71220
ggggccatca ttcaagttag attggggagtc cttgtgcttg tttcttccct ttctttctat    71280
gatgagagcc tcatggtggc tcgagacacc ttgctccttt ctcctagcct cctcattaag    71340
```

```
catatagtct ttcaccattg ccaaggctat cgaactatct ggtgaagaat tgcttagaga    71400
caccaccaaa gtctcctaac tatcgagtaa gaaacttaac aatagtaaag cctagagctc    71460
ctcatctaac agcatcttca tcacagtaag ctggttcacc acgttctaaa agttgcttag    71520
atgctccacc atataagctc cctccttata tttcatattt atcagtttgt gaattaggaa    71580
caccttgttc tataccatct ctcttgtata gactttttag tttcaaccaa aggccatgag    71640
cattaacctc cattgaaata tggtggaaga tgctatcatc aatccactgt tggataatcc    71700
caacgatttt atgattcaat ttctcccatt ctttatttga catcttatca aactgaataa    71760
taacatcctc gattggatca tgaaaatctt agcagtaaag gaggtcttcc atgtaaggat    71820
tccagattga gtagttagtt aatgtcagct tgatcgtagt gcccgacgaa gattggttct    71880
ccatctatta gcatcttaat ttcttttttga atactttaga ttttgtaaaa tttggctctg    71940
ataccactta ttgggatttg agtactaaaa gataatagaa aaagcaaaag caaaaatcac    72000
gccaacgata ataccaaagg cacaaagaat catagcaatc gcaagagcac tagaatttt     72060 tatggctcga tcaaagtcta tgtctgcaca gggatgaaaa taaaaagaaa cttttactat    72120
aataatagtt tagagtataa aaacttctct gacactacgc cgacaatact acttctaata    72180
caagaaagaa gaaattcaag attaaacaaa cctccagaag aatcctttt gatggaatat     72240 gaaagaataa tattctacaa gtcaatcgca tgagtaatgc aataagtat tgttctatat     72300 tttatcttcc aaattcatat atttgatatt aattattaat aaaattagat attttatttc    72360
attatatgct gcattttaat acttgtttaa aattataatg aactccatag gttaggacaa    72420
taattttaag gtcatgatga gatcatacca gtgagattta aatctttgat aaccttaatc    72480
taaaatattc tcaatagtag gatcattaag tcaaaaatca atgatactga taaaactggt    72540
acatcctata tattctcgac agagagggtg gttgatgtca taatcacttg tgtggagaca    72600
ctaatacgaa gatgtggtgc tcattagaga ataagttcat tgaatttact gatcgagaga    72660
atatatgatg caagtgatcc tttgacctaa gatcaccatg gtgccttgta tatatgaatc    72720
tatgttttgg ttcattcttt agcttcattt tttgagcctt gtgtgggtg ctccggacat      72780 ggtgcagtat gtatggaggt tgtgagtggt caacaaaaaa tcaatcactc cttgtaaaag    72840
gagcgaatat cttatgtgat cttataggtt gatccaaaaa atctttgacc aaagcagaat    72900
gataattaga aagagttttt aatatatcat taactgaatc aatatcttct gatcgagata    72960
catataaata agtatttgaa tttgacatga ttttatatcc ataactaatc tgaaatattg    73020
tatgattgaa gaattgaatt gtacaatttt ttaccattga aaaaaatttt tgatattttt    73080
tttcaaattt aatatctttt tgatagtcat gacatgttgc tagacatcaa tcttgacttg    73140
tgggctcaca aaaattaaaa agatttatt tgaaagttaa ttagaaagta ttctgattaa       73200
ttgatgtatt tggactgacc taatctaatt ggattgattt aggtcatgag cttgagccca    73260
ctgctggcta gatgatcgct gtcgtaggca gtcaagaata aaaatcaact caaactatat    73320
agatagggtg agtagggatc atttctatgg agatctagga tgattatctt ttttttttaag    73380 aaaaaataaa aagagaattg attgtagaag aattaaaaga aatagaatag caagaattaa    73440
attaaaagta tgaattaatt tatgaaaaaa aataagtcag agaaataact cagaaatttt    73500
gaatccacca tgcaaattag atttatttc ttcttttttt tatgttgcaa cattaattct      73560
tgtgattaag gtattagtat agcttatctc taagagatac ggactgtatc agtagattac    73620
aactcgtcct gttgaagtat aaactatcta aattcaatta caaaatataa gattcaatct    73680
```

```
aacatactac gatctatctc tccaaagcac gtatcgtatc tagggatcac gatacgtcaa   73740
tagagggtat aagccgtgta ggctggatca atacctcaaa aaaaaataaa aagatatgaa   73800
ataaaagtat aattttatta cataaaaatt taatataaaa aaaaaccgtt tacaggcttt   73860
atcatatttc tggattgaag agatttagcc acgcatcaag ctctctagct ccataatctc   73920
tcaataattg atccctaaag ctctttaatt ttttttttta ttattttttt gtttttcttt   73980 taatttttt ctcttcttat ttttgctgcc atctgctgcc tctgttttct ctgctcctgc   74040
tgcctccttt tatagagcac agcttcttcg aattataagc atctatggac tttcaattcc   74100
cactatcttt tattttgatt gggattttaa aactttatcc gcatcccagc atcttgtttc   74160
acgcgagatc ctagcgtcca catgtgtttt gaattcctta tgggccacag accatttaaa   74220
ccaccaaaga ccactttact attttgattt gaatcccatg gaagccggct gcctctggtc   74280
tcattcaccc ttccagtgct tcacatgggt cccattaatt tgaattccta tgagccacat   74340
ccaagctttt gaatccaagc cttccttatt ttttaaatca attaaaactt tgctttaaat   74400
gccttgtaga ccctcctatt tgcatgctac gtgagaacat tgttaagctc ctcttggccc   74460
acttaagaac ttctatgggc tacatgcttt tggctagctt taaaatggtt ttgggcctaa   74520
ctttggatca ccattcgaag tccatttga attcaattta tttttatttt ttttttaac    74580 ctacaaatcg agctctttta ttggtgatca ttttcctat aaaacaaaaa caaaaagcat    74640
caagtcttaa gaaataaaag ttaattaata tatattttga tacttttatt gggatattta   74700
atgtacttat cactagatat gaaatccaat gggtcacaca ctttgaaatt tgatcttagt   74760
ctaatctaac taggatttat tataaatctt atgggttaaa tttacatgct agcacatgaa   74820
ttaactcaag tttcaattg gatttagttc taaggtgttt gagctaaccc tatcctgata    74880
ccttaaacct aattagatta gatttgaacc tatggttttc ttgatgcctt atgcttatta   74940
catgaaagag tttcatgtga cttaaattcc tccatgccac cacatcttca tccatgccaa   75000
attaatatgg aacaccccat ttaattgtgc atttaagaag gaatagtcct tcttaaacac   75060
tcctcttaat ttcccacact ttcctttgtt ctacacacca tcaaatggct tttggaaata   75120
tgcgggcgca gaagtggagg tgtcctatat gaaggctctt ccacattata agttatcaca   75180
tggtgaatta aattattgtg tgagaaaatc atgcgccaag agttggcacc ccttgggagt   75240
tttaggcact ccttcttatc ctataaataa ggggcacccc atatggataa atacaaggga   75300
attcaagttt aggcatgaga ttgagaggag aaaaagacac aaaaatctga aaaaaagata   75360
agaaaaaaaa agagagaaaa atagaaagaa aagacgagag aaaacgaaag gcaagggttg   75420
ctaatcctag ggttcaattt ttcaatagtt ggatttctga atcaatttgg ggtggtgaga   75480
ttttttgaga aaaagtttct gatgtggccc tagtagaaga ttgaaggcat tcagatgatg   75540
gtgcaatccg ttttgaaaa agaaaagtga gtagtatact tgtgaagaaa gctgcaacac    75600
tacatcaaat tggaaaggac cttgatcaaa cccatatgga tcaccgttgc aggatatcta   75660
ctttggtatc ttgtgaaggt tattttttt atcagatcat catcttcaaa aaggtataat    75720
tttctaccta atatgcatgc ttgatttgtt tgattaaaat ctataaagtg ttcataaggt   75780
ttgtgttctg attgtattgt tttaagtatt aaaacttact ttaaaaatat aaaaaaattt   75840
gaaaactatc ttctactgtg caactaaaat ccaacagaat aaccctaata tgagattgag   75900
cgatctccgt caaccgatgt tctctgatct tcttttcttg aatgaagcct cttcaagcct   75960
ttcttcttct ctctctctcc ctatcttctt ttgtggccca cggcctcctc ttcttttat    76020 gttttgtatt tctcatgtca catccataaa ctcccttta tagataaaaa attagagtcc    76080
```

```
attttggact cctttccat gcttcccacg ccattggttc tgtgcacacg actttttcca    76140
tgctacaaaa gttttcatg tctcacgtag tttccatgcg ccataaaatt ttgcatactt    76200
ctccaagact tttatgctc gaccctttt ggttttcatt taaatcagtg ggtcccatat    76260
gacgagggat cacaccaaca tcatatgctc tcctcaccat accaaatggt atccccaact    76320
ataagacaaa acattcatca agttgctaac agggttgaag atcagcattc actatagaaa    76380
ttttgttttt ttgctaacag acgaaaagca tcaccaaagg catcaaaacc attggcatag    76440
accctggggt gttttaccga cagacacaaa aagcatcaaa aatatccct atcagcaaag    76500
agttttgctg atgctttttt tttcatcacc ctttatcgat actttttac tcgtcgataa    76560
atcatcgaca taactctcaa aaaattgatg atccctattg aatgtcagca taactctaaa    76620
gcctttagtc atgcctgact aaaccatcag caaaaggctt atttttagtg atacctgagc    76680
agtctattac gaaaaatctg aataatatgc tagcaatttt attgtaaatg cacaggagtt    76740
tcatgcatac atttcaaaaa ttttaataa aaaatatta gattaaatta tttaatctac    76800
aaatgcatgt ataagatctg accttaaaac tactataaat ggatcgatga catgaattta    76860
tatacataaa aatctgaatc taaaatgaca agcatatgaa ccaaaaacag catttagtaa    76920
tagatctaat ctaccacttc tagaattccg aatccaatac ctaagtgtgg gtagttgaac    76980
tccatgatca aaaatgtaga tctgaaaatc ttctctggtc gctcatagcc gcacaagcat    77040
ccgacctcta cggatggttc acacgaagct cctcggacct atcagctctc tgcgggagtg    77100
ctagcttgtg cagtcagttt ctgatggtag attgacttga tctccttctt cgattatctc    77160
gaacctttt aatgttgaag atggatcaga ggaagatgtt ggatggtaga gaaaaaatag    77220
atgaagactc tcttctcttt gattttttc ttacccaaaa atctgaaaca gttctaggtc    77280
tctcacccga gaggagaatg gtctcttctt ttgttcatgc caaggaagaa agaaaaccac    77340
ccaaacctta caccccaaag aaaaatttg gcccctcttt ctctctagta tcacacaatg    77400
aaaagttctc tcttgttggc acacaaaatt atggtcattt tatggttgtc gcacaaacca    77460
ggtaagacag gataagagcc agagtttgtt gcaattcaaa ccattttaaa tttcaattta    77520
tcttcaactt tttctcactc ttatctgact taaagagaga cttataagag aaaattgggt    77580
ataaaaaacc atcagaaaga cttccttttc ttacacacaa taggcccctt caaaaataac    77640
caacgtgtgg aaggatatgg ataaggtttt aggttgaaat tcaaatcatt ttgaattcaa    77700
atcaaaatca atcaattcct atccttaatg gatgataaaa gaagggttat cttctaattt    77760
tatcatacat aaactaattt tgtacggtga gaaaagacgt aagataattt gggtggtgca    77820
agggagagag tcccattcat ttaggactct agggtttaac caattgaatt tttttcaaa    77880
cccaatccaa ttagatccaa ttaaaatatg atgaacctaa tctaattagg ctcctataat    77940
ctttattaaa tttaatcaat caataaatta attgagccat agacctgatc aaattaggat    78000
catttctctt ttaccgatta ggtcatctca taacctaatc agacttgacc tgattgaatc    78060
caattcaatc aaacttgata cagacttcaa tgctcaatca aattaagcta attagtgatc    78120
tattcactaa ttaatcttct attaatgata gtgatccaga ctcttctcta gagtctccgt    78180
ccagtgggac tctccagcag agtcccaatc tagtgggact cttcaccaga gtctccattc    78240
attgggactc ttcagattag ccatgtgatt ggagagaaac ttttaatgtg aatccatcat    78300
ccacatttta tgtgaatgac a                                             78321
```

<210> SEQ ID NO 2

```
<211> LENGTH: 15569
<212> TYPE: DNA
<213> ORGANISM: Elaeis guineensis
<220> FEATURE:
<221> NAME/KEY: misc_feature
<222> LOCATION: (11900)..(12834)
<223> OTHER INFORMATION: n is a, c, g, or t

<400> SEQUENCE: 2
```

| | | | | | |
|---|---|---|---|---|---|
| actacatttt | aacaccaagc | tcgataatag | tgataaagaa | acatctagat | cagctttata | 60 |
| atcaaaaatt | ttgacttaca | attttacgtg | tgtctcaaaa | tcttgaataa | atataaataa | 120 |
| gatcttttat | cttgatccaa | aaatagtaat | caaggatttc | attagtaact | tcaacaacaa | 180 |
| tggtaaaaaa | attttctatc | cattgataaa | cccaaatttt | gaattgaagt | ttcatgcata | 240 |
| ccatatagcc | tttaataaga | tctattattt | ggatctaaag | atagtaatta | aaattgttaa | 300 |
| tgattccact | aagatgaata | ctttacaatc | tcataattaa | tttcttcaat | aaaaatagac | 360 |
| ttcttgataa | tgtctccaat | tgtatatttt | tttttatttc | tacaagaaaa | cttcatacat | 420 |
| tttttacgtt | ccaatataaa | tcttaaaaag | ttattccaat | caaatatcat | aaaagatctt | 480 |
| cttagtccaa | ccttaaataa | cttttatgaa | tgaatcttta | tcttgccact | aaataatgaa | 540 |
| ttttaaaatc | aagagcaaca | tcacagcatt | ctgtcatgtc | aaatttgtgt | tagatgtatg | 600 |
| tcctagaaat | caattagatt | gacaatgtaa | atttttaag | gatataattt | atatattttg | 660 |
| atttattaat | aaaataaaat | ttaaattaat | ttttattcat | attttttat | ctatgaatca | 720 |
| tctaaagaat | aataagatg | atgatacata | ttcttaagag | ttcaaaattt | gaaatatatg | 780 |
| tcattgatga | ttaatttctg | aatactttg | aattcttaag | agtttagaag | atcttgaccc | 840 |
| aagtagtgtg | aatagtgaaa | aaagttttc | acatacttca | catcaaaaat | ttaagttgaa | 900 |
| taaattgtac | atatgacagg | tattatagtt | tgacgagtaa | tctataacct | ctatcttatc | 960 |
| aaaattctga | tagaaagatt | gtattgtatg | ataactgtac | ttagaggttc | accttttatt | 1020 |
| ttactggatt | accactacat | gttgctagat | gtcactggtg | gattgtgaga | tctacgaaga | 1080 |
| ttatcttgat | gatcgataat | tctcattgaa | aagattgaaa | ctattttaat | gatgttgtga | 1140 |
| tagagatcat | aatatatctt | attatcagac | agaaatagaat | tctatgggat | catacacaat | 1200 |
| aggagattaa | gactgatcaa | atagttgaat | gatgattaag | aatcattacg | gagttcagat | 1260 |
| tatcaatata | attgataatt | agactaactt | ataattgtta | caagtagcaa | ggacttaact | 1320 |
| gctaaaggtt | aataggttca | aaaagaactt | atgtataaat | gttgtgcatc | ttaatttgat | 1380 |
| tggatcaaat | tagttatggc | tgaattcaag | atgaatcaaa | taggaatttg | gttcaattga | 1440 |
| atttgggtca | agcttaggc | ttaggtcaca | tatacccaaa | atcatttgga | tgcatcaggt | 1500 |
| gtgtgacacc | tgaatcaggc | ctttctaaac | tattttgagt | aagtttgatc | aagtcaaaag | 1560 |
| gatccacacc | ctaaggtttc | ttgaataaaa | ccttaggcac | cacattgagg | acctatagga | 1620 |
| aactttgacc | ctctctcata | tggggtggca | cactgaggtt | ttataaaaac | cttaggcacc | 1680 |
| cattttagcc | ataaaaaaaa | agctccaagg | gatgggggcag | tagccatgaa | gaatccttgg | 1740 |
| ctgtcaggac | tctattcaaa | agagttctca | aggttttgga | ctcttatgga | gccctaggat | 1800 |
| ttgtttgcct | ataaatagat | ggccacccca | aggcttaga | taatgttaga | gacttgtgaa | 1860 |
| gctctcccct | ttctcttggt | tgccggccca | ccctctctcc | tctctcttcc | atgccccaag | 1920 |
| acttctttct | tgtctccatc | atcttgctga | aatttagatt | tcagcaagaa | aagtcaagta | 1980 |
| gaagtcaaag | ttctaatgta | gctcacaaga | tgttgagaac | ttcctccatc | tggcaaaggt | 2040 |
| tctgcaagag | agctagcatc | ctgagaaaca | aaaagattgc | tgatcagccc | tcatctccat | 2100 |

```
atggatattt gtagagatca gatgcatgca tagctagaag agaatcttat cacgatcatc   2160
actcgtgaag atcatctacc tgtgcaaagg tatgagataa gaaaaatatt tttttatca    2220 taattcatga atcctttgct tatattatac tgagattctt ggaatggatt ttttctctag   2280
taaaactcta gagatcagat ctcgaagtct tcttcatata aaggttttga aagttcttta   2340
tattttcgct gctttgattc aaaataaatt agatctattt tgccttttcaa cctttctcat  2400 atttattgac atataaagct ttaattaatg agattaatga aaagcatgtg cgaaatactg   2460
agaaaatcct aacagtgata tcagagctac ttttgtacat aagaaaagga ttcaagttaa   2520
ataaaatctg tttgatttaa gtaaatgaat caatcaaaat ttatcctaac ataagtttgt   2580
cctggtataa tggtcaagac cattatgttg aaaggttatc ctaggacaaa aagtctaagt   2640
aaaatctatt ttatttaagt aaatgaatca attaaagttt attctaatat aagattgcct   2700
tagcataatg gtgaagaccc ttatgttgaa aggttgtcct aggatggaaa gtgattgatg   2760
agacaaatat atcatgaaag tatttttcac agatggaata aaatatatat attttgtttg   2820
tgaaaatgag atttcatgaa tgtgtttgtc attcaatatg tgtggtgatc atcttgaatt   2880
gccacaaatc cttttggat tagggttgta tcatgactca caaatcctga tggtttgcaa    2940
aattttgcat tctgtagtga tagaaaccaa aagttaatcc agttttggaa taagattgat   3000
caattggtat ctaaggcaag tatttttataa tggtggttac ttaattagtt ataaaagtac  3060
gaagagtctc ctaccaatct tacacttatc tagccaattt ggttgattga attctgaatt   3120
tgggttgctt aagtgttaag ttcactacaa atatattgca accatgattc cgacttagtc   3180
aaccaagcct agatctcttg aatagattca tgttaattat ggatttacat aggatataaa   3240
taaataatta aaacttgaag agatctaaat gaaaccttct cgtacatatt aaatcgaatg   3300
atcttccatc attgtagata tacggatact ctactgatgt tgatgatttt cgactagata   3360
tagtactttg gttgcatcga aaaagtacaa ccactttata acatgagatg ttgcagggta   3420
gagatggggt tgggcccaat aattgttagg tgaggatcca aatgatggct gcacttgcgt   3480
gtgaatggcg agtctgactt aattaagaaa tagagctaat aactattaga tgaggcttca   3540
ggacttagag acttatgacc actacaactt acttgagaag caatggataa agagtcgtct   3600
atttatcaac tgacgcatca ccaataacta tcagatggag tgatgtataa ttagtgggac   3660
tatagtatcc acttgaaatc ttaatcgtaa aaattttgt ttctccacct gaagagcatg    3720
ggagattcga aaaatagtg ggggtagttt attttttaaaa taaagctcct aaaataaact   3780
aaaataagtt aaatacaaag tctaactaga atcttcttct ctctgtagaa aatatctgct   3840
tccaacctct atttcatatc cttaagacta attgtttgac tagacccagt tataaagatt   3900
gactctaaaa cttaaagata gtcttgagtt ttgaaaagat gagctatgtc ctggatcaag   3960
atatcctctc tctaccagct tgtcccaccc ctaatcaagg ggcatcctat gaaaagtggt   4020
taaacgatga taacaaggct tggtgctgtg tgctgacatc tatgtccatt gaactccaat   4080
gccagcataa gggtacaaac tgtccaaggt atattgactc atctacaaga gttatatagt   4140
gagtagagcc atgtatctca ctaggaagta tttaagagac tcttcaagat gaagaagtat   4200
gatggatagt ctgttaatga tcattgtctg ataatgatca agaacttgaa agaacttgag   4260
aagctcgata tgtctatcaa taagaaattg cagattgatt tgatcctaca attccttact   4320
gattcatatg tgtagtttat tataaactac catatgaata aaatacagtg caccaaggtt   4380
gagttgttaa atatactgat aactactgaa gggacctcga agagttcaag aggcactgtt   4440
```

```
cttattatgg agcagacctc atctttcaag aaaaagtcta ctgaaaagaa gaaaaagttt       4500
gtgaagaagc agaagttaga gaataggcca aagaaagaag ttttcaagaa gaaggccaca       4560
aaaaaggaaa agtattttca ctgcaactct gatgaccatt ggaagagaaa ctattctgat       4620
tatgtggcaa gcttgaagaa caaaaaagat agcataccett ctgaagatat gtctgatctt       4680
ctcgttattg aaactaatct tacaatttct tttactttca gttaggttat agactctagc       4740
tctagtgctc atctatgcac ttctatacag gatctggagg aaagtagaag gctgaggaaa       4800
gaagaaataa tccaacaagt tgaaaatgat gcaagagttg ttactatggc tgtggagatc       4860
tatcctctac gactaccatc tgatcttagt ttaattctta gagactgtta ttttatacct       4920
actgctagca aaaaattgat ctctattca tctctagcat aggataatta tgtattaaat       4980
tttaataaag attattatac catttatttg aaaaataaaa tggttggacg taattttta         5040 attgacagtc tctatcattt acatgttgat gtatctatga atgtaaccaa gcagaaagtg       5100
aatgccatag gatctaaaag atctaaagat gaaataaatt atatgtggca cattaggcta       5160
gatcatataa gagaagaaag gattaacaga ttggagaaag atgggctctt gggcttattg       5220
actactgagt tatatccgat ctgtgaattc tgccttcaag aaaaaatgat caagctgccc       5280
tttatgaaac aaggagaaaa gaccattaag atatttgccc tggtacatat tgatatatgt       5340
ggcccattaa ttcgatgcgc tggtcaaaga aggttgtctc tatttcatca tctttatcga       5400
taattattca cagtatggat atgtgtatct tatgagatac aaatatgaag tctttgaaaa       5460
atttaaaaaa tttagaaatg aagtaaaaaa ataaactaaa atttttttaa agattttca        5520 atcagattga aaagttgaat accttaatgg agaatttcta aattatctca aaaaaaatag       5580
catagtctta taatggactc catttggaat gtcttaactc aatagagttt cgaaatagag       5640
aaatcaaact ttattagata tggttcggtc catgattagt ttcattgacc ttctcttatt       5700
tctttggaga tatagtttac ttaccactaa ttatctattg aatagggttt cctctaaaat       5760
catttctacc acattgtatg agatatggta ttgtagaaaa tcaagtcttg atcatatcaa       5820
gatttaagga tatccgaccc atatcaaaat atttcagacg gacaagttag aggtcagatc       5880
tatgaaagct cggttcaaaa gtatcttaag gagtctttag gatattattt ctacttttca       5940
gaggatcaca atatgattat aagccaacat gctctcttcc ttaaaaaata gttcatgcaa       6000 gatgaagta gtaggaggca gattgagctt gaagagagtc tctgaagagc aatgagtctc        6060
agaacttacg taaaacctat ttaagttgag ccaatacaca cacctcttcc tccatctcgt       6120
agatccagta aaattttca ttctcctgag agatacttag gtatcatcat agagaatgta       6180
gagaaaatat ttctcgtgaa aaatgagaca tatgaaaatg accccaaaac ctatagcgag       6240
gcaatatcaa atatcgacta taagaaatgg ttagaggcta tgaagttaga aattaactca       6300
atacacttaa accaagtctg aacctttatg gatccgtcag aaggtatggt acctattatg       6360
tataaataga tctacaaaag aaagattggt tttgatggaa aggtagagac ctttaaggta       6420
aagcctgtga ctaaaggtta tagctgacac gaaagcattg actatcaata tatttttca        6480 ctagtagtta tgctaagtcc atttgaacat tacttgcgat tgcagcatat tatgattata       6540
agatatgaca gatagatgtg aaaactattt ttctaaatga atatctttag gaagttatct       6600
atatagagta gactttgtgt ttcacttcca gtgatggcga tcacaaagtt tacaaattgt       6660
aaagatctat ttatgcactc aaacaagcat cttggagctg gaatacttat ttcaatgatg       6720
taatcaaatc atttagtttc atcaaaaatg agaaagaatc gtgtgtgttt aagaaaatca       6780
gtgggagtac tgttacttt cttgtattgt acgtggatga catcctcctg atcgaaaatg        6840
```

```
atatttttat gttaatttta gtcaaaatat agttgtctaa gaaattctcc atgaaggatc    6900
ttggggaagc atcctatatt ttggagataa atgtctatag tgataaatct atgaggatgc    6960
caggcctttc acagaagatg tacattaagg aagtgctgaa gaagttcagc atgaaaaact    7020
ccaagtggag acttctatcc ttcaggtatg ggattcatct ctccaagaag gtgtgcctca    7080
acacatctta agagatacag tacatgagca aaatccctta tactgcggct ataggaagtc    7140
tcatgtatgt catgttatgt acatgacctg atatagctta tgttgtgagt gtcacaagta    7200
gatatcagtt gaatgcaggt gaaaaacact ggacatctat gaaatgtatc cttaagtact    7260
tgagaaggat taaggatatg ttcttgatct ttagaggagg agaattaagg gtgcaagaat    7320
ataccgactt aaattttatg tttgatattg atgatcgaaa attgacatca gattatattt    7380
ttttatgcaa cggtggtact gtgagttaga aaagtttcaa gttgcctatc atagcagact    7440
ccattataga agatgagttt ataatcacat ggaagctac caaagaggca ttctggttta    7500
aaaaatttat tacagagctg gatataatgc catcagatgt cataccactc tactgcgaca    7560
acaatagtgc cataactcta gctaaggagc tgaggtctca ccaaaagtct aagcacatag    7620
agcaatgatt taatctcatt cgcaattatc tcgaaaaaaa tatatcaagg tatagaaagt    7680
agatactatg gataatatga cagacccact aactaagtag ctgagtcaat aaaaaatcga    7740
agtccatctt gagaagatgg gacttagatt tgtggccaat tgattttagt gcaaatagga    7800
gattgttaga tgtatactct aaaagtcaat tagactgaca aatataaatt ttctaaggac    7860
ataatttata tattttgact tattaataaa ataaaatttg gattaatttt ttattcatat    7920
tttagtatcc atgaattatc caagagatta atatgataat gatatatatt ctcaagagtt    7980
gaaaatttga acatacgtc attgatgatt aattttgaa tgctttcgat taatggatga    8040
tcataaggat agtaattaat ccgatcaatg tacaaatcac ttcttttttg atagacgagt    8100
ctcgagtcta tactatggag acactggagc aagagtgcag gtatttgtta gagaacaaag    8160
gtatcgagcg tgactaatac gagaagtcaa ttggatggct atccactcgt taatgactta    8220
tttgatacta cagtagtatg tctagtcctt agatctgcaa tgcctcaggt gttcataatg    8280
agactgttag agtttgactg tacataaact tgatttctag ccatatggat ctttatagtg    8340
catgttggct acagtaggtt cgttgtagga ataggatgtg cacatagata gaatctatca    8400
tccttgatag acaaaaaaaa tgatcctata taatttatga gactgagttc aaaaaatctt    8460
gactaagaca gtgtgaataa tgaaaagaag tttccacata tacttcac atcagcaatt    8520 ccagttaaat aaatcctaca tataataggt attgtagttt gatgaataat ctataacctc    8580
catcttattg aaactctgat agaaggactg tatcatatgg taactgtatc aagagattca    8640 tctactatt tgctgaattg tcactacaaa ctgctagatg tcactgatag attgtgggac    8700
ctatgaagat tatcttgatg atcgatgatt ctcatggaga agattgaaac tatttcaatg    8760
atgttgtggt agaaatcaca atatatctta ctactagata gaatagaacc tatgaggtca    8820
cacataataa aaatttgaga ttgatcagat tgttgaatga tgattaagaa ttgttacagg    8880
attcagatta tcaatataat tgataattgg actaacttgt aattattata agtagcaaag    8940
atttaattgc taaggttag cagattcaag gaggacttat gtgtaaataa tgtacatctt    9000
aatttgattg gatcaactta gttatggcta aatttaagat gaatcaaaca gggatttagt    9060
ttaatcgaat ttgggtcaag ctttgggctt aggtcacatg cactcaaaag ggtttggatg    9120
catcaagtgt gtgacaccca aaccaagcct ccctaaacta ttttgagttg gttttgacca    9180
```

```
agtcaaaagg gtccacaccc tagggtttct tgaataaaac cctaggtgcc acattgagga    9240
ccaattagga aactttgaca ttctttcaca cggagcagca cactagggtt tcatgaaaac    9300
cctaggcacc cattttagcc ataaaaggaa agctccaagg gatgggatgg tgccatgaag    9360
aatccctggc cattgggact ccattcaaaa gttctctagg ttttgggctc ttatagagcc    9420
ctagggtttg tttgcctata aataggtcgc taccccaagg ctttagataa tgctagaggc    9480
ttgtgaagct ctctcctttc tcttgtttgc catcccacct tctctcctct ctcctccatg    9540
cctcaagact tctttcttct ctccatcatc ttgttgaaat ttagatttca atgagaagga    9600
tcaagtagag tcagagttct actgcagttc tcaaggtgtt gagaactttc ttcatcaggc    9660
aaagattctg caaggagtt agcacctcaa agaaccaaga aagttgctaa tctgccctca    9720
tctccatgtg gatacttata gaggccaagc atgacgagaa gagccttatc acgatcatca    9780
ctcgtggaga tcatctaccc gcgcaaaggt atgagataag aaaaaaatat ttttcttatc    9840
atgattcatg aatcctttgc ttatgttaca ttgagactct tggattagat tttttctcta    9900
ataaaatttc aaagattaga tctcgaagtc ttcttcacct aaaggtattg aaagttcttt    9960
atattttcgc tactttgatt caaaatagat tagatttgtt ttgccttttca attttttctca   10020 tatttattga gatatgaagc tttaattaat gagattaata aaaagcatat gtgaaatact   10080
gagaacatcc taacaatttg agcttacaat tcacttaaac aactaatgat caaattaata   10140
atcacaatgc acaataaaaa ttcatgataa atcttttgt tgttacttta gatcaaaatc   10200
caactaatca taacatgatc cacggattgc ctatcatata tcaaaccctc tgaattatta   10260
atcttaaacg atcttttcat tcatgatcat aagatttagt taaaaatcat gaagacaact   10320
tatattgtaa tcatcataga tctgtatctt aacatcctta gtgtttaccct acctatactc   10380 atcctatgtt tgattctata tatcataatt tattcactaa tactttgata tcatataaat   10440
tatcgcatcc ccaatctaag atcatattgg tactttaata tttcattagt ggggggttatg   10500 cattagtact ttgataccctt atcagttgaa tggttaaaca ctggtacttt gatatccctat   10560 cagtggaggt tatacgctgg tactttaata tcctatcagt aagatggtta aatactgata   10620
ctttgataac ctcccagtgg gtgttgtatg ctagtacttt attatcctac caatggggca   10680
gttaaatgct actactttga tacgctacca atgggatagt taaacgctag taatctaatc   10740
ttagcttgac ataaagtaac gtcgactcga gtttagggtc gactcgagag aatgttaggg   10800
ttagcttgat atgaaagagg gtcgctcgtc aatattttgg agtcaactct tgtttatgga   10860
tgatctagaa agtgtcagag tgagctcgag tactgcatat ttctgataca ttgtctatgc   10920
tagaatgtgc tagaactgat tatcttcttt atcaaagttg attttttgagt aacttgatga   10980 tcaatttttc taggctagac ttgctttgtc aaaatgagca cttgttagtt tagagaatct   11040
tcacctacac atgatctcaa gcattcatta gtaccaaaaa tacttaagta ttttgatatc   11100
atcaaaatca attcttgggt taacacaata cttttcaaat aataagcata cagatataat   11160
cctataacaa tttaaatttt gttcatatat caatttctttt aaaatatta tattcatctt   11220 gatagctatg aactaaatca aaatacatac tagtatacaa cttttactgg gagagtatta   11280
gattaccagc atttaaccat cccactggca aggtatcaaa ttaccaatac acaaccccta   11340
tttataaagt atcaaagtac cagtgttcaa ctgcctcact ggcaggatat catagtacta   11400
gtatttaact accacattga caggatatgg aattatcagt atttaaccat cattagtaga   11460
attttgatgc atagtcaggc tgcgagtcaa aatctatctc aaatcaaaat attgatcaca   11520
tgtctaattc tgtatcataa ttcattccct tatgctctaa tattatatta attgtcatac   11580
```

```
ttctagctcg agatcatgag ccaaggattg cagtaactac cgcatactta tagagaactc    11640
tttctataag catacaagat attctaaata tactatcaat atatcataga gaaattaatt    11700
taaataacta aaagttaata ttcaattaat aaattcaact ggcaaatgta tttaaaaatt    11760
ttacatcaaa taaatcttga ttaataaata ttaattaata acaatagatt taaatcgaaa    11820
caaggttgat attgttagaa tttgatgcct caagattcag cccacattga gtccacagtg    11880
aggttcgcga cgaaaaatgn nnnnnnnnnn nnnnnnnnnn nnnnnnnnnn nnnnnnnnnn    11940
nnnnnnnnnn nnnnnnnnnn nnnnnnnnnn nnnnnnnnnn nnnnnnnnnn nnnnnnnnnn    12000
nnnnnnnnnn nnnnnnnnnn nnnnnnnnnn nnnnnnnnnn nnnnnnnnnn nnnnnnnnnn    12060
nnnnnnnnnn nnnnnnnnnn nnnnnnnnnn nnnnnnnnnn nnnnnnnnnn nnnnnnnnnn    12120
nnnnnnnnnn nnnnnnnnnn nnnnnnnnnn nnnnnnnnnn nnnnnnnnnn nnnnnnnnnn    12180
nnnnnnnnnn nnnnnnnnnn nnnnnnnnnn nnnnnnnnnn nnnnnnnnnn nnnnnnnnnn    12240
nnnnnnnnnn nnnnnnnnnn nnnnnnnnnn nnnnnnnnnn nnnnnnnnnn nnnnnnnnnn    12300
nnnnnnnnnn nnnnnnnnnn nnnnnnnnnn nnnnnnnnnn nnnnnnnnnn nnnnnnnnnn    12360
nnnnnnnnnn nnnnnnnnnn nnnnnnnnnn nnnnnnnnnn nnnnnnnnnn nnnnnnnnnn    12420
nnnnnnnnnn nnnnnnnnnn nnnnnnnnnn nnnnnnnnnn nnnnnnnnnn nnnnnnnnnn    12480
nnnnnnnnnn nnnnnnnnnn nnnnnnnnnn nnnnnnnnnn nnnnnnnnnn nnnnnnnnnn    12540
nnnnnnnnnn nnnnnnnnnn nnnnnnnnnn nnnnnnnnnn nnnnnnnnnn nnnnnnnnnn    12600
nnnnnnnnnn nnnnnnnnnn nnnnnnnnnn nnnnnnnnnn nnnnnnnnnn nnnnnnnnnn    12660
nnnnnnnnnn nnnnnnnnnn nnnnnnnnnn nnnnnnnnnn nnnnnnnnnn nnnnnnnnnn    12720
nnnnnnnnnn nnnnnnnnnn nnnnnnnnnn nnnnnnnnnn nnnnnnnnnn nnnnnnnnnn    12780
nnnnnnnnnn nnnnnnnnnn nnnnnnnnnn nnnnnnnnnn nnnnnnnnnn nnnnaagata    12840
ttactaaatt ttgcttctaa tctcactctt aaatagtact taccttttgaa actaggcatt    12900 tgaatctgaa aaagaaagag gagattatga gcttgatagt tcagtaaatc atgaataaat    12960
tagctaaata aatctatgaa taatagtata ttaaaaataa atatgtaaga tacaataatt    13020
caaaaatgaa ttcatatata taatactttc caaataataa gtatgtggct gcaatccttt    13080
cgtaattcaa attttgttca ttaattattt ttttcaaaac atcacatgga tagtcatgaa    13140
ctaaatcaaa gtaccagtgc ataacccctta ttgataaaga atcaaataac aagtgtttga    13200
ctgcctcatt atcaggatat caaattatta atgcataacc tccactgcta gggtatcaaa    13260
gtagcaacct caatcacctc actggaaggg catctagttt cagtatttaa ctactccact    13320
ggcaaggtgt taaattatca atatttaacc tccactgata ggattttgat atatagtcag    13380
actgcgagcc aaaattcatt tcaaaccaaa atattttttct caaagacata ttttatgttt    13440
cacattgaaa aattcacaaa aattatgcga tattgaaatc aattggataa aatccacgtc    13500
aaatttagta tattcaatca taaatcattt actattctag aaaaggtata ttaaaagtat    13560
aatgcatcaa tttcataaat cataaatatc tcaatataaa aaatatttta ttatttatta    13620
ataaatctag gagaagtgaa gcattactta tcttgtaagt aaaactaacc aactgatcaa    13680
attaattctg agaatctttc tcaaaactca tcaccactat atcaaaaact tgtgcttctt    13740
gctatgtaag agcatagacc ctttcttcga tctggggttc caagtttcta ttttatttg     13800 ttcaactatc aaattagact gacttttcat tttttttgtgg atattcagct attttatggc    13860
ctttctaaca ataaccaaag tatgtaccaa tattccaaca ataatcattt attgcatgat    13920
```

-continued

```
tttcaccgca tcgaaatatt tgatattatc aatcaatcca aacttgttat tcactgacct   13980
cttattcaaa cccttagtat atttaatatt ctacctttgt gattcattca atcgatttct   14040 tttttttttat tttcttccc tttctatatg ctcttcatta acttttcttt caattatcaa   14100
tgctttattc aatacatctg tataagtagt taactcatat agtaccattt attttctaat   14160
ttctatcctc aattccaact caaatttatc tactcagtca cattcatctt caaccaatct   14220
cgaagcaaac ttgacaagct ccataaattt agcttcatat tctacaacta ttatatttct   14280
ttatttcaga taaataaatt tttattcttt ctgaatcctc atactctaag aaaaatattt   14340
ttatcataaa atatcttttg aaatcactcc caagcgagtt gttctccatc ttgttcatat   14400
ttaggtttca ttctctatta tcaattaaat gtctcatctt tcaacatgta tgatgcatat   14460
aagatttttt catcatcatg gtatctctta acaataaatg ctttctccat ctccataagc   14520 taattttttag ctcctatttc atagttttct taaaagtcaa tggagacaac ttcttaaatt   14580
ctatgatatt actttattgc tcctattgct cttatgtcct tgtggtgaca atatttattg   14640
ttgcacttgc tgtagaggca gttactgtta ctgcaattgc tattacgatt ccatcaagcc   14700
gactagtgtc tgcattattt ggataatagt tgattttgc tactttattt agatgttggt   14760
ggcaaaatca atgacttctt tttgctgaga gatgccacca acctactaag tatcatcatc   14820
ttattggttg ataccttagt cagcacctcg agtggttctt tttatctgat atggaaccat   14880
cttaatcttg catgaaaaac aaacttcgca aaattttctt ttaaaatcta atatctaata   14940
ttatactttt attaaaattt aattatgatt attttaagaa taaaaatttt aaattttgaa   15000
atcctcacaa ggctggccaa gagataatga ccatcatcct agtcggtttg acgtaggaca   15060
tccaaagatc aactataatt caagcatcat attgagatgc taggatataa tcgatggtga   15120
aatttaatga tgctcgactg atcaagatgg gggccggccc gatggcctgt tcaacaatca   15180
ttgatcaaaa ttttttaacc aaggtctatc aagatcatta aaaagtcttt ctaagatcta   15240
taaattgtaa taaagagaca caatctgagg agagacactt tttacataaa gaaagtagaa   15300
attttaggga gagaaattag agagaaaggg gaaagagaga ggaagctgag aggaagaaag   15360
aaaagagaaa gactctctct ctttttcttt tctttctttt ctctctttttc tttttctttt   15420 ctttttttttc ttccttttct ttctttcttt ctttggctca ttagaaaaat aggggaccta   15480
ttgatcccct tgtttcctaa ataggggagg aatctcatct tggtagctat ggccggcgat   15540
gtgagccaaa gtggcaaaat catgaatct                                     15569
```

<210> SEQ ID NO 3
<211> LENGTH: 3181
<212> TYPE: DNA
<213> ORGANISM: Elaeis guineensis

<400> SEQUENCE: 3

```
ttcaaaatga tgaacagatg catctcaagt cagcactaga ccatcttcta aaataggaag     60
atctatggaa gcaacactcc caaatgcagt ggcttcaaaa tggggattgc aatacgaagt    120
ttatccatgt ttgggcaagt aacaggaaaa aaagaatact atcactgaac tctagcaagg    180
cgatcagaag attatcgaat agcagcaaat ccaatccaca ttctacaact tttttttctac   240 cctactaggc tcgactgagg aatgactcat ccaagctgat tagaagattc tttatccaga    300
aggacctctg gatcttgctg acattgagta tccatttatg gagaaagaaa tccatgatac    360
agtgtatgac ttggctttgg aaaagtcacc cggatgatat tttcccattc tccttctata    420
tgcacttcta gtgtatcatc aaacatgacc tgatgaacct actgtaaaat cagctaatgt    480
```

```
agaccatctg aactacttgt tcatcaccct tatcccaaaa aaaaattggt gtgtattcag    540
ttagagactt caggccaata agcctgatta atggagtaat aaaaaatatt tcaaaaactc    600
tatcgaaaag gctctcacag aaaatgaatt tgttaatttt atccacagag cttgctttca    660
acaaaggaag aaatatctct gaatattttg taatgactat ggaaactata cacttctgca    720
aagctgaagt acacaaggat ctcaattata agtcgactt cgagaaagct tttgacaatg    780
tggattggag ctttctattg aaattgctat ccagcacggg gctttgattc gaggtggtgt    840
caatggatag aatatctgat ttatacagct aaattctcag tccttattaa tggtgataaa    900
ggtaaacttt ttaaattgag gaaagatctc aggcaaggag atcctctatt cgcctagctc    960
tttctcttag ttgttgatat agaatgatca agggagcaag taggttcaat cttttgttg   1020 gaattggatc atataatatc atgggataac ttcaaagctt ttagttcact gatgacacac   1080
ttatattttg cagatatgat ctaaaataca tcaaaactct taaattttta ctctatagtt   1140
atgagctact gatgggtctc aaaattaact ttgaaaaatt ccaatttttt ggcttgagaa   1200
ttgcaaagat gtcagtacag caagttgcat ctatcctaga aagcaaggtg gctacatttt   1260
ccattactta tttgggtctc ccactccatc attctaaact gaggaaaact tattggaatc   1320
cactccttga gaaggttcag aagaaattga tcgggtagaa aggtaaactt cttaacctct   1380
agggtaggct tatactaact aatgcagtgc ttacagggat cccactactc tggagggata   1440
cattccttct ccctcaattc attatcaaat aaattgataa aatccatcga tcattcattt   1500
ggagaggaaa cgaggagtat aactaagggc actctagaat atgttggtcg aatatttgtc   1560
gatcaaaaaa atttggagga ctgggggttc ctcaatctaa aaattttcaa tacaattctt   1620
ctttgtaaat ggtggtggaa gctctactct aatgctggtg acccgtggtg tagttttatt   1680
gccactatcc acccaacttc acactagaga tctaaaggta tacacaaatc aacctcttca   1740
ttttggaatg gtttacagca cacatgaaat atttctactc ctaatccact ttcaagttag   1800
caactagtat tattttggaa agatagttgg ttacataatc atccactgaa ggatcgacttt   1860 cctcaccttt acacaatagc attgaagtgc aacaactcag tggcaaaggt attaagcaat   1920
ctacttgata atagctcttt tagtactcct cttcctcaaa gataccaaga agattttcag   1980
agtctatagg aaagcattga acaaattaca ttaacggaac gacctgatac tatacaatgg   2040 aaatggtttta gtagcaatat ttttttggca tgaaggatct actattttct gcaagatgga   2100
ggagtttggc ctctactgag taatattata taaaaactcc taataccaaa gaaagccaag   2160
ttatttgctt ggctaagtgc tcacaacaaa atcccaatga aagctaatct tcttaataga   2220
ggaataattg gaactgatta ctgtacactt tgcgatgact tatcagaaac taatgatcat   2280
ctaatgctca tctatacttt ttcaaaagca atttggaatc aagtactttc agacctgcaa   2340
ttgtcgaaac ttttatgcat gcttaacacc ctatgggata cttggagact catcaatatg   2400
caacacgata gaagacctaa actagctgct ctattcgtaa ttggtcaatg gtgtctttgg   2460
aaggaaagaa ataaaagatt attcgacttc tatactttt atccacgatc gattgctgaa   2520
actgtgtcac tttttctttc ttgggcatca cacctaacaa cggagcaact aaagatgtta   2580
gctcctgttc gagaagttct cttatctaag aatgaaaaca cacaatcttt agtgagaatt   2640
acagatgcta acaggcgcag atgaatgttt tatgagcatt tttatagctg cagcttatat   2700
gtgatctatg gtgcaaggag ttaattataa ccatggatat tagttaggtt gactatcaga   2760
aatcatctcc aatacattct atgtaaccac tgatcaattc catgttcaac tagataggaa   2820
```

| | |
|---|---|
| cctgcctata tacaggtatg tccctgatgt aactatagta tactattatt cataaataaa | 2880 |
| taacgaaggt tttaccttct tctcataaaa aaaaagtatc ttcatgtcat cctatatgtc | 2940 |
| atgcatctcc tttgctactt cttttattta cttcttaaac ttggttctac catatattat | 3000 |
| cagcccettt taaatttgct tttggatatt gcatattcca ctcttcaatc acctcatgcc | 3060 |
| aagcaaaaca tttattcaca cttgaaaacc aatataagaa taccaaagaa tttatccatg | 3120 |
| aaattctaga aactttggtt ttactccttt ctccatcatt caaaaaggtt caaaatgatg | 3180 |
| a | 3181 |

<210> SEQ ID NO 4
<211> LENGTH: 14184
<212> TYPE: DNA
<213> ORGANISM: Artificial Sequence
<220> FEATURE:
<223> OTHER INFORMATION: synthetic predicted full EgDEF1 cDNA transcript

<400> SEQUENCE: 4

| | |
|---|---|
| aggagagaga ggggcttggt ggctgactgt cagaagaagc ctcgatgctc gaagattaga | 60 |
| tggaagaaaa aaaaatttct caaaacttct cttttctata agcaaaacc tcactattat | 120 |
| aaatagggtt atgtatctca gtttatgatg tgaagaatta atgaaaaatt ggactttagc | 180 |
| tctattttg taattctttc atcttctatt tttatgaaat tcaagttgag ccgattaaaa | 240 |
| gaaataatct ttctttccga ttggatcaat ccattaacta gatacttcaa aaatcaaaat | 300 |
| gacctatcta aaatcctaaa tcaaatacaa accaaaata actaaattaa gatagaacaa | 360 |
| actacaatta caaaaaactg gctaaagtgt ttaaatgctt ttactcctaa gtttcttctt | 420 |
| gctcaccatt aatgcttgat ctttagctgg gatcatatca gccttatgac cactataaga | 480 |
| ccaacataac aactcacttg tattgctcct ttaaaattat acaaaactag tgtctaaatat | 540 |
| gtaccatgcg aatgtctgtt tctcaccaga aaatggatgg gcttcttgtg caagcacctt | 600 |
| cttcctacaa ataataaaat atgcatccct tctctcatct tactaaataa aataattaaa | 660 |
| ggctttacta tcaggaaatc tggctttatc catataattt tggaagtttt atttgaacat | 720 |
| aacattacga gtactagatt acatcaggag gtggttcctc ttatttctat taagagaaaa | 780 |
| atcaattttc ttttaagaaa gatcatttca ttttcatcag gtagcgtact ctactaatat | 840 |
| acttccacaa caatatatag ggattagatt ataggatgga cttaaggct tcttttcgag | 900 |
| agccctgatt tctcaatcac attcccttt cttttctcatg taatggcatt taagagtgca | 960 |
| tccagggccc aacaattagt cacaagtgtt cttttatac atggtacata tttgctattt | 1020 |
| tttagcttat tttaacttga ttgtgaagat atcatgagaa aattagattt aaagcctagc | 1080 |
| aatcttgaac ccataatttc aagttaacag gtggaagagt ccattattat gtgagaccaa | 1140 |
| cttagactgc aaaactatct gatattggac tatttactaa cacccttttt catgtgcaat | 1200 |
| gtttgtaaag agaagatata tgatgtagcg agataggata gtttggctct aatattgtgt | 1260 |
| taatattcaa accaaaatcc taagctaata gatggaagag aaatgactta tatacatgtg | 1320 |
| cattattgga tatatcttta tgggagaaat aatcacatgg atgtttatat cacacatctc | 1380 |
| atatgtgcat gttgttgtaa ggcttcaaaa gacagacgat gagattggtc ttggatcaaa | 1440 |
| ttggaatgtt tcttagttga atttggagaa gtctgcaaca aatcctataa aagaagtccc | 1500 |
| gaaattggtg gggcaccttt cgatccaaga cccttcgatg gataagtcaa ataaagcctt | 1560 |
| gagaacagat tgtggaaatg gaagaataga aggatgagaa aagagattgt gaacaaatgg | 1620 |
| agagaggact cttgtttcct tcagtggagg agttgaaaat gattcaacaa agtctccact | 1680 |

```
ctatctatcc cgacttacct tatggagggt atgttaccct cctttatata gaggggtgag    1740
gaggcttgct caagttgtta ggccgttaat ttattataat agaatggtca gctatataaa    1800
gatcatggga tgtttatcca tgtgatgatt agctatagga tagctagaaa atatctaatg    1860
cttaattaga tgatagctgt cagataaccg tctgcattct tatagtacat cgatatttta    1920
tcgacgtgac tagcttaaat cagcaactga ctgaactgaa tattatgatt cttttagtta    1980
acaatcatat tggttagaga ccgatgtaat tcatagtaga tcgatcacaa gctgagatga    2040
gtatcatatt ttaagaacaa tactagcaag ttagatcgat caaatgtcag atgaaaaagt    2100
agatcagtaa acgttcgatg gaacctgaaa gaatatttat gatttagata taatctatc     2160 atcacgtatc cagataatga gatcatataa catgtaccaa tatatgccct ccatttttca    2220
caccgaagtg aagttcttca catcgggtgt ggaaagtctc ttcagaagat ctcacctgac    2280
ctgtattgtc atcataaatg ctccatacca cgatggttgg aagtattaat tttttaatca    2340
ctcaaagtca tacacaattt cttgaaaatg atttgttgaa cttagtaatg atgagcgctt    2400
agaaaatcgg gagctcacaa ttatttgggt ggctagtccc taatgtgtat gtgctaggtg    2460
tcatactgta attggccact tcagctatca catggatcct gcttgcatgg cttaatcaag    2520
aagaggtgcg tcgcaacaac tctctgcaga accatcggat aactgacaag tggcattgat    2580
ctaatggcat atcaaatgga ttgagactgt tagtaaattt tataaatagg tctatactct    2640
gttcaaaaat tactttacta ttttttttcac atgacagtct tgctgaaatt ttttcagagc    2700
ccctaacatc attggtatcg gagtagagac cccccaaagt cattggagcc ggagaagaaa    2760
gaagtaaaga agtcttttaa aagcttcctc aaattcctct ttacatatta ggcagactct    2820
ttcatcttca acttcttttc catgaacatc tgagattta ggttttacaa tctttatttt      2880
tttttttgga tagttattcc cttttctctc ttttttttttc tgtttctctt ttcccattca    2940
cctttacttt cttctttcct ttcaaaaata tcttttgata ggactaatga gataagtcag    3000
gaccaatgga tatctcggtc aacccaacca ctgctcaagt ttgagatgga aaatctatct    3060
cggacaacag ctgaagttag tacctcaggt taggatgatc tagaatctcc tataagagat    3120
tttttagatt atttcggccc aagtactgaa caatctgtcc tgaccaatct cgatctttag    3180
gaacttaaga aaaaatattc gattcagctt ataactccaa gttgggatgg taggattatt    3240
gaacctccag aaggttatgt cgtatttttat gatgaggcac ttcgatctgg actttaattt    3300
ctcttacatc ctttcttcag taatgtttta gacttctata aactccatcc aatctaggtt    3360
actcccaatg ccattaggat gatcatagtt ttcattatct atcgtaaatt ttttgctata    3420
gaactaagaa tttctctctt taggatgctg gtcatcctaa gaaaacatcc ttatgaaaaa    3480
gactgatggt atttcttacc ttggcctcaa tataaattcg gtcccactct tcctttttca    3540
atacataatt gaaaaaatca ttttttcttt atttcttcta atgtttcgta gggttttatt    3600
tgtaaatagt ctaagcctaa aaccaaatgg aactcaaata acaaaatatt atctgaggat    3660
gaggagactt ttgtagagct tttagatatg aaagtatcca agttgagcct actggtgtcc    3720
aatcagtcct tgtttgacac cgacatcagt cagatctctc cttaagataa gtctgatgtt    3780
aattcttttt ctttattgct ttatcatttt tcatcatttt tcttttctaa caatcttttt    3840
ccttatatag tagcaataat gaagttcaac ctacaaaggc tggctaactc aaagaagagg    3900
aagaaggatc taaccgattg ctctcaagaa gagtaaggag actgctcctc taagatcgat    3960
tggcccccga tcatcacctg ggccaatatt aattgacata gatgctacat cgatctccac    4020
```

```
tataccacca gcaaaatcaa ctcatcaacc tactaaggtg gcttgtccac ctcctaaaga    4080
gtctgcacat ccaaagtagg catcttcccc aacacctcca acatcggcca agttagtttg    4140
gctgagcaat cagcatctga ggtcacagac tcctgatgtc aacccaccaa ctttctcatc    4200
aaaaaaaaat tgacttggcg aaggtatcac ttttggagac acccagacta ggcaaggact    4260
tgctctgtac aatgatgcct caaaaggacc tagatgctga taggagggat ctttctttgg    4320
agcaaataat aaattatgga ttcaacagta tcatgaacgt gagtcttcat tctcttccac    4380
tctcttcttt cttttttctt tttttttttta cattggctat ttgttgatct gaatatatct    4440
ttcttttttgc agtcggttgt gtatttcaag ttgctcaatg agcacttgac atggttcttc    4500
aaaaataaaa attttttttga agagaggct caaggccaag aaagaggcca aaaagcagt     4560
tgaggaggtc aagaaggcag taagaagaa ggctgtcaaa gaaagcaaaa tgatggaggg     4620
gctgaagaaa cagctccaag aaaaaataga ttccattaag gagactggac aaccaatgac    4680
agatgaatga taaagatgac aagttgtaaa aacagcctga aaaaaatctc aaagttggag    4740
gccaagctga aggaggtcga gtcaataatt gaaaagcatg atgaagctct tgtcccatat    4800
tagagacaac ttgataaaga caaagagtgg atgtcaagga ttattgaaga ttataagaat    4860
tccgacactt tcaagatga cgttactgag gcctcaaaag gagcttttcaa ttatggcttt    4920
ttgagctaca ggagtttaat tatcaagctc tttcctaacc ttgatctcag caaggtcata    4980
atagaagcag ctctagaagt agtagccgaa gtgacttctg caacaactac tgagcttgct    5040
tccacttcta tcattggagt ttctccgatc gaagtcccaa acagtccaat cgaggcctcc    5100
atcatcgaag ctatttcgaa ggaatcagtc ggcaaagacc ttacctcaac tcctccaaca    5160
aataactccc aagctaaggc ctgaattatc ttcttctttt ttttctaaac atttgtatta    5220
gcccgatgtg ggcttctata aatacttttt acattaatga atgagttttt caatgtcaat    5280
atttttttctt tttaactaat actaatcttg gatgatccga tctgggttgg atgtctcaaa    5340
aaatatcatt cacgatagat agttattttc tgacttcggt tagatgatta tgagtatatg    5400
taattcaacc ttggttaggt aagtaatcaa atattaacta ttctcaaacc aagtagataa    5460
cgaagtcaat gtgattaact ttaacaagta agattgttat ggaatgaaat tgaatcagat    5520
caactaacta tagataactt aatctctcat aattcactgt aaaggttcta aaagtacctt    5580
tatctaagtt cgaagtgaca agtcgggttc ttttattcgt ggatttatga cccatgctgt    5640
cttttttgtga tcttcattat taatcaccctt aaatcgatat agcaaaatcc agtttataga    5700
tctgagtgct ttcttgtcag attgagtcta tcctattatc tgtgaaacct gatctagaga    5760
tcaagtattt taggtttttt atttaaggtc caattcgaag attgagtatc caatgtcata    5820
ttgttaggtc caatttggag attggatgtc tcactatcat ctcgtgaggt ccaatccaaa    5880
gatcgaatat ctcactatca tctcatgagg tccaatccag agattggatg tctcacatca    5940
tcttgtgaga tccaattcga agattggatg tctcacatca tctcatccta ttgtggttgg    6000
aatttttgta gccttagttt gacttttttct gacctcattt ggacacctaa atcttattat    6060
catcgtttga tcgatttta ctaatctact ttggatgaaa aagaattctt caatggaact    6120
tttgattaga actttatctt cattgggata gaaatcgaat gctttattga agatttttat    6180
tgataataca ttctgagatt tttaatattt catgttctcg aaatgatcgt accatctaaa    6240
tttttaattc gataagctct tggatggatc acctcagtaa tctgataagg tccttcccaa    6300
ttcgggatga gttttctta ctccattggt tttgagactt cagctcattg gagaaccaaa     6360
tctccttata aaaaatttta ggctttacct gagagttgta atatctggct acttttttgtt   6420
```

```
tataaactac catatgaatc tgggcttttt ctcgagtttt ctcaaataaa ttgagatcag    6480
tcctcagttg atctgaatta ttttcttcat gaaaattttc tattctggtt gtaggtaaac    6540
tgatctcgac tagtattata gcctctgttc cgaaagtaag tttaaaagat atttctctag    6600
ttggtctctg aggtgtagtt ctgtataccc ataaaatatt ataaaattat tctaccccga    6660
gacttttagc ctcaatgagt tttattttta ggccttgaaa gatagttcta taaataaatt    6720
tagcttctcc atttgattgt agatgtccaa tcgaagtaaa tatatgatct atgtagagct    6780
cagaataaat ttttttaaaa ttttgattat caaattattg ctcattatta gtaattataa    6840
ctcaaggcaa accaaaatgg taaataatta tttttcacat aaaatctcat attttttctc    6900
agtgatttat gtcagaggtt caatttctat ccattgggta aaataatcaa tagtcacaac    6960
taaaaatttt ctttgctcca tggccattag aaaggatccc agaatatcca ttctccatat    7020
agcaaaaggc cacagcactg taatagaaat aagttcagtt gtaggctgat gttatatatt    7080
ggcgtacctt tgacactgat cgcagtactt attaataaag tcggttgaat cttttttgaat   7140 agtaggccaa taataatctt actgaattat ttcataagct aaaattttac cccccaaatg    7200
gttactagag attcctttat gaacttctcg aaggatgtaa tcagcttccg atggccttag    7260
gcataggagc agtgggagtg aatataacct ctgatataat tgattatctt gaacaacata    7320
ccatggggcc tgtcttttaa ttcttgttcc ttcgactgga tcaaccggta gaggttcttt    7380
agtaatatac tccattaatg ggtcaatgga acttagctca tattaaattt ggacaattag    7440
taaggcctcg atactagact ttttaagaat atcaataaga acaccttgat ttagtttgaa    7500
aaaatctgat gtggctaaat gagatagggc atcagctcag acattttgtc cttggtattt    7560
gcatgatctt cagattttca agttttttta ataattcttt catattatat aaatattgaa    7620
acatcataaa atctttagct tcaaattaat ctcatacctg actgacgata aattgagaat    7680
caataaaaat tttaattttt ttaacattaa gctccttagc cattttgagt cctacaatta    7740
gcgtttcata ttctactcca ttgtttgagt gttaaaatta aatctcaaag cacgctcact    7800
aacaatgcct tctagactcg ttagaattaa actagttcta ctttctttcg aatttgaggc    7860
tccatcaatg tacagtatca aataagaatc tttgatattt ttcaattctt ttaagattgg    7920
ttcttcatta ggaatagagc attcaataat aaaatcagct aatacttaaa ctttcaatga    7980
agatcgaggc ccatattgat atcaaattca tttaattcaa tagcctattt gaatatcctt    8040
cttaaagtat caagctactg taaaattaat tttaaaggtt gatcgatcag aattataata    8100
gaatgagcct aaaaatacga tcaaagtcat cttgctaatg caatgagggt ataaattatc    8160
ttctcaattt tagaatatcg agtttcaaca tctctaaata atttatttgt ataataaatg    8220
gatctttgta tccctgcatc atttcaagct aaaatcgaac taacagcatt tgctgaaata    8280
gatagataca tgaataattt ttgacctttg atcggctttg atagtaatgg agctgtgccg    8340
agatatttct tgagatcatc gaaggctgct tgacattcat cttatcaatc gaagtctttg    8400
atctgcctta gaatttttaaa gaaaggaaga tatttatcag ctgatctgaa ataaaattaa    8460
ctaagcaatg ctactcatcc agtaagttgg tgtacttctt tgatggagct cggatgcttc    8520
atttcacata gagcttgaat tttcttaaga ttgactttaa ttcctctttg agttacaaaa    8580
aaatctaaaa aaatttttga agttacttca aaagcatatt tgttgggatt gagcttcatt    8640
tgatattttc gtagtctcta aaggcttctt ccagattggc aatatactga tctgactcag    8700
tattttttac taatatatca tcaacataaa ctttgatatt aatttcaatt tgttacttaa    8760
```

```
aaatcttatt aatcaagtat tagtatgtag cacctacatt tttaagatca aaagacatca    8820 tttttataaca atgcaaatct ttttcagtga tgaaggccat attttcttca tcctcaagtg    8880
ccattttgat ctgatataac cagaaaaagt atccataaag cttagtaatt tgtgtcttga    8940
agtagcatca acaagctgat caattttga gagagaaaaa ctatctttta ggcaagcttt     9000
attgagatcg gtataatcaa catagatcct tcatttttca ttagccttt taaccatgac     9060 aacatttaca atccactttg gatattatgc ttctctgatg aatttgtctt tcaagagttt    9120
gtcgacttcc tcatctatta ttttttatct tttcggggtg aaacttcttt tcttctgttg    9180
cattggttta tgctttggat caacattcag cttatgtaca ataagatcag ttaaaatctc    9240
aggcatatta gagactgact aaacaaagac atcggcattc atccgaagaa aagatattaa    9300
tttctccctc agatcaggct tcaatagaga tccaatttgg acagttttt ttggatcatc     9360 acacaaaaga acagtaataa gtttctcgac tggttctcct cgattttga tgatatcaac     9420 tttactttct tgatcaagta ttttaattgg tagagcttcc acagaccttt tcattttac     9480 agctatcaga aaatactact tagcaagtat ctgatttcct catatttctc caactccata    9540
cttagtttgg aattggatta gtaaatgata agtgaagact atagccttaa gggcgttgag    9600
cctaggtcgg tcaagaatag cattataagc tgatggtatt ttgacaataa aaaaagtgag    9660
tcttacagtt gactggcatg gttctatccc tgcagtgacg gacaaagtga cctctccttc    9720
cacagctaca ggatttctag aaaatccaat tacgggggta ccaacctatt tagctaattt    9780
atcatattca ttcttggaa tgtatcatag aacaatatat tagcagagct ttcattatca    9840
ataagtattc ttttatatc atatttggct attgccataa agatgacaac agcatcatta    9900
cgaggagttt gaactctaac atcatcatcg aaaaatgaaa ttatgtgatc catgcactga    9960
tgctttggaa ggctttcagt aatctcagcc acctcctcag ttccgtcgag atctgagatc   10020
atattgatga ctgcagcagt agacttgttg tgatcattct cattgttggg cttctatcat   10080
tggtcagtag cttgacttgc ccgatctcga acatatttac taaagtaaca ttagtggatc   10140
aatacttcaa ttttatcttt taattatcga tgctcctcag tatcatggcc atagtctcga   10200
tggaaatgac agtatttcct cttatctctc tttgctggag gggctttcat aggattaggt   10260
tggcgaatat atcctaaatc ctcgatttct atcagtatct gagctcgagg agtagatagt   10320
gaggtataga tgtcgaatca ccgaggtggg cttttgaact tcagattctt ctgaggtcgt   10380
tcagagttat cctgttggtt tttatgatct tcttcctagg gccactttt tccatctctt    10440 tttttcttca cctaacgaag tatgcatgct ctctttcttt tcagcttgag catacttaca   10500
aacctagatc aatatttgtt cataattgtt tgggtagttc ttattaagag agaagatcag   10560
gcgattactc ttgagtcctt gcttcaaagc tgccattgca atggactcat tgaagttctt   10620
cactttcagt atggcggcat taaagcatgc cacatattct tgaagagatt caccttccta   10680
ctatttgata gtaaaaagat tgctagtatt tttcaaatga atccatttat tatcaaaata   10740
cgtgatgaat atttgctaac tgtgtgaaag atgaaataga tcatgtctgg aggtcagaga   10800
actagattct tgcagatgtt ttgagagtga ttggaaaagt gatgcaaaat agggcattag   10860
ataccccttg tagtcttata atggctctga agccttcaag atgatttaag ggattgatgg   10920
agccatcgaa tgtttccact gtaggtatct tgaatcgagg aggaactgat ttaccaagaa   10980
ttttttgaga aaaagagat cgtaagttga aatctcttct accttgagaa tggcttccaa     11040
tctatatctc catcattttc ttctcaagat tttgaatctt ttgtccaaga ccctcctcca   11100
tacatggctt cttatgtgga gcagatttca cttcccaaga gtgatcagta tggtcaagaa   11160
```

```
gatgatcatg atgaagatct tgaggagttg gttgctaagt gtgatgtgat tggactactt   11220 gggggctac ttttgctac cgttctgtcg tatactacag cagtaagagc ttggacctgc   11280
tgaaccaaga gactaaacta ttgtggatca ataataattg aaggttaggt attctcctga   11340
acatcttcag gagaagatga agtaggtaaa ggatgatttg gtgccttctt gttcaccatt   11400
tctactaaaa tattttaagt gcccttcctc taacactaat ctattactgc aaggcttcaa   11460
aagacaggca acgagatggg tcttgaatcg aactagaatg tttcttggtt gaatttggcg   11520
aagtctgtaa caaatcttgc aaagaaaatc tcgaaaccta cgggtacctt ctggttcaag   11580
atcctctgat ggataagtta ggtaaagtct tgagaatagg ttgtgaaaat agaagaatag   11640
aaggatgaga agagagattg tcggtaaatg gagagatgac tcttatttct ttcaatgggg   11700
gagctgaaaa taattcagca gagtttccac tctatcaatc ctgacttatt ttgtggaggg   11760
taccttggcc ccttcatata taggggatga agaggcctgg taaggttgtt agactattag   11820
gagagtttgt tagatcgtta atttattata atagaatgac cagctatata aaaatcatgg   11880
agtatttacc cacatggtga ttgactgtag tataactgaa agatagctaa tgcttagctg   11940
gatgactgct gttagataac tgtctgcatt cttacggtac attgatattt taccaatgtg   12000
acatagctta aatcggcaac tggctgaact aaatattatg tatcccttta gttaacaatc   12060
atgtcggtta gagatcaatg taattcgcag cagatcgatc ataagctgag atgagtatca   12120
tattttaaga acaacgctgg gcgagttagg ccgatcaaat gtcagactga aaaagcagat   12180
caataaacct ctgatgtgat ctgaaagaat atttatgatt taaataataa tctatcacca   12240
cgtatccaga taatgaggtc atataacatg taccaacagt gcattttcc atctagttaa   12300 gaggttggtt agtggcattt gtcttcgata tgtaatgttc acataactaa tgtgcttagt   12360
agcattcttt tgtaaggtta aatcttcaat gatcttaagt tcacataatt gcctttgtgc   12420
cctattagtt tatagttgac cttttaattc aagagacagt caccttagca atcgatgtct   12480
gcttagattg ggccaattag gtactcacat taatatattg aatcatgttt gaatataaag   12540
gattagattg atttataagt ttccttttat tgtttacata ctgatactta gattgactta   12600
ctacattatt tgatatgtta tgttctaatt tttggattaa aattgttgtt tctgatttct   12660
ccttacatct aatactttgt ataatttatt attttttagc atgattgagt gtagaggatt   12720
agattgattt ttaagtttat tttgattatt tacatgccga tacttaaatt gacttactac   12780
attattcaat atgttatgtt tcaattattg agttaaaatt tttatttctg atttctactg   12840
atgtccagtg tgtgtgtgtg tacgtatgtg tgtatatatt tatttacata tatatgtatg   12900
tatgtataca gacatacata catacataca tacatacgta cacacacaca cacacacaca   12960
cacacacaca cacacacaca tatatatata tatatatctg tgtgtgtgtg tgtctctctc   13020
tctatatatg tataagtatg tatgtatgta tgtgtatata tatatatata tatatatata   13080
tatctatatg tgtgtatgca tgtatgtata tgtatgtatg tatatacata tatgtatata   13140
tatgtatata tatgtgtata tatgtatata tatgtgtgtg tgtgtataca tatgtataca   13200
tacatatcta tacatacata tgtatacata catacatata tatgtatata tacatataca   13260
tgtatacata catgtataca catacatgta tacatataca tgtatacata tatgtataca   13320
tatacatata tacatatata tatatatatg tatatacgtg tgtgtgtgtg tgtaagtaat   13380
taagtatgta gtgtgtgtgt gtgtgtgtat atatatttat atctgtgtgt gtgtgtatat   13440
atgtatgtat gtatgtatgt atatatatat aaatacatac atacatattt atacacacat   13500
```

```
atctatacac aaatatgtat acatatagac acacacacac gcgtgcgcgc gcgcgcgcac    13560
acacacacat atatatatat atatatagat agatagatat atgtatgtat gtatatatat    13620
atgtatatat atgtatacat atgtgtatat atgtatatat atatgtgtgt gtgtgtgtgt    13680
gtgtgtacat atgtatacat acatatctat acatatatat atatatacat atatatatac    13740
atatacatat atatatatat acataaatat atatacatat acatacatac atatatatat    13800
atatatatat atatatatat atatatatat acacatacat acatacatat acatatatac    13860
atacacacac acacatacac acatgtatac gtacatgtat gcatatacat gtatacgtac    13920
atgtatacat atacatgtat acacatat atagatatat atatacacat atatgtatat      13980
atatatatat atatacacat ataggttta tttggaacct aagaaacttg caaagttact    14040
agatgcaatg ttcggaaacc atggaccgta acaactggag tagtatttgg gtcatgaatt    14100
catggctaga tcatgaattg agtgggagtc aaccgaagta gggccagctc agacacttgt    14160
atttaggtcc catgcttgcg tgca                                          14184

<210> SEQ ID NO 5
<211> LENGTH: 678
<212> TYPE: DNA
<213> ORGANISM: Elaeis guineensis

<400> SEQUENCE: 5
atggggaggg ggaagataga gatcaagaag atagagaatc ctacaaacag gcaggtgacc      60
tactccaaga ggaggacggg gatcatgaag aaggctaagg aactgacggt gctttgcgat     120
gctgaggtct cgcttatcat gttctccagc accggcaagt tctccgagta ttgcagcccc     180
ctttccgaca ccaagaccat atttgatcgc taccagcagg tgtcagggat caacctgtgg     240
agcgcccaat acgagaaaat gcaaaacact ttgaaccatc tgagggagat caaccagaac     300
ctccgcagag aaataaggca gcggatgggt gaagatctcg acagtttggg catccatgaa     360
ctgcgcggtc ttgagcaaaa tttagatgag gctttgaagg ttgttcgtca cagaaaatac     420
catgtgatca ccacgcagac ggatacctac aagaaaaagt tgaagaactc taatgaagct     480
cacaaaaatt tactgcatga acttgaaatg aaggacgagc acccagttta tggttttgtg     540
gatgatgacc ctagcaacta cgcaggtgca ctggctcttg ccaatggggc ttcccacatg     600
tatgctttcc gtgttcagcc gagccagccg aatctccatc gaatgggggtt tggctcccat    660 gacctgcgcc ttgcttga                                                 678

<210> SEQ ID NO 6
<211> LENGTH: 225
<212> TYPE: PRT
<213> ORGANISM: Artificial Sequence
<220> FEATURE:
<223> OTHER INFORMATION: synthetic

<400> SEQUENCE: 6

Met Gly Arg Gly Lys Ile Glu Ile Lys Lys Ile Glu Asn Pro Thr Asn
  1               5                  10                  15

Arg Gln Val Thr Tyr Ser Lys Arg Arg Thr Gly Ile Met Lys Lys Ala
             20                  25                  30

Lys Glu Leu Thr Val Leu Cys Asp Ala Glu Val Ser Leu Ile Met Phe
         35                  40                  45

Ser Ser Thr Gly Lys Phe Ser Glu Tyr Cys Ser Pro Leu Ser Asp Thr
     50                  55                  60

Lys Thr Ile Phe Asp Arg Tyr Gln Gln Val Ser Gly Ile Asn Leu Trp
```

```
                65                  70                  75                  80
Ser Ala Gln Tyr Glu Lys Met Gln Asn Thr Leu Asn His Leu Arg Glu
                    85                  90                  95

Ile Asn Gln Asn Leu Arg Arg Glu Ile Arg Gln Arg Met Gly Glu Asp
                100                 105                 110

Leu Asp Ser Leu Gly Ile His Glu Leu Arg Gly Leu Glu Gln Asn Leu
                115                 120                 125

Asp Glu Ala Leu Lys Val Val Arg His Arg Lys Tyr His Val Ile Thr
    130                 135                 140

Thr Gln Thr Asp Thr Tyr Lys Lys Leu Lys Asn Ser Asn Glu Ala
145                 150                 155                 160

His Lys Asn Leu Leu His Glu Leu Glu Met Lys Asp Glu His Pro Val
                165                 170                 175

Tyr Gly Phe Val Asp Asp Pro Ser Asn Tyr Ala Gly Ala Leu Ala
                180                 185                 190

Leu Ala Asn Gly Ala Ser His Met Tyr Ala Phe Arg Val Gln Pro Ser
                195                 200                 205

Gln Pro Asn Leu His Arg Met Gly Phe Gly Ser His Asp Leu Arg Leu
    210                 215                 220

Ala
225

<210> SEQ ID NO 7
<211> LENGTH: 61
<212> TYPE: DNA
<213> ORGANISM: Artificial Sequence
<220> FEATURE:
<223> OTHER INFORMATION: synthetic

<400> SEQUENCE: 7
aaattaatat tgcaaactag ctcaaaataa ttttgatcac tacatttctg ctgtgcattc    60
t                                                                   61

<210> SEQ ID NO 8
<211> LENGTH: 61
<212> TYPE: DNA
<213> ORGANISM: Artificial Sequence
<220> FEATURE:
<223> OTHER INFORMATION: synthetic

<400> SEQUENCE: 8
actacatttt aacaccaagc tcgataatag tgataaagaa acatctagat cagctttata    60
a                                                                   61

<210> SEQ ID NO 9
<211> LENGTH: 61
<212> TYPE: DNA
<213> ORGANISM: Artificial Sequence
<220> FEATURE:
<223> OTHER INFORMATION: synthetic

<400> SEQUENCE: 9
tgcatgcata gctagaagag aatcttatca cgatcatcac tcgtgaagat catctacctg    60
t                                                                   61

<210> SEQ ID NO 10
<211> LENGTH: 61
<212> TYPE: DNA
<213> ORGANISM: Artificial Sequence
```

<220> FEATURE:
<223> OTHER INFORMATION: synthetic

<400> SEQUENCE: 10
gctcgagtac tgcatatttc tgatacattg tctatgctag aatgtgctag aactgattat    60
c                                                                    61

<210> SEQ ID NO 11
<211> LENGTH: 61
<212> TYPE: DNA
<213> ORGANISM: Artificial Sequence
<220> FEATURE:
<223> OTHER INFORMATION: synthetic

<400> SEQUENCE: 11
tatattaatt gtcatacttc tagctcgaga tcatgagcca aggattgcag taactaccgc    60
a                                                                    61

<210> SEQ ID NO 12
<211> LENGTH: 61
<212> TYPE: DNA
<213> ORGANISM: Artificial Sequence
<220> FEATURE:
<223> OTHER INFORMATION: synthetic

<400> SEQUENCE: 12
ggaatctcat cttggtagct atggccggcg atgtgagcca aagtggcaaa atcatgaatc    60
t                                                                    61

<210> SEQ ID NO 13
<211> LENGTH: 61
<212> TYPE: DNA
<213> ORGANISM: Artificial Sequence
<220> FEATURE:
<223> OTHER INFORMATION: synthetic

<400> SEQUENCE: 13
tataactaat ctccaactct gccgactcct tagtagtatg agcacatgga aagcttgacc    60
t                                                                    61

<210> SEQ ID NO 14
<211> LENGTH: 61
<212> TYPE: DNA
<213> ORGANISM: Artificial Sequence
<220> FEATURE:
<223> OTHER INFORMATION: synthetic

<400> SEQUENCE: 14
ataaatgagt gatagattct aatccagaga caaagagcac acctcgaatt cacttgccat    60
c                                                                    61

<210> SEQ ID NO 15
<211> LENGTH: 61
<212> TYPE: DNA
<213> ORGANISM: Artificial Sequence
<220> FEATURE:
<223> OTHER INFORMATION: synthetic

<400> SEQUENCE: 15
aagaagaact aatacagctt tcatcacttc aaaatgatga acagatgcat ctcaagtcag    60
c                                                                    61

```
<210> SEQ ID NO 16
<211> LENGTH: 61
<212> TYPE: DNA
<213> ORGANISM: Artificial Sequence
<220> FEATURE:
<223> OTHER INFORMATION: synthetic

<400> SEQUENCE: 16
ttgatataga atgatcaagg gagcaagtag gttcaatctt tttgttggaa ttggatcata     60
t                                                                    61

<210> SEQ ID NO 17
<211> LENGTH: 61
<212> TYPE: DNA
<213> ORGANISM: Artificial Sequence
<220> FEATURE:
<223> OTHER INFORMATION: synthetic

<400> SEQUENCE: 17
ggcgcagatg aatgttttat gagcattttt atagctgcag cttatatgtg atctatggtg     60
c                                                                    61

<210> SEQ ID NO 18
<211> LENGTH: 61
<212> TYPE: DNA
<213> ORGANISM: Artificial Sequence
<220> FEATURE:
<223> OTHER INFORMATION: synthetic

<400> SEQUENCE: 18
atttgctttt ggatattgca tattccactc ttcaatcacc tcatgccaag caaaacattt     60
a                                                                    61

<210> SEQ ID NO 19
<211> LENGTH: 61
<212> TYPE: DNA
<213> ORGANISM: Artificial Sequence
<220> FEATURE:
<223> OTHER INFORMATION: synthetic

<400> SEQUENCE: 19
cggttgcatg ccctgcagag tttgactcat gaggcatgca aggtattgaa tagtagtcta     60
g                                                                    61

<210> SEQ ID NO 20
<211> LENGTH: 61
<212> TYPE: DNA
<213> ORGANISM: Artificial Sequence
<220> FEATURE:
<223> OTHER INFORMATION: synthetic

<400> SEQUENCE: 20
cgtcagctgc tcaatcatgg attctgatag ctcaaatggt ggtaagtaga aagagagaga     60
t                                                                    61

<210> SEQ ID NO 21
<211> LENGTH: 61
<212> TYPE: DNA
<213> ORGANISM: Artificial Sequence
<220> FEATURE:
<223> OTHER INFORMATION: synthetic

<400> SEQUENCE: 21
```

```
aagattgtgc aactcatgaa gattgtctcc agattgaaga taatttcaat acaagcacaa    60
a                                                                    61

<210> SEQ ID NO 22
<211> LENGTH: 61
<212> TYPE: DNA
<213> ORGANISM: Artificial Sequence
<220> FEATURE:
<223> OTHER INFORMATION: synthetic

<400> SEQUENCE: 22
atcggtggat caaatgataa tacttatgat agaaacataa tcaatccact taggactata    60
c                                                                    61

<210> SEQ ID NO 23
<211> LENGTH: 61
<212> TYPE: DNA
<213> ORGANISM: Artificial Sequence
<220> FEATURE:
<223> OTHER INFORMATION: synthetic

<400> SEQUENCE: 23
ttgaggagat taatctgacg caaggaaaaa agaagagctg acaactagcc aatgatcgag    60
a                                                                    61

<210> SEQ ID NO 24
<211> LENGTH: 61
<212> TYPE: DNA
<213> ORGANISM: Artificial Sequence
<220> FEATURE:
<223> OTHER INFORMATION: synthetic

<400> SEQUENCE: 24
tgatctcagc aaggtcataa tagaagcagc tctagaagta gtagccgaag tgacttctgc    60
a                                                                    61

<210> SEQ ID NO 25
<211> LENGTH: 61
<212> TYPE: DNA
<213> ORGANISM: Artificial Sequence
<220> FEATURE:
<223> OTHER INFORMATION: synthetic

<400> SEQUENCE: 25
atattttcgt agtctctaaa ggcttcttcc agattggcaa tatactgatc tgactcagta    60
t                                                                    61

<210> SEQ ID NO 26
<211> LENGTH: 61
<212> TYPE: DNA
<213> ORGANISM: Artificial Sequence
<220> FEATURE:
<223> OTHER INFORMATION: synthetic

<400> SEQUENCE: 26
atagctaatg cttagctgga tgactgctgt tagataactg tctgcattct tacggtacat    60
t                                                                    61

<210> SEQ ID NO 27
<211> LENGTH: 61
<212> TYPE: DNA
```

<213> ORGANISM: Artificial Sequence
<220> FEATURE:
<223> OTHER INFORMATION: synthetic

<400> SEQUENCE: 27
aattattgag ttaaaattttt tatttctgat ttctactgat gtccagtgtg tgtgtgtgta    60
c                                                                     61

<210> SEQ ID NO 28
<211> LENGTH: 61
<212> TYPE: DNA
<213> ORGANISM: Artificial Sequence
<220> FEATURE:
<223> OTHER INFORMATION: synthetic

<400> SEQUENCE: 28
tcttcctcag atgacatgtg atttatgcta cggcctagtt ctaaggactt ttctctgtca    60
t                                                                     61

<210> SEQ ID NO 29
<211> LENGTH: 61
<212> TYPE: DNA
<213> ORGANISM: Artificial Sequence
<220> FEATURE:
<223> OTHER INFORMATION: synthetic

<400> SEQUENCE: 29
cctagattaa tgctgttatt ggatgctggc agtcagatga agattatgtt tgattgtacc    60
t                                                                     61

<210> SEQ ID NO 30
<211> LENGTH: 61
<212> TYPE: DNA
<213> ORGANISM: Artificial Sequence
<220> FEATURE:
<223> OTHER INFORMATION: synthetic

<400> SEQUENCE: 30
taaatgagtg ctcatagtga caatgtttag cctccacgta taatgtgtgc cagctaacta    60
g                                                                     61

<210> SEQ ID NO 31
<211> LENGTH: 61
<212> TYPE: DNA
<213> ORGANISM: Artificial Sequence
<220> FEATURE:
<223> OTHER INFORMATION: synthetic

<400> SEQUENCE: 31
atcctctttt gtggctcaca acctcctctc cttttatgt tctatgttcc tcacatcaca     60
t                                                                     61

<210> SEQ ID NO 32
<211> LENGTH: 61
<212> TYPE: DNA
<213> ORGANISM: Artificial Sequence
<220> FEATURE:
<223> OTHER INFORMATION: synthetic

<400> SEQUENCE: 32
atcctttcaa tctcataaga agttaaatga catggatgac atgaagcttt gatatgcatc    60
g                                                                     61

<210> SEQ ID NO 33
<211> LENGTH: 61
<212> TYPE: DNA
<213> ORGANISM: Artificial Sequence
<220> FEATURE:
<223> OTHER INFORMATION: synthetic

<400> SEQUENCE: 33

```
accatcaaat ggcttttgga aatatgcggg cgcagaagta gaggtgtcct atatgaaggc    60
t                                                                    61
```

<210> SEQ ID NO 34
<211> LENGTH: 61
<212> TYPE: DNA
<213> ORGANISM: Artificial Sequence
<220> FEATURE:
<223> OTHER INFORMATION: synthetic

<400> SEQUENCE: 34

```
gacgagggat cacaccaaca tcatatgctc tcctcaccat accaaatggt atccccaact    60
a                                                                    61
```

<210> SEQ ID NO 35
<211> LENGTH: 4061
<212> TYPE: DNA
<213> ORGANISM: Artificial Sequence
<220> FEATURE:
<223> OTHER INFORMATION: synthetic

<400> SEQUENCE: 35

```
aaatctatta gtatctgaca aaagttaaat tagagtcgaa acactaaatg acaattaggg     60
atcaacttga tcaagtagat agagaatatt agaaaagaga gaaattaaca agatagaaca    120
tgattaatta ggtgacatag cccgacaatc caattggtct aagcaagttg atttaatcaa    180
atcacggttg aactaatata tagatagctc aataaaaatc atacataatt gaatctaatg    240
atatttggat ctgaccaaga tggaatttga catgctgtcc gatgatcgtg aatcaagact    300
ctctttgcta attaagatca aattagaatc attgaaagag aatcttttac tggatcaaga    360
gagagaaata tataaagaga gtgaaatagt ctatagaaaa aaattttaga gagagaaatt    420
aagaagaaaa aataaatttt ttagagaaag aaagtgggta tacaagctca gagaagggag    480
agaggaaaga gagagaaatg ctctcttatt ttcttttttt tctttttttct tcttttcttt    540
ttttttttcct attcttcttt cccttttctg cttaatggaa taggggacct cccattcccc    600
ttctatttct agagttgggg gctcaaaatt gatgatagct atcattgggg atgtaggcta    660
tggtgatgca gtagaggatc accgaccgat gatcgatggt gatgttgcaa tcaaaaaatc    720
aagaaagata gatggaaaat aaaggaaaat aaggagaaat agatctcaac ttgtttggat    780
gctaacccac tcactgacga ctccacttca actatggccg gagcttgcta tggaaaagaa    840
gccaaggcct tcaaggatga acaccaatgg tgaggaagat ggtcgaaaat agaagaatgg    900
ctggctttc taatcgacaa ataggggtat cgcccttctt agcaaatatt cggcaataaa    960
tatctagaat ccaggatcct aggactatgg aagagggaga ggagggcaag tcaaggatg   1020
ccagattctt atctagcttc gacaatgat ggggccctat tttcgataaa cacaattgag   1080
gatgttcgga aaagggtttt ttcgatgatg attctagtga ccaactatga gatttcaaag   1140
ggggtgaggg gggtttaaat aagatgggag ggaagtttga atcctcctta aatctgaacc   1200
```

-continued

```
ttttcgaca aagccaagag cgtgaaggag actccttcgt gaagtcaaag atggaataga    1260
ctcccttcgg gagtttggtt catcacccaa cttccctagc atgtgcggag tatgtgctag    1320
ccttttctct cttttttttt cattttttt catcctttaa gatccatgca gtttctaggt    1380
tgagggattg gggtatcaca ttctctctcc taaaaaaaaa ttattttcaa aattttttta    1440
cctatatttt caaaagttgg gattcatggt ccaaatctca tccttgaatt tttttgatat    1500
tctaattctc gaaaaatttt catcgttaaa tcatttcata agagaaaagt caatacctca    1560
agagttgatc tgaatcaaaa ttattatctc tagtaatcga aatcaatatc ttaatttcaa    1620
ataagaatat ccagtttatt gtcaaaatta ttaactactc ttgacttaat tgatctatta    1680
cataatcgta ataaaattct aacatactct tgaagtgtag aatataagat tgataaacaa    1740
tcctatatcc gttctaatag atataaaagc ataaacttta aatattttaa atccaagatt    1800
aagaatcaat gatccactta tcctagactc aagatattag aaatttttttt ttgtacaata    1860
gatagaggat gtactggtga aaatcatgta gcgatatcca aaataatttt taattaaaaa    1920
tattatcctt ttcattatca atgaattta tctataagaa agatcaaatc atatgatcca    1980
tcttaaattt ttaactcaaa aaattaatat tgcaaactag ctcaaaataa ttttgatcac    2040
tacatttctg ctgtgcattc taatttaaac cgttcacatt ttttagattc atgaaataat    2100
tttgaccaaa gtattactcc atactatagt caaaaaagat taaaatatta gattctaatt    2160
aaagccaaag ataaactttt gattctcatc cttaattttg cctaaagtat aattattttg    2220
attaaccctt aagcgcaata acacattcaa aaccaacaga taggtttact ataatccaaa    2280
tgaattaaat cttaattctt ttatcaattc atttagacaa tttcaaatca aaattctata    2340
agtaatatca ataaaaaaa ttttgatgc tccaataagt tagaacttaa atcaaaatat    2400
ataagtaaaa ttgatttaat catctcttct aaagtttctt ctattaagat ctttaatatc    2460
tatcaaatac attccacaat aatcatgcaa acctttaaa aattaaattc tcaatgcctt    2520
tactacattt taacaccaag ctcgataata gtgataaaga aacatctaga tcagctttat    2580
aatcaaaaat tttgacttac aattttacgt gtgtctcaaa atcttgaata aatataaata    2640
agatcttta tcttgatcca aaaatagtaa tcaaggattt cattagtaac ttcaacaaca    2700
atggtaaaaa aattttctat ccattgataa acccaaattt tgaattgaag tttcatgcat    2760
accatatagc ctttaataag atctattatt tggatctaaa gatagtaatt aaaattgtta    2820
atgattccac taagatgaat actttacaat ctcataatta atttcttcaa taaaaataga    2880
cttcttgata atgtctccaa ttgtatattt tttttattt ctacaagaaa acttcataca    2940
tttttttacgt tccaatataa atcttaaaaa gttattccaa tcaaatatca taaaagatct    3000
tcttagtcca accttaaata actttttatga atgaatcttt atcttgccac taaataatga    3060
atttttaaaat caagagcaac atcacagcat tctgtcatgt caaatttgtg ttagatgtat    3120
gtcctagaaa tcaattagat tgacaatgta aattttttaa ggatataatt tatatatttt    3180
gatttattaa taaaataaaa tttaaattaa tttttattca tatttttta tctatgaatc    3240
atctaaagaa ttaataagat gatgatacat attcttaaga gttcaaaatt tgaaatatat    3300
gtcattgatg attaatttct gaatactttt gaattcttaa gagtttagaa gatcttgacc    3360
caagtagtgt gaatagtgaa aaaagttttt cacatacttc acatcaaaaa tttaagttga    3420
ataaattgta catatgacag gtattatagt ttgacgagta atctataacc tctatcttat    3480
caaaattctg atagaaagat tgtattgtat gataactgta cttagaggtt cacctttat    3540
tttactggat taccactaca tgttgctaga tgtcactggt ggattgtgag atctacgaag    3600
```

```
attatcttga tgatcgataa ttctcattga aaagattgaa actattttaa tgatgttgtg    3660
atagagatca taatatatct tattatcaga cagaatagaa ttctatggga tcatacacaa    3720
taggagatta agactgatca aatagttgaa tgatgattaa gaatcattac ggagttcaga    3780
ttatcaatat aattgataat tagactaact tataattgtt acaagtagca aggacttaac    3840
tgctaaaggt taataggttc aaaaagaact tatgtataaa tgttgtgcat cttaatttga    3900
ttggatcaaa ttagttatgg ctgaattcaa gatgaatcaa ataggaattt ggttcaattg    3960
aatttgggtc aagctttagg cttaggtcac atatacccaa aatcatttgg atgcatcagg    4020
tgtgtgacac ctgaatcagg cctttctaaa ctattttgag t                       4061

<210> SEQ ID NO 36
<211> LENGTH: 4061
<212> TYPE: DNA
<213> ORGANISM: Artificial Sequence
<220> FEATURE:
<223> OTHER INFORMATION: synthetic

<400> SEQUENCE: 36
cttttttctt cttttctttt ttttttccta ttcttcttttc ccttttctgc ttaatggaat     60
aggggacctc ccattcccct tctatttcta gagttggggg ctcaaaattg atgatagcta    120
tcattgggga tgtaggctat ggtgatgcag tagaggatca ccgaccgatg atcgatggtg    180
atgttgcaat caaaaaatca agaaagatag atggaaaata aaggaaaata aggagaaata    240
gatctcaact tgtttggatg ctaacccact cactgacgac tccacttcaa ctatggccgg    300
agcttgctat ggaaaagaag ccaaggcctt caaggatgaa caccaatggt gaggaagatg    360
gtcgaaaata aagaatggc tggcttttct aatcgacaaa atagggtatc gcccttctta    420
gcaaatattc ggcaataaat atctagaatc caggatccta ggactatgga agaggagag    480 gagggcaagt caaggatgc cagattctta tctagcttcc gacaatgatg gggccctatt    540
ttcgataaac acaattgagg atgttcggaa aagggttttt tcgatgatga ttctagtgac    600
caactatgag atttcaaagg gggtgagggg ggtttaaata agatgggagg gaagtttgaa    660
tcctccttaa atctgaacct ttttcgacaa agccaagagc gtgaaggaga ctccttcgtg    720
aagtcaaaga tggaatagac tcccttcggg agtttggttc atcacccaac ttccctagca    780
tgtgcggagt atgtgctagc cttttctctc tttttttttc attttttttc atcctttaag    840
atccatgcag tttctaggtt gagggattgg ggtatcacat tctctctcct aaaaaaaaat    900
tattttcaaa attttttttac ctatattttc aaaagttggg attcatggtc caaatctcat    960
ccttgaattt ttttgatatt ctaattctcg aaaaaatttc atcgttaaat catttcataa   1020
gagaaaagtc aataccctcaa gagttgatct gaatcaaaat tattatctct agtaatcgaa   1080
atcaatatct taatttcaaa taagaatatc cagtttattg tcaaaattat taactactct   1140
tgacttaatt gatctattac ataatcgtaa ataaattcta acatactctt gaagtgtaga   1200
atataagatt gataaacaat cctatatccg ttctaataga tataaaagca taaactttaa   1260
atattttaaa tccaagatta agaatcaatg atccacttat cctagactca agatattaga   1320
aatttttttt tgtacaatag atagaggatg tactggtgaa atcatgtag cgatatccaa   1380 aataattttt aattaaaaat attatccttt tcattatcaa tgaattttat ctataagaaa   1440
gatcaaatca tatgatccat cttaaatttt taactcaaaa aattaatatt gcaaactagc   1500
tcaaaataat tttgatcact acattctgc tgtgcattct aatttaaacc gttcacattt   1560
```

```
tttagattca tgaaataatt ttgaccaaag tattactcca tactatagtc aaaaaagatt    1620
aaaatattag attctaatta aagccaaaga taaacttttg attctcatcc ttaattttgc    1680
ctaaagtata attattttga ttaacccttta agcgcaataa cacattcaaa accaacagat    1740
aggtttacta taatccaaat gaattaaatc ttaattcttt tatcaattca tttagacaat    1800
ttcaaatcaa aattctataa gtaatatcaa taaaaaaaat ttttgatgct ccaataagtt    1860
agaacttaaa tcaaaatata taagtaaaat tgatttaatc atctcttcta aagtttcttc    1920
tattaagatc tttaatatct atcaaataca ttccacaata atcatgcaaa cctttaaaaa    1980
attaaattct caatgccttt actacatttt aacaccaagc tcgataatag tgataaagaa    2040
acatctagat cagctttata atcaaaaatt ttgacttaca attttacgtg tgtctcaaaa    2100
tcttgaataa atataaataa gatcttttat cttgatccaa aaatagtaat caaggatttc    2160
attagtaact tcaacaacaa tggtaaaaaa attttctatc cattgataaa cccaaatttt    2220
gaattgaagt tcatgcata ccatatagcc tttaataaga tctattattt ggatctaaag    2280
atagtaatta aaattgttaa tgattccact aagatgaata ctttacaatc tcataattaa    2340
tttcttcaat aaaaatagac ttcttgataa tgtctccaat tgtatatttt tttttatttc    2400
tacaagaaaa cttcatacat tttttacgtt ccaatataaa tcttaaaaag ttattccaat    2460
caaatatcat aaaagatctt cttagtccaa ccttaaataa cttttatgaa tgaatcttta    2520
tcttgccact aaataatgaa ttttaaaatc aagagcaaca tcacagcatt ctgtcatgtc    2580
aaatttgtgt tagatgtatg tcctagaaat caattagatt gacaatgtaa attttttaag    2640
gatataattt atatattttg atttattaat aaaataaaat ttaaattaat ttttattcat    2700 attttttat  ctatgaatca tctaaagaat taataagatg atgatacata ttcttaagag    2760
ttcaaaattt gaaatatatg tcattgatga ttaatttctg aatactttg aattcttaag    2820 agtttagaag atcttgaccc aagtagtgtg aatagtgaaa aaagttttc acatacttca    2880 catcaaaaat ttaagttgaa taaattgtac atatgacagg tattatagtt tgacgagtaa    2940
tctataacct ctatcttatc aaaattctga tagaaagatt gtattgtatg ataactgtac    3000
ttagaggttc acctttttat ttactggatt accactacat gttgctagat gtcactggtg    3060
gattgtgaga tctacgaaga ttatcttgat gatcgataat tctcattgaa aagattgaaa    3120 ctatttaat  gatgttgtga tagagatcat aaatatatctt attatcagac agaatagaat    3180
tctatgggat catacacaat aggagattaa gactgatcaa atagttgaat gatgattaag    3240
aatcattacg gagttcagat tatcaatata attgataatt agactaactt ataattgtta    3300
caagtagcaa ggacttaact gctaaaggtt aataggttca aaaagaactt atgtataaat    3360
gttgtgcatc ttaatttgat tggatcaaat tagttatggc tgaattcaag atgaatcaaa    3420
taggaatttg gttcaattga atttgggtca agctttaggc ttaggtcaca tatacccaaa    3480
atcatttgga tgcatcaggt gtgtgacacc tgaatcaggc ctttctaaac tatttgagt    3540 aagtttgatc aagtcaaaag gatccacacc ctaaggtttc ttgaataaaa ccttaggcac    3600
cacattgagg acctatagga aactttgacc ctctctcata tggggtggca cactgaggtt    3660
ttataaaaac cttaggcacc catttagcc ataaaaaaaa agctccaagg gatggggcag    3720
tagccatgaa gaatccttgg ctgtcaggac tctattcaaa agagttctca aggttttgga    3780
ctcttatgga gccctaggat ttgtttgcct ataaatagat ggccacccca aggctttaga    3840
taatgttaga gacttgtgaa gctctcccct ttctcttggt tgccggccca ccctctctcc    3900
tctctcttcc atgccccaag acttctttct tgtctccatc atcttgctga aatttagatt    3960
```

| | | |
|---|---|---|
| tcagcaagaa aagtcaagta gaagtcaaag ttctaatgta gctcacaaga tgttgagaac | 4020 |
| ttcctccatc tggcaaaggt tctgcaagag agctagcatc c | 4061 |

<210> SEQ ID NO 37
<211> LENGTH: 4061
<212> TYPE: DNA
<213> ORGANISM: Artificial Sequence
<220> FEATURE:
<223> OTHER INFORMATION: synthetic

<400> SEQUENCE: 37

| | |
|---|---|
| tcttttatct tgatccaaaa atagtaatca aggatttcat tagtaacttc aacaacaatg | 60 |
| gtaaaaaaat tttctatcca ttgataaacc caaattttga attgaagttt catgcatacc | 120 |
| atatagcctt taataagatc tattatttgg atctaaagat agtaattaaa attgttaatg | 180 |
| attccactaa gatgaatact ttacaatctc ataattaatt tcttcaataa aaatagactt | 240 |
| cttgataatg tctccaattg tatattttt tttatttcta caagaaaact tcatacattt | 300 |
| tttacgttcc aatataaatc ttaaaagtt attccaatca aatatcataa aagatcttct | 360 |
| tagtccaacc ttaaataact tttatgaatg aatctttatc ttgccactaa ataatgaatt | 420 |
| ttaaaatcaa gagcaacatc acagcattct gtcatgtcaa atttgtgtta gatgtatgtc | 480 |
| ctagaaatca attagattga caatgtaaat tttttaagga tataatttat atattttgat | 540 |
| ttattaataa aataaaattt aaattaattt ttattcatat tttttttatct atgaatcatc | 600 |
| taaagaatta ataagatgat gatacatatt cttaagagtt caaaatttga atatatgtc | 660 |
| attgatgatt aatttctgaa tacttttgaa ttcttaagag tttagaagat cttgacccaa | 720 |
| gtagtgtgaa tagtgaaaaa aagttttcac atacttcaca tcaaaatttt aagttgaata | 780 |
| aattgtacat atgacaggta ttatagtttg acgagtaatc tataacctct atcttatcaa | 840 |
| aattctgata gaaagattgt attgtatgat aactgtactt agaggttcac cttttatttt | 900 |
| actggattac cactacatgt tgctagatgt cactggtgga ttgtgagatc tacgaagatt | 960 |
| atcttgatga tcgataattc tcattgaaaa gattgaaact atttaatga tgttgtgata | 1020 |
| gagatcataa tatatcttat tatcagacag aatagaattc tatgggatca tacacaatag | 1080 |
| gagattaaga ctgatcaaat agttgaatga tgattaagaa tcattacgga gttcagatta | 1140 |
| tcaatataat tgataattag actaacttat aattgttaca agtagcaagg acttaactgc | 1200 |
| taaaggttaa taggttcaaa aagaacttat gtataaatgt tgtgcatctt aatttgattg | 1260 |
| gatcaaatta gttatggctg aattcaagat gaatcaaata ggaatttggt tcaattgaat | 1320 |
| ttgggtcaag ctttaggctt aggtcacata tacccaaaat catttggatg catcaggtgt | 1380 |
| gtgacacctg aatcaggcct ttctaaacta ttttgagtaa gtttgatcaa gtcaaaagga | 1440 |
| tccacaccct aaggtttctt gaataaaacc ttaggcacca cattgaggac ctataggaaa | 1500 |
| ctttgaccct ctctcatatg gggtggcaca ctgaggtttt ataaaaacct taggcaccca | 1560 |
| ttttagccat aaaaaaaaag ctccaaggga tggggcagta gccatgaaga atccttggct | 1620 |
| gtcaggactc tattcaaaag agttctcaag gttttggact cttatggagc cctaggattt | 1680 |
| gtttgcctat aaatagatgg ccaccccaag gctttagata atgttagaga cttgtgaagc | 1740 |
| tctcccttt ctcttggttg ccggcccacc ctctctcctc tctcttccat gccccaagac | 1800 |
| ttctttcttg tctccatcat cttgctgaaa tttagatttc agcaagaaaa gtcaagtaga | 1860 |
| agtcaaagtt ctaatgtagc tcacaagatg ttgagaactt cctccatctg gcaaaggttc | 1920 |

| | |
|---|---|
| tgcaagagag ctagcatcct gagaaacaaa aagattgctg atcagccctc atctccatat | 1980 |
| ggatatttgt agagatcaaa tgcatgcata gctagaagag aatcttatca cgatcatcac | 2040 |
| tcgtgaagat catctacctg tgcaaaggta tgagataaga aaaatatttt ttttatcata | 2100 |
| attcatgaat cctttgctta tattatactg agattcttgg aatggatttt ttctctagta | 2160 |
| aaactctaga gatcagatct caaagtcttc ttcacataaa ggttttgaaa gttctttata | 2220 |
| tttccgctgc tttgattcaa ataaattag atctattttg cctttcaacc tttctcatat | 2280 |
| ttattgacat ataaagcttt aattaatgag attaatgaaa agcatgtgcg aaatactgag | 2340 |
| aaaatcctaa cagtgatatc agagctactt ttgtacataa gaaaaggatt caagttaaat | 2400 |
| aaaatatgtt tgatttaagt aaatgaatca atcaaaattt atcctaacat aagtttgtcc | 2460 |
| tggtataatg gtcaagacca ttatgttgaa aggttatcct aggacaaaaa gtctaagtaa | 2520 |
| aatctatttt atttaagtaa atgaatcaat taaagtttat tctaatataa gattgcctta | 2580 |
| gcataatggt gaagacccctt atgttgaaag gttgtcctag gatggaaagt gattgatgag | 2640 |
| acaaatatat catgaaagta ttttcacag atggaataaa atatatatat tttgtttgtg | 2700 |
| aaaatgagat tcatgaatg tgtttgtcat tcaatatgtg tggtgatcat cttgaattgc | 2760 |
| cacaaatcct ttttggatta gggttgtatc atgactcaca atcctgatg gtttgcaaaa | 2820 |
| ttttgcattc tgtagtgata gaaaccaaaa gttaatccaa ttttggaata agattgatca | 2880 |
| attggtatct aaggcaagta ttttataatg gtggttactt aattagttat aaaagtacga | 2940 |
| agagtctcct accaatctta cacttatcta gccaatttgg ttgattgaat tctgaatttg | 3000 |
| ggttgcttaa gtgttaagtt cactacaaat atattgcaac catgattccg acttagtcaa | 3060 |
| ccaagcctag atctcttgaa tagattcatg ttaattatgg atttacatag gatataaata | 3120 |
| aataattaaa acttgaagag atctaaatga aaccttctcg tacatattaa atcgaatgat | 3180 |
| cttccatcat tgtagatata cggatactct actgatgttg atgattttcg actagatata | 3240 |
| gtactttggt tgcatcgaaa aagtacaacc actttataac atgagatgtt gcagggtaga | 3300 |
| gatggggttg ggcccaataa ttgttaggtg aggatccaaa tgatggctgc acttgcgtgt | 3360 |
| gaatggcgag tctgacttaa ttaagaaata gagctaataa ctattagatg aggcttcagg | 3420 |
| acttagagac ttatgaccac tacaacttac ttgagaagca atggataaag agtcgtctat | 3480 |
| ttatcaactg acgcatcacc aataactatc agatggagtg atgtataatt agtgggacta | 3540 |
| tagtatccac ttgaaatctt aatcgtaaaa attttgttt ctccacctga agagcatggg | 3600 |
| agattcgaaa aaatagtggg ggtagtttat ttttaaaata aagctcctaa aataaactaa | 3660 |
| aataagttaa atacaaagtc taactagaat cttcttctct ctgtagaaaa tatctgcttc | 3720 |
| caacctctat ttcatatcct taagactaat tgtttgacta gacccagtta taaagattga | 3780 |
| ctctaaaact taaagatagt cttgagtttt gaaaagatga gctatgtcct ggatcaagat | 3840 |
| atcctctctc taccagcttg tcccacccct aatcaagggg catcctatga aaagtggtta | 3900 |
| aacgatgata acaaggcttg gtgctgtgtg ctgacatcta tgtccattga actccaatgc | 3960 |
| cagcataagg gtacaaactg tccaaggtat attgactcat ctacaagagt tatatagtga | 4020 |
| gtagagccat gtatctcact aggaagtatt taagagactc t | 4061 |

```
<210> SEQ ID NO 38
<211> LENGTH: 4061
<212> TYPE: DNA
<213> ORGANISM: Artificial Sequence
<220> FEATURE:
<223> OTHER INFORMATION: synthetic
```

-continued

```
<220> FEATURE:
<221> NAME/KEY: misc_feature
<222> LOCATION: (3017)..(3951)
<223> OTHER INFORMATION: n is a, c, g, or t

<400> SEQUENCE: 38
cagattatca atataattga taattggact aacttgtaat tattataagt agcaaagatt      60
taattgctaa aggttagcag attcaaggag gacttatgtg taaataatgt acatcttaat     120
ttgattggat caacttagtt atggctaaat ttaagatgaa tcaaacaggg atttagttta    180
atcgaatttg ggtcaagctt tgggcttagg tcacatgcac tcaaagggt tggatacat     240 caagtgtgtg acacccaaac caagcctccc taaactattt tgagttggtt ttgaccaagt   300
caaaagggtc cacaccctag ggtttcttga ataaaccct aggtgccaca ttgaggacca   360
attaggaaac tttgacattc tttcacacgg agcagcacac tagggtttca tgaaaaccct  420
aggcacccat tttagccata aaaggaaagc tccaagggat gggatggtgc catgaagaat  480
ccctggccat tgggactcca ttcaaaagtt ctctaggttt tgggctctta tagagcccta   540
gggtttgttt gcctataaat aggtcgctac cccaaggctt tagataatgc tagaggcttg   600
tgaagctctc tcctttctct tgtttgccat cccaccttct ctcctctctc ctccatgcct   660
caagacttct ttcttctctc catcatcttg ttgaaattta gatttcaatg agaaggatca   720
agtagagtca gagttctact gcagttctca aggtgttgag aactttcttc atcaggcaaa   780
gattctgcaa aggagttagc acctcaaaga accagaaaag ttgctaatct gccctcatct   840
ccatgtggat acttatagag gccaagcatg acgagaagag ccttatcacg atcatcactc   900
gtggagatca tctacccgcg caaaggtatg agataagaaa aaatatttt tcttatcatg     960 attcatgaat cctttgctta tgttacattg agactcttgg attagatttt ttctctaata   1020
aaatttcaaa gattagatct cgaagtcttc ttcacctaaa ggtattgaaa gttctttata  1080
ttttcgctac tttgattcaa aatagattag atttgtttg cctttcaatt tttctcatat    1140
ttattgagat atgaagcttt aattaatgag attaataaaa agcatatgtg aaatactgag   1200
aacatcctaa caatttgagc ttacaattca cttaaacaac taatgatcaa attaataatc  1260
acaatgcaca ataaaaattc atgataaatc tttttgttgt tactttagat caaaatccaa   1320
ctaatcataa catgatccac ggattgccta tcatatatca aaccctctga attattaatc  1380
ttaaacgatc ttttcattca tgatcataag atttagttaa aaatcatgaa gacaacttat   1440
attgtaatca tcatagatct gtatcttaac atccttagtg tttacctacc tatactcatc   1500
ctatgtttga ttctatatat cataatttat tcactaatac tttgatatca tataaattat   1560
cgcatcccca atctaagatc atattggtac tttaatattt cattagtggg ggttatgcat   1620
tagtactttg ataccttatc agttgaatgg ttaaacactg gtactttgat atcctatcag   1680
tggaggttat acgctggtac tttaatatcc tatcagtaag atggttaaat actgatactt   1740
tgataacctc ccagtgggtg ttgtatgcta gtactttatt atcctaccaa tggggcagtt   1800
aaatgctact actttgatac gctaccaatg ggatagttaa acgctagtaa tctaatctta   1860
gcttgacata aagtaacgtc gactcgagtt tagggtcgac tcgagagaat gttagggtta   1920
gcttgatatg aaagagggtc gctcgtcaat attttggagt caactcttgt ttatggacga   1980
tctagaaagt gtcagagtga gctcgagtac tgcatatttc tgatacattg tctatgctag   2040
aatgtgctag aactgattat cttctttatc aaagttgatt tttgagtaac ttgatgatca   2100 attttttctag gctagacttg ctttgtcaaa atgagcactt gttagtttag agaatcttca  2160
```

```
cctacacatg atctcaagca ttcattagta ccaaaaatac ttaagtattt tgatatcatc   2220
aaaatcaatt cttgggttaa cacaatactt ttcaaataat aagcatacag atataatcct   2280
ataacaattt aaattttgtt catatatcaa tttctttaaa aatattatat tcatcttgat   2340
agctatgaac taaatcaaaa tacatactag tatacaactt ttactgggag agtattagat   2400
taccagcatt taaccatccc actggcaagg tatcaaatta ccaatacaca acccctattt   2460
ataaagtatc aaagtaccag tgttcaactg cctcactggc aggatatcat agtactagta   2520
tttaactacc acattgacag gatatggaat tatcagtatt taaccatcat tagtagaatt   2580
ttgatgcata gtcaggctgc gagtcaaaat ctatctcaaa tcaaaatatt gatcacatgt   2640
ctaattctgt atcataattc attcccttat gctctaatat tatattaatt gtcatacttc   2700
tagctcgaga tcatgagcca aggattgcag taactaccgc atacttatag agaactcttt   2760
ctataagcat acaagatatt ctaaatatac tatcaatata tcatagagaa attaatttaa   2820
ataactaaaa gttaatattc aattaataaa ttcaactggc aaatgtattt aaaaatttta   2880
catcaaataa atcttgatta ataaatatta attaataaca atagatttaa atcgaaacaa   2940
ggttgatatt gttagaattt gatgcctcaa gattcagccc acattgagtc cacagtgagg   3000
ttcgcgacga aaaatgnnnn nnnnnnnnnn nnnnnnnnnn nnnnnnnnnn nnnnnnnnnn   3060
nnnnnnnnnn nnnnnnnnnn nnnnnnnnnn nnnnnnnnnn nnnnnnnnnn nnnnnnnnnn   3120
nnnnnnnnnn nnnnnnnnnn nnnnnnnnnn nnnnnnnnnn nnnnnnnnnn nnnnnnnnnn   3180
nnnnnnnnnn nnnnnnnnnn nnnnnnnnnn nnnnnnnnnn nnnnnnnnnn nnnnnnnnnn   3240
nnnnnnnnnn nnnnnnnnnn nnnnnnnnnn nnnnnnnnnn nnnnnnnnnn nnnnnnnnnn   3300
nnnnnnnnnn nnnnnnnnnn nnnnnnnnnn nnnnnnnnnn nnnnnnnnnn nnnnnnnnnn   3360
nnnnnnnnnn nnnnnnnnnn nnnnnnnnnn nnnnnnnnnn nnnnnnnnnn nnnnnnnnnn   3420
nnnnnnnnnn nnnnnnnnnn nnnnnnnnnn nnnnnnnnnn nnnnnnnnnn nnnnnnnnnn   3480
nnnnnnnnnn nnnnnnnnnn nnnnnnnnnn nnnnnnnnnn nnnnnnnnnn nnnnnnnnnn   3540
nnnnnnnnnn nnnnnnnnnn nnnnnnnnnn nnnnnnnnnn nnnnnnnnnn nnnnnnnnnn   3600
nnnnnnnnnn nnnnnnnnnn nnnnnnnnnn nnnnnnnnnn nnnnnnnnnn nnnnnnnnnn   3660
nnnnnnnnnn nnnnnnnnnn nnnnnnnnnn nnnnnnnnnn nnnnnnnnnn nnnnnnnnnn   3720
nnnnnnnnnn nnnnnnnnnn nnnnnnnnnn nnnnnnnnnn nnnnnnnnnn nnnnnnnnnn   3780
nnnnnnnnnn nnnnnnnnnn nnnnnnnnnn nnnnnnnnnn nnnnnnnnnn nnnnnnnnnn   3840
nnnnnnnnnn nnnnnnnnnn nnnnnnnnnn nnnnnnnnnn nnnnnnnnnn nnnnnnnnnn   3900
nnnnnnnnnn nnnnnnnnnn nnnnnnnnnn nnnnnnnnnn nnnnnnnnnn nagatattac   3960
taaattttgc ttctaatctc actcttaaat agtacttacc tttgaaacta ggcatttgaa   4020
tctgaaaaag aaagaggaga ttatgagctt gatagttcag t                       4061
```

<210> SEQ ID NO 39
<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2337)..(3271)
<223> OTHER INFORMATION: n is a, c, g, or t

<400> SEQUENCE: 39

```
catcatcttg ttgaaattta gatttcaatg agaaggatca agtagagtca gagttctact    60
```

```
gcagttctca aggtgttgag aactttcttc atcaggcaaa gattctgcaa aggagttagc    120
acctcaaaga accaagaaag ttgctaatct gccctcatct ccatgtggat acttatagag    180
gccaagcatg acgagaagag ccttatcacg atcatcactc gtggagatca tctacccgcg    240
caaaggtatg agataagaaa aaaatatttt tcttatcatg attcatgaat cctttgctta    300
tgttacattg agactcttgg attagatttt ttctctaata aaatttcaaa gattagatct    360
cgaagtcttc ttcacctaaa ggtattgaaa gttctttata ttttcgctac tttgattcaa    420
aatagattag atttgttttg cctttcaatt tttctcatat ttattgagat atgaagcttt    480
aattaatgag attaataaaa agcatatgtg aaatactgag aacatcctaa caatttgagc    540
ttacaattca cttaaacaac taatgatcaa attaataatc acaatgcaca ataaaaattc    600
atgataaatc tttttgttgt tactttagat caaaatccaa ctaatcataa catgatccac    660
ggattgccta tcatatatca aaccctctga attattaatc ttaaacgatc ttttcattca    720
tgatcataag atttagttaa aaatcatgaa gacaacttat attgtaatca tcatagatct    780
gtatcttaac atccttagtg tttacctacc tatactcatc ctatgtttga ttctatatat    840
cataatttat tcactaatac tttgatatca tataaattat cgcatcccca atctaagatc    900
atattggtac tttaatattt cattagtggg ggttatgcat tagtactttg ataccttatc    960
agttgaatgg ttaaacactg gtactttgat atcctatcag tggaggttat acgctggtac   1020
tttaatatcc tatcagtaag atggttaaat actgatactt tgataacctc ccagtgggtg   1080
ttgtatgcta gtactttatt atcctaccaa tggggcagtt aaatgctact actttgatac   1140
gctaccaatg ggatagttaa acgctagtaa tctaatctta gcttgacata agtaacgtc    1200 gactcgagtt tagggtcgac tcgagagaat gttagggtta gcttgatatg aaagagggtc   1260
gctcgtcaat attttggagt caactcttgt ttatggacga tctagaaagt gtcagagtga   1320
gctcgagtac tgcatatttc tgatacattg tctatgctag aatgtgctag aactgattat   1380
cttctttatc aaagttgatt tttgagtaac ttgatgatca atttttctag gctagacttg   1440
ctttgtcaaa atgagcactt gttagtttag agaatcttca cctacacatg atctcaagca   1500
ttcattagta ccaaaaatac ttaagtattt tgatatcatc aaaatcaatt cttgggttaa   1560
cacaatactt ttcaaataat aagcatacag atataatcct ataacaattt aaattttgtt   1620
catatatcaa tttctcttaaa aatattatat tcatcttgat agctatgaac taaatcaaaa   1680
tacatactag tatacaactt ttactgggag agtattagat taccagcatt taaccatccc   1740
actggcaagg tatcaaatta ccaatacaca accsctattt ataaagtatc aaagtaccag   1800
tgttcaactg cctcactggc aggatatcat agtactagta tttaactacc acattgacag   1860
gatatggaat tatcagtatt taaccatcat tagtagaatt ttgatgcata gtcaggctgc   1920
gagtcaaaat ctatctcaaa tcaaaatatt gatcacatgt ctaattctgt atcataattc   1980
attcccttat gctctaatat tatattaatt gtcatacttc tagctcgaga tcatgagcca   2040
aggattgcag taactaccgc atacttatag agaactcttt ctataagcat acaagatatt   2100
ctaaatatac tatcaatata tcatagagaa attaatttaa ataactaaaa gttaatattc   2160
aattaataaa ttcaactggc aaatgtattt aaaaatttta catcaaataa atcttgatta   2220
ataaatatta attaataaca atagatttaa atcgaaacaa ggttgatatt gttagaattt   2280
gatgcctcaa gattcagccc acattgagtc cacagtgagg ttcgcgacga aaaatgnnnn   2340
nnnnnnnnnn nnnnnnnnnn nnnnnnnnnn nnnnnnnnnn nnnnnnnnnn nnnnnnnnnn   2400
```

```
nnnnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnnnn nnnnnnnnnn nnnnnnnnnn nnnnnnnnnn nnnnnnnnnn nnnnnnnnnn    2580
nnnnnnnnnn nnnnnnnnnn nnnnnnnnnn nnnnnnnnnn nnnnnnnnnn nnnnnnnnnn    2640
nnnnnnnnnn nnnnnnnnnn nnnnnnnnnn nnnnnnnnnn nnnnnnnnnn nnnnnnnnnn    2700
nnnnnnnnnn nnnnnnnnnn nnnnnnnnnn nnnnnnnnnn nnnnnnnnnn nnnnnnnnnn    2760
nnnnnnnnnn nnnnnnnnnn nnnnnnnnnn nnnnnnnnnn nnnnnnnnnn nnnnnnnnnn    2820
nnnnnnnnnn nnnnnnnnnn nnnnnnnnnn nnnnnnnnnn nnnnnnnnnn nnnnnnnnnn    2880
nnnnnnnnnn nnnnnnnnnn nnnnnnnnnn nnnnnnnnnn nnnnnnnnnn nnnnnnnnnn    2940
nnnnnnnnnn nnnnnnnnnn nnnnnnnnnn nnnnnnnnnn nnnnnnnnnn nnnnnnnnnn    3000
nnnnnnnnnn nnnnnnnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nagatattac taaattttgc ttctaatctc    3300
actcttaaat agtacttacc tttgaaacta ggcatttgaa tctgaaaaag aaagaggaga    3360
ttatgagctt gatagttcag taaatcatga ataaattagc taaataaatc tatgaataat    3420
agtatattaa aaataaatat gtaagataca ataattcaaa aatgaattca tatatataat    3480
actttccaaa taataagtat gtggctgcaa tcctttcgta attcaaattt tgttcattaa    3540
ttattttttt caaaacatca catggatagt catgaactaa atcaaagtac cagtgcataa    3600
cccctattga taaagaatca aataacaagt gtttgactgc tcattatca ggatatcaaa     3660 ttattaatgc ataacctcca ctgctagggt atcaaagtag caacctcaat cacctcactg    3720
gaagggcatc tagtttcagt atttaactac tccactggca aggtgttaaa ttatcaatat    3780
ttaacctcca ctgataggat tttgatatat agtcagactg cgagccaaaa ttcatttcaa    3840
accaaaatat ttttctcaaa gacatatttt atgtttcaca ttgaaaaatt cacaaaaatt    3900
atgcgatatt gaaatcaatt ggataaaatc cacgtcaaat ttagtatatt caatcataaa    3960
tcatttacta ttctagaaaa ggtatattaa aagtataatg catcaatttc ataaatcata    4020
aatatctcaa tataaaaaat attttattat ttattaataa a                        4061
```

<210> SEQ ID NO 40
<211> LENGTH: 4061
<212> TYPE: DNA
<213> ORGANISM: Artificial Sequence
<220> FEATURE:
<223> OTHER INFORMATION: synthetic

<400> SEQUENCE: 40

```
agtatattca atcataaatc atttactatt ctagaaaagg tatattaaaa gtataatgca     60
tcaatttcat aaatcataaa tatctcaata taaaaaatat tttattattt attaataaat    120
ctaggagaag tgaagcatta cttatcttgt aagtaaaact aaccaactga tcaaattaat    180
tctgagaatc tttctcaaaa ctcatcacca ctatatcaaa aacttgtgct tcttgctatg    240
taagagcata gacccttct tcgatctggg gttccaagtt tctattttat tttgttcaac     300
tatcaaatta gactgacttt tcattttttt gtggatattc agctatttta tggcctttct    360
aacaataacc aaagtatgta ccaatattcc aacaataatc atttattgca tgattttcac    420
```

```
cgcatcgaaa tatttgatat tatcaatcaa tccaaacttg ttattcactg acctcttatt      480
caaacccttt gtatatttaa tattctacct ttgtgattca ttcaatcgat ttctttttt       540 tattttcttt ccctttctat atgctcttca ttaacttttc tttcaattat caatgctttta    600 ttcaatacat ctgtataagt agttaactca tatagtacca tttattttct aatttctatc     660
ctcaattcca actcaaattt atctactcag tcacattcat cttcaaccaa tctcgaagca     720
aacttgacaa gctccataaa tttagcttca tattctacaa ctattatatt tctttatttc    780
agataaataa attttttattc tttctgaatc ctcatactct aagaaaaata ttttttatcat   840 aaaatatctt ttgaaatcac tcccaagcga gttgttctcc atcttgttca tatttaggtt     900
tcattctcta ttatcaatta aatgtctcat ctttcaacat gtatgatgca tataagattt     960
tttcatcatc atggtatctc ttaacaataa atgctttctc catctccata agctaatttt    1020
tagctcctat ttcatagttt tcttaaaagt caatggagac aacttcttaa attctatgat     1080
attactttat tgctcctatt gctcttatgt ccttgtggtg acaatattta ttgttgcact     1140
tgctgtagag gcagttactg ttactgcaat tgctattacg attccatcaa gccgactagt    1200
gtctgcatta tttggataat agttgatttt tgctacttta tttagatgtt ggtggcaaaa    1260
tcaatgactt cttttttgctg agagatgcca ccaacctact aagtatcatc atcttattgg    1320
ttgatacctt tagcagcacc tcgagtggtt ctttttatct gatatggaac catcttaatc     1380
ttgcatgaaa acaaacttc gcaaaattt cttttaaaat ctaatatcta atattatact       1440
tttattaaaa tttaattatg attattttaa gaataaaaaa tttaaatttt gaaatcctca    1500
caaggctggc caagagataa tgaccatcat cctagtcggt ttgacgtagg acatccaaag    1560
atcaactata attcaagcat catattgaga tgctaggata taatcgatgg tgaaattaa     1620 tgatgctcga ctgatcaaga tgggggccgg cccgatggcc tgttcaacaa tcattgatca    1680
aaatttttta accaaggtct atcaagatca ttaaaaagtc tttctaagat ctataaattg     1740
taataaagag acacaatcta gagagagaca cttttacat aaagaaagta gaaatttag     1800 ggagagaaat tagagagaaa ggggaaagag agaggaagct gagaggaaga agaaaaagag    1860
aaagactctc tctcttttc ttttctttct tttctttctt ttcttttcct tttctttttt     1920
tcttcctttt ctttctttct ttctttggct cattagaaaa ataggggacc tattgatccc    1980
cttgtttcct aaataggggga ggaatctcat cttggtagct atggccggcg atgtgagcca    2040
aagtggcaaa atcatgaatc tcccaacttg cagccgacat tgacttttgg cactggaaaa    2100
tcaaagaaat ttgacaaaaa atgggaaaaa attgaaacca aaatagggac caaaatccgg    2160
taatagctag ccaaaaatcc ttgatctttg ctcatggagg ataggaaaaa agattattca    2220
agagattaag ggaatcttat ctcatttttt tgctgtgctt cggccatggt ggttgcagaa    2280
atcgtttgtg aaagctcgac aaactctgca atttcctcgg gcttgggcct cgatctttaa    2340
taggagaaga gagaagtcct cttttctttta aatagagtcg gagggaagga gtttgatttc    2400
ctccttatgg tggtttcaaa ctctgatcgg aagtccattg gaaagaaga ctcccattag      2460 ttttaaaatc taataagatt tattgattag aaaattgata aaaatgatt attaaaaaag     2520 tagcataatt atttaaatca atgatgctta gattgttgga ggtaaatagt aataaaatca    2580
aaaaattaaa attcatggga ccaaaaaata atgaacaaga tttgaaagaa atgtctataa     2640
ataagaattt atgaaacagg ggaacattga tcaaaggtgt gttaaatagt gtccttaaag    2700
tgttattgtc cctctcacgt agactttgtg tgttgggaga gaacatagta attctctcaa    2760
```

| cctatgcaac | ctaaatcttt | tgaaaagaaa | tttaaaatta | tagaaaaatt | ggcaaactag | 2820 |
| aattttggtc | attttcttta | ttagtaaaaa | atatactaag | ttatatgtct | ttatttatac | 2880 |
| tagtgaggtc | tatctttgca | caattcagac | caaatttata | ttctagttaa | aagaggtata | 2940 |
| gatttttaa | aatagatata | actagtggaa | atagtcatag | aaaagttaaa | aatcaatgaa | 3000 |
| aggtagattt | cacttctata | ttggctttat | tgtggtcac | tttatctaat | tcttttttt | 3060 |
| gatggagcaa | tataccctgt | taaaatcttc | tcgatttttt | tttcacttta | agcaacctat | 3120 |
| ttcgatgcct | aaacaatgga | atttagttta | accacttaat | atgctacact | tttaaaagga | 3180 |
| gcaccatatt | gtagggcttg | aaaagttact | tgatttaaaa | aaagagcatc | ttaattggac | 3240 |
| atcatacaag | taagttatga | cctctgaaaa | tttgatacat | gatttatcat | cttgatatgg | 3300 |
| taaatcttgt | taagatttcc | tcatggtgtc | taaagtggcc | ggttcatact | gagtttggtg | 3360 |
| attcttctgg | tcaatggtta | attgctcgaa | tattttaag | atataactaa | tctccaactc | 3420 |
| tgccgactcc | ttagtagtat | gagcacatgg | aaagcttgac | ctaattgatt | tcttaaattg | 3480 |
| cttgaaatca | gtacttagaa | aatatgcaaa | atggatgaaa | tgtttattgc | agcgagagct | 3540 |
| ttctgatctg | tacgaccgag | agcttactag | tttttatga | gctatacgtt | ttgcacttaa | 3600 |
| gcctaattta | aatagtgaaa | tagttttgca | acaattcaaa | acaattaaaa | tcaaaagaca | 3660 |
| agctgctatg | catgttcaac | tgactcggct | ttcaatcgca | atatgtcaca | taggctggcc | 3720 |
| tagaatgcag | atgcgtgcgt | ggtgagcatc | ctaaaaacct | acatatccaa | taaattccca | 3780 |
| ctagttggtg | aagtattaaa | tgtaactcgt | attaactttt | taatgtagga | ctaaagttta | 3840 |
| ttcgactaat | taagaactaa | atactttaat | aattgaactt | ttccaaccag | aaatcagaaa | 3900 |
| atatttaagt | aattaaatat | tacataataa | ctagatcaaa | atatcatggt | tcctctctcg | 3960 |
| ctcgagatca | attgggatgt | tggtttatct | tggtcatcca | tcgagatgac | tctatcttag | 4020 |
| cctttcaaaa | cggcgcggta | ccacgggtct | caccgcttcg | t | | 4061 |

<210> SEQ ID NO 41
<211> LENGTH: 4061
<212> TYPE: DNA
<213> ORGANISM: Artificial Sequence
<220> FEATURE:
<223> OTHER INFORMATION: synthetic

<400> SEQUENCE: 41

| caaaattttc | ttttaaaatc | taatatctaa | tattatactt | ttattaaaat | ttaattatga | 60 |
| ttattttaag | aataaaaaat | ttaaattttg | aaatcctcac | aaggctggcc | aagagataat | 120 |
| gaccatcatc | ctagtcggtt | tgacgtagga | catccaaaga | tcaactataa | ttcaagcatc | 180 |
| atattgagat | gctaggatat | aatcgatggt | gaaatttaat | gatgctcgac | tgatcaagat | 240 |
| gggggccggc | ccgatggcct | gttcaacaat | cattgatcaa | aattttttaa | ccaaggtcta | 300 |
| tcaagatcat | taaaaagtct | ttctaagatc | tataaattgt | aataaagaga | cacaatctag | 360 |
| agagagacac | ttttacata | aagaaagtag | aaatttagg | gagagaaatt | agagagaaag | 420 |
| gggaaagaga | gaggaagctg | agaggaagaa | agaaaagaga | aagactctct | ctcttttct | 480 |
| tttcttcttt | ttctttctt | tctttttctt | ttcttttttt | cttcctttc | tttcttctt | 540 |
| tctttggctc | attagaaaaa | tagggggacct | attgatcccc | ttgtttccta | aataggggag | 600 |
| gaatctcatc | ttggtagcta | tggccggcga | tgtgagccaa | agtggcaaaa | tcatgaatct | 660 |
| cccaacttgc | agccgacatt | gactttggc | actggaaaat | caagaaatt | tgacaaaaaa | 720 |
| tgggaaaaaa | ttgaaaccaa | aatagggacc | aaaatccggt | aatagctagc | caaaaatcct | 780 |

```
tgatctttgc tcatggagga taggaaaaaa gattattcaa gagattaagg gaatcttatc      840
tcattttttt gctgtgcttc ggccatggtg gttgcagaaa tcgttgtga aagctcgaca       900 aactctgcaa tttcctcggg cttgggcctc gatctttaat aggagaagag agaagtcctc      960
tttcttttaa atagagtcgg agggaaggag tttgatttcc tccttatggt ggtttcaaac     1020
tctgatcgga agtccattgg aaaagaagac tcccattagt tttaaaatct aataagattt     1080
attgattaga aaattgataa aaatgatta ttaaaaaagt agcataatta tttaaatcaa      1140
tgatgcttag attgttggag gtaaatagta ataaaatcaa aaaattaaaa ttcatgggac     1200
caaaaaataa tgaacaagat ttgaaagaaa tgtctataaa taagaattta tgaaacaggg     1260
gaacattgat caaggtgtg ttaaatagtg tccttaaagt gttattgtcc ctctcacgta      1320
gactttgtgt gttgggagag aacatagtaa ttctctcaac ctatgcaacc taaatctttt     1380
gaaaagaaat ttaaaattat agaaaaattg gcaaactaga attttggtca ttttctttat     1440
tagtaaaaaa tatactaagt tatatgtctt tatttatact agtgaggtct atctttgcac     1500
aattcagacc aaatttatat tctagttaaa agaggtatag attttttaaa atagatataa     1560
ctagtggaaa tagtcataga aaagttaaaa atcaatgaaa ggtagatttc acttctatat     1620
tggctttatt tgtggtcact ttatctaatt ctttttttg atggagcaat ataccctgtt      1680
aaaatcttct cgattttttt ttcactttaa gcaacctatt tcgatgccta acaatggaa      1740 tttagtttaa ccacttaata tgctacactt ttaaaaggag caccatattg tagggcttga     1800
aaagttactt gatttaaaaa aagagcatct taattggaca tcatacaagt aagttatgac     1860
ctctgaaaat ttgatacatg atttatcatc ttgatatggt aaatcttgtt aagatttcct     1920
catggtgtct aaagtggccg gttcatactg agtttggtga ttcttctggt caatggttaa     1980
ttgctcgaat atttttaaga tataactaat ctccaactct gccgactcct tagtagtatg     2040
agcacatgga aagcttgacc taattgattt cttaaattgc ttgaaatcag tacttagaaa     2100
atatgcaaaa tggatgaaat gtttattgca gcgagagctt tctgatctgt acgaccgaga     2160
gcttactagt ttttatgag ctatacgttt tgcacttaag cctaatttaa atagtgaaat      2220
agttttgcaa caattcaaaa caattaaaat caaaagacaa gctgctatgc atgttcaact     2280
gactcggctt tcaatcgcaa tatgtcacat aggctggcct agaatgcaga tgcgtgcgtg     2340
gtgagcatcc taaaaaccta catatccaat aaattcccac tagttggtga agtattaaat     2400
gtaactcgta ttaacttttt aatgtaggac taaagtttat tcgactaatt aagaactaaa     2460
tactttaata attgaacttt tccaaccaga aatcagaaaa tatttaagta attaaatatt     2520
acataataac tagatcaaaa tatcatggtt cctctctcgc tcgagatcaa ttgggatgtt     2580
ggtttatctt ggtcatccat cgagatgact ctatcttagc ctttcaaaac ggcgcggtac     2640
cacgggtctc accgcttcgt tacatcgaat gccaccatcc cttttttttt tttttttatt     2700
tatttatgct ttcttgctcc tagattggtg cggcctcatt acaactccac tgctacttga     2760
tgcttccctc tagcatctcc tttgcagctc tctcacttcc accactcttc ggcctaatgt     2820
tgggaaacga cgaaggggcc ttacaaaaat gtcatccatg atggcagtgg agaagaaaac     2880
atcgctgggg ctttccttcg atatccttcg cagccaaagc tcttataggg ttatatggga     2940
gaacgctgca ttatttgggt gatcttttg gatggtgttg ttgactgatg ctagttttgc      3000
ttcatgaatt gaatatttac acaagatgag aatacaatct agtacaattg gtaccaatta     3060
cctgggtttg actcctgctc gcatctgatt gaagcttggt taatgtgcat ctcaattaat     3120
```

| | |
|---|---|
| tcagaaagat catcggactt catgtgaatt attttgacta gcatgaatag ggctaaataa | 3180 |
| ggctgaaata tgtgttaaat ttttaaaatt ataacttgat catatgatgt ccaattgaga | 3240 |
| tgttttcaaa tcaaaaattt ttttcgagat ttatcactta atgttaaact cttagaaggt | 3300 |
| cgaaacagac tgaaagtttt cttttcaaga tgtattttga ccgagtatat aacttgatga | 3360 |
| tcatatgatg cccaattgag atgttttcaa atgaaaattt tttttgagat ttatgactta | 3420 |
| atgttaaact cttaaaaggt cgaaacagac tgaaagtttt cttttcaaga tgtattttga | 3480 |
| ccaaatatat ctcataatct ataaagaata tatttcataa tctatgaata attagataga | 3540 |
| gcgacagaag ataatgctaa tgtaaaaatc acgatctatt ttttataaaa tttaatattt | 3600 |
| ttatataatc acttttacta tagtcatatt tattttaaaa aatttagtta tatttaaaat | 3660 |
| atcaaaaaaa tttgacttga attatataag aaaggatctt cctactatta tagatagaag | 3720 |
| ctttatatca tagtttacag tgtatggatc atcaatgaaa gaaagaggga tgtaaacctt | 3780 |
| acttttgaaa ttttctatt tgtttctaaa tttttaaag gatccaagtt gagaattgag | 3840 |
| agaattcttt ctttctgcaa atcaaatcat tagtataatc cacatggaga cgttgtaata | 3900 |
| gaaagtagaa actatatttt atgaataata gaaagggagt tgatttacgc caagcctttt | 3960 |
| gtttgcttga ttaattattt attttatgg tgttagctgg accccatgaa tagcaaccat | 4020 |
| cgttgggtca gggtcgtgta tttgttttgg ggtcttcatt a | 4061 |

<210> SEQ ID NO 42
<211> LENGTH: 4061
<212> TYPE: DNA
<213> ORGANISM: Artificial Sequence
<220> FEATURE:
<223> OTHER INFORMATION: synthetic

<400> SEQUENCE: 42

| | |
|---|---|
| caagtactcc agaatcaaaa ttgtgaaaga aaaataggat aaatctggtt aagctgtaat | 60 |
| ttatttactt actttctatc tatattaaaa ttattcagat tattttgcaa atttatggat | 120 |
| atgcttgaat cacgtatctg atactttctc ttcatctgga tggcagtacc atgtgatcac | 180 |
| cacgcagacg gataacctaca agaaaaaggc aaggctaaca tgctttctta ccatcattct | 240 |
| ttacggtctt tgatccggtt ttgcgtgtcc acttcttacg tagtcttttt caaacattcc | 300 |
| tatctaagac tgaaggtaat gatttgcaaa ggaatagctt tactgttttc ctctaagtag | 360 |
| atgaaatatt actcacgtag aaaggagcca tcataattgc agaaagaata aaactgaatg | 420 |
| gaatatgagt agaattgtca aaatcttggt ttaagggttt taatagccag atgagaaagc | 480 |
| aacctacttt tcttgaacaa cttgtttgtg actgtcttgt tgctcccatc ttgcatctat | 540 |
| gattagcaaa atatatgata aatagatatt cagatttgat cgaaaagaag gaagattttc | 600 |
| tttaatccat ttaatttgaa tctcacaaaa aaaagtaga gatttggac acgatcgctg | 660 |
| ggggcagcac gctcttaata gaatggtgtc acgttgcaga tctcgaaaaa ttattcaatt | 720 |
| tttttttaaaa aaaagagtc attgaaatta gacgttgtat gaccatgtta tgatctctga | 780 |
| aagtttgact tctgactcaa cttcccaatg tagcagattt tactcctgaa ccatgtttaa | 840 |
| cctcctgact catagtggcc aaagtatcta catcgagttc actggtcttc ttggatcaca | 900 |
| ttcataagaa tacttcccat aatttttgctc aacgttgttt ttctcatcaa ccaaaggtat | 960 |
| atgcttttta aaattgaaat gcccatgaat attatggcat tcttttattt gacattttgg | 1020 |
| ttgatcctat attgttgtt tggcattcaa cacttcttca tgggaacctt tgaaatgagg | 1080 |
| taggtgctag gattttttctt tttacctatc catatcatat ttccaatgtc ttcttttaca | 1140 |

```
ttaggttctt tagtgacaat aggggaaacg acccaatata ataccccttga aaatttgggc    1200 aatatctact aaaactaact tgaataaaat attaacataa aaagggattt agtaacataa    1260
aagcataact caaaatcact caccttgtgt gccacgttct cattgcccct tattattttg    1320
cattgtgaat tgtgtccccc aataaagcaa cgtgaatggt ggaagagagt tgaatggctt    1380
tgttgagtaa ttgttttgag ttactatagc attgctctac taaaattgaa atcttgctgt    1440
gaggctatgt atgagaagca agttcatgct ttttgactgt tgggatggaa gtatgagcaa    1500 tcttttttaat agaaaatgga cgaatcatga agttttttcct ttttattgaa aaagatgatc    1560
gaaaaatatg tgcaagatag aaaaacactg aaaagataaa atgagaagta aaagtggaag    1620
tctaggagaa gaaaatttaa gagaaatatc ttcaatgaga ggatgtgtgc accaacaaag    1680
ccaactttca ctaaagaatg taatgactca cctctacttt cttcgaataa ggggttccca    1740
gttgtggaaa gtatatagaa tcttctgaaa gactgagtaa atggagcaat tccttctaag    1800
aaatattatg gcatttctct cccacgaaat ttcaaagcaa agagcagcta gtagttgatc    1860
ctctaatctc ttaattgaag tttggaattt ctcttgcctc tatttggccc aaaggtcatg    1920
aagatctacc ggccaacctc ttaagttgaa ttagatctta atagaagtcc aaatgcttct    1980
tgtagaagaa catctaataa ataaatgagt gatagattct aatccagaga caaagagcac    2040
acctcgaatt cacttgccat cctttttctag ctagaacttc tctagcatga aacttgttcc    2100
ttaaggcaag ccaaataaat actcacattt taggaatgac tgccttccaa ataatttttat    2160 aatatggaca aattagacca ccattattga taaacttgca atgaacaatt ataaatgagt    2220
tttcaggttg gcacattagc aatataggat ggtttgatta ttaaaaggat gatatgaagg    2280
gtttcaaggt ggtttgcctc gttcaaatca aaggattttg aagattaata ttccaagata    2340
aggttctcca actccattag gaaagtgtct tcatgtcatc ttagagaagc agctcgtacc    2400
aaacttgaca gatgtttttat ttatttagag tgacacagat acccttttggc aatactctcc    2460 atccttgtcc gaacaacttc taatcacacc tcacttatct tgcatctaac tcagaggcta    2520
caagttacac ctttcaacaa accttttcgg tttgaaaatt tgtgatttca ttatttagag    2580
ttcgaagagc atatcaagta ttggtcggag ttggcaccca aagcaaacga aacagttact    2640
gacatggtcc aaaagctgag atttctaaga tcccaactta agcactgaat aaagccatta    2700
tgggaaatat cattttaacg aaagaggaat ttagagtaag aattgattct cttgataccg    2760
aagaagaact aatacagctt tcatcacttc aaaatgatga acagatgcat ctcaagtcag    2820
cactagacca tcttctaaaa taggaagatc tatggaagca acactcccaa atgcagtggc    2880
ttcaaaatgg ggattgcaat acgaagttta tccatgtttg ggcaagtaac aggaaaaaaa    2940
gaatactatc actgaactct agcaaggcga tcagaagatt atcgaatagc agcaaatcca    3000
atccacattc tacaactttt tttctaccct actaggctcg actgaggaat gactcatcca    3060
agctgattgg aagattcttt atccagaagg acctctggat cttgctgaca ttgagtatcc    3120
atttatggag aaagaaatcc atgatacagt gtatgacttg gctttggaaa agtcacccgg    3180
atgatatttt cccattctcc ttctataagc acttctagtg tatcatcaaa catgacctga    3240
tgaacctact gtaaaatcag ctaatgtaga ccatctgaac tacttgttca tcacccttat    3300
cccaaaaaaa aattggtgtg tattcagtta gagacttcag gccaataagc ctgattaatg    3360
gagtaataaa aaatatttca aaaactctat cgaaaaggct cccacagaaa atgaatttgt    3420 taatttatc cacagagctt gctttcaaca gaggaagaaa tatctctgaa tattttgtaa    3480
```

| | |
|---|---:|
| tgactatgga aactatacac ttctgcaaag ctgaagtaca caaggatctc aattataaag | 3540 |
| tcgacttcga gaaagctttt gacaatgtgg attggagctt tctattgaaa ttgctatcca | 3600 |
| gcacggggct ttgattcgag gtggtgtcaa tggatagaat atctgattta tacagctaaa | 3660 |
| ttctcagtcc ttattaatgg tgataaaggt aaactttta aattgaggaa agatctcagg | 3720 |
| caaggagatc ctctattcgc ctagctcttt ctcttagttg ttgatataga atgatcaagg | 3780 |
| gagcaagtag gttcaatctt tttgttggaa ttggatcata taatatcatg ggataacttc | 3840 |
| aaagctttta gttcactgat gacacactta tattttgcag atatgatcta aaatacatca | 3900 |
| aaactcttaa atttttactc tatagttatg agctactgat gggtctcaaa attaactttg | 3960 |
| aaaaattcca atttttggc ttgagaattg caaagatgtc agtacagcaa gttgcatcta | 4020 |
| tcctagaaag caaggtggct acattttcca ttacttattt g | 4061 |

<210> SEQ ID NO 43
<211> LENGTH: 4061
<212> TYPE: DNA
<213> ORGANISM: Artificial Sequence
<220> FEATURE:
<223> OTHER INFORMATION: synthetic

<400> SEQUENCE: 43

| | |
|---|---:|
| gaccatgtta tgatctctga aagtttgact tctgactcaa cttcccaatg tagcagattt | 60 |
| tactcctgaa ccatgtttaa cctcctgact catagtggcc aaagtatcta catcgagttc | 120 |
| actggtcttc ttggatcaca ttcataagaa tacttcccat aattttgctc aacgttgttt | 180 |
| ttctcatcaa ccaaaggtat atgctttta aaattgaaat gcccatgaat attatggcat | 240 |
| tcttttattt gacattttgg ttgatcctat attgtttgtt tggcattcaa cacttcttca | 300 |
| tgggaacctt tgaaatgagg taggtgctag gattttttctt tttacctatc catatcatat | 360 |
| ttccaatgtc ttcttttaca ttaggttctt tagtgacaat aggggaaacg acccaatata | 420 |
| ataccccttga aaatttgggc aatatctact aaaactaact tgaataaaat attaacataa | 480 |
| aaagggattt agtaacataa aagcataact caaaatcact caccttgtgt gccacgttct | 540 |
| cattgccctt attattttg cattgtgaat tgtgtccccc aataaagcaa cgtgaatggt | 600 |
| ggaagagagt tgaatggctt tgttgagtaa ttgttttgag ttactatagc attgctctac | 660 |
| taaaattgaa atcttgctgt gaggctatgt atgagaagca agttcatgct ttttgactgt | 720 |
| tgggatggaa gtatgagcaa tcttttaat agaaaatgga cgaatcatga agttttcct | 780 |
| ttttattgaa aaagatgatc gaaaatatg tgcaagatag aaaacactg aaagataaa | 840 |
| atgagaagta aaagtggaag tctaggagaa gaaaatttaa gagaaatatc ttcaatgaga | 900 |
| ggatgtgtgc accaacaaag ccaacttca ctaaagaatg taatgactca cctctacttt | 960 |
| cttcgaataa ggggttccca gttgtggaaa gtatatagaa tcttctgaaa gactgagtaa | 1020 |
| atggagcaat tccttctaag aaatatatg gcatttctct cccacgaaat ttcaaagcaa | 1080 |
| agagcagcta gtagttgatc ctctaatctc ttaattgaag tttggaattt ctcttgcctc | 1140 |
| tatttggccc aaaggtcatg aagatctacc ggccaacctc ttaagttgaa ttagatctta | 1200 |
| atagaagtcc aaatgcttct tgtagaagaa catctaataa ataaatgagt gatagattct | 1260 |
| aatccagaga caaagagcac cctcgaatt cacttgccat cctttctag ctagaacttc | 1320 |
| tctagcatga aacttgttcc ttaaggcaag ccaaataaat actcacattt taggaatgac | 1380 |
| tgccttccaa ataattttat aatatggaca aattagacca ccattattga taaacttgca | 1440 |
| atgaacaatt ataaatgagt tttcaggttg gcacattagc aatataggat ggtttgatta | 1500 |

```
ttaaaaggat gatatgaagg gtttcaaggt ggtttgcctc gttcaaatca aaggattttg    1560
aagattaata ttccaagata aggttctcca actccattag gaaagtgtct tcatgtcatc    1620
ttagagaagc agctcgtacc aaacttgaca gatgttttat ttatttagag tgacacagat    1680 acccttttggc aatactctcc atccttgtcc gaacaacttc taatcacacc tcacttatct    1740
tgcatctaac tcagaggcta caagttacac ctttcaacaa accttttcgg tttgaaaatt    1800
tgtgatttca ttatttagag ttcgaagagc atatcaagta ttggtcggag ttggcaccca    1860
aagcaaacga aacagttact gacatggtcc aaaagctgag atttctaaga tcccaactta    1920
agcactgaat aaagccatta tgggaaatat cattttaacg aaagaggaat ttagagtaag    1980
aattgattct cttgataccg aagaagaact aatacagctt tcatcacttc aaaatgatga    2040
acagatgcat ctcaagtcag cactagacca tcttctaaaa taggaagatc tatgaaagca    2100
acactcccaa atgcagtggc ttcaaaatgg ggattgcaat acgaagttta tccatgtttg    2160
ggcaagtaac aggaaaaaaa gaatactatc actgaactct agcaaggcga tcagaagatt    2220
atcgaatagc agcaaatcca atccacattc tacaactttt tttctaccct actaggctcg    2280
actgaggaat gactcatcca agctgattgg aagattcttt atccagaagg acctctggat    2340
cttgctgaca ttgagtatcc atttatggag aaagaaatcc atgatacagt gtatgacttg    2400
gctttggaaa agtcacccgg atgatatttt cccattctcc ttctataagc acttctagtg    2460
tatcatcaaa catgacctga tgaacctact gtaaaatcag ctaatgtaga ccatctgaac    2520
tacttgttca tcacccttat cccaaaaaaa aattggtgtg tattcagtta gagacttcag    2580
gccaataagc ctgattaatg gagtaataaa aaatatttca aaaactctat cgaaaaggct    2640
cccacagaaa atgaatttgt taattttatc cacagagctt gctttcaaca gaggaagaaa    2700
tatctctgaa tattttgtaa tgactatgga aactatacac ttctgcaaag ctgaagtaca    2760
caaggatctc aattataaag tcgacttcga gaaagctttt gacaatgtgg attggagctt    2820
tctattgaaa ttgctatcca gcacggggct ttgattcgag gtggtgtcaa tggatagaat    2880
atctgattta tacagctaaa ttctcagtcc ttattaatgg tgataaaggt aaactttta    2940 aattgaggaa agatctcagg caaggagatc ctctattcgc ctagctcttt ctcttagttg    3000
ttgatataga atgatcaagg gagcaagtag gttcaatctt tttgttggaa ttggatcata    3060
taatatcatg ggataacttc aaagctttta gttcactgat gacacactta tattttgcag    3120
atatgatcta aaatacatca aaactcttaa attttactc tatagttatg agctactgat    3180
gggtctcaaa attaactttg aaaaattcca attttttggc ttgagaattg caagatgtc    3240 agtacagcaa gttgcatcta tcctagaaag caaggtggct acattttcca ttacttattt    3300
gggtctccca ctccatcatt ctaaactgag gaaaacttat tggaatccac tccttgagaa    3360
ggttcagaag aaattgatcg ggtagaaagg taaacttctt aacctctagg gtaggcttat    3420
actaactaat gcagtgctta cagggatccc actactctgg agggatacat tccttctccc    3480
tcaattcatt atcaaataaa ttgataaaat ccatcgatca ttcatttgga gaggaaacga    3540
ggagtataac taagggcact ctagaatatg ttggtcgaat atttgtcgat caaaaaaatt    3600
tggaggactg ggggttcctc aatctaaaaa ttttcaatac aattcttctt tgtaaatggt    3660
ggtggaagct ctactctaat gctggtgacc cgtggtgtag ttttattgcc actgtccacc    3720
caacttcaca ctagagatct aaaggtatac acaaatcaac ctcttcattt tggaatggtt    3780
tacagcacac atgaaatatt tctactccta atccactttc aagttagcaa ctagtattat    3840
```

| tttggaaaga tagttggtta cataatcatc cactgaagga tcgatttcct cacctttaca | 3900 |
| caatagcatt gaagtgcaac aactcagtgg caaaggtatt aagcaatcta cttgataata | 3960 |
| gctcttttag tactcctctt cctcaaagat accaagaaga ttttcagagt ctataggaaa | 4020 |
| gcattgaaca aattacatta acggaacgac ctgatactat a | 4061 |

```
<210> SEQ ID NO 44
<211> LENGTH: 4061
<212> TYPE: DNA
<213> ORGANISM: Artificial Sequence
<220> FEATURE:
<223> OTHER INFORMATION: synthetic

<400> SEQUENCE: 44
```

| tcttctgaaa gactgagtaa atggagcaat tccttctaag aaatattatg gcatttctct | 60 |
| cccacgaaat ttcaaagcaa agagcagcta gtagttgatc ctctaatctc ttaattgaag | 120 |
| tttggaattt ctcttgcctc tatttggccc aaaggtcatg aagatctacc ggccaacctc | 180 |
| ttaagttgaa ttagatctta atagaagtcc aaatgcttct tgtagaagaa catctaataa | 240 |
| ataaatgagt gatagattct aatccagaga caaagagcac acctcgaatt cacttgccat | 300 |
| cctttctag ctagaacttc tctagcatga aacttgttcc ttaaggcaag ccaaataaat | 360 |
| actcacattt taggaatgac tgccttccaa ataattttat aatatggaca aattagacca | 420 |
| ccattattga taaacttgca atgaacaatt ataaatgagt tttcaggttg gcacattagc | 480 |
| aatataggat ggtttgatta ttaaaaggat gatatgaagg gtttcaaggt ggtttgcctc | 540 |
| gttcaaatca aaggatttg aagattaata ttccaagata aggttctcca actccattag | 600 |
| gaaagtgtct tcatgtcatc ttagagaagc agctcgtacc aaacttgaca gatgttttat | 660 |
| ttatttagag tgacacagat acccttggc aatactctcc atccttgtcc gaacaacttc | 720 |
| taatcacacc tcacttatct tgcatctaac tcagaggcta caagttacac cttttcaacaa | 780 |
| acctttcgg tttgaaaatt tgtgatttca ttatttagag ttcgaagagc atatcaagta | 840 |
| ttggtcggag ttggcaccca aagcaaacga acagttact gacatggtcc aaaagctgag | 900 |
| atttctaaga tcccaactta agcactgaat aaagccatta tgggaaatat cattttaacg | 960 |
| aaagaggaat ttagagtaag aattgattct cttgataccg aagaagaact aatacagctt | 1020 |
| tcatcacttc aaaatgatga acagatgcat ctcaagtcag cactgagacca tcttctaaaa | 1080 |
| taggaagatc tatggaagca acactcccaa atgcagtggc ttcaaaatgg ggattgcaat | 1140 |
| acgaagttta tccatgtttg ggcaagtaac aggaaaaaaa gaatactatc actgaactct | 1200 |
| agcaaggcga tcagaagatt atcgaatagc agcaaatcca atccacattc tacaacttt | 1260 |
| tttctacccct actaggctcg actgaggaat gactcatcca agctgattgg aagattctt | 1320 |
| atccagaagg acctctggat cttgctgaca ttgagtatcc atttatggag aaagaaatcc | 1380 |
| atgatacagt gtatgacttg gctttggaaa agtcacccgg atgatatttt cccattctcc | 1440 |
| ttctataagc acttctagtg tatcatcaaa catgacctga tgaacctact gtaaaatcag | 1500 |
| ctaatgtaga ccatctgaac tacttgttca tcacccttat cccaaaaaaa aattggtgtg | 1560 |
| tattcagtta gagacttcag gccaataagc ctgattaatg gagtaataaa aaatatttca | 1620 |
| aaaactctat cgaaaaggct cccacagaaa atgaatttgt taatttatc cacagagctt | 1680 |
| gcttccaaca gaggaagaaa tatctctgaa tattttgtaa tgactatgga aactatacac | 1740 |
| ttctgcaaag ctgaagtaca caaggatctc aattataaag tcgacttcga gaaagctttt | 1800 |
| gacaatgtgg attggagctt tctattgaaa ttgctatcca gcacggggct tgattcgag | 1860 |

-continued

```
gtggtgtcaa tggatagaat atctgattta tacagctaaa ttctcagtcc ttattaatgg    1920
tgataaaggt aaactttta aattgaggaa agatctcagg caaggagatc ctctattcgc    1980
ctagctcttt ctcttagttg ttgatataga atgatcaagg gagcaagtag gttcaatctt    2040
tttgttggaa ttggatcata taatatcatg ggataacttc aaagcttta gttcactgat    2100 gacacactta tattttgcag atatgatcta aaatacatca aaactcttaa attttttactc   2160 tatagttatg agctactgat gggtctcaaa attaactttg aaaaattcca attttttggc    2220
ttgagaattg caaagatgtc agtacagcaa gttgcatcta tcctagaaag caaggtggct    2280
acattttcca ttacttattt gggtctccca ctccatcatt ctaaactgag gaaaacttat    2340
tggaatccac tccttgagaa ggttcagaag aaattgatcg ggtagaaagg taaacttctt    2400
aacctctagg gtaggcttat actaactaat gcagtgctta cagggatccc actactctgg    2460
agggatacat tccttctccc tcaattcatt atcaaataaa ttgataaaat ccatcgatca    2520
ttcatttgga gaggaaacga ggagtataac taagggcact ctagaatatg ttggtcgaat    2580
atttgtcgat caaaaaaatt tggaggactg ggggttcctc aatctaaaaa ttttcaatac    2640
aattcttctt tgtaaatggt ggtggaagct ctactctaat gctggtgacc cgtggtgtag    2700
ttttattgcc actgtccacc caacttcaca ctagagatct aaaggtatac acaaatcaac    2760
ctcttcattt tggaatggtt tacagcacac atgaaatatt tctactccta atccactttc    2820
aagttagcaa ctagtattat tttggaaaga tagttggtta cataatcatc cactgaagga    2880
tcgatttcct cacctttaca caatagcatt gaagtgcaac aactcagtgg caaaggtatt    2940
aagcaatcta cttgataata gctcttttag tactcctctt cctcaaagat accaagaaga    3000
ttttcagagt ctataggaaa gcattgaaca aattacatta acggaacgac ctgatactat    3060
acaatggaaa tggtttagta gcaatatttt tttggcatga aggatctact attttctgca    3120
agatggagga gtttggcctc tactgagtaa tattatataa aaactcctaa taccaaagaa    3180
agccaagtta tttgcttggc taagtgctca caacaaaatc ccaatgaaag ctaatcttct    3240
taatagagga ataattggaa ctgattactg tacactttgc gatgacttat cagaaactaa    3300
tgatcatcta atgctcatct atactttttc aaaagcaatt tggaatcaag tactttcaga    3360
cctgcaattg tcgaaacttt tatgcatgct taacaccta tgggatactt ggagactcat    3420
caatatgcaa cacgatagaa gacctaaact agctgctcta ttcgtaattg gtcaatggtg    3480
tctttggaag gaaagaaata aaagattatt cgacttctat acttttatc cacgatcgat    3540 tgctgaaact gtgtcacttt ttctttcttg ggcatcacac ctaacaacgg agcaactaaa    3600
gatgttagct cctgttcgag aagttctctt atctaagaat gaaaacacac aatctttagt    3660
gagaattaca gatgctaaca ggcgcagatg aatgttttat gagcattttt atagctgcag    3720
cttatatgtg atctatggtg caaggagtta attataacca tggatattag ttaggttgac    3780
tatcagaaat catctccaat acattctatg taaccactga tcaattccat gttcaactag    3840
ataggaacct gcctatatac aggtatgtcc ctgatgtaac tatagtatac tattattcat    3900
aaataaataa cgaaggtttt accttcttct cataaaaaaa aagtatcttc atgtcatcct    3960
atatgtcatg catctccttt gctacttctt ttatttactt cttaaacttg gttctaccat    4020
atattatcag ccccttttaa atttgctttt ggatattgca t                       4061
```

<210> SEQ ID NO 45
<211> LENGTH: 4061
<212> TYPE: DNA

<213> ORGANISM: Artificial Sequence
<220> FEATURE:
<223> OTHER INFORMATION: synthetic

<400> SEQUENCE: 45

```
gctttcaaca gaggaagaaa tatctctgaa tattttgtaa tgactatgga aactatacac      60
ttctgcaaag ctgaagtaca caaggatctc aattataaag tcgacttcga gaaagctttt     120
gacaatgtgg attggagctt tctattgaaa ttgctatcca gcacgggct ttgattcgag      180
gtggtgtcaa tggatagaat atctgattta tacagctaaa ttctcagtcc ttattaatgg    240
tgataaaggt aaacttttta aattgaggaa agatctcagg caaggagatc ctctattcgc    300
ctagctcttt ctcttagttg ttgatataga atgatcaagg gagcaagtag gttcaatctt    360
tttgttggaa ttggatcata taatatcatg ggataacttc aaagctttta gttcactgat    420
gacacactta tattttgcag atatgatcta aaatacatca aaactcttaa attttactc     480
tatagttatg agctactgat gggtctcaaa attaactttg aaaaattcca attttttggc    540
ttgagaattg caaagatgtc agtacagcaa gttgcatcta tcctagaaag caaggtggct    600
acattttcca ttacttattt gggtctccca ctccatcatt ctaaactgag gaaaacttat    660
tggaatccac tccttgagaa ggttcagaag aaattgatcg ggtagaaagg taaacttctt    720
aacctctagg gtaggcttat actaactaat gcagtgctta cagggatccc actactctgg    780
agggatacat tccttctccc tcaattcatt atcaaataaa ttgataaaat ccatcgatca    840
ttcatttgga gaggaaacga ggagtataac taagggcact ctagaatatg ttggtcgaat    900
atttgtcgat caaaaaaatt tggaggactg ggggttcctc aatctaaaaa ttttcaatac    960
aattcttctt tgtaaatggt ggtggaagct ctactctaat gctggtgacc cgtggtgtag   1020
ttttattgcc actgtccacc caacttcaca ctagagatct aaaggtatac acaaatcaac   1080
ctcttcattt tggaatggtt tacagcacac atgaaatatt tctactccta atccactttc   1140
aagttagcaa ctagtattat tttggaaaga tagttggtta cataatcatc cactgaagga   1200
tcgatttcct caccttttaca caatagcatt gaagtgcaac aactcagtgg caaaggtatt   1260
aagcaatcta cttgataata gctcttttag tactcctctt cctcaaagat accaagaaga   1320
ttttcagagt ctataggaaa gcattgaaca aattacatta acggaacgac ctgatactat   1380
acaatggaaa tggtttagta gcaatatttt tttggcatga aggatctact attttctgca   1440
agatggagga gtttggcctc tactgagtaa tattatataa aaactcctaa taccaaagaa   1500
agccaagtta tttgcttggc taagtgctca caacaaaatc ccaatgaaag ctaatcttct   1560
taatagagga ataattggaa ctgattactg tacactttgc gatgacttat cagaaactaa   1620
tgatcatcta atgctcatct atacttttttc aaaagcaatt tggaatcaag tactttcaga   1680
cctgcaattg tcgaaacttt tatgcatgct taacacccta tgggatactt ggagactcat   1740
caatatgcaa cacgatagaa gacctaaact agctgctcta ttcgtaattg gtcaatggtg   1800
tctttggaag gaaagaaata aaagattatt cgacttctat acttttatc cacgatcgat    1860
tgctgaaact gtgtcacttt ttcttcttg ggcatcacac ctaacaacgg agcaactaaa   1920
gatgttagct cctgttcgag aagttctctt atctaagaat gaaacacac aatctttagt    1980
gagaattaca gatgctaaca ggcgcagatg aatgttttat gagcattttt atagctgcag   2040
cttatatgtg atctatggtg caaggagtta attataacca tggatattag ttaggttgac   2100
tatcagaaat catctccaat acattctatg taaccactga tcaattccat gttcaactag   2160
ataggaacct gcctatatac aggtatgtcc ctgatgtaac tatagtatac tattattcat   2220
```

| | | |
|---|---|---|
| aaataaataa cgaaggtttt accttcttct cataaaaaaa aagtatcttc atgtcatcct | 2280 | |
| atatgtcatg catctccttt gctacttctt ttatttactt cttaaacttg gttctaccat | 2340 | |
| atattatcag ccccttttaa atttgctttt ggatattgca tattccactc ttcaatcacc | 2400 | |
| tcatgccaag caaacatttt attcacactt gaaaaccaat ataagaatac caagaatttt | 2460 | |
| atccatgaaa ttctagaaac tttggtttta ctcctttctc catcattcaa aaaggttcaa | 2520 | |
| aatgatgata actctatata gcttatttat caaatttacg aggttggtgt tcaatgtttt | 2580 | |
| tgtgaaaaaa atatcttgct atccacatag tttgaatcca tacttttgct atcttgagtt | 2640 | |
| tcaaaaattt taatttgcta caatttgttg ctattagcat atgactactt ttaagaagat | 2700 | |
| aagccaatat actattttcc taagaattta aaaaatcaaa ataaaaatt tttatttaag | 2760 | |
| atttttttaag ggttgttttc caaatgtgca atggggctta atcttggcat cattttctaa | 2820 | |
| cttgtagaat tttgacccaa gtaacatttg tccaatcact tagaacttct ataacttcgt | 2880 | |
| acaatcattt gttaatgttg ttcatctatt tatctatatt atctatctgg aatatagttg | 2940 | |
| ctcttaatta ttttttatata tcgcctatta tccaccctaa gctttcatgt tcatcctcat | 3000 | |
| gttgttggag gtgcatgtct tattccaaac tatttaccat tgctgtagat tttaaaaaat | 3060 | |
| ttgctagttt aggactttt aatcttttga tatcatgttg atgtaagcta accctctaag | 3120 | |
| gctagtcata atacatttta aggatttatg ttatatgaga ccaaaatttt aacaaaatga | 3180 | |
| agtgttggaa attggtagaa tggaagtgta aagatgctta gagacataga actagccctg | 3240 | |
| ggccatgtaa atcttccaaa agaagaagaa aataataaaa ttaagatcat attcaatctc | 3300 | |
| tacagaaaag ttggtctttg ttgtataata agccatctta acatatgatg gacaataaaa | 3360 | |
| tatataaact tatgagtttt aatacttaga tggaagaaaa gggacagata tgtcacaccc | 3420 | |
| catcctacta gcatgagtag gcacatgata cacggttgca tgccctgcag agtttgactc | 3480 | |
| atgaggcatg caaggtattg aatagtagtc taggtaaaat taaaaaactt ggagcattct | 3540 | |
| aaaaataaat caagttcatt ttataaaatc aatatttatt atggactcca tcaaatatta | 3600 | |
| tgcgcataac atttttatttg caaatagaag aagataagtc ctagatccta agtctcctac | 3660 | |
| tcttagtctc ataattcatc caagctatcc accaaatatc taaaacgaaa aagaaaaacg | 3720 | |
| atagtatgct aatagctttg taagtcacct tttatctcta attagatcaa gcatattaga | 3780 | |
| tataaaacaa taattttcaa agtatatgat ttgcaattag gaataaatat ttgataaata | 3840 | |
| cagaataaat tttcataaag catatttact aacattattt ataaaatata taatgcttat | 3900 | |
| atcaataaat taatttctaa atcaatatat ataaactatc cattctgtct tagccttaca | 3960 | |
| actattgcta ccattccctg tagcatggtt aggaagagac tagctcttga atactcatgt | 4020 | |
| catttatcaa catatgcgaa tgatcattcg actaatatag t | 4061 | |

<210> SEQ ID NO 46
<211> LENGTH: 4061
<212> TYPE: DNA
<213> ORGANISM: Artificial Sequence
<220> FEATURE:
<223> OTHER INFORMATION: synthetic

<400> SEQUENCE: 46

| | | |
|---|---|---|
| tttgttggaa ttggatcata taatatcatg ggataacttc aaagctttta gttcactgat | 60 | |
| gacacactta tattttgcag atatgatcta aaatacatca aaactcttaa atttttactc | 120 | |
| tatagttatg agctactgat gggtctcaaa attaactttg aaaaattcca atttttggc | 180 | |

-continued

```
ttgagaattg caaagatgtc agtacagcaa gttgcatcta tcctagaaag caaggtggct    240
acattttcca ttacttattt gggtctccca ctccatcatt ctaaactgag gaaaacttat    300
tggaatccac tccttgagaa ggttcagaag aaattgatcg ggtagaaagg taaacttctt    360
aacctctagg gtaggcttat actaactaat gcagtgctta cagggatccc actactctgg    420
agggatacat tccttctccc tcaattcatt atcaaataaa ttgataaaat ccatcgatca    480
ttcatttgga gaggaaacga ggagtataac taagggcact ctagaatatg ttggtcgaat    540
atttgtcgat caaaaaaatt tggaggactg ggggttcctc aatctaaaaa ttttcaatac    600
aattcttctt tgtaaatggt ggtggaagct ctactctaat gctggtgacc cgtggtgtag    660
ttttattgcc actgtccacc caacttcaca ctagagatct aaaggtatac acaaatcaac    720
ctcttcattt tggaatggtt tacagcacac atgaaatatt tctactccta atccactttc    780
aagttagcaa ctagtattat tttggaaaga tagttggtta cataatcatc cactgaagga    840
tcgatttcct cacctttaca caatagcatt gaagtgcaac aactcagtgg caaaggtatt    900
aagcaatcta cttgataata gctctttag tactcctctt cctcaaagat accaagaaga    960
ttttcagagt ctataggaaa gcattgaaca aattacatta acggaacgac ctgatactat   1020
acaatggaaa tggtttagta gcaatatttt tttggcatga aggatctact attttctgca   1080
agatggagga gtttggcctc tactgagtaa tattatataa aaactcctaa taccaaagaa   1140
agccaagtta tttgcttggc taagtgctca caacaaaatc ccaatgaaag ctaatcttct   1200
taatagagga ataattggaa ctgattactg tacactttgc gatgacttat cagaaactaa   1260
tgatcatcta atgctcatct atactttttc aaaagcaatt tggaatcaag tactttcaga   1320
cctgcaattg tcgaaacttt tatgcatgct taacacccta tgggatactt ggagactcat   1380
caatatgcaa cacgatagaa gacctaaact agctgctcta ttcgtaattg gtcaatggtg   1440
tctttggaag gaaagaaata aaagattatt cgacttctat acttttttatc cacgatcgat   1500 tgctgaaact gtgtcacttt ttcttctctg ggcatcacac ctaacaacgg agcaactaaa   1560
gatgttagct cctgttcgag aagttctctt atctaagaat gaaaacacac aatctttagt   1620
gagaattaca gatgctaaca ggcgcagatg aatgttttat gagcattttt atagctgcag   1680
cttatatgtg atctatggtg caaggagtta attataacca tggatattag ttaggttgac   1740
tatcagaaat catctccaat acattctatg taaccactga tcaattccat gttcaactag   1800
ataggaacct gcctatatac aggtatgtcc ctgatgtaac tatagtatac tattattcat   1860
aaataaataa cgaaggtttt accttcttct cataaaaaaa aagtatcttc atgtcatcct   1920
atatgtcatg catctccttt gctacttctt ttatttactt cttaaacttg gttctaccat   1980
atattatcag ccccttttaa atttgctttt ggatattgca tattccactc ttcaatcacc   2040
tcatgccaag caaaacattt attcacactt gaaaccaat ataagaatac caaagaattt   2100
atccatgaaa ttctagaaac tttggtttta ctcctttctc catcattcaa aaaggttcaa   2160
aatgatgata actctatata gcttatttat caaatttacg aggttggtgt tcaatgtttt   2220
tgtgaaaaaa atatcttgct atccacatag tttgaatcca tactttgct atcttgagtt   2280 tcaaaaattt taatttgcta caattgttg ctattagcat atgactactt ttaagaagat   2340
aagccaatat actattttcc taagaattta aaaaatcaaa aataaaaatt tttatttaag   2400 atttttaag ggttgttttc caaatgtgca atggggctta atcttggcat cattttctaa   2460
cttgtagaat tttgacccaa gtaacatttg tccaatcact agaacttct ataacttcgt   2520 acaatcattt gttaatgttg ttcatctatt tatctatatt atctatctgg aatatagttg   2580
```

```
ctcttaatta ttttatata tcgcctatta tccaccctaa gctttcatgt tcatcctcat      2640
gttgttggag gtgcatgtct tattccaaac tatttaccat tgctgtagat tttaaaaaat     2700
ttgctagttt aggactttt aatctttga tatcatgttg atgtaagcta accctctaag       2760
gctagtcata atacatttta aggatttatg ttatatgaga ccaaaatttt aacaaaatga    2820
agtgttggaa attggtagaa tggaagtgta aagatgctta gagacataga actagccctg    2880
ggccatgtaa atcttccaaa agaagaagaa aataataaaa ttaagatcat attcaatctc    2940
tacagaaaag ttggtctttg ttgtataata agccatctta acatatgatg acaataaaa     3000 tatataaact tatgagtttt aatacttaga tggaagaaaa gggacagata tgtcacaccc   3060
catcctacta gcatgagtag gcacatgata cacggttgca tgccctgcag agtttgactc    3120
atgaggcatg caaggtattg aatagtagtc taggtaaaat taaaaaactt ggagcattct    3180
aaaaataaat caagttcatt ttataaaatc aatatttatt atggactcca tcaaatatta    3240
tgcgcataac atttttatttg caaatagaag aagataagtc ctagatccta agtctcctac   3300
tcttagtctc ataattcatc caagctatcc accaaatatc taaaacgaaa aagaaaaacg   3360
atagtatgct aatagctttg taagtcacct tttatctcta attagatcaa gcatattaga    3420
tataaaacaa taattttcaa agtatatgat ttgcaattag gaataaatat ttgataaata   3480
cagaataaat tttcataaag catatttact aacattattt ataaaatata taatgcttat   3540
atcaataaat taatttctaa atcaatatat ataaactatc cattctgtct tagccttaca   3600
actattgcta ccattccctg tagcatggtt aggaagagac tagctcttga atactcatgt   3660
catttatcaa catatgcgaa tgatcattcg actaatatag tcaaaaaaaa attactctga   3720 ttatataaa ttaaaaatta gtaaataata tatgctagta atcaccttac cagctaagct    3780
ctaaagaaaa ttagcttttg aatatacatc atgctattga ttattatatg tcagtgcttg   3840
tctcattttg tggcatgcaa gaagactaga tcctaaactt atatgcatag tcagattaaa   3900
gagcaaatgt tgcatctgat tatatgaaca tctattatga tgtagagttt gtatcatgta    3960
tatttaattt aaacacaaat ataattatac ataaataata ttcatatttt aaattttaaa   4020
tatttagata ttattctag tgcaggtata aaaataagca a                         4061

<210> SEQ ID NO 47
<211> LENGTH: 4061
<212> TYPE: DNA
<213> ORGANISM: Artificial Sequence
<220> FEATURE:
<223> OTHER INFORMATION: synthetic

<400> SEQUENCE: 47
ttggcctcta ctgagtaata ttatataaaa actcctaata ccaagaaaag ccaagttatt      60
tgcttggcta agtgctcaca acaaaatccc aatgaaagct aatcttctta atagaggaat    120
aattggaact gattactgta cactttgcga tgacttatca gaaactaatg atcatctaat    180
gctcatctat actttttcaa aagcaatttg gaatcaagta ctttcagacc tgcaattgtc     240
gaaactttta tgcatgctta acaccctatg ggatacttgg agactcatca atatgcaaca    300
cgatagaaga cctaaactag ctgctctatt cgtaattggt caatggtgtc tttggaagga    360
aagaaataaa agattattcg acttctatac tttttatcca cgatcgattg ctgaaactgt    420
gtcacttttt ctttcttggg catcacacct aacaacggag caactaaaga tgttagctcc    480
tgttcgagaa gttctcttat ctaagaatga aaacacacaa tctttagtga gaattacaga   540
```

```
tgctaacagg cgcagatgaa tgttttatga gcatttttat agctgcagct tatatgtgat    600
ctatggtgca aggagttaat tataaccatg gatattagtt aggttgacta tcagaaatca    660
tctccaatac attctatgta accactgatc aattccatgt tcaactagat aggaacctgc    720
ctatatacag gtatgtccct gatgtaacta tagtatacta ttattcataa ataaataacg    780
aaggttttac cttcttctca taaaaaaaaa gtatcttcat gtcatcctat atgtcatgca    840
tctcctttgc tacttctttt atttacttct taaacttggt tctaccatat attatcagcc    900 cctttaaat ttgcttttgg atattgcata ttccactctt caatcacctc atgccaagca    960
aaacatttat tcacacttga aaccaatat aagaatacca agaatttat ccatgaaatt    1020 ctagaaactt tggttttact cctttctcca tcattcaaaa aggttcaaaa tgatgataac    1080
tctatatagc ttatttatca aatttacgag gttggtgttc aatgttttg tgaaaaaat    1140 atcttgctat ccacatagtt tgaatccata cttttgctat cttgagtttc aaaaatttta    1200
atttgctaca atttgttgct attagcatat gactacttt aagaagataa gccaatatac    1260
tattttccta agaatttaaa aaatcaaaaa taaaattttt tatttaagat ttttaaggg    1320 ttgttttcca aatgtgcaat ggggcttaat cttggcatca ttttctaact tgtagaattt    1380
tgacccaagt aacattgtc caatcactta gaacttctat aacttcgtac aatcatttgt    1440
taatgttgtt catctatta tctatattat ctatctggaa tatagttgct cttaattatt    1500
tttatatatc gcctattatc caccctaagc tttcatgttc atcctcatgt tgttggaggt    1560
gcatgtctta ttccaaacta tttaccattg ctgtagattt taaaaaattt gctagtttag    1620 gacttttaa tcttttgata tcatgttgat gtaagctaac cctctaaggc tagtcataat    1680
acattttaag gatttatgtt atatgagacc aaaattttaa caaatgaag tgttggaaat    1740 tggtagaatg gaagtgtaaa gatgcttaga gacatagaac tagccctggg ccatgtaat    1800 cttccaaaag aagaagaaaa taataaaatt aagatcatat tcaatctcta cagaaaagtt    1860
ggtctttgtt gtataataag ccatcttaac atatgatgga caataaaata tataaactta    1920
tgagtttaaa tacttagatg gaagaaagg gacagatatg tcacacccca tcctactagc    1980
atgagtaggc acatgataca cggttgcatg ccctgcagag tttgactcat gaggcatgca    2040
aggtattgaa tagtagtcta ggtaaaatta aaaacttgg agcattctaa aaataaatca    2100 agttcattt ataaaatcaa tatttattat ggactccatc aaatattatg cgcataacat    2160 ttatttgca aatagaagaa gataagtcct agatcctaag tctcctactc ttagtctcat    2220
aattcatcca agctatccac caaatatcta aaacgaaaaa gaaaaacgat agtatgctaa    2280
tagctttgta agtcaccttt tatctctaat tagatcaagc atattagata taaaacaata    2340
attttcaaag tatatgattt gcaattagga ataaatattt gataaataca gaataaattt    2400
tcataaagca tatttactaa cattatttat aaaatatata atgcttatat caataaatta    2460
atttctaaat caatatatat aaactatcca ttctgtctta gccttacaac tattgctacc    2520
attccctgta gcatggttag gaagagacta gctcttgaat actcatgtca tttatcaaca    2580
tatgcgaatg atcattcgac taatatagtc aaaaaaaaat tactctgatt tatataaatt    2640
aaaaattagt aaataatata tgctagtaat caccttacca gctaagctct aaagaaaatt    2700
agcttttgaa tatacatcat gctattgatt attatatgtc agtgcttgtc tcattttgtg    2760
gcatgcaaga agactagatc ctaaacttat atgcatagtc agattaaaga gcaaatgttg    2820
catctgatta tatgaacatc tattatgatg tagagtttgt atcatgtata tttaatttaa    2880
acacaaatat aattatacat aaataatatt catattttaa attttaaata tttagataat    2940
```

```
tattctagtg caggtataaa aataagcaat ataaaatttt aaatcgattt atataacatg   3000
cataataaaa aaaattaagg atagaggtac ttactgctca actcataaaa cataagaaat   3060
ctctttaact aactttagtg caacctagat agaacatatt aatgattaag ttttcatcta   3120
aaataaacat agatatcatt ttaaaatctt aggcatttaa atggtctcat gatttgtgag   3180
gctttcttca gattctacaa ttttgaaatt ttttcaaatt ataattttt taccttgatt    3240 gataacaaag ccaataatac acctcaaatc caaatgtatt cctaatagtt ttcaataaat   3300
ctaatatcaa taaatcataa ttaagatatc aatccattct atgaatttga ccataaatcc   3360
tacttgtttc tctgaccttc actataaatt aatcatcaaa ctaataagt gaggggatca    3420 taattctttt acgacaatcc aagaattcaa gtctagcatc cacattagat ggcttcctgt   3480
ccagatattt gcgcctctcc aaaattgaga ttatcagatt aagaaaaata aataagaga    3540 gagggttaaa ggacaatgcc ttctaggtag tgatgtccga catcataatt ttgatcaaat   3600
ctatggggca accaataata ttagggaaag aggattggaa ttgagcaaga atagcaaagt   3660
cattgtcatc aatggcctga ttcattgagt tcaatgaagg attggtggtt gagtggtgga   3720
ggtggcatct aggaaggaga gagaaagaaa aagatagaga gaaagagata agaaaaatag   3780
agagaaggtg gcagttaaga tcccttttg tgattaatat atagccgtaa gatactcaaa    3840
gatctcacct tatcgacctc aaacactaag ggaggtggaa ggaggacta ctacccatga    3900 agctagagaa agggatgatg atgattggag gaaggaagaa ggaaaaatag tagactcgat   3960
gatgataaga ctaaaagaaa agggtttgac ttagccactt ggtatataat gaggtttggt   4020
atggagtcaa tagcttgagt aatagcatgg aaagagagaa g                       4061
```

<210> SEQ ID NO 48
<211> LENGTH: 4061
<212> TYPE: DNA
<213> ORGANISM: Artificial Sequence
<220> FEATURE:
<223> OTHER INFORMATION: synthetic

<400> SEQUENCE: 48

```
aaatatctaa aacgaaaaag aaaaacgata gtatgctaat agctttgtaa gtcaccttt      60 atctctaatt agatcaagca tattagatat aaaacaataa ttttcaaagt atatgatttg    120
caattaggaa taaatatttg ataaatacag aataaatttt cataaagcat atttactaac    180
attatttata aaatatataa tgcttatatc aataaattaa tttctaaatc aatatatata    240
aactatccat tctgtcttag ccttacaact attgctacca ttccctgtag catggttagg    300
aagagactag ctcttgaata ctcatgtcat ttatcaacat atgcgaatga tcattcgact    360
aatatagtca aaaaaaaatt actctgattt atataaatta aaaattagta aataatatat    420
gctagtaatc accttaccag ctaagctcta agaaaatta gcttttgaat atacatcatg    480
ctattgatta ttatatgtca gtgcttgtct cattttgtgg catgcaagaa gactagatcc    540
taaacttata tgcatagtca gattaaagag caaatgttgc atctgattat atgaacatct    600
attatgatgt agagttttgta tcatgtatat ttaatttaaa cacaaatata attatacata    660
aataatattc atattttaaa ttttaaatat ttagataatt attctagtgc aggtataaaa    720
ataagcaata taaattttta aatcgattta tataacatgc ataataaaaa aaattaagga    780
tagaggtact tactgctcaa ctcataaaac ataagaaatc tctttaacta actttagtgc    840
aacctagata gaacatatta atgattaagt tttcatctaa aataaacata gatatcattt    900
```

```
taaaatctta ggcatttaaa tggtctcatg atttgtgagg ctttcttcag attctacaat    960
tttgaaattt tttcaaatta taattttttt accttgattg ataacaaagc caataataca   1020
cctcaaatcc aaatgtattc ctaatagttt tcaataaatc taatatcaat aaatcataat   1080
taagatatca atccattcta tgaatttgac cataaatcct acttgtttct ctgaccttca   1140
ctataaatta atcatcaaac taaataagtg aggggatcat aattctttta cgacaatcca   1200
agaattcaag tctagcatcc acattagatg gcttcctgtc cagatatttg cgcctctcca   1260
aaattgagat tatcagatta agaaaaataa aataagagag agggttaaag gacaatgcct   1320
tctaggtagt gatgtccgac atcataattt tgatcaaatc tatggggcaa ccaataatat   1380
tagggaaaga ggattggatt tgagcaagaa tagcaaagtc attgtcatca atggcctgat   1440
tcattgagtt caatgaagga ttggtggttg agtggtggag gtggcatcta ggaaggagag   1500
agaaagaaaa agatagagag aaagagataa gaaaaataga gagaaggtgg cagttaagat   1560
cccttttgt gattaatata tagccgtaag atactcaaag atctcacctt atcgacctca   1620
aacactaagg gaggtggaag gagggactac tacccatgaa gctagagaaa gggatgatga   1680
tgattggagg aaggaagaag gaaaaatagt agactcgatg atgataagac taaaagaaaa   1740
gggtttgact tagccacttg gtatataatg aggtttggta tggagtcaat agcttgagta   1800
atagcatgga aagagagaag gagctgaaga gagtactaag tcttattaga ataaagaaag   1860
atagaatctt agcgaaaaat agggcctcaa atctttcagg tagaggaaaa agagggatca   1920
acgaatgaaa gactaaggaa aaggtgtgga gtaggatata ctctcgatta gtctctcaat   1980
catggattct agtagggctt cgtcagctgc tcaatcatgg attctgatag ctcaaatggt   2040
ggtaagtaga aagagagaga tctaaagaga ttgatagtgg ccttaaaacc agcacggtca   2100
aggataggca tgccttagag agaggaaaag agagagagat taatgaaaat aagcgagaaa   2160
aatatattct tagagaatag attggcgata agaagaggag gtggttgggg catgcttaaa   2220
gaaataaaga aaattgagta ggcggaaagt ggtgatgctt ggcgatgaga agatttgaga   2280
gagagagcaa aaaaatgtgg atgatggtca taggataggg aaaggaaaga acaaagaagg   2340
gggtgctaag ctaactcttt ctaccttcct cacaccctga agcaaaggat ttggccaagg   2400
atggacaaat gggcgagggc tttggtggat ccatgcctac cctttctccc tctcacgatg   2460
attctagtca agctatctat ctttgatagc ttgagccaag ccaattgact tgatccaatc   2520
tctctaaatc catacaaact taagagagtg tattgattca cttattctct tctaagttga   2580
taagaaacat aattaagtgg agctcattaa gtatttcagg tagttgctaa cttggcaaaa   2640
tggaagcaat aataaatctt aaaagactat agcttggtat aatctcaacc atccatgatt   2700
tagaaagatc ttcagactca atatagatta ctttggctac tacaggtaag agctaaaatag   2760
gatccaaaag taagatccat cacattagta agtcaaatta tatgtcaaat tttagtaggt   2820
atacttagtc ctacgatgcc taattaaaat gatcatcatt tgaaccttaa aatggactag   2880
tcaactaaaa ttttctttt tgaagaagat ttagaccata aaatatcttc taatctgtga   2940
agaattagat agagcgagga atataaaatt gatgtagaaa tcaagatcta tcatatatac   3000
aatttttaata tttttttcat aattttttaaa tatttatctt cttttttttat aggtctagtc   3060
ctatttaaac taggaagagg agtccaactt gacttatgca ataggggatg tccttctaga   3120
agataagaat aatttgatca gaattatata agagcaaacc tcattattat aaataggggc   3180
tatatacatc aatttatgag atagagaatc aatgaaacaa aagtagactt aagtttttatt   3240
ttcataattc ttctatcttc tactttttttt ctaggagatt caagttgagt ggattgaaga   3300
```

```
aaatctttca tcttctcgat cggatcatat tggtattaga gcgttggtct tctatattta    3360
tggagagctt taatgtattg tttaaatacg tgaacaatac aaacaatcaa gagaagtgct    3420
atccatgctt caaatacatc gaaatataaa agcaaatatg ctactaatt cttttcaat     3480 ggacaatgag ataaaaggat gtcttacaca actcaaggag aagattgtgc aactcatgaa    3540
gattgtctcc agattgaaga taatttcaat acaagcacaa acaccagcaa ctcatgttgt    3600
gaaactgttt cctatgtttg gagatgaaga tcttctatct agtgaggaga ttgaattacc    3660
taaaagtatg aaaaatcttt cttcaatcat tgaaagttaa agcttgaatt gagatcccca    3720
tatataatgg aaccattgat gaaaaaaagc tagataattg gctaaactaa ttacaaacct    3780
attttattat ctatagatat tatggcatct agaagatagc ttttacttat ctcaagcttt    3840
ctagccatgc tcttatctga tgaaattcat atatgagaaa taataatatt tttaatatgg    3900
tgcagagcca attcaaaggt ttaatcaaga agtaatttta tctaattggc cataaggaag    3960
atcggtggat caaatgataa tacttatgat agaaacataa tcaatccact taggactata    4020
ccaccaagtt ccacaaacag gcaatctgcc ttggaatctt t                        4061
```

<210> SEQ ID NO 49
<211> LENGTH: 4061
<212> TYPE: DNA
<213> ORGANISM: Artificial Sequence
<220> FEATURE:
<223> OTHER INFORMATION: synthetic

<400> SEQUENCE: 49

```
aaagagataa gaaaaataga gagaaggtgg cagttaagat ccctttttgt gattaatata      60
tagccgtaag atactcaaag atctcacctt atcgacctca aacactaagg gaggtggaag     120
gagggactac tacccatgaa gctagagaaa gggatgatga tgattggagg aaggaagaag     180
gaaaaatagt agactcgatg atgataagac taaagaaaaa gggtttgact tagccacttg     240
gtatataatg aggtttggta tggagtcaat agcttgagta atagcatgga aagagagaag     300
gagctgaaga gagtactaag tcttattaga ataagaaaag atagaatctt agcgaaaaat     360
agggcctcaa atctttcagg tagaggaaaa agagggatca acgaatgaaa gactaaggaa     420
aaggtgtgga gtaggatata ctctcgatta gtctctcaat catggattct agtagggctt     480
cgtcagctgc tcaatcatgg attctgatag ctcaaatggt ggtaagtaga aagagagaga     540
tctaaagaga ttgatagtgg ccttaaaacc agcacggtca aggataggca tgccttagag     600
agaggaaaag agagagagat taatggaaat aagcgagaaa aatatattct tagagaatag     660
attggcgata agaagaggag gtggttgggg catgcttaaa gaaataaaga aaattgagta     720
ggcgaaaagt ggtgatgctt ggcgatgaga agatttgaga gagagagcaa aaaaatgtgg     780
atgatggtca taggatagggg aaaggaaaga acaaagaagg gggtgctaag ctaactcttt     840
ctaccttcct cacaccctga agcaaaggat ttggccaagg atggacaaat gggcgagggc     900
tttggtggat ccatgcctac cctttctccc tctcacgatg attctagtca agctatctat     960
ctttgatagc ttgagccaag ccaattgact tgatccaatc tctctaaatc catacaaact    1020
taagagagtg tattgattca cttattctct tctaagttga taagaaacat aattaagtgg    1080
agctcattaa gtatttcagg tagttgctaa cttggcaaaa tggaagcaat aataaatctt    1140
aaaagactat agcttggtat aatctcaacc atccatgatt tagaaagatc ttcagactca    1200
atatagatta ctttggctac tacaggtaag agctaaatag gatccaaaag taagatccat    1260
```

| | | | | | |
|---|---|---|---|---|---|
| cacattagta | agtcaaatta | tatgtcaaat | tttagtaggt | atacttagtc | ctacgatgcc | 1320 |
| taattaaaat | gatcatcatt | tgaaccttaa | aatggactag | tcaactaaaa | tttttctttt | 1380 |
| tgaagaagat | ttagaccata | aaatatcttc | taatctgtga | agaattagat | agagcgagga | 1440 |
| atataaaatt | gatgtagaaa | tcaagatcta | tcatatatac | aattttaata | ttttttttcat | 1500 |
| aattttttaaa | tatttatctt | cttttttttat | aggtctagtc | ctatttaaac | taggaagagg | 1560 |
| agtccaactt | gacttatgca | ataggggatg | tccttctaga | agataagaat | aatttgatca | 1620 |
| gaattatata | agagcaaacc | tcattattat | aaataggggc | tatatacatc | aatttatgag | 1680 |
| atagagaatc | aatgaaacaa | aagtagactt | aagttttatt | ttcataattc | ttctatcttc | 1740 |
| tactttttttt | ctaggagatt | caagttgagt | ggattgaaga | aaatctttca | tcttctcgat | 1800 |
| cggatcatat | tggtattaga | gcgttggtct | tctatatttta | tggagagctt | taatgtattg | 1860 |
| tttaaatacg | tgaacaatac | aaacaatcaa | gagaagtgct | atccatgctt | caaatacatc | 1920 |
| gaaatataaa | agcaaatatg | gctactaatt | cttttttcaat | ggacaatgag | ataaaaggat | 1980 |
| gtcttacaca | actcaaggag | aagattgtgc | aactcatgaa | gattgtctcc | agattgaaga | 2040 |
| taatttcaat | acaagcacaa | acaccagcaa | ctcatgttgt | gaaactgttt | cctatgtttg | 2100 |
| gagatgaaga | tcttctatct | agtgaggaga | ttgaattacc | taaaagtatg | aaaaatcttt | 2160 |
| cttcaatcat | tgaaagttaa | agcttgaatt | gagatcccca | tatataatgg | aaccattgat | 2220 |
| gaaaaaaagc | tagataattg | gctaaactaa | ttacaaacct | attttattat | ctatagatat | 2280 |
| tatggcatct | agaagatagc | ttttacttat | ctcaagcttt | ctagccatgc | tcttatctga | 2340 |
| tgaaattcat | atatgagaaa | taataatatt | tttaatatgg | tgcagagcca | attcaaaggt | 2400 |
| ttaatcaaga | agtaatttta | tctaattggc | cataaggaag | atcggtggat | caaatgataa | 2460 |
| tacttatgat | agaaacataa | tcaatccact | taggactata | ccaccaagtt | ccacaaacag | 2520 |
| gcaatctgcc | ttggaatctt | tatcaacaat | tatacaattt | ttataaagta | tgttgaaagt | 2580 |
| cttcatgaga | gcatctaaaa | aaagatgaaa | ctctttaagg | ttgatgatat | cagtaaagct | 2640 |
| aacatgaaag | tcatagagat | tgaggagaaa | aatcaaatta | gagaagataa | ggaaggcaaa | 2700 |
| aagcatatca | acataactca | aaaaaaaaaa | ttatgatcat | tgaaatcttt | gaaaatacat | 2760 |
| caaggagaag | tattgaaagt | ttcatcctga | attggagcta | aagtagaaga | agcccaagga | 2820 |
| tgataattttt | aagaaaaata | aaaagtggtc | ctcaattcta | tagagattga | ggagctatct | 2880 |
| gaacttgagt | aagcaaactt | caaattgagc | ttgatggtga | gaaaacctaa | tacaacaatt | 2940 |
| aaaacggatc | tagaggtaca | tgacaactca | cccacttaaa | gattcaagtg | aagcagagta | 3000 |
| tcattaaggc | tattataaat | ctttgaagct | agaagaacct | cattttccaa | tatttggttc | 3060 |
| agaaatcgag | gttgtagatc | aagcctcatc | catatcctta | tcctcttagt | tggattcaga | 3120 |
| aggatgtcaa | gttaaaaatt | atgagatagt | gtaccttcaa | gttagccatc | actgagaggt | 3180 |
| ttatttgtga | ggtaacttttt | gaaatagttt | ctttggatat | ttgtcaagtt | atccttagaa | 3240 |
| atgtgtacct | ttagaatcaa | gatgcaattt | tctatagacg | atagagaaag | tatcatctta | 3300 |
| taagggatga | gaaaaagttc | atgatcaaca | cctcaagaac | ataaggtaac | tttgaccttg | 3360 |
| caactgttgc | ccaagtgaag | tgatttgtta | atgtttgtga | tgagtgcatg | atgatggtat | 3420 |
| aaagaaccga | tatcactcat | gagaggtcaa | ggccttgtcc | tttggttcca | tcaatcgatc | 3480 |
| aatagagatt | gagattaagg | aggagtcact | atagtccttg | tcgatgagga | aggatgacaa | 3540 |
| caagcattcc | taccatgaag | tctagatttg | agagcaaatg | aaagtaatcc | actgagacct | 3600 |
| gagagcaaaa | aaaggcgaga | ccaaaaaatca | tcttcaagta | aagtcaaatg | gttcaaccat | 3660 |

| | |
|---|---|
| gagatgggga agtaagtatt ttcccacctt caattctaac tttgtagaaa ctaaatccct | 3720 |
| taaacagggg agccctaatt taagaggatc ctcagattca ttgtggacta ctttggctat | 3780 |
| tacaataaga gctggatagg aatcgaaagc aaaattcacc acattaggaa gccaaattgt | 3840 |
| atggcaaact tcaagagacc ataacttgat cacatgaaat ccaattaaga tgattttatt | 3900 |
| tttgaatttg aatattttt tgagatctat aactttagat ctaaatcaag ctaaaatttt | 3960 |
| attgcttatg ccttcaaaat aggctagtca aatcaaaact tttctttca aaaaagactt | 4020 |
| tgactgaaag atatctttca atctatgaag aatcaagtag a | 4061 |

<210> SEQ ID NO 50
<211> LENGTH: 4061
<212> TYPE: DNA
<213> ORGANISM: Artificial Sequence
<220> FEATURE:
<223> OTHER INFORMATION: synthetic

<400> SEQUENCE: 50

| | |
|---|---|
| ctctcgatta gtctctcaat catggattct agtagggctt cgtcagctgc tcaatcatgg | 60 |
| attctgatag ctcaaatggt ggtaagtaga aagagagaga tctaaagaga ttgatagtgg | 120 |
| ccttaaaacc agcacggtca aggataggca tgccttagag agaggaaaag agagagagat | 180 |
| taatggaaat aagcgagaaa aatatattct tagagaatag attggcgata agaaggggag | 240 |
| gtggttgggg catgcttaaa gaaataaaga aaattgagta ggcggaaagt ggtgatgctt | 300 |
| ggcgatgaga agatttgaga gagagagcaa aaaaatgtgg atgatggtca taggataggg | 360 |
| aaaggaaaga acaaagaagg gggtgctaag ctaactcttt ctaccttcct cacaccctga | 420 |
| agcaaaggat ttggccaagg atggacaaat gggcgagggc tttggtggat ccatgcctac | 480 |
| cctttctccc tctcacgatg attctagtca agctatctat ctttgatagc ttgagccaag | 540 |
| ccaattgact tgatccaatc tctctaaatc catacaaact taagagagtg tattgattca | 600 |
| cttattctct tctaagttga taagaaacat aattaagtgg agctcattaa gtatttcagg | 660 |
| tagttgctaa cttggcaaaa tggaagcaat aataaatctt aaaagactat agcttggtat | 720 |
| aatctcaacc atccatgatt tagaaagatc ttcagactca atatagatta ctttggctac | 780 |
| tacaggtaag agctaaatag gatccaaaag taagatccat cacattagta agtcaaatta | 840 |
| tatgtcaaat tttagtaggt atacttagtc ctacgatgcc taattaaaat gatcatcatt | 900 |
| tgaaccttaa aatggactag tcaactaaaa tttttctttt tgaagaagat ttagaccata | 960 |
| aaatatcttc taatctgtga agaattagat agagcgagga atataaaatt gatgtagaaa | 1020 |
| tcaagatcta tcatatatac aattttaata tttttttcat aattttaaa tatttatctt | 1080 |
| cttttttat aggtctagtc ctatttaaac taggaagagg agtccaactt gacttatgca | 1140 |
| ataggggatg tccttctaga agataagaat aatttgatca gaattatata agagcaaacc | 1200 |
| tcattattat aaaataggggc tatatacatc aatttatgag atagagaatc aatgaaacaa | 1260 |
| aagtagactt aagtttatt ttcataattc ttctatcttc tacttttttt ctaggagatt | 1320 |
| caagttgagt ggattgaaga aaatctttca tcttctcgat cggatcatat tggtattaga | 1380 |
| gcgttggtct tctatattta tggagagctt taatgtattg tttaaatacg tgaacaatac | 1440 |
| aaacaatcaa gagaagtgct atccatgctt caaatacatc gaaatataaa agcaaatatg | 1500 |
| gctactaatt cttttttcaat ggacaatgag ataaaaggat gtcttacaca actcaaggag | 1560 |
| aagattgtgc aactcatgaa gattgtctcc agattgaaga taatttcaat acaagcacaa | 1620 |

```
acaccagcaa ctcatgttgt gaaactgttt cctatgtttg gagatgaaga tcttctatct   1680
agtgaggaga ttgaattacc taaaagtatg aaaaatcttt cttcaatcat tgaaagttaa   1740
agcttgaatt gagatcccca tatataatgg aaccattgat gaaaaaaagc tagataattg   1800
gctaaactaa ttacaaacct attttattat ctatagatat tatggcatct agaagatagc   1860
ttttacttat ctcaagcttt ctagccatgc tcttatctga tgaaattcat atatgagaaa   1920
taataatatt tttaatatgg tgcagagcca attcaaaggt ttaatcaaga agtaatttta   1980
tctaattggc cataaggaag atcggtggat caaatgataa tacttatgat agaaacataa   2040
tcaatccact taggactata ccaccaagtt ccacaaacag gcaatctgcc ttggaatctt   2100
tatcaacaat tatacaattt ttataaagta tgttgaaagt cttcatgaga gcatctaaaa   2160
aaagatgaaa ctctttaagg ttgatgatat cagtaaagct aacatgaaag tcatagagat   2220
tgaggagaaa aatcaaatta gagaagataa ggaaggcaaa aagcatatca acataactca   2280
aaaaaaaaaa ttatgatcat tgaaatcttt gaaaatacat caaggagaag tattgaaagt   2340
ttcatcctga attggagcta aagtagaaga agcccaagga tgataatttt aagaaaaata   2400
aaaagtggtc ctcaattcta tagagattga ggagctatct gaacttgagt aagcaaactt   2460
caaattgagc ttgatggtga gaaaacctaa tacaacaatt aaaacggatc tagaggtaca   2520
tgacaactca cccacttaaa gattcaagtg aagcagagta tcattaaggc tattataaat   2580
ctttgaagct agaagaacct cattttccaa tatttggttc agaaatcgag ttgtagatc    2640
aagcctcatc catatcctta tcctcttagt tggattcaga aggatgtcaa gttaaaaatt   2700
atgagatagt gtaccttcaa gttagccatc actgagaggt ttatttgtga ggtaacttt    2760
gaaatagttt ctttggatat ttgtcaagtt atccttagaa atgtgtacct ttagaatcaa   2820
gatgcaattt tctatagacg atagagaaag tatcatctta taagggatga gaaaaagttc   2880
atgatcaaca cctcaagaac ataaggtaac tttgaccttg caactgttgc ccaagtgaag   2940
tgatttgtta atgtttgtga tgagtgcatg atgatggtat aaagaaccga tatcactcat   3000
gagaggtcaa ggccttgtcc tttggttcca tcaatcgatc aatagagatt gagattaagg   3060
aggagtcact atagtccttg tcgatgagga aggatgacaa caagcattcc taccatgaag   3120
tctagatttg agagcaaatg aaagtaatcc actgagacct gagagcaaaa aaggcgaga    3180
ccaaaaatca tcttcaagta aagtcaaatg gttcaaccat gagatgggga agtaagtatt   3240
ttcccacctt caattctaac tttgtagaaa ctaaatccct taaacagggg agccctaatt   3300
taagaggatc ctcagattca ttgtggacta cttttggctat tacaataaga gctggatagg   3360
aatcgaaagc aaaattcacc acattaggaa gccaaattgt atggcaaact tcaagagacc   3420
ataacttgat cacatgaaat ccaattaaga tgattttatt tttgaatttg aatattttt    3480
tgagatctat aactttagat ctaaatcaag ctaaaatttt attgcttatg ccttcaaaat   3540
aggctagtca aatcaaaact tttctttca aaaaagactt tgactgaaag atatctttca    3600
atctatgaag aatcaagtag agtgatgaaa gataaagttg atataaaaat tgagatctat   3660
ctcttataaa attttagtaa ttttattttt tttaatattt atctttattt agagatctat   3720
tcctatttaa actagaaaga attgtccaac ctaacttgtt caatgatcaa catcctccta   3780
aaagataaaa agaagaatct gactcaaatt ataaagggc ggaccttttt ttttgatgaa    3840
aagggaggaa aaaatccat caaaatttat taagaaaaaa agagtacaag aaaagaagga    3900
tatgaaagag taagagaagc cccacaacat ccatcaatat ttaaaattta aatttaaatc   3960
tccccccatca ttctatcaat atttgatatt caaatttaaa ttcttcgcag catcccacca   4020
```
acatttgaaa ttcaaatcct ttcatacaaa caaaataata t    4061

<210> SEQ ID NO 51
<211> LENGTH: 4061
<212> TYPE: DNA
<213> ORGANISM: Artificial Sequence
<220> FEATURE:
<223> OTHER INFORMATION: synthetic

<400> SEQUENCE: 51

| | |
|---|---|
| caaggagaag tattgaaagt tcatcctga attggagcta agtagaaga agcccaagga | 60 |
| tgataatttt aagaaaaata aaaagtggtc ctcaattcta tagagattga ggagctatct | 120 |
| gaacttgagt aagcaaactt caaattgagc ttgatggtga gaaacctaa tacaacaatt | 180 |
| aaaacggatc tagaggtaca tgacaactca cccacttaaa gattcaagtg aagcagagta | 240 |
| tcattaaggc tattataaat ctttgaagct agaagaacct cattttccaa tatttggttc | 300 |
| agaaatcgag gttgtagatc aagcctcatc catatcctta tcctcttagt tggattcaga | 360 |
| aggatgtcaa gttaaaaatt atgagatagt gtaccttcaa gttagccatc actgagaggt | 420 |
| ttatttgtga ggtaacttt gaaatagttt ctttggatat ttgtcaagtt atccttagaa | 480 |
| atgtgtacct ttagaatcaa gatgcaattt tctatagacg atagagaaag tatcatctta | 540 |
| taagggatga gaaaagttc atgatcaaca cctcaagaac ataaggtaac tttgaccttg | 600 |
| caactgttgc ccaagtgaag tgatttgtta atgtttgtga tgagtgcatg atgatggtat | 660 |
| aaagaaccga tatcactcat gagaggtcaa ggccttgtcc tttggttcca tcaatcgatc | 720 |
| aatagagatt gagattaagg aggagtcact atagtccttg tcgatgagga aggatgacaa | 780 |
| caagcattcc taccatgaag tctagatttg agagcaaatg aaagtaatcc actgagacct | 840 |
| gagagcaaaa aaaggcgaga ccaaaaatca tcttcaagta aagtcaaatg gttcaaccat | 900 |
| gagatgggga agtaagtatt tccccaccctt caattctaac tttgtagaaa ctaaatccct | 960 |
| taaacagggg agccctaatt taagaggatc ctcagattca ttgtggacta ctttggctat | 1020 |
| tacaataaga gctggatagg aatcgaaagc aaaattcacc acattaggaa gccaaattgt | 1080 |
| atggcaaact tcaagagacc ataacttgat cacatgaaat ccaattaaga tgattttatt | 1140 |
| tttgaatttg aatattttt tgagatctat aactttagat ctaaatcaag ctaaaatttt | 1200 |
| attgcttatg ccttcaaaat aggctagtca aatcaaaact tttctttca aaaaagactt | 1260 |
| tgactgaaag atatctttca atctatgaag aatcaagtag agtgatgaaa gataaagttg | 1320 |
| atataaaaat tgagatctat ctcttataaa attttagtaa tttttatttt tttaatattt | 1380 |
| atctttattt agagatctat tcctatttaa actagaaaga attgtccaac ctaacttgtt | 1440 |
| caatgatcaa catcctccta aaagataaaa agaagaatct gactcaaatt ataaaagggc | 1500 |
| ggacctttt ttttgatgaa agggaggaa aaaatccat caaatttat taagaaaaaa | 1560 |
| agagtacaag aaaagaagga tatgaaagag taagagaagc cccacaacat ccatcaatat | 1620 |
| ttaaaattta aatttaaatc tcccccatca ttctatcaat atttgatatt caaatttaaa | 1680 |
| ttcttcgcag catcccacca acatttgaaa ttcaaatcct ttcatacaaa caaaataata | 1740 |
| tttttcaaat tctcaacttt gagtttcaaa attgagaagc ctacatattg tctgctcttc | 1800 |
| accaaagagg ggagattgtt ggcttagctt ggcccaagag aagagaagaa ggccaaggcc | 1860 |
| caatctgtag cctagagaag gagggttttgg tagctactta ataatcggat ctaaccgata | 1920 |
| aagacactat ctctattaga agaaaaggta gagagaaaaa gaggcaattg gttaacttca | 1980 |

```
gaggggagg aggtaagctg ttgaggagat taatctgacg caaggaaaaa agaagagctg    2040
acaactagcc aatgatcgag aagggctgga gacaatccaa gcccagcacc aagaagcaag    2100
agaaagaatt tggaggtcaa aggaggagtc caggaagaga gagcgaaaca caatgttcgg    2160
atctagccga caacgatacc aattatacta ggaaagaagg taaaaaggga aagagcaatc    2220
gatcatcttc agcaaagaaa aataaaagag gcacccgaca gtcaagccca tggccaaatc    2280
agtcagcaag aggacctcac aagatctaga cggtgctaag gggaagggag gaagaaaaga    2340
gatccagtaa ctgtccaaca ccaggaaaag gaggagataa gaggaaggga gaagtcattt    2400
ttctatcttg ggccgaagga gggagaagga agaaagagga agaacatcc tcaaagtcga     2460 aggaaggaag gaaagagagg ggggaagggg tcacagtcag atataccaga agggatagat    2520
ccagtgtcaa agagagaaaa gagagaggag atcagaaaat aaaatttgat gactgactaa    2580
ttgtcatgaa aggctaatga caactcataa aaaagtata gtagtaaaga gaggggata      2640 ggcttggtta gggaagagat tccgacaaca aagagaaaga aagagagaga gagagagaac    2700
cggctcccag ccaaaaatag cttgacccac catcgagaag gaccgacaaa gagagagaaa    2760
gatagaatag ggagaatagc ttggcttcga atcaaaaatg atctaacaca ctgctgaaaa    2820
ggactaggaa gagagagaga gggggtaggg gagtatctcg gctcgcaatc agaatcaact    2880
ggccaatgcc agaaaagaga ggaagagaga gatagagaag atatagcaaa agagaagaga    2940
tggacaaaag gagagaggaa gggagggaga gagaaaaaa ataggagaga gaggggcttg      3000
gtggctgact gtcagaagaa gcctcgatgc tcgaagatta gatggaagaa aaaaaaattt    3060
ctcaaaactt ctctttctta taagagcaaa cctcactatt ataaataggg ttatgtatct    3120
cagtttatga tgtgaagaat taatgaaaaa ttggacttta gctctatttt tgtaattctt    3180
tcatcttcta tttttatgaa attcaagttg agccgattaa aagaaataat ctttctttcc    3240
gattggatca atccattaac tagatacttc aaaaatcaaa atgacctatc taaaatccta    3300
aatcaaatac aaaaccaaaa taactaaatt aagatagaac aaactacaat tacaaaaaac    3360
tggctaaagt gttaaatgc ttttactcct aagtttcttc ttgctcacca ttaatgcttg      3420
atctttagct gggatcatat cagccttatg accactataa gaccaacata acaactcact    3480
tgtattgctc ctttaaaatt atacaaaact agtgtctaat atgtaccatg cgaatgtctg    3540
tttctcacca gaaatggat gggcttcttg tgcaagcacc ttcttcctac aaataataaa      3600
atatgcatcc cttctctcat cttactaaat aaaataatta aaggctttac tatcaggaaa    3660
tctggcttta tccatataat tttggaagtt ttatttgaac ataacattac gagtactaga    3720
ttacatcagg aggtggttcc tcttatttct attaagagaa aaatcaattt tcttttaaga    3780
aagatcattt cattttcatc aggtagcgta ctctactaat atacttccac aacaatatat    3840
agggattaga ttataggatg gactttaagg cttcttttcg agagccctga tttctcaatc    3900
acattccctt ttctttctca tgtaatggca tttaagagtg catccagggc ccaacaatta    3960
gtcacaagtg ttctttttat acatggtaca tatttgctat tttttagctt attttaactt    4020
gattgtgaag atatcatgag aaaattagat ttaaagccta g                        4061
```

<210> SEQ ID NO 52
<211> LENGTH: 4061
<212> TYPE: DNA
<213> ORGANISM: Artificial Sequence
<220> FEATURE:
<223> OTHER INFORMATION: synthetic

<400> SEQUENCE: 52

```
ctttcaaaaa tatcttttga taggactaat gagataagtc aggaccaatg gatatctcgg      60
tcaacccaac cactgctcaa gtttgagatg gaaaatctat ctcggacaac agctgaagtt     120
agtacctcag gttaggatga tctagaatct cctataagag atttttttaga ttatttcggc    180 ccaagtactg aacaatctgt cctgaccaat ctcgatcttt aggaacttaa gaaaaaatat    240
tcgattcagc ttataactcc aagttgggat ggtaggatta ttgaacctcc agaaggttat    300
gtcgtatttt atgatgaggc acttcgatct ggactttaat ttctcttaca tccttctttc    360
agtaatgttt tagacttcta taaactccat ccaatctagg ttactcccaa tgccattagg    420
atgatcatag ttttcattat ctatcgtaaa ttttttgcta tagaactaag aatttctctc    480
tttaggatgc tggtcatcct aagaaaacat ccttatgaaa aagactgatg gtatttctta    540
ccttggcctc aatataaatt cggtcccact cttccttttt caatacataa ttgaaaaaat    600 catttttttct ttatttcttc taatgtttcg tagggtttta tttgtaaata gtctaagcct    660
aaaaccaaat ggaactcaaa taacaaaata ttatctgagg atgaggagac ttttgtagag    720
cttttagata tgaaagtatc caagttgagc ctactggtgt ccaatcagtc cttgtttgac    780
accgacatca gtcagatctc tccttaagat aagtctgatg ttaattcttt ttctttattg    840
ctttatcatt tttcatcatt tttcttttct aacaatcttt ttccttatat agtagcaata    900
atgaagttca acctacaaag gctggctaac tcaagaagaa ggaagaagga tctaaccgat    960
tgctctcaag aagagtaagg agactgctcc tctaagatcg attggccccc gatcatcacc   1020
tgggccaata ttaattgaca tagatgctac atcgatctcc actataccac cagcaaaatc   1080
aactcatcaa cctactaagg tggcttgtcc acctcctaaa gagtctgcac atccaaagta   1140
ggcatcttcc ccaacacctc caacatcggc caagttagtt tggctgagca atcagcatct   1200
gaggtcacag actcctgatg tcaacccacc aactttctca tcaaaaaaaa ttgacttggc   1260
gaaggtatca cttttggaga cacccagact aggcaaggac ttgctctgta caatgatgcc   1320 tcaaaggac ctagatgctg ataggaggga tctttctttg gagcaaataa taaattatgg    1380
attcaacagt atcatgaacg tgagtcttca ttctcttcca ctctcttctt tcttttttctt   1440 tttttttta cattggctat ttgttgatct gaatatatct ttcttttttgc agtcggttgt    1500 gtatttcaag ttgctcaatg agcacttgac atggttcttc aaaaataaaa ttttttttgaa   1560 agagaggctc aaggccaaga aagaggccaa aaaagcagtt gaggaggtca agaaggcagt   1620
aaagaagaag gctgtcaaag aaagcaaaat gatggcgggg ctgaagaaac agctccaaga   1680
aaaaatagat tccattaagg agactggaca accaatgaca gatgaatgat aaagatgaca   1740
agttgtaaaa acagcctgaa aaaaatctca agttggagg ccaagctgaa ggaggtcgag    1800
tcaataattg aaaagcatga tgaagctctt gtcccatatt agacacaact tgataaagac   1860
aaagagtgga tgtcaaggat tattgaagat tataagaatt ccgacacttt tcaagatgac   1920
gttactgagg cctcaaaagg agctttcaat tatggctttt tgagctacag gagtttaatt   1980
atcaagctct ttcctaacct tgatctcagc aaggtcataa tagaagcagc tctagaagta   2040
gtagccgaag tgacttctgc aacaactact gagcttgctt ccacttctat cattggagtt   2100
tctccgatcg aagtcccaaa cagtccaatc gaggcctcca tcatcgaagc tatttcgaag   2160
gaatcagtcg gcaaagacct tacctcaact cctccaacaa ataactccca agctaaggcc   2220
tgaattatct tcttcttttt ttctaaacat ttgtattagc ccgatgtggg cttctataaa   2280 tacttttac attaatgaat gagttttcca atgtcaatat ttttctttt taactaatac    2340
```

```
taatcttgga tgatccgatc tgggttggat gtctcaaaaa atatcattca cgatagatag    2400
ttattttctg acttcggtta gatgattatg agtatatgta attcaacctt ggttaggtaa    2460
gtaatcaaat attaactatt ctcaaaccaa gtagataacg aagtcaatgt gattaacttt    2520
aacaagtaag attgttatgg aatgaaattg aatcagatca actaactata gataacttaa    2580
tctctcataa ttcactgtaa aggttctaaa agtaccttta tctaagttcg aagtgacaag    2640
tcgggttctt ttattcgtgg atttatgacc catgctgtct ttttgtgatc ttcattatta    2700
atcaccttaa atcgatatag caaaatccag tttatagatc tgagtgcttt cttgtcagat    2760
tgagtctatc ctattatctg tgaaacctga tctagagatc aagtatttta ggttttttat    2820
ttaaggtcca attcgaagat tgagtatcca atgtcatatt gttaggtcca atttggagat    2880
tggatgtctc actatcatct cgtgaggtcc aatccaaaga tcgaatatct cactatcatc    2940
tcatgaggtc caatccagag attggatgtc tcacatcatc ttgtgagatc caattcgaag    3000
attggatgtc tcacatcatc tcatcctatt gtggttggaa ttttttgtagc cttagtttga    3060 cttttctga cctcatttgg acacctaaat cttattatca tcgtttgatc gatttttact    3120
aatctacttt ggatgaaaaa gaattcttca atggaacttt tgattagaac tttatcttca    3180
ttgggataga aatcgaatgc tttattgaaa gattttattg ataatacatt ctgagatttt    3240
taatatttca tgttctcgaa atgatcgtac catctaaatt tttaattcga taagctcttg    3300
gatggatcac ctcagtaatc tgataaggtc cttcccaatt cgggatgagt ttttcttact    3360
ccattggttt tgagacttca gctcattgga gaaccaaatc tccttataaa aaattttagg    3420
ctttacctga gagttgtaat atctggctac ttttttgttta taaactacca tatgaatctg    3480
ggctttttct cgagttttct caaataaatt gagatcagtc ctcagttgat ctgaattatt    3540
ttcttcatga aaattttcta ttctggttgt aggtaaactg atctcgacta gtattatagc    3600
ctctgttccg aaagtaagtt taaagatat ttctctagtt ggtctctgag gtgtagttct    3660
gtatacccat aaaatattat aaaattattc taccccgaga cttttagcct caatgagttt    3720 tattttagg ccttgaaaga tagttctata aataaattta gcttctccat ttgattgtag    3780
atgtccaatc gaagtaaata tatgatctat gtagagctca gaataaattt ttttaaaatt    3840
ttgattatca aattattgct cattattagt aattataact caaggcaaac caaaatggta    3900
aataattatt tttcacataa aatctcatat ttttctcag tgatttatgt cagaggttca    3960
atttctatcc attgggtaaa ataatcaata gtcacaacta aaattttct ttgctccatg    4020 gccattagaa aggatcccag aatatccatt ctccatatag c                       4061

<210> SEQ ID NO 53
<211> LENGTH: 4061
<212> TYPE: DNA
<213> ORGANISM: Artificial Sequence
<220> FEATURE:
<223> OTHER INFORMATION: synthetic

<400> SEQUENCE: 53
aaaattattc taccccgaga cttttagcct caatgagttt tattttagg ccttgaaaga      60 tagttctata aataaattta gcttctccat ttgattgtag atgtccaatc gaagtaaata   120
tatgatctat gtagagctca gaataaattt ttttaaaatt ttgattatca aattattgct   180
cattattagt aattataact caaggcaaac caaaatggta aataattatt tttcacataa   240
aatctcatat ttttctcag tgatttatgt cagaggttca atttctatcc attgggtaaa   300
ataatcaata gtcacaacta aaattttct ttgctccatg gccattagaa aggatcccag   360
```

```
aatatccatt ctccatatag caaaaggcca cagcactgta atagaaataa gttcagttgt    420
aggctgatgt tatatattgg cgtacctttg acactgatcg cagtacttat taataaagtc    480
ggttgaatct ttttgaatag taggccaata ataatcttac tgaattattt cataagctaa    540
aattttaccc cccaaatggt tactagagat tcctttatga acttctcgaa ggatgtaatc    600
agcttccgat ggccttaggc ataggagcag tgggagtgaa tataacctct gatataattg    660
attatcttga caacatacc atggggcctg tcttttaatt cttgttcctt cgactggatc    720
aaccggtaga ggttctttag taatatactc cattaatggg tcaatggaac ttagctcata    780
ttaaatttgg acaattagta aggcctcgat actagacttt taagaatat caataagaac     840 accttgattt agtttgaaaa atctgatgt ggctaaatga datagggcat cagctcagac     900
attttgtcct tggtatttgc atgatcttca gattttcaaa gttttttaat aattctttca    960
tattatataa atattgaaac atcataaaat ctttagcttc aaattaatct catacctgac   1020
tgacgataaa ttgagaatca ataaaaattt taatttttt aacattaagc tccttagcca    1080
ttttgagtcc tacaattagc gtttcatatt ctactccatt gtttgagtgt taaaattaaa   1140
tctcaaagca cgctcactaa caatgccttc tagactcgtt agaattaaac tagttctact   1200 ttcttttcgaa tttgaggctc catcaatgta cagtatcaaa taagaatctt tgatattttt   1260
caattctttt aagattggtt cttcattagg aatagagcat tcaataataa aatcagctaa   1320
tacttaaact ttcaatgaag atcgaggccc atattgatat caaattcatt taattcaata   1380
gcctatttga atatccttct taaagtatca agctactgta aaattaattt taaaggttga   1440
tcgatcagaa ttataataga atgagcctaa aaatacgatc aaagtcatct tgctaatgca   1500
atgagggtat aaattatctt ctcaatttta gaatatcgag tttcaacatc tctaaataat   1560
ttatttgtat aataaatgga tctttgtatc cctgcatcat ttcaagctaa aatcgaacta   1620
acagcatttg ctgaaataga tagatacatg aataattttt gacctttgat cggctttgat   1680
agtaatggag ctgtgccgag atatttcttg agatcatcga aggctgcttg acattcatct   1740
tatcaatcga agtctttgat ctgccttaga atttttaaaga aaggaagata tttatcagct   1800
gatctgaaaa taaattaact aagcaatgct actcatccag taagttggtg tacttctttg   1860
atggagctcg gatgcttcat ttcacataga gcttgaattt tcttaagatt gactttaatt   1920
cctctttgag ttacaaaaaa atctaaaaaa attttttgaag ttacttcaaa agcatatttg   1980
ttgggattga gcttcatttg atattttcgt agtctctaaa ggcttcttcc agattggcaa   2040
tatactgatc tgactcagta ttttttacta atatatcatc aacataaact ttgatattaa   2100
tttcaatttg ttacttaaaa atcttattaa tcaagtatta gtatgtagca cctacatttt   2160
taagatcaaa agcatcatt ttataacaat gcaaatcttt ttcagtgatg aaggccatat    2220
tttcttcatc ctcaagtgcc attttgatct gatataacca gaaaaagtat ccataaagct   2280
tagtaatttg tgtcttgaag tagcatcaac aagctgatca attttgaga gagaaaaact    2340 atcttttagg caagctttat tgagatcggt ataatcaaca tagatccttc attttttcatt  2400 agccttttta accatgacaa catttacaat ccactttgga tattatgctt ctctgatgaa   2460
tttgtctttc aagagtttgt cgacttcctc atctattatt ttttatcttt tcggggtgaa   2520
acttcttttc ttctgttgca ttggtttatg ctttggatca acattcagct tatgtacaat   2580
aagatcagtt aaaatctcag gcatattaga gactgactaa acaaagacat cggcattcat   2640
ccgaagaaaa gatattaatt tctccctcag atcaggcttc aatagagatc caatttggac   2700
```

```
agtttttttt ggatcatcac acaaaagaac aataataagt ttctcgactg gttctcctcg    2760
atttttgatg atatcaactt tactttcttg atcaagtatt ttaattggta gagcttccac    2820
agacctttc attttacag ctatcagaaa atactactta gcaagtatct gatttcctca      2880
tatttctcca actccatact tagtttgaa ttggattagt aaatgataag tgaagactat     2940
agccttaagg gcgttgagcc taggtcggtc aagaatagca ttataagctg atggtatttt    3000
gacaataaaa aaagtgagtc ttacagttga ctggcatggt tctatccctg cagtgacgga    3060
caaagtgacc tctccttcca cagctacagg atttctagaa aatccaatta cggggtacc     3120
aacctattta gctaatttat catattcatt ctttggaatg tatcatagaa caatatatta    3180
gcagagcttt cattatcaat aagtattctt tttatatcat atttggctat tgccataaag    3240
atgacaacag catcattacg aggagtttga actctaacat catcatcgaa aaatgaaatt    3300
atgtgatcca tgcactgatg ctttggaagg ctttcagtaa tctcagccac ctcctcagtt    3360
ccgtcgagat ctgagatcat attgatgact gcagcagtag acttgttgtg atcattctca    3420
ttgttgggct tctatcattg gtcagtagct tgacttgccc gatctcgaac atatttacta    3480
aagtaacatt agtggatcaa tacttcaatt ttatctttta attatcgatg ctcctcagta    3540
tcatggccat agtctcgatg gaaatgacag tattttctct tatctctctt tgctggaggg    3600
gctttcatag gattaggttg gcgaatatat cctaaatcct cgatttctat cagtatctga    3660
gctcgaggag tagatagtga ggtatagatg tcgaatcacc gaggtgggct tttgaacttc    3720
agattcttct gaggtcgttc agagttatcc tgttggtttt tatgatcttc ttcctagggc    3780
cacttttttc catctctttt tttcttcacc taacgaagta tgcatgctct ctttcttttc    3840
agcttgagca tacttacaaa cctagatcaa tatttgttca taattgtttg ggtagttctt    3900
attaagagag aagatcaggc gattactctt gagtccttgc ttcaaagctg ccattgcaat    3960
ggactcattg aagttcttca ctttcagtat ggcggcatta aagcatgcca catattcttg    4020
aagagattca ccttcctact atttgatagt aaaaagattg c                        4061
```

<210> SEQ ID NO 54
<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2978)..(3705)
<223> OTHER INFORMATION: n is a, c, g, or t

<400> SEQUENCE: 54

```
catcatcgaa aaatgaaatt atgtgatcca tgcactgatg ctttggaagg ctttcagtaa      60
tctcagccac ctcctcagtt ccgtcgagat ctgagatcat attgatgact gcagcagtag     120
acttgttgtg atcattctca ttgttgggct tctatcattg gtcagtagct tgacttgccc     180
gatctcgaac atatttacta aagtaacatt agtggatcaa tacttcaatt ttatctttta    240
attatcgatg ctcctcagta tcatggccat agtctcgatg gaaatgacag tattttctct    300
tatctctctt tgctggaggg gctttcatag gattaggttg gcgaatatat cctaaatcct    360
cgatttctat cagtatctga gctcgaggag tagatagtga ggtatagatg tcgaatcacc    420
gaggtgggct tttgaacttc agattcttct gaggtcgttc agagttatcc tgttggtttt    480
tatgatcttc ttcctagggc cacttttttc catctctttt tttcttcacc taacgaagta   540
tgcatgctct ctttcttttc agcttgagca tacttacaaa cctagatcaa tatttgttca    600
```

```
taattgtttg ggtagttctt attaagagag aagatcaggc gattactctt gagtccttgc      660
ttcaaagctg ccattgcaat ggactcattg aagttcttca ctttcagtat ggcggcatta      720
aagcatgcca catattcttg aagagattca ccttcctact atttgatagt aaaaagattg      780
ctagtatttt tcaaatgaat ccatttatta tcaaaatacg tgatgaatat ttgctaactg      840
tgtgaaagat gaaatagatc atgtctggag gtcagagaac tagattcttg cagatgtttt      900
gagagtgatt ggaaaagtga tgcaaaatag ggcattagat accccttgta gtcttataat      960
ggctctgaag ccttcaagat gatttaaggg attgatggag ccatcgaatg tttccaatgt     1020
aggtatcttg aatcgaggag gaactgattt accaagaatt ttttgagaaa aaagagatcg     1080
taagttgaaa tctcttctac cttgagaatg gcttccaatc tatatctcca tcattttctt     1140
ctcaagattt tgaatctttt gtccaagacc ctcctccata catggcttct tatgtggagc     1200
agatttcact tcccaagagt gatcagtatg gtcaagaaga tgatcatgat gaagatcttg     1260
aggagttggt tgctaagtgt gatgtgattg gactacttgg ggggctactt tttgctaccg     1320
ttctgtcgta tactacagca gtaagagctt ggacctgctg aaccaagaga ctaaactatt     1380
gtggatcaat aataattgaa ggttaggtat tctcctgaac atcttcagga gaagatgaag     1440
taggtaaagg atgatttggt gccttcttgt tcaccatttc tactaaaata ttttaagtgc     1500
ccttcctcta acactaatct attactgcaa ggcttcaaaa gacaggcaac gagatgggtc     1560
ttgaatcgaa ctagaatgtt tcttggttga atttggcgaa gtctgtaaca aatcttgcaa     1620
agaaaatctc gaaacctacg ggtaccttct ggttcaagat cctctgatgg ataagttagg     1680
taaagtcttg agaataggtt gtgaaaatag aagaatagaa ggatgagaag agagattgtc     1740
ggtaaatgga gagatgactc ttatttcttt caatggggga gctgaaaata attcagcaga     1800
gtttccactc tatcaatcct gacttatttt gtggagggta ccttggcccc ttcatatata     1860
ggggatgaag aggcctggta aggttgttag actattagga gagtttgtta gatcgttaat     1920
ttattataat agaatgacca gctatataaa aatcatggag tatttaccca catggtgatt     1980
gactgtagta taactgaaag atagctaatg cttagctgga tgactgctgt tagataactg     2040
tctgcattct tacggtacat tgatatttta ccaatgtgac atagcttaaa tcggcaactg     2100
gctgaactaa atattatgta tcccttttagt taacaatcat gtcggttaga gatcaatgta     2160
attcgcagca gatcgatcat aagctgagat gagtatcata ttttaagaac aacgctgggc     2220
gagttaggcc gatcaaatgt cagactgaaa aagcagatca ataaacctct gatgtgatct     2280
gaaagaatat ttatgattta aataataatc tatcaccacg tatccagata atgaggtcat     2340
ataacatgta ccaacagtgc attttttccat ctagttaaga ggttggttag tggcatttgt     2400
cttcgatatg taatgttcac ataactaatg tgcttagtag cattcttttg taaggttaaa     2460
tcttcaatga tcttaagttc acataattgc ctttgtgccc tattagttta tagttgaccct     2520 tttaattcaa gagacagtca ccttagcaat cgatgtctgc ttagattggg ccaattaggt     2580
actcacatta atatattgaa tcatgtttga atataaagga ttagattgat ttataagttt     2640
ccttttattg tttacatact gatacttaga ttgacttact acattatttg atatgttatg     2700
ttctaatttt tggattaaaa ttgttgtttc tgatttctcc ttacatctaa tactttgtat     2760
aatttattat ttttttagcat gattgagtgt agaggattag attgattttt aagtttattt     2820
tgattattta catgcccata cttaaattga cttactacat tattcaatat gttatgtttc     2880
aattattgag ttaaaatttt tatttctgat ttctactgat gtccagtgtg tgtgtgtgta     2940
```

-continued

```
cgtatgtgtg tatatattta tttacatata tatgtatnnn nnnnnnnnnn nnnnnnnnnn    3000
nnnnnnnnnn nnnnnnnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnatgta tacatataca    3720
tgtatacata catatataga tatatatata tacatatatg tatatatata tatatatata    3780
cacatatata ggttatttgg aacctaagaa acttgcaaag ttactagatg caatgttcgg    3840
aaaccatgga ccgtaacaac tggagtagta tttgggtcat gaattcatgg ctagatcatg    3900
aattgagtgg gagtcaaccg aagtagggcc agctcagaca cttgtattta ggtcccatgc    3960
ttgcgtgcat tctcttccct gatatccttt ggctttgctg cctcaaatcc tcgagctatc    4020
ttatcatcat cgcattgagc tccataccct gctctttcct a                        4061
```

<210> SEQ ID NO 55
<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2098)..(2825)
<223> OTHER INFORMATION: n is a, c, g, or t

<400> SEQUENCE: 55

```
tagattcttg cagatgtttt gagagtgatt ggaaaagtga tgcaaaatag ggcattagat     60
accccttgta gtcttataat ggctctgaag ccttcaagat gatttaaggg attgatggag    120
ccatcgaatg tttccaatgt aggtatcttg aatcgaggag gaactgattt accaagaatt    180
ttttgagaaa aaagagatcg taagttgaaa tctcttctac cttgagaatg gcttccaatc    240
tatatctcca tcattttctt ctcaagattt tgaatctttt gtccaagacc tcctcccata    300
catggcttct tatgtggagc agatttcact tcccaagagt gatcagtatg gtcaagaaga    360
tgatcatgat gaagatcttg aggagttggt tgctaagtgt gatgtgattg gactacttgg    420
ggggctactt tttgctaccg ttctgtcgta tactacagca gtaagagctt ggacctgctg    480
aaccaagaga ctaaactatt gtggatcaat aataattgaa ggttaggtat tctcctgaac    540
atcttcagga gaagatgaag taggtaaagg atgatttggt gccttcttgt tcaccatttc    600
tactaaaata tttaagtgc ccttcctcta acactaatct attactgcaa ggcttcaaaa    660
gacaggcaac gagatgggtc ttgaatcgaa ctagaatgtt tcttggttga atttggcgaa    720
gtctgtaaca aatcttgcaa agaaaatctc gaaacctacg ggtaccttct ggttcaagat    780
cctctgatgg ataagttagg taaagtcttg agaataggtt gtgaaaatag aagaatagaa    840
```

```
ggatgagaag agagattgtc ggtaaatgga gagatgactc ttatttcttt caatggggga    900
gctgaaaata attcagcaga gtttccactc tatcaatcct gacttatttt gtggagggta    960
ccttggcccc ttcatatata ggggatgaag aggcctggta aggttgttag actattagga   1020
gagtttgtta gatcgttaat ttattataat agaatgacca gctatataaa aatcatggag   1080
tatttacccca catggtgatt gactgtagta taactgaaag atagctaatg cttagctgga   1140
tgactgctgt tagataactg tctgcattct tacggtacat tgatatttta ccaatgtgac   1200
atagcttaaa tcggcaactg gctgaactaa atattatgta tccctttagt taacaatcat   1260
gtcggttaga gatcaatgta attcgcagca gatcgatcat aagctgagat gagtatcata   1320
ttttaagaac aacgctgggc gagttaggcc gatcaaatgt cagactgaaa aagcagatca   1380
ataaacctct gatgtgatct gaaagaatat ttatgattta aataataatc tatcaccacg   1440
tatccagata atgaggtcat ataacatgta ccaacagtgc attttccat ctagttaaga    1500
ggttggttag tggcatttgt cttcgatatg taatgttcac ataactaatg tgcttagtag   1560
cattctttg taaggttaaa tcttcaatga tcttaagttc acataattgc ctttgtgccc    1620
tattagttta tagttgacct tttaattcaa gagacagtca ccttagcaat cgatgtctgc   1680
ttagattggg ccaattaggt actcacatta atatattgaa tcatgtttga atataaagga   1740
ttagattgat ttataagttt ccttttattg tttacatact gatacttaga ttgacttact   1800
acattatttg atatgttatg ttctaatttt tggattaaaa ttgttgtttc tgatttctcc   1860
ttacatctaa tactttgtat aatttattat tttttagcat gattgagtgt agaggattag   1920
attgattttt aagtttattt tgattattta catgcccata cttaaattga cttactacat   1980
tattcaatat gttatgtttc aattattgag ttaaaatttt tatttctgat ttctactgat   2040
gtccagtgtg tgtgtgtgta cgtatgtgtg tatatattta tttacatata tatgtatnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nnnnnnnnnn   2400
nnnnnnnnnn nnnnnnnnnn nnnnnnnnnn nnnnnnnnnn nnnnnnnnnn nnnnnnnnnn   2460
nnnnnnnnnn nnnnnnnnnn nnnnnnnnnn nnnnnnnnnn nnnnnnnnnn nnnnnnnnnn   2520
nnnnnnnnnn nnnnnnnnnn nnnnnnnnnn nnnnnnnnnn nnnnnnnnnn nnnnnnnnnn   2580
nnnnnnnnnn nnnnnnnnnn nnnnnnnnnn nnnnnnnnnn nnnnnnnnnn nnnnnnnnnn   2640
nnnnnnnnnn nnnnnnnnnn nnnnnnnnnn nnnnnnnnnn nnnnnnnnnn nnnnnnnnnn   2700
nnnnnnnnnn nnnnnnnnnn nnnnnnnnnn nnnnnnnnnn nnnnnnnnnn nnnnnnnnnn   2760
nnnnnnnnnn nnnnnnnnnn nnnnnnnnnn nnnnnnnnnn nnnnnnnnnn nnnnnnnnnn   2820
nnnnnatgta tacatataca tgtatacata catatataga tatatatata tacatatatg   2880
tatatatata tatatatata cacatatata ggttatttgg aacctaagaa acttgcaaag   2940
ttactagatg caatgttcgg aaaccatgga ccgtaacaac tggagtagta tttgggtcat   3000
gaattcatgg ctagatcatg aattgagtgg gagtcaaccg aagtagggcc agctcagaca   3060
cttgtattta ggtcccatgc ttgcgtgcat tctcttccct gatatccttt ggctttgctg   3120
cctcaaatcc tcgagctatc ttatcatcat cgcattgagc tccataacctt gctctttcct  3180
```

```
aactgccccc atcaaacctc cggagatcct ctttcttctc caatgttgag atttgttgga    3240
gtcttcccac cttctcactt caatgggtgg caatttcaag tgccagttcc cttatttgtc    3300
ccagctatat tgacaatggg gcttattcta gggtttctca tggacatagt gataataata    3360
atcaagggac caagagagaa aaatctttct agtctgtgtt ctttaagttt gagagatagg    3420
cagcacattt ttttaataag cctttttcac tcatcggatc ctgattttca gttgttcgac    3480
ctgaacagtt caagcaattg aactgcttgg gtcactattt tggacgattt tcagccattt    3540
ttaagtattg tttgactgga tccacgctgc gtagtgggca ttgcgttgat caagtagacc    3600
tgtaagggtc aacaaggtct gagaacactg aatggatgct ccataatcct cttgttatct    3660
gtcaaccatt tggaatcttt taaaacaaca tgtggtgata atatatatga taaactgtga    3720
tagattcatg tatagattat acatatgaaa atgtagagtg cttagtaaaa gtgatgaaga    3780
gcaatgcgtt agaatgtgct agcctttgac ctaaaaattg gaatgcccaa tgatgagtta    3840
tgataaaatt gtgacgtgat ttatgaagtc taatgtttag ttggcttgca gtttcagatg    3900
cgataaagaa ttttatgatt tagctctttg gtttttttaac atgcaaacat ttaattgtac    3960
tgaaaaacat ttatttcgaa acatgtagga gactattgga tattgaaatt aaaattgact    4020
ttttggtgtt tcacaatatt tcttaataaa cactacgact a                        4061
```

<210> SEQ ID NO 56  
<211> LENGTH: 4061  
<212> TYPE: DNA  
<213> ORGANISM: Artificial Sequence  
<220> FEATURE:  
<223> OTHER INFORMATION: synthetic  
<220> FEATURE:  
<221> NAME/KEY: misc_feature  
<222> LOCATION: (218)..(1631)  
<223> OTHER INFORMATION: n is a, c, g, or t

<400> SEQUENCE: 56

```
aagctccgtg cttctgtctt tgagaagtgt ctgagtaggt agtcgatccc aggcaacctt      60
ctagaggaaa agtctgatcc tagagtggat agccatgtgt atatatatat atatatatat     120
gtatgtatgt atgtatgtat gtatgtatgt atgtacgtac atacatacat acacacacat     180
acatacatat acatacatac atatacatac atacatannn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
```

```
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn ntatatatat atagtatact atatagtata tatatagtat atatagtata    1680
tatatatata tatatatata gtatatatat atatatatat atatatatgt gtgtgtgtgt    1740
gtgtgcgcgt gcgcgcacgc acgtgtgtat ctcgatctgt gtgtgtgtgg tccatcttca    1800
cactttcccc tcaaaaaaac cccccttgag attttgttca gctgaaaggg gttcataaaa    1860
cttgcccttg cttggtccta gggtttaaga tttatatgca atattcatta agacgtctaa    1920
atgtcataat attttgaggt tacaaatatt aacaaacagc cttggataca aaccttttc    1980 tcgaagaatc ttgtatctgt tcttcctcag atgacatgtg attatgcta cggcctagtt    2040 ctaaggactt ttctctgtca ttaacataaa aaaaaacaga aatatattcc ttagtaagga    2100
aatagttgtg cactatgatt gctatgtctc tcaaaattat accaaacttt ttatgatata    2160
gagtgaaaat caaatcagca tgtctggtct atttgccaaa tagggttgag cataggtcgg    2220
gttcggtcga gttgagagaa aaatttcatc cgatcaaatt caatcggatt gaagaaaatt    2280
caatccactg ccaatcattc attatgcata aactatctaa aactgaaatg aatagtttgt    2340
agcaggatca ggtgttatgt cagttttggac ttcaatgtta acccaatatt gattttaaat    2400
ccaacattgg tccacttaga cttatttatt tatttttatc aatttaatat aaaaaagatc    2460
taaacctcat aagtcataaa ttttggattt attttttgaac atgtacaaaa taaaacagaa    2520
aaaagaaaaa attacttatc taaaagtaac tatatctgaa aactttcact ttagaattgt    2580
cttaaattaa tgtacttcca tcaacaattc aatgttaata tttttatgaa tccaaatgga    2640
tgatagagta ttttttagaa tgaagtattg aagtctaaat gacatcgtcc caaaataaaa    2700
gtgaatttat gaaatactac atctgtcgga ttcggtttca tacggattaa aagtgtagga    2760
atagaatccg attataaata attatttttt tataaattct aattcaattt tattcgattt    2820
atatttttta accggtcaaa attaatattt attaagtagg attggatgga tttattcgta    2880
tctcgattat ttgctcagcc cattgccaaa tctaaactct tttcagatag gttccatgtg    2940
aacatgatac atgagatgca gtgtgatagt acacaccatt gctaagaaaa ctttggagtt    3000
tgcgtaacaa tatctgttta ccatttaaaa aatggcagtt ttgaattta acacgctctc    3060 ctccagattc agcttatgaa cttttcgaat aaaaatacccc ctggactatt tttccaaaaa    3120
gtaccagcat cttttgaact tgaatggaaa ttcggccaat aaaatgtttt catttattga    3180
agaaataaac agggtaacgc agtagctcta tttcctctgc ttttcttttc tatattaata    3240
acatgattat tcatctctct cggatcacaa aaaaattaag ctattcaagc tttatttata    3300 tttcatttt aaatttttta cttaaataca aaatctccca tcccactact acggcagcat    3360
gttttctatg tatgattatt ttcattcaaa tgatatcatt ttttataatt tatattgtat    3420
```

| | |
|---|---|
| gtaattaatt catttatagt tcttacattt tcctgtttct agtagataca ataaagcggt | 3480 |
| tttggactag tagcttgttc tctgtatcga agtttaacta aagctttgac aataatatat | 3540 |
| gaatccatat cactgggtag gagaggaata tgttgggtat aaaggattta aggaattaga | 3600 |
| tattttcata caattgtatt gcattgcaga cagtaattag attactatgc aattattctc | 3660 |
| tctctccatg tttgttgcag ttgaagaact ctaatgaagc tcacaaaaat ttactgcatg | 3720 |
| aacttgtaag tggaattaga cgactccgtt gtcctccatt ttcttttatt ttctttaaaa | 3780 |
| tcatctgcca ttcaaataga cagaaaaaaa aggattgatt agctattgga tgcctcttga | 3840 |
| attcaggaaa tgaaggacga gcacccagtt tatggttttg tggatgatga ccctagcaac | 3900 |
| tacgcaggtg cactagctct tgccaatggg gcttcccaca tgtatgcttt ccgtgttcag | 3960 |
| ccgagccagc cgaatctcca tcgaatgggg tttggctccc atgacctgcg ccttgcttga | 4020 |
| ttttattgta gcttaaagac cttacaactt ccagagtggt g | 4061 |

<210> SEQ ID NO 57
<211> LENGTH: 4061
<212> TYPE: DNA
<213> ORGANISM: Artificial Sequence
<220> FEATURE:
<223> OTHER INFORMATION: synthetic

<400> SEQUENCE: 57

| | |
|---|---|
| cagtttggac ttcaatgtta acccaatatt gattttaaat ccaacattgg tccacttaga | 60 |
| cttatttatt tattttatc aatttaatat aaaaaagatc taaacctcat aagtcataaa | 120 |
| ttttggattt attttgaac atgtacaaaa taaaacagaa aaaagaaaaa attacttatc | 180 |
| taaaagtaac tatatctgaa aactttcact ttagaattgt cttaaattaa tgtacttcca | 240 |
| tcaacaattc aatgttaata ttttatgaa tccaaatgga tgatagagta tttttagaa | 300 |
| tgaagtattg aagtctaaat gacatcgtcc caaaataaaa gtgaatttat gaaatactac | 360 |
| atctgtcgga ttcggtttca tacgattaa aagtgtagga atagaatccg attataaata | 420 |
| attattttt tataaattct aattcaattt tattcgattt atatttttta accggtcaaa | 480 |
| attaatattt attaagtagg attggatgga tttattcgta tctcgattat ttgctcagcc | 540 |
| cattgccaaa tctaaactct tttcagatag gttccatgtg aacatgatac atgagatgca | 600 |
| gtgtgatagt acacaccatt gctaagaaaa cttggagtt tgcgtaacaa tatctgttta | 660 |
| ccatttaaaa aatggcagtt tgaatttta acacgctctc ctccagattc agcttatgaa | 720 |
| cttttcgaat aaaaatacc ctggactatt ttccaaaaa gtaccagcat cttttgaact | 780 |
| tgaatggaaa ttcggccaat aaaatgtttt catttattga agaaataaac agggtaacgc | 840 |
| agtagctcta tttcctctgc ttttcttttc tatattaata acatgattat tcatctctct | 900 |
| cggatcacaa aaaattaag ctattcaagc tttatttata tttcatttt aaattttta | 960 |
| cttaaataca aaatctccca tcccactact acggcagcat gttttctatg tatgattatt | 1020 |
| ttcattcaaa tgatatcatt ttttataatt tatattgtat gtaattaatt catttatagt | 1080 |
| tcttacattt tcctgtttct agtagataca ataaagcggt tttggactag tagcttgttc | 1140 |
| tctgtatcga agtttaacta aagctttgac aataatatat gaatccatat cactgggtag | 1200 |
| gagaggaata tgttgggtat aaaggattta aggaattaga tattttcata caattgtatt | 1260 |
| gcattgcaga cagtaattag attactatgc aattattctc tctctccatg tttgttgcag | 1320 |
| ttgaagaact ctaatgaagc tcacaaaaat ttactgcatg aacttgtaag tggaattaga | 1380 |
| cgactccgtt gtcctccatt ttcttttatt ttctttaaaa tcatctgcca ttcaaataga | 1440 |

```
cagaaaaaaa aggattgatt agctattgga tgcctcttga attcaggaaa tgaaggacga    1500
gcacccagtt tatggttttg tggatgatga ccctagcaac tacgcaggtg cactagctct    1560
tgccaatggg gcttcccaca tgtatgcttt ccgtgttcag ccgagccagc cgaatctcca    1620
tcgaatgggg tttggctccc atgacctgcg ccttgcttga ttttattgta gcttaaagac    1680
cttacaactt ccagagtggt gttatatatt agtatcttaa gctatgacag tggtaagcct    1740
ctctatccgc tacttgttat cctttaggta ctttgcatgt ggtgcaaggt tataattgcc    1800
ttgtgtttct attgtcttcc tcatggtact tactggactg atgatgtcaa gtgaaatgga    1860
gttgtttgaa tcctgactga aatttctctt ggtccatcaa gtgcaagagt aagtttagac    1920
atcactcgca agcttttgct aggaaataag tagtttcatt gcactaatga tttcgaattt    1980
ttgttttcgg gttagagaaa cctagattaa tgctgttatt ggatgctggc agtcagatga    2040
agattatgtt tgattgtacc tcgttggaca gatgctcatg cgtagatcca taactctatt    2100
tcatttcatt tccctgtaca caattgaaac agggcatata tgaataggta tagaacagat    2160
gattcctgca atattggagg tggctagctc agcttagact aaagttggtc tagctgggat    2220
attctgaaca cctgagatgt tcaaataatg tgggataact tggcccaact caactaaaca    2280
ttggctcaaa gcatagtcaa ggtaaagctt gagcaagctc ttttgagctt ggttcgagtc    2340
cgagctgagc ccgggccgct tgtttagctg atgaactgaa ttcaaatagc cggtactcag    2400
cttggctcca ctcgattcat gagttcgaat cccctcaagt tcaacctcga acttgacggt    2460
gtagtcccac aacctggcc acctataat gtgggacggc cattatgcat tcctctagtg    2520
cctgctccat atgacttttg ttctcattat accatgcacc taaatgagtg ctcatagtga    2580
caatgtttag cctccacgta taatgtgtgc cagctaacta gaagcctaaa ctttggtgaa    2640
atttctgcaa tgttgtggtt gtaaaacgct cctacgttga gacatgatgg tatctaagat    2700
tatagacaaa ctatcatgct gaatcaaccc aaatccaagg tgaataaaac ttgatacaaa    2760
gccgagctcc attgaaatag tacaatggat tctgcacttg aagaacatta caaaatcatt    2820
ttttcccaaa aagaaacatt gcgaacagac caaagcgtaa agaaattaca tgattcaact    2880
aattcaagct ttccatgatg taggcactcg ctagatgtag tagggtgata acttgctttg    2940
tgagggtgga tcataagctt aacctcaatc tatcccaatc tatccttttcc cttgacctat    3000 ccatgccaat ctaggccatt tctgcataaa tataacttaa tcccagtgga tccggcctag    3060
tttcactcac tccaacacat tcctactcaa tggtagccaa tcctttcttt agccctcaaa    3120
tataatccta atctagcata gccaaccatc aatcatgcct aataaagccc gactacacca    3180
acccgatcat tcctgatcgt acacaatcaa gacttatcct aattgatcct agctttttt    3240 aggcctctct tatagaacct gtgccaattc tggacaagct aatccaatct tagcagccaa    3300
aaatattaca tgtttaatta gccaaatcga acctatcata aacccaatat ataatcggac    3360
cataccaaga tcatcatcct atatttcctt ctcttgttat aactcacct aaaaggaat    3420 ttcttcatac ttatgagggg tatattatga taaaaattcc ttcatttag ccctccatcc    3480 ttgtctattt ttgggaccac tagccaagta acaccttaag agccctccat cttaatattc    3540
cctctaacta gctcgatttc ttcttcattc tttctttgcg atgtgtcccc tccaatttaa    3600
ttcttacatg ttgggatttg agtactgaaa aataatagat aaagagaaag taaaaactat    3660
gctaatgata ataccaaagg cataagaaa tcacagcagt cgcaaaaaca tcaaattttt    3720
ttatggttcg gcctaagcct atatctacat agggacgaga gtaagaagaa gcttccacta    3780
```

| taataatagt ttagagtaca aaaacttctc tgacaccatg tagggaacat cgcttctaat | 3840 |
| acaagaaaga agaaatccaa gattaaacaa acctctagaa aaattcttct cgatggaata | 3900 |
| actctaatct gagattgaac aatcttctcc aatcgatgat ctccaatctt cttttcttaa | 3960 |
| atgaagcacc cttcaagcct ctcttctttt ctctcttcct atcctctttt gtggctcaca | 4020 |
| acctcctctc cttttatgt tctatgttcc tcacatcaca t | 4061 |

<210> SEQ ID NO 58
<211> LENGTH: 4061
<212> TYPE: DNA
<213> ORGANISM: Artificial Sequence
<220> FEATURE:
<223> OTHER INFORMATION: synthetic

<400> SEQUENCE: 58

| tttcagatag gttccatgtg aacatgatac atgagatgca gtgtgatagt acacaccatt | 60 |
| gctaagaaaa ctttggagtt tgcgtaacaa tatctgttta ccatttaaaa aatggcagtt | 120 |
| ttgaatttta acacgctctc ctccagattc agcttatgaa cttttcgaat aaaaatacccc | 180 |
| ctggactatt tttccaaaaa gtaccagcat cttttgaact tgaatggaaa ttcggccaat | 240 |
| aaaatgtttt catttattga agaaataaac agggtaacgc agtagctcta tttcctctgc | 300 |
| ttttctttc tatattaata acatgattat tcatctctct cggatcacaa aaaaattaag | 360 |
| ctattcaagc tttatttata tttcattttt aatttttta cttaaataca aatctccca | 420 |
| tcccactact acggcagcat gttttctatg tatgattatt tcattcaaa tgatatcatt | 480 |
| ttttataatt tatattgtat gtaattaatt catttatagt tcttacattt tcctgtttct | 540 |
| agtagataca ataaagcggt tttggactag tagcttgttc tctgtatcga agtttaacta | 600 |
| aagctttgac aataatatat gaatccatat cactgggtag agaggaata tgttgggtat | 660 |
| aaaggattta aggaattaga tattttcata caattgtatt gcattgcaga cagtaattag | 720 |
| attactatgc aattattctc tctctccatg tttgttgcag ttgaagaact ctaatgaagc | 780 |
| tcacaaaaat ttactgcatg aacttgtaag tggaattaga cgactccgtt gtcctccatt | 840 |
| ttcttttatt ttctttaaaa tcatctgcca ttcaaataga cagaaaaaaa aggattgatt | 900 |
| agctattgga tgcctcttga attcaggaaa tgaaggacga gcacccagtt tatggttttg | 960 |
| tggatgatga ccctagcaac tacgcaggtg cactagctct tgccaatggg gcttcccaca | 1020 |
| tgtatgcttt ccgtgttcag ccgagccagc cgaatctcca tcgaatgggg tttggctccc | 1080 |
| atgacctgcg ccttgcttga ttttattgta gcttaaagac cttacaactt ccagagtggt | 1140 |
| gttatatatt agtatcttaa gctatgacag tggtaagcct ctctatccgc tacttgttat | 1200 |
| cctttaggta ctttgcatgt ggtgcaaggt tataattgcc ttgtgtttct attgtcttcc | 1260 |
| tcatggtact tactggactg atgatgtcaa gtgaaatgga gttgtttgaa tcctgactga | 1320 |
| aatttctctt ggtccatcaa gtgcaagagt aagtttagac atcactcgca agcttttgct | 1380 |
| aggaaataag tagtttcatt gcactaatga tttcgaattt ttgttttcgg gttagagaaa | 1440 |
| cctagattaa tgctgttatt ggatgctggc agtcagatga agattatgtt tgattgtacc | 1500 |
| tcgttggaca gatgctcatg cgtagatcca taactctatt tcatttcatt tccctgtaca | 1560 |
| caattgaaac agggcatata tgaataggta tagaacagat gattcctgca atattggagg | 1620 |
| tggctagctc agcttagact aaagttggtc tagctgggat attctgaaca cctgagatgt | 1680 |
| tcaaataatg tgggataact tggcccaact caactaaaca ttggctcaaa gcatagtcaa | 1740 |
| ggtaaagctt gagcaagctc ttttgagctt ggttcgagtc cgagctgagc ccgggccgct | 1800 |

```
tgtttagctg atgaactgaa ttcaaatagc cggtactcag cttggctcca ctcgattcat    1860
gagttcgaat cccctcaagt tcaacctcga acttgacggt gtagtccac  aaccatggcc    1920
accttataat gtgggacggc cattatgcat tcctctagtg cctgctccat atgacttttg    1980
ttctcattat accatgcacc taaatgagtg ctcatagtga caatgtttag cctccacgta    2040
taatgtgtgc cagctaacta gaagcctaaa ctttggtgaa atttctgcaa tgttgtggtt    2100
gtaaaacgct cctacgttga gacatgatgg tatctaagat tatagacaaa ctatcatgct    2160
gaatcaaccc aaatccaagg tgaataaaac ttgatacaaa gccgagctcc attgaaatag    2220
tacaatggat tctgcacttg aagaacatta caaaatcatt ttttcccaaa aagaaacatt    2280
gcgaacagac caaagcgtaa agaaattaca tgattcaact aattcaagct ttccatgatg    2340
taggcactcg ctagatgtag tagggtgata acttgctttg tgagggtgga tcataagctt    2400
aacctcaatc tatcccaatc tatccttttcc cttgacctat ccatgccaat ctaggccatt    2460
tctgcataaa tataacttaa tcccagtgga tccggcctag tttcactcac tccaacacat    2520
tcctactcaa tggtagccaa tcctttcttt agccctcaaa tataatccta atctagcata    2580
gccaaccatc aatcatgcct aataaagccc gactacacca acccgatcat tcctgatcgt    2640
acacaatcaa gacttatcct aattgatcct agctttttttt aggcctctct tatagaacct    2700
gtgccaattc tggacaagct aatccaatct tagcagccaa aaatattaca tgtttaatta    2760
gccaaatcga acctatcata aacccaatat ataatcggac cataccaaga tcatcatcct    2820
atatttcctt ctcttgttat aactacacct aaaaaggaat tcttcatac  ttatgagggg    2880
tatattatga taaaaattcc ttcattttag ccctccatcc ttgtctattt ttgggaccac    2940
tagccaagta acaccttaag agccctccat cttaatattc cctctaacta gctcgatttc    3000
ttcttcattc tttctttgcg atgtgtcccc tccaatttaa ttcttacatg ttgggatttg    3060
agtactgaaa aataatagat aaagagaaag taaaaactat gctaatgata ataccaaagg    3120
cataaagaaa tcacagcagt cgcaaaaaca tcaaattttt ttatggttcg gcctaagcct    3180
atatctacat agggacgaga gtaagaagaa gcttccacta taataatagt ttagagtaca    3240
aaaacttctc tgacaccatg tagggaacat cgcttctaat acaagaaaga agaaatccaa    3300
gattaaacaa acctctagaa aaattcttct cgatggaata actctaatct gagattgaac    3360
aatcttctcc aatcgatgat ctccaatctt cttttcttaa atgaagcacc cttcaagcct    3420
ctcttctttt ctctcttcct atcctctttt gtggctcaca acctcctctc ctttttatgt    3480
tctatgttcc tcacatcaca tccacagact catttttata gataaaaaat tagagtctat    3540
ttcggactcc ttttccacac acaagatggc ttcccacgcc attggttccg tgcgcatgac    3600
tttttttcatg ccacaaagga ttccgtgctg caaaagtttt ccatatccat gcagtttcca    3660
cacaccacaa aaactttcgc acacttctcg aaggcttttc atgctcgacc cttttttggtt    3720
ttcaattaaa ttgatggatc ccatatgagg agggaccaca ccaataaatc tcctccttct    3780
aactcatatg gtaggttcca tcaagcctgt agcaccttttg catttttatca gttttgttcc    3840
tgaagccggc ttcatcaata tattagaact attttcttca gtgtcaactt ttttaagctt    3900
gaaccacttc atctctagca tattgacatg cttttggaaa gtatgtcaaa ttgctcaaaa    3960
ttaatcttac ggttctcttt ttcgttagat tctagtgcat attacgcact ttaacataag    4020
atctaaggaa ggaagaggac tgaggtaagg tgaagtgatt t                        4061
```

<210> SEQ ID NO 59

<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3947)..(4061)
<223> OTHER INFORMATION: n is a, c, g, or t

<400> SEQUENCE: 59

| | | | | | |
|---|---|---|---|---|---|
| cctagattaa | tgctgttatt | ggatgctggc | agtcagatga | agattatgtt | tgattgtacc | 60 |
| tcgttggaca | gatgctcatg | cgtagatcca | taactctatt | tcatttcatt | tccctgtaca | 120 |
| caattgaaac | agggcatata | tgaataggta | tagaacagat | gattcctgca | atattggagg | 180 |
| tggctagctc | agcttagact | aaagttggtc | tagctgggat | attctgaaca | cctgagatgt | 240 |
| tcaaataatg | tgggataact | tggcccaact | caactaaaca | ttggctcaaa | gcatagtcaa | 300 |
| ggtaaagctt | gagcaagctc | ttttgagctt | ggttcgagtc | cgagctgagc | ccgggccgct | 360 |
| tgtttagctg | atgaactgaa | ttcaaatagc | cggtactcag | cttggctcca | ctcgattcat | 420 |
| gagttcgaat | cccctcaagt | tcaacctcga | acttgacggt | gtagtcccac | aaccatggcc | 480 |
| acctataat | gtgggacggc | cattatgcat | tcctctagtg | cctgctccat | atgacttttg | 540 |
| ttctcattat | accatgcacc | taaatgagtg | ctcatagtga | caatgtttag | cctccacgta | 600 |
| taatgtgtgc | cagctaacta | aagcctaaa | ctttggtgaa | atttctgcaa | tgttgtggtt | 660 |
| gtaaaacgct | cctacgttga | gacatgatgg | tatctaagat | tatagacaaa | ctatcatgct | 720 |
| gaatcaaccc | aaatccaagg | tgaataaaac | ttgatacaaa | gccgagctcc | attgaaatag | 780 |
| tacaatggat | tctgcacttg | aagaacatta | caaaatcatt | ttttcccaaa | agaaacatt | 840 |
| gcgaacagac | caaagcgtaa | agaaattaca | tgattcaact | aattcaagct | ttccatgatg | 900 |
| taggcactcg | ctagatgtag | tagggtgata | acttgctttg | tgagggtgga | tcataagctt | 960 |
| aacctcaatc | tatcccaatc | tatcctttcc | cttgacctat | ccatgccaat | ctaggccatt | 1020 |
| tctgcataaa | tataacttaa | tcccagtgga | tccggcctag | tttcactcac | tccaacacat | 1080 |
| tcctactcaa | tggtagccaa | tccttttcttt | agccctcaaa | tataatccta | atctagcata | 1140 |
| gccaaccatc | aatcatgcct | aataaagccc | gactacacca | acccgatcat | tcctgatcgt | 1200 |
| acacaatcaa | gacttatcct | aattgatcct | agcttttttt | aggcctctct | tatagaacct | 1260 |
| gtgccaattc | tggacaagct | aatccaatct | tagcagccaa | aaatattaca | tgtttaatta | 1320 |
| gccaaatcga | acctatcata | aacccaatat | ataatcggac | cataccaaga | tcatcatcct | 1380 |
| atatttcctt | ctcttgttat | aactacacct | aaaaaggaat | ttcttcatac | ttatgagggg | 1440 |
| tatattatga | taaaaattcc | ttcattttag | ccctccatcc | ttgtctattt | ttgggaccac | 1500 |
| tagccaagta | acaccttaag | agccctccat | cttaatattc | cctctaacta | gctcgatttc | 1560 |
| ttcttcattc | tttctttgcg | atgtgtcccc | tccaatttaa | ttcttacatg | ttgggatttg | 1620 |
| agtactgaaa | ataatagat | aaagagaaag | taaaaactat | gctaatgata | ataccaaagg | 1680 |
| cataagaaa | tcacagcagt | cgcaaaaaca | tcaaattttt | ttatggttcg | gcctaagcct | 1740 |
| atatctacat | agggacgaga | gtaagaagaa | gcttccacta | taataatagt | ttagagtaca | 1800 |
| aaaacttctc | tgacaccatg | tagggaacat | cgcttctaat | acaagaaaga | agaaatccaa | 1860 |
| gattaaacaa | acctctagaa | aaattcttct | cgatggaata | actctaatct | gagattgaac | 1920 |
| aatcttctcc | aatcgatgat | ctccaatctt | cttttcttaa | atgaagcacc | cttcaagcct | 1980 |
| ctcttctttt | ctctcttcct | atcctctttt | gtggctcaca | acctcctctc | cttttatgt | 2040 |

```
tctatgttcc tcacatcaca tccacagact catttttata gataaaaaat tagagtctat    2100
ttcggactcc ttttccacac acaagatggc ttcccacgcc attggttccg tgcgcatgac    2160
ttttttcatg ccacaaagga ttccgtgctg caaaagtttt ccatatccat gcagtttcca    2220
cacaccacaa aaactttcgc acacttctcg aaggcttttc atgctcgacc cttttggtt     2280 ttcaattaaa ttgatggatc ccatatgagg agggaccaca ccaataaatc tcctccttct    2340
aactcatatg gtaggttcca tcaagcctgt agcacctttg cattttatca gttttgttcc    2400
tgaagccggc ttcatcaata tattagaact attttcttca gtgtcaactt ttttaagctt    2460
gaaccacttc atctctagca tattgacatg cttttggaaa gtatgtcaaa ttgctcaaaa    2520
ttaatcttac ggttctcttt ttcgttagat tctagtgcat attacgcact ttaacataag    2580
atctaaggaa ggaagaggac tgaggtaagg tgaagtgatt ttttttgagt tggtaatggt    2640
acaaaagtta tactagaccg tgggtaccta atctcggaga ttaccattta gatttggttc    2700
ttgatcattt gtatagtgat gcatttaaaa aattatttga gcaaaacagt gaatgccatt    2760
gggtctgaga gatccaaaac caaataacct aaagtatata gatggttcct ttagctagat    2820
catgtatgag aaaaaatgat ctgccgactg gaaaaaatag atctttgagc tcattgattg    2880
ttaagtcata tctagtctgt gaatcatctc tttgaggatt aatgatcaag ctatctttta    2940
tgggttaaaa gaataggatc actgaaatac ttatcctagt atacatataa tgtgcatggc    3000
ctatttgatg agtcagacta gaaggttatc actacttcat cacctttact gatgagcaat    3060
catgatatag atatgtatgt gagatacaaa tctaaaagat tttgaatggt tcaaagaatt    3120
cagatatgaa gtagaaaaga taaatcaaaa aattttttaaa ggtacttgat cggatctaga    3180
atgcaatacc aaataaaaaa tttgttgatt atctaaaaaa agtgatatag tttcatgatg    3240
gaattcttct tgtacacctc agctcaacgg tatatatatg aggagcaata gcactatatg    3300
agatatggtc cggtccatca tgaatatcac taatttaatt attatttatt taagagcaag    3360
atttaatttt taaaatttaa attagatttt ttctaaaatt ggtttcaccg caccatatga    3420
gatatgattt ggtggataag ttagaggata ggtctgtgag aactcattta tagggtatcc    3480
caaaaggtat ttaaaatatt acttttctt tctagtagtt gacaatatga ttgtgagcaa     3540
tcatactgtt ttcttaaaaa cagtggaagg atgaactcaa aagaaagtc tctaaagaac      3600 aacgagtcac aagacctata caacctattt aagatgagcc agtatatgta gtacttcctt    3660
cacctcatca atttagtagg atctcctatc ctttagaaag atactcggta ttcttacaaa    3720
ggatttagag aaagtgtttc ttgagggaga ttgagaatat agggatgatc tcaaaaccta    3780
caatgacata atataaggaa tcatgtagtt acatgaaggt cagtgggagg gttccatact    3840
gacatcgatt atgatgtggt tacatataga attttttttt caaagatcta gatcaaacat    3900
tctgaaaata aaaggtctat agagataaat ccgaaaagga tgtttgnnnn nnnnnnnnn     3960 nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn n                        4061
```

<210> SEQ ID NO 60
<211> LENGTH: 4061
<212> TYPE: DNA
<213> ORGANISM: Artificial Sequence
<220> FEATURE:
<223> OTHER INFORMATION: synthetic

<400> SEQUENCE: 60

```
tataccatag attttctgt taaccacatg tcaattcttc tcctccattg attttcatta        60
caatattcag gaacagctgc tttcatcttc tcaacaaata agtcaacatt aaaatggtta       120
gactttagat cattcttcca atgcctccac atagcccta ttttttccag tagagactt         180 cttatggcat ccatgtactt agataaaaat ataaatatat cctacaccta gaaactgact       240
tttagaaaaa gtgtatatat acctaaataa aatgatttaa gatgaaaata ttcactatac      300
ctctagttca gctatcatct tttccttgaa gcctgatggc acatcatgcc aagagtcata      360
atcgattgga gcattatcaa attgtcttac cattgactgt atataatttg acaaattagt     420
agcttccacc cggattgatt gtccaagttc acttaggttg caacaacat gctctccctc      480 ttttagatca cgtaactcag acatacgtat gtatcctctc cttctaggcc agctagtcga     540
acctacaaat atgtatacac aattaaaaaa atacataaaa tgtaagaaaa tgatccctca    600
aaattaataa ttatcatatg caccatcctt tatttggtta ttagtgatct atttatgcaa    660
ttcattcgaa gaagattata tatgtatacc tagttgactt tcattggtag ctaagggagg    720
tagctcttag gcaactgatt cagttttctc ataattttgg gcttcaagtg actgctccta    780
ttgattatga gatggaggct caccttgatt ctgactttaa gagttttctg taccactaat    840
attgacaatt gtctgcttgt gttttgccat tattaatgta atttgaaaga aaaaaataga   900
attcatatat ctgaatgtta gtgaccaaaa aaacttgcaa gtatctcccc aaccatctaa   960
agattatacg ctattttatt tttcaaatct taaaaggcta acaaggcaca tagcaattac  1020
atgaagcaaa aaagaaaat aaataaagca ccaaggaaac cattacactg tcattactga   1080
aattacattc aatagtatta tgcattaaaa caaaaactac attgataaaa taaaattgaa  1140
aataagaaac tacaagctcg tgggtgttcc ctcttgatca aaacatatcc tcaaactcta  1200
aatcttcatc gtgttggtgc acttcttgaa caaccacttc tttaaatggc tcttcacctc  1260
gaatcaaatc tgaaggttga agctgatcct catacatttg ttgtggcaca tgatcactaa  1320
caatagagtt cacatctccc aaatcataat tgtctctaac tttaaccgac ttaacaataa  1380
ccacatcttt atgtctagga gtattaatat agaacatctt tgcttgagat gcaaatacga  1440
aaggatcgtc aagcacacct tcaccagtat gtgctaagta agaaaaattc acaagtacaa  1500
taaaatttat ctttcttgca tcctttattg atatcaaccc aatcgcactt gaataaatca  1560
atcttgattt tgcaatgata atttaattga ataatgtcct ttaatatacc ataatactct  1620
attttttctt tcaacaggct acctatctct agtcctagtg taacccattg attcaactat  1680
caccacaacc ccactatttt gagttctcaa cttcctctca agtgctttg tgtggaatct   1740 aaagccattc ataacgtaac cggtatatca tcgtgcaaca tcaagtggct ttcgagcaag  1800
gcacctaatt tgtttagtaa tatagacatc accttgttga ttcatgcatg caacctaaat  1860
taacatggat ttcaaatagt atattacaag atagaacatt atgaggtaaa tatatggtgt  1920
ttatatattc aaattataaa ttataaagga gcatataaaa cactcattta tgaaaccact  1980
cgaaaaattc ctgactatga atcctttcaa tctcataaga agttaaatga catggatgac  2040
atgaagcttt gatatgcatc gaaacatatt cacatggtta ttaatgagat gagtgatagt  2100
ttggtagact tgccaactta ataactaact taataacaaa atctccttac tctcgaaata  2160
cggtaattgc atcgtagtta aataggatat atctgtgcgc ttgcatcaac tctttctcat  2220
caagatggac ccttggcact cgacttcacc tttctggcct ccatgacttt tgctacttcc  2280
tttctaaaga ttttctggc ctaaacattc ttgaatcgac atcaagttgg tcttcaccat  2340
catcgcctac aagttggtct tcaccatcat ctcctacaag tagatcttcg ctattatcat  2400
```

```
tccttcatgg ccaattgaac cttatttgaa tcccacttaa gtgtcgtaag cagaatgtac    2460
attatacatt catttgcaag atatgcttct gctattgagc cctctggagg agctctattg    2520
cacacatata tcttaaggta accaagaagc ctaaataaaa aattgaaaga aatgataaca    2580
taaattaatc atcaaaaaat atcataacac ataatgaacc aaattttaac tataacacat    2640
ccaaaattat acctctcaat aggatacatt catctatgat gaactggatc agtcatctta    2700
gcctcgctcg ctagatgaac cactaagtga accataactg tgaaaaaaga tggtggaaaa    2760
atcttcctat ttgacaaaag gtaagagcag ctcaagattg aagccgctca agattatcca    2820
catccaaaac cttgctataa agttctatga aaaaattgca tagatcaata acagctaaag    2880
aaacatggtc aggaaaagac ccaggggtag caattggaag gatttcttca atcaggacat    2940
gacagtcata cgacttaagg tgagcaagct tgtgttgtct caactacaca cacctctaaa    3000
tgttggatga acactcttct ggaaatttca attccttaat cacattgcaa aaatcatcct    3060
tttcttttgc attcatttga ggcataaact tcaaataagt attgttgggt ataaaatacc    3120
ccccggctga agtctgtaaa agaccgaccc ttccaggact ctttcggctt ccgaccttgt    3180
gtgtggcatc actccaaacc cccatgaccg tccggacttc tccgatagag aacttctgca    3240
ttcgtctacc gagccgcccc aaaatgctct ctgggcctca ccaccagccg accttctaca    3300
gtgatcaact attctccgaa ctccttccga actctgccaa tatccaagct tcttcgacaa    3360
cgagatttct acagtaatca gactccatcc aagtttctac gacggtcgac cgccttcagg    3420
attccaactg ggctcctgtg agagccaaac ttctactacg gacagtctac tccgaactca    3480
tacagtgagc ggtctactct ggatatccac tataagcaaa ctccattcga gcctctgctg    3540
taaacaaatt tcttccaaac tttcgttaca ggtagacttc gatcgagctt cttcgtagcc    3600
ggatcccata cgagcttcta cgatggggca ggatccaccg gccaggtcgt tactccgagc    3660
tcccacgaca accgatcttc gatcgagctc aacaataag tggcttcctt tcggcctccc     3720
acaagaacca gactccgtcc gagcttccac agtggatgga ttctggatga gctttcgcaa    3780
tggacgagct ctagcagctg gatttctaca atgactgatc acctccgacg tctgtcgaac    3840
ctccccagcg ccatccgaag tccatcacca gctgacctcc tgccagatcc ttcatgaaat    3900
caaagttctc caatggatca tcttcagatg agcttccaca tcaggtaaat ctcagacgga    3960
ctcctctagc aatcgaactt ctgttgggct tcaccaacga aaagtctcca tccgagcttc    4020
tacaacagat gactcccacc tgtggtatca gcgcctaagg t                        4061
```

<210> SEQ ID NO 61
<211> LENGTH: 4061
<212> TYPE: DNA
<213> ORGANISM: Artificial Sequence
<220> FEATURE:
<223> OTHER INFORMATION: synthetic

<400> SEQUENCE: 61

```
atttaaaat ttttaatagg ataaaaaatt ttagttagct ttgtgatagg cctagcgaat     60
ccacgagcta ccattctttg cttttggaca aattgcagat gcacgaagcc aatcatgata    120
tagttagcaa aactccttca ataggacagg aatgacaaac tggctggcca aagcctcagt    180
cggtgctttc aaagtgtatc gtcacctaac aataaagtag atattagaat caccacaagg    240
taaaaaattt ttaacgataa aattatttgt gatagataaa attttttatta taataataa    300 tgtcaatgat ggtaaaaaat tttcatcgat aataaaaaaa tatttacgat gaataaattt    360
```

```
tttcattata aataaaagta attaacgacg aaaatattgc ttacgtcgta acaaacagaa    420
tatttgcgat gaaaatttta atcataaata agaaaatatt ttttaaataa aaatatagag    480
atattaccga tgaaattatt tttgttagaa atattaaaag ttttttcgat gaaatcaggt    540
tttgcatcat caataacatt atttacgata aattttttt gtcactaata aatcaaaaaa    600
aattaaaaat tagatatttt caattatttg tgatgtaaat tttagtcgta aataaatttga  660 ctatttgaaa actgagacat acctttaaaa aaaataaata aataaaaatt gatccagctc   720
gagatgatga tatatattta atatattaat tatatctatc tatataacaa taataaaatg   780
atatacaggt attaggggta gcattcttta ttgacacata aagattataa gatgatccct   840
aaagtcttct ttaatttttt ttttatttat tttttgtttt tctttaattt tttctcttct   900
tatttttgct gccatctgct gcctctgttt tctctgctcc tgctgcctcc ttttatagag   960
cacagcttct tcgaattata agcatctatg gactttcaat tcccactatc ttttattttg  1020
attgggattt taaaacttta tccgcatccc agcatcttgt ttcacgcgag atcctagcgt  1080
ccacatgtgt tttgaattcc ttatgggcca cagaccattt aaaccaccaa agaccacttt  1140
actattttga tttgaatccc atggaagccg gctgcctctg gtctcattca cccttccagt  1200
gcttcacatg ggtcccatta atttgaattc ctatgagcca catccaagct tttgaatcca  1260
agccttcctt attttttaaa tcaattaaaa ctttgcttta aatgccttgt agaccctcct  1320
atttgcatgc tacgtgagaa cattgttaag ctcctcttgg cccacttaag aacttctatg  1380
ggctacatgc ttttggctag ctttaaaatg gttttgggcc taactttgga tcaccattcg  1440
aagtccattt tgaattcaat ttatttttat tttttttttt aaccttacaa atcgagctct  1500
tttattggtg atcatttttc ctataaaaca aaaacaaaaa gcatcaagtc ttaagaaata  1560
aaagttaatt aatatatatt ttgatacttt tattgggata tttaatgtac ttatcactag  1620
atatgaaatc caatgggtca cacactttga aatttgatct tagtctaatc taactaggat  1680
ttattataaa tcttatgggt taaatttaca tgctagcaca tgaattaact caagttttca  1740
attggattta gttctaaggt gtttgagcta accctatcct gataccttaa acctaattag  1800
attagatttg aacctatggt tttcttgatg ccttatgctt attacatgaa agagtttcat  1860
gtgacttaaa ttcctccatg ccaccacatc ttcatccatg ccaaattaat atggaacgcc  1920
ccatttaatt gtgcatttaa gaaggaatag tccttcttaa acactcctct taatttccca  1980
cactttcctt tgttctacac accatcaaat ggcttttgga aatatgcggg cgcagaagta  2040
gaggtgtcct atatgaaggc tcttccacat tataagttat cacatggtga attaaatcat  2100
tgtgtgagaa aatcatgcgc caagagttgg cacccttgg gagttttagg cactccttat  2160
cctataaata aggggcaccc catatggata aatacaaggg aattcaagtt taggcatgag  2220
attgagagga gaaaaagaca caaaaatctg agaaaaagat aagaaaaaa aagagagaaa  2280 aatagaaaga aaagacgaga gaaatgaaa ggcaagggtt gctaatccta gggttcaatt   2340
tttcaatagt tggatttctg aatcaatttg gggtggtgag attttttgag aaaaagtttc  2400
tgatgtggcc ctagtagaag attgaaggca ttcagatgat ggtgcaatcc gttttgaaa   2460 aagaaaagtg agtagtatac ttatgaagaa agctgcaaca ctacatcaaa ttggaaagga  2520
ccttgatcaa acccatatgg atcaccgttg caggatatct actttggtat cttgtgaagg  2580
ttattttttt tatcagatca tcatcttcaa aaaggtataa ttttctacct aatatgcatg  2640
cttgatttgt ttgattaaaa tctataaagt gttcataagg tttgtgttct gattgtattg  2700
ttttaagtat taaaacttac tttaaaaata taaaaaaatt tgaaaactat cttctactgt  2760
```

```
gcaactaaaa tccaacagaa taaccctaat atgagattga gcgatctccg ccaatgttct    2820
cgatcttctt ttcttgaatg aagccttttc aagcctctct tcttctctct ctctccctat    2880
cttcttttgt ggcccacggc ctcctcttct ttttatgttt tgtgtttctc atgtcacatc    2940
cataaactcc cttttataga taaaaaatta gagtccattt tggactcctt ttccatgcat    3000
aagaaggctt cccacgccat tggttctgtg cacacgactt tttccatgct acaaaagttt    3060
ttcatgtctc acgtagtttc catgcgccat aaaattttgc atacttctcc aagcttttt     3120
atgctcgacc ctttttggtt ttcatttaaa tcagtgggtc ccatatgacg agggatcaca    3180
ccaacatcat atgctctcct caccatacca atggtatcc  ccaactataa gacaaaacat    3240
tcatcaaatt gctaacaggg ttgaggatca gcattcacta tagaaatttt gtttttcaat    3300
ctgtaacccc tcccaccatc ctggcctctt ggatatcgga cccatcaagt gggtcccgcg    3360
agcccgcacg gcactgtcag tccccaaact caattttttt tttaggaaaa atgttacctg    3420
cagtagaaga aagagacctc caaaaaaatt atgaaaaaaa agccttaaaa taaaaatgaa    3480
aaggatgaag attaaaaggg gtgcaacagg aggagttccc aggggtcat  ccatccctgt    3540
acgactctcg cccaagcacg ctcgactgtg gagttctgat gggatccggt gcattagtgc    3600
tggtatgatc gcacccatca tgatctcttc gaaattcata gatataacat agcttccgtt    3660
gcacgccatc cataaccctc ccaccgtccg ggcctgcagg gtaccagact catcaagtgg    3720
gctcgcgagc ccgcacgtca ctataggtct ccagacttag ttttttttga tagagaacat    3780
taaccatggt agaagaaaga gatctccata aaaattatga aaaaaaatat tgaaataaaa    3840
ataaaaggct taaaaattat ggaaaaaaag gcttgaaata gaaataaaaa ggacgaagat    3900
taaaagggat gcaacatgag gtcctcccag gggttcatcc atcttagaac tactctcgcc    3960
caagcatgct taactacgaa gttctgatgg gatctgacgt attggtgctg gcatgatctc    4020
ctcgaaattc ttagatataa cgtagcgacc gtcgcacccc a                       4061
```

<210> SEQ ID NO 62
<211> LENGTH: 4061
<212> TYPE: DNA
<213> ORGANISM: Artificial Sequence
<220> FEATURE:
<223> OTHER INFORMATION: synthetic

<400> SEQUENCE: 62

```
gccggctgcc tctggtctca ttcacccttc cagtgcttca catgggtccc attaatttga      60
attcctatga gccacatcca agcttttgaa tccaagcctt ccttattttt taaatcaatt     120
aaaactttgc tttaaatgcc ttgtagaccc tcctatttgc atgctacgtg agaacattgt     180
taagctcctc ttggcccact taagaacttc tatgggctac atgcttttgg ctagctttaa    240
aatggttttg ggcctaactt tggatcacca ttcgaagtcc attttgaatt caatttattt    300
ttattttttt ttttaacctt acaaatcgag ctcttttatt ggtgatcatt tttcctataa    360
aacaaaaaca aaaagcatca agtcttaaga aataaaagtt aattaatata tattttgata    420
cttttattgg gatatttaat gtacttatca ctagatatga aatccaatgg gtcacacact    480
ttgaaatttg atcttagtct aatctaacta ggatttatta taaatcttat gggttaaatt    540
tacatgctag cacatgaatt aactcaagtt ttcaattgga tttagttcta aggtgtttga    600
gctaacccta tcctgatacc ttaaacctaa ttagattaga tttgaaccta tggttttctt    660
gatgccttat gcttattaca tgaaagagtt tcatgtgact taaattcctc catgccacca    720
```

```
catcttcatc catgccaaat taatatggaa cgccccattt aattgtgcat ttaagaagga    780
atagtccttc ttaaacactc ctcttaattt cccacacttt cctttgttct acacaccatc    840
aaatggcttt tggaaatatg cgggcgcaga agtagaggtg tcctatatga aggctcttcc    900
acattataag ttatcacatg gtgaattaaa tcattgtgtg agaaaatcat gcgccaagag    960
ttggcacccc ttgggagttt taggcactcc ttatcctata aataagggc acccccatatg   1020
gataaataca agggaattca agtttaggca tgagattgag aggagaaaaa gacacaaaaa   1080
tctgagaaaa agataagaaa aaaaagaga gaaaaataga aagaaaagac gagagaaaat    1140
gaaaggcaag ggttgctaat cctagggttc aattttttcaa tagttggatt tctgaatcaa   1200
tttggggtgg tgagattttt tgagaaaaag tttctgatgt ggccctagta gaagattgaa   1260
ggcattcaga tgatggtgca atccgttttt gaaaagaaa agtgagtagt atacttatga    1320
agaaagctgc aacactacat caaattggaa aggaccttga tcaaacccat atggatcacc   1380
gttgcaggat atctactttg gtatcttgtg aaggttattt ttttttatcag atcatcatct   1440
tcaaaaggt ataatttctc acctaatatg catgcttgat ttgtttgatt aaaatctata    1500
aagtgttcat aaggtttgtg ttctgattgt attgtttta gtattaaaaac ttactttaaa   1560
aatataaaaa aatttgaaaa ctatcttcta ctgtgcaact aaaatccaac agaataaccc   1620
taatatgaga ttgagcgatc tccgccaatg ttctcgatct tcttttcttg aatgaagcct   1680
tttcaagcct ctcttcttct ctctctctcc ctatcttctt ttgtggccca cggcctcctc   1740
ttctttttat gttttgtgtt tctcatgtca catccataaa ctccctttta tagataaaaa   1800
attagagtcc attttggact ccttttccat gcataagaag gcttcccacg ccattggttc   1860
tgtgcacacg acttttttcca tgctacaaaa gttttcatg tctcacgtag tttccatgcg    1920
ccataaaatt ttgcatactt ctccaagact ttttatgctc gaccctttt ggttttcatt    1980
taaatcagtg ggtcccatat gacgagggat cacaccaaca tcatatgctc tcctcaccat   2040
accaaatggt atccccaact ataagacaaa acattcatca aattgctaac agggttgagg   2100
atcagcattc actatagaaa ttttgttttt caatctgtaa cccctcccac catcctggcc   2160
tcttggatat cggacccatc aagtgggtcc cgcgagcccg cacggcactg tcagtcccca   2220
aactcaattt tttttttagg aaaaatgtta cctgcagtag aagaaagaga cctccaaaaa   2280
aattatgaaa aaaagccctt aaaataaaaa tgaaaaggat gaagattaaa aggggtgcaa   2340
caggaggagt tcccaggggg tcatccatcc ctgtacgact ctcgcccaag cacgctcgac   2400
tgtggagttc tgatgggatc cggtgcatta gtgctggtat gatcgcaccc atcatgatct   2460
cttcgaaatt catagatata acatagcttc cgttgcacgc catccataac cctcccaccg   2520
tccgggcctg cagggtacca gactcatcaa gtgggctcgc gagcccgcac gtcactatag   2580
gtctccagac ttagtttttt ttgatagaga acattaacca tggtagaaga aagagatctc   2640
cataaaaatt atgaaaaaaa atattgaaat aaaaataaaa ggcttaaaaa ttatggaaaa   2700
aaaggcttga aatagaaata aaaaggacga agattaaaag ggatgcaaca tgaggtcctc   2760
ccaggggttc atccatctta gaactactct cgcccaagca tgcttaacta cgaagttctg   2820
atgggatctg acgtattggt gctggcatga tctcctcgaa attcttagat ataacgtagc   2880
gaccgtcgca ccccatcaat aaccctccca cgtccaggcc tgtagggcac cggaccttc    2940
atgtgcatcc ccataaaaat tgtggaaaaa agtattgaat taaaaataaa atagacaaag   3000
attaaaaaaa atgcaacacg cccatcccag tacaactctc acccaagctc gttcgactgc   3060
ggagttttga tgggatccgg tgcattagtg ctggtatgat cacacccatc acgatctctt   3120
```

```
cgaaattcat gtatataacg tagcttcaat tgcacgccat ctgtaaccct cccaccattc    3180
gggcctgtag ggtatcggac ccttcatgcg agctcgtacg gcactgtagg tctccagacc    3240
cagttttttt ttgagagaaa acgttaacct tggcagaaga aagagatctc tataaaaatt    3300
gtagaagaaa gtgtttgaat aaaaataaaa agcataaaaa ttacaaaaaa aatcttgaaa    3360
tagaaataaa aaggatgaag attaaaaggg atgcaacatg tggacctcgc tgggggttac    3420
ccttcctagt tctactctcg atcaagcatg cttaactacg gagttctgat gggatccaat    3480
gtattagtgc tggcatgatc gcacccatca tgatctctta gaaattctta gatataacgt    3540
agcggccgtt gcatgccatc agtaaacctc ccacgtccag gcctgtaggg cactagacct    3600
atcaagtgga tccggtgagg ccgcacggca ctgcctgtct ccagactcaa tttatttttt    3660
taagaattgt ggaaagtgat ccccataaaa attatgaaaa aaagtgttga attaaaaata    3720
aaatagatga agattaaaaa agatgcaaca cgaggacttc ccaggggtag atataacgta    3780
gcggccgttg catgccatca gtaaacctcc cacgtccagg cctgtagggc actagaccta    3840
tcaagtggat cccgcgaggc cgcacggcac tgcctgtctc cagactcaat ttatttttt    3900 aagaattgtg gaaagtgatc cccataaaaa ttatggaaaa aagtgttgaa ttaaaaataa    3960
aatagatgaa gattaaaaaa gatgcaacaa gaggacttcc caggggttca cccatcctaa    4020
tattactctc gtccaagcac gcttaactat agagttctga a                        4061
```

<210> SEQ ID NO 63
<211> LENGTH: 6704
<212> TYPE: DNA
<213> ORGANISM: Artificial Sequence
<220> FEATURE:
<223> OTHER INFORMATION: synthetic

<400> SEQUENCE: 63

```
aaatctatta gtatctgaca aaagttaaat tagagtcgaa acactaaatg acaattaggg      60
atcaacttga tcaagtagat agagaatatt agaaaagaga gaaattaaca agatagaaca     120
tgattaatta ggtgacatag cccgacaatc caattggtct aagcaagttg atttaatcaa     180
atcacggttg aactaatata tagatagctc aataaaaatc atacataatt gaatctaatg     240
atatttggat ctgaccaaga tggaatttga catgctgtcc gatgatcgtg aatcaagact     300
ctctttgcta attaagatca aattagaatc attgaaagag aatcttttac tggatcaaga     360
gagagaaata tataaagaga gtgaaatagt ctatagaaaa aaatttaga gagagaaatt     420 aagaagaaaa aataaattt ttagagaaag aaagtgggta tacaagctca gagaaggga     480 agaggaaaga gagagaaatg ctctcttatt ttcttttttt tctttttct tcttttcttt     540 ttttttcct attcttcttt ccctttttctg cttaatggaa taggggacct cccattcccc     600
ttctatttct agagttgggg gctcaaaatt gatgatagct atcattgggg atgtaggcta     660
tggtgatgca gtagaggatc accgaccgat gatcgatggt gatgttgcaa tcaaaaaatc     720
aagaaagata gatggaaaat aaaggaaaat aaggagaaat agatctcaac ttgtttggat     780
gctaacccac tcactgacga ctccacttca actatggccg gagcttgcta tggaaaagaa     840
gccaaggcct tcaaggatga acaccaatgg tgaggagat ggtcgaaaat agaagaatgg     900
ctggcttttc taatcgacaa aatagggtat cgcccttctt agcaaatatt cggcaataaa     960
tatctagaat ccaggatcct aggactatgg aagaggagag gagggcaag tcaaaggatg    1020 ccagattctt atctagcttc cgacaatgat ggggccctat tttcgataaa cacaattgag    1080
```

```
gatgttcgga aaagggtttt ttcgatgatg attctagtga ccaactatga gatttcaaag      1140
ggggtgaggg gggtttaaat aagatgggag ggaagtttga atcctcctta aatctgaacc      1200
ttttcgaca aagccaagag cgtgaaggag actccttcgt gaagtcaaag atggaataga      1260
ctcccttcgg gagtttggtt catcacccaa cttcccctagc atgtgcggag tatgtgctag     1320
ccttttctct cttttttttt cattttttt catcctttaa gatccatgca gtttctaggt      1380
tgagggattg gggtatcaca ttctctctcc taaaaaaaaa ttattttcaa aatttttta      1440
cctatatttt caaaagttgg gattcatggt ccaaatctca tccttgaatt ttttgatat      1500
tctaattctc gaaaaaattt catcgttaaa tcatttcata agagaaaagt caatacctca     1560
agagttgatc tgaatcaaaa ttattatctc tagtaatcga aatcaatatc ttaatttcaa     1620
ataagaatat ccagtttatt gtcaaaatta ttaactactc ttgacttaat tgatctatta    1680
cataatcgta aataaattct aacatactct tgaagtgtag aatataagat tgataaacaa    1740
tcctatatcc gttctaatag atataaaagc ataaacttta aatatttta atccaagatt     1800
aagaatcaat gatccactta tcctagactc aagatattag aaatttttt ttgtacaata    1860
gatagaggat gtactggtga aaatcatgta gcgatatcca aaataatttt taattaaaaa   1920
tattatcctt ttcattatca atgaattta tctataagaa agatcaaatc atatgatcca    1980
tcttaaattt ttaactcaaa aaattaatat tgcaaactag ctcaaaataa ttttgatcac    2040
tacatttctg ctgtgcattc taatttaaac cgttcacatt ttttagattc atgaaataat    2100
tttgaccaaa gtattactcc atactatagt caaaaaagat taaaatatta gattctaatt    2160
aaagccaaag ataaacttt gattctcatc cttaattttg cctaaagtat aattatttg     2220
attaacccctt aagcgcaata acacattcaa aaccaacaga taggtttact ataatccaaa    2280
tgaattaaat cttaattctt ttatcaattc atttagacaa tttcaaatca aaattctata    2340
agtaatatca ataaaaaaaa ttttgatgc tccaataagt tagaacttaa atcaaaatat    2400
ataagtaaaa ttgatttaat catctcttct aaagtttctt ctattaagat ctttaatatc   2460
tatcaaatac attccacaat aatcatgcaa accttttaaa aattaaattc tcaatgcctt    2520
tactacattt taacaccaag ctcgataata gtgataaaga aacatctaga tcagctttat   2580
aatcaaaaat tttgacttac aattttacgt gtgtctcaaa atcttgaata aatataaata    2640
agatcttta tcttgatcca aaaatagtaa tcaaggattt cattagtaac ttcaacaaca    2700
atggtaaaaa aattttctat ccattgataa acccaaattt tgaattgaag tttcatgcat    2760
accatatagc ctttaataag atctattatt tggatctaaa gatagtaatt aaaattgtta   2820
atgattccac taagatgaat actttacaat ctcataatta atttcttcaa taaaaataga    2880
cttcttgata atgtctccaa ttgtatattt tttttatttt ctacaagaaa acttcataca    2940
tttttacgt tccaatataa atcttaaaaa gttattccaa tcaaatatca taaaagatct    3000
tcttagtcca accttaaata actttttatga atgaatcttt atcttgccac taaataatga   3060
attttaaaat caagagcaac atcacagcat tctgtcatgt caaatttgtg ttagatgtat    3120
gtcctagaaa tcaattagat tgacaatgta aatttttaa ggatataatt tatatatttt   3180
gatttattaa taaaataaaa tttaaattaa ttttattca tattttta tctatgaatc      3240
atctaaagaa ttaataagat gatgatacat attcttaaga gttcaaaatt tgaaatatat    3300
gtcattgatg attaattct gaatactttt gaattcttaa gagtttagaa gatcttgacc    3360
caagtagtgt gaatagtgaa aaaaagtttt cacatacttc acatcaaaaa tttaagttga    3420
ataaattgta catatgacag gtattatagt ttgacgagta atctataacc tctatcttat    3480
```

```
caaaattctg atagaaagat tgtattgtat gataactgta cttagaggtt cacctttat    3540 tttactggat taccactaca tgttgctaga tgtcactggt ggattgtgag atctacgaag    3600
attatcttga tgatcgataa ttctcattga aaagattgaa actatttaa tgatgttgtg    3660 atagagatca taatatatct tattatcaga cagaatagaa ttctatggga tcatacacaa    3720
taggagatta agactgatca aatagttgaa tgatgattaa gaatcattac ggagttcaga    3780
ttatcaatat aattgataat tagactaact tataattgtt acaagtagca aggacttaac    3840
tgctaaaggt taataggttc aaaagaact tatgtataaa tgttgtgcat cttaatttga    3900
ttggatcaaa ttagttatgg ctgaattcaa gatgaatcaa ataggaattt ggttcaattg    3960
aatttgggtc aagctttagg cttaggtcac atatacccaa aatcatttgg atgcatcagg    4020
tgtgtgacac ctgaatcagg ccttctaaa ctatttgag taagtttgat caagtcaaaa    4080
ggatccacac cctaaggttt cttgaataaa accttaggca ccacattgag gacctatagg    4140
aaactttgac cctctctcat atggggtggc acactgaggt tttataaaaa ccttaggcac    4200
ccattttagc cataaaaaaa aagctccaag ggatggggca gtagccatga agaatccttg    4260
gctgtcagga ctctattcaa aagagttctc aaggttttgg actcttatgg agccctagga    4320
tttgtttgcc tataaataga tggccaccc aaggctttag ataatgttag agacttgtga    4380
agctctcccc tttctcttgg ttgccggccc ccctctctc ctctctcttc catgccccaa    4440
gacttctttc ttgtctccat catcttgctg aaatttagat ttcagcaaga aaagtcaagt    4500
agaagtcaaa gttctaatgt agctcacaag atgttgagaa cttcctccat ctggcaaagg    4560
ttctgcaaga gagctagcat cctgagaaac aaaaagattg ctgatcagcc ctcatctcca    4620
tatggatatt tgtagagatc aaatgcatgc atagctagaa gagaatctta tcacgatcat    4680
cactcgtgaa gatcatctac ctgtgcaaag gtatgagata agaaaaatat ttttttatc    4740 ataattcatg aatcctttgc ttatattata ctgagattct tggaatggat tttttctcta    4800
gtaaaactct agagatcaga tctcaaagtc ttcttcacat aaaggttttg aaagttcttt    4860
atatttccgc tgctttgatt caaaataaat tagatctatt ttgcctttca acctttctca    4920
tatttattga catataaagc tttaattaat gagattaatg aaaagcatgt gcgaaatact    4980
gagaaaatcc taacagtgat atcagagcta cttttgtaca taagaaaagg attcaagtta    5040
aataaaatat gtttgattta agtaaatgaa tcaatcaaaa tttatcctaa cataagtttg    5100
tcctggtata atggtcaaga ccattatgtt gaaaggttat cctaggacaa aaagtctaag    5160
taaaatctat tttatttaag taaatgaatc aattaaagtt tattctaata taagattgcc    5220
ttagcataat ggtgaagacc cttatgttga aaggttgtcc taggatggaa agtgattgat    5280
gagacaaata tatcatgaaa gtattttcca cagatggaat aaaatatata tattttgttt    5340
gtgaaaatga gatttcatga atgtgtttgt cattcaatat gtgtggtgat catcttgaat    5400
tgccacaaat ccttttggga ttagggttgt atcatgactc acaaatcctg atggtttgca    5460
aaattttgca ttctgtagtg atagaaacca aaagttaatc caattttgga ataagattga    5520
tcaattggta tctaaggcaa gtattttata atggtggtta cttaattagt tataaaagta    5580
cgaagagtct cctaccaatc ttacacttat ctagccaatt tggttgattg aattctgaat    5640
ttgggttgct taagtgttaa gttcactaca aatatattgc aaccatgatt ccgacttagt    5700
caaccaagcc tagatctctt gaatagattc atgttaatta tggatttaca taggatataa    5760
ataaataatt aaaacttgaa gagatctaaa tgaaaccttc tcgtacatat taaatcgaat    5820
```

-continued

| | |
|---|---|
| gatcttccat cattgtagat atacggatac tctactgatg ttgatgattt tcgactagat | 5880 |
| atagtacttt ggttgcatcg aaaaagtaca accactttat aacatgagat gttgcagggt | 5940 |
| agagatgggg ttgggcccaa taattgttag gtgaggatcc aaatgatggc tgcacttgcg | 6000 |
| tgtgaatggc gagtctgact taattaagaa atagagctaa taactattag atgaggcttc | 6060 |
| aggacttaga gacttatgac cactacaact tacttgagaa gcaatggata aagagtcgtc | 6120 |
| tatttatcaa ctgacgcatc accaataact atcagatgga gtgatgtata attagtggga | 6180 |
| ctatagtatc cacttgaaat cttaatcgta aaaattttg tttctccacc tgaagagcat | 6240 |
| gggagattcg aaaaaatagt gggggtagtt tatttttaaa ataaagctcc taaaataaac | 6300 |
| taaaataagt taaatacaaa gtctaactag aatcttcttc tctctgtaga aaatatctgc | 6360 |
| ttccaacctc tatttcatat ccttaagact aattgtttga ctagacccag ttataaagat | 6420 |
| tgactctaaa acttaaagat agtcttgagt tttgaaaaga tgagctatgt cctggatcaa | 6480 |
| gatatcctct ctctaccagc ttgtcccacc cctaatcaag gggcatccta tgaaaagtgg | 6540 |
| ttaaacgatg ataacaaggc ttggtgctgt gtgctgacat ctatgtccat tgaactccaa | 6600 |
| tgccagcata agggtacaaa ctgtccaagg tatattgact catctacaag agttatatag | 6660 |
| tgagtagagc catgtatctc actaggaagt atttaagaga ctct | 6704 |

<210> SEQ ID NO 64
<211> LENGTH: 4741
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3017)..(3951)
<223> OTHER INFORMATION: n is a, c, g, or t

<400> SEQUENCE: 64

| | |
|---|---|
| cagattatca atataattga taattggact aacttgtaat tattataagt agcaaagatt | 60 |
| taattgctaa aggttagcag attcaaggag gacttatgtg taaataatgt acatcttaat | 120 |
| ttgattggat caacttagtt atggctaaat ttaagatgaa tcaaacaggg atttagttta | 180 |
| atcgaatttg ggtcaagctt tgggcttagg tcacatgcac tcaaagggt ttggatacat | 240 |
| caagtgtgtg acacccaaac caagcctccc taaactattt tgagttggtt ttgaccaagt | 300 |
| caaaagggtc cacaccctag ggtttcttga ataaaccct aggtgccaca ttgaggacca | 360 |
| attaggaaac tttgacattc tttcacacgg agcagcacac tagggtttca tgaaaaccct | 420 |
| aggcacccat tttagccata aaaggaaagc tccaagggat gggatggtgc catgaagaat | 480 |
| ccctggccat tgggactcca ttcaaaagtt ctctaggttt tgggctctta tagagcccta | 540 |
| gggtttgttt gcctataaat aggtcgctac cccaaggctt tagataatgc tagaggcttg | 600 |
| tgaagctctc tcctttctct tgtttgccat cccaccttct ctcctctctc tccatgcct | 660 |
| caagacttct ttcttctctc catcatcttg ttgaaattta gatttcaatg agaaggatca | 720 |
| agtagagtca gagttctact gcagttctca aggtgttgag aacttcttc atcaggcaaa | 780 |
| gattctgcaa aggagttagc acctcaaaga accaagaaag ttgctaatct gccctcatct | 840 |
| ccatgtggat acttatagag gccaagcatg acgagaagag ccttatcacg atcatcactc | 900 |
| gtggagatca tctacccgcg caaaggtatg agataagaaa aaatatttt tcttatcatg | 960 |
| attcatgaat cctttgctta tgttacattg agactcttgg attagatttt ttctctaata | 1020 |
| aaatttcaaa gattagatct cgaagtcttc ttcacctaaa ggtattgaaa gttctttata | 1080 |

-continued

```
ttttcgctac tttgattcaa aatagattag atttgttttg cctttcaatt tttctcatat    1140
ttattgagat atgaagcttt aattaatgag attaataaaa agcatatgtg aaatactgag    1200
aacatcctaa caatttgagc ttacaattca cttaaacaac taatgatcaa attaataatc    1260
acaatgcaca ataaaaattc atgataaatc tttttgttgt tactttagat caaaatccaa    1320
ctaatcataa catgatccac ggattgccta tcatatatca aaccctctga attattaatc    1380
ttaaacgatc ttttcattca tgatcataag atttagttaa aaatcatgaa gacaacttat    1440
attgtaatca tcatagatct gtatcttaac atccttagtg tttacctacc tatactcatc    1500
ctatgtttga ttctatatat cataatttat tcactaatac tttgatatca tataaattat    1560
cgcatcccca atctaagatc atattggtac tttaatattt cattagtggg ggttatgcat    1620
tagtactttg atccttatc agttgaatgg ttaaacactg gtactttgat atcctatcag    1680
tggaggttat acgctggtac tttaatatcc tatcagtaag atggttaaat actgatactt    1740
tgataacctc ccagtgggtg ttgtatgcta gtactttatt atcctaccaa tggggcagtt    1800
aaatgctact actttgatac gctaccaatg ggatagttaa acgctagtaa tctaatctta    1860
gcttgacata aagtaacgtc gactcgagtt tagggtcgac tcgagagaat gttagggtta    1920
gcttgatatg aaagagggtc gctcgtcaat attttggagt caactcttgt ttatggacga    1980
tctagaaagt gtcagagtga gctcgagtac tgcatatttc tgatacattg tctatgctag    2040
aatgtgctag aactgattat cttctttatc aaagttgatt tttgagtaac ttgatgatca    2100 attttctag gctagacttg ctttgtcaaa atgagcactt gttagtttag agaatcttca    2160
cctacacatg atctcaagca ttcattagta ccaaaaatac ttaagtattt tgatatcatc    2220
aaaatcaatt cttgggttaa cacaatactt ttcaaataat aagcatacag atataatcct    2280
ataacaattt aaattttgtt catatatcaa tttctttaaa aatattatat tcatcttgat    2340
agctatgaac taaatcaaaa tacatactag tatacaactt ttactgggag agtattagat    2400
taccagcatt taaccatccc actggcaagg tatcaaatta ccaatacaca acccctattt    2460
ataaagtatc aaagtaccag tgttcaactg cctcactggc aggatatcat agtactagta    2520
tttaactacc acattgacag gatatggaat tatcagtatt taaccatcat tagtagaatt    2580
ttgatgcata gtcaggctgc gagtcaaaat ctatctcaaa tcaaaatatt gatcacatgt    2640
ctaattctgt atcataattc attcccttat gctctaatat tatattaatt gtcatacttc    2700
tagctcgaga tcatgagcca aggattgcag taactaccgc atacttatag agaactcttt    2760
ctataagcat acaagatatt ctaaatatac tatcaatata tcatagagaa attaatttaa    2820
ataactaaaa gttaatattc aattaataaa ttcaactggc aaatgtattt aaaaatttta    2880
catcaaataa atcttgatta ataaatatta attaataaca atagatttaa atcgaaacaa    2940
ggttgatatt gttagaattt gatgcctcaa gattcagccc acattgagtc cacagtgagg    3000
ttcgcgacga aaaatgnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 3480 |
| nnnnnnnnnn | nnnnnnnnnn | nnnnnnnnnn | nnnnnnnnnn | nnnnnnnnnn | nnnnnnnnnn | 3540 |
| nnnnnnnnnn | nnnnnnnnnn | nnnnnnnnnn | nnnnnnnnnn | nnnnnnnnnn | nnnnnnnnnn | 3600 |
| nnnnnnnnnn | nnnnnnnnnn | nnnnnnnnnn | nnnnnnnnnn | nnnnnnnnnn | nnnnnnnnnn | 3660 |
| nnnnnnnnnn | nnnnnnnnnn | nnnnnnnnnn | nnnnnnnnnn | nnnnnnnnnn | nnnnnnnnnn | 3720 |
| nnnnnnnnnn | nnnnnnnnnn | nnnnnnnnnn | nnnnnnnnnn | nnnnnnnnnn | nnnnnnnnnn | 3780 |
| nnnnnnnnnn | nnnnnnnnnn | nnnnnnnnnn | nnnnnnnnnn | nnnnnnnnnn | nnnnnnnnnn | 3840 |
| nnnnnnnnnn | nnnnnnnnnn | nnnnnnnnnn | nnnnnnnnnn | nnnnnnnnnn | nnnnnnnnnn | 3900 |
| nnnnnnnnnn | nnnnnnnnnn | nnnnnnnnnn | nnnnnnnnnn | nnnnnnnnnn | nagatattac | 3960 |
| taaattttgc | ttctaatctc | actcttaaat | agtacttacc | tttgaaacta | ggcatttgaa | 4020 |
| tctgaaaaag | aaagaggaga | ttatgagctt | gatagttcag | taaatcatga | ataaattagc | 4080 |
| taaataaatc | tatgaataat | agtatattaa | aaataaatat | gtaagataca | ataattcaaa | 4140 |
| aatgaattca | tatatataat | actttccaaa | taataagtat | gtggctgcaa | tcctttcgta | 4200 |
| attcaaattt | tgttcattaa | ttattttttt | caaaacatca | catggatagt | catgaactaa | 4260 |
| atcaaagtac | cagtgcataa | cccctattga | taagaatca | ataacaagt | gtttgactgc | 4320 |
| ctcattatca | ggatatcaaa | ttattaatgc | ataacctcca | ctgctagggt | atcaaagtag | 4380 |
| caacctcaat | cacctcactg | gaagggcatc | tagtttcagt | atttaactac | tccactggca | 4440 |
| aggtgttaaa | ttatcaatat | ttaacctcca | ctgataggat | tttgatatat | agtcagactg | 4500 |
| cgagccaaaa | ttcatttcaa | accaaaatat | ttttctcaaa | gacatatttt | atgtttcaca | 4560 |
| ttgaaaaatt | cacaaaaatt | atgcgatatt | gaaatcaatt | ggataaaatc | cacgtcaaat | 4620 |
| ttagtatatt | caatcataaa | tcatttacta | ttctagaaaa | ggtatattaa | aagtataatg | 4680 |
| catcaatttc | ataaatcata | aatatctcaa | tataaaaaat | attttattat | ttattaataa | 4740 |
| a | | | | | | 4741 |

<210> SEQ ID NO 65
<211> LENGTH: 5462
<212> TYPE: DNA
<213> ORGANISM: Artificial Sequence
<220> FEATURE:
<223> OTHER INFORMATION: synthetic

<400> SEQUENCE: 65

| | | | | | | |
|---|---|---|---|---|---|---|
| agtatattca | atcataaatc | atttactatt | ctagaaaagg | tatattaaaa | gtataatgca | 60 |
| tcaatttcat | aaatcataaa | tatctcaata | taaaaatat | tttattattt | attaataaat | 120 |
| ctaggagaag | tgaagcatta | cttatcttgt | aagtaaaact | aaccaactga | tcaaattaat | 180 |
| tctgagaatc | tttctcaaaa | ctcatcacca | ctatatcaaa | aacttgtgct | tcttgctatg | 240 |
| taagagcata | gacccttcct | tcgatctggg | gttccaagtt | tctattttat | tttgttcaac | 300 |
| tatcaaatta | gactgacttt | tcatttttt | gtggatattc | agctatttta | tggccttct | 360 |
| aacaataacc | aaagtatgta | ccaatattcc | aacaataatc | atttattgca | tgattttcac | 420 |
| cgcatcgaaa | tatttgatat | tatcaatcaa | tccaaacttg | ttattcactg | acctcttatt | 480 |
| caaaccctta | gtatatttaa | tattctacct | ttgtgattca | ttcaatcgat | ttctttttt | 540 |
| tattttcttt | cccttctat | atgctcttca | ttaactttc | tttcaattat | caatgcttta | 600 |
| ttcaatacat | ctgtataagt | agttaactca | tatagtacca | tttatttct | aatttctatc | 660 |
| ctcaattcca | actcaaattt | atctactcag | tcacattcat | cttcaaccaa | tctcgaagca | 720 |

-continued

```
aacttgacaa gctccataaa tttagcttca tattctacaa ctattatatt tctttatttc    780
agataaataa attttttattc tttctgaatc ctcatactct aagaaaaata tttttatcat   840
aaaatatctt ttgaaatcac tcccaagcga gttgttctcc atcttgttca tatttaggtt    900
tcattctcta ttatcaatta aatgtctcat ctttcaacat gtatgatgca tataagattt    960
tttcatcatc atggtatctc ttaacaataa atgctttctc catctccata agctaatttt   1020
tagctcctat ttcatagttt tcttaaaagt caatggagac aacttcttaa attctatgat   1080
attactttat tgctcctatt gctcttatgt ccttgtggtg acaatattta ttgttgcact   1140
tgctgtagag gcagttactg ttactgcaat tgctattacg attccatcaa gccgactagt   1200
gtctgcatta tttggataat agttgatttt tgctactttta tttagatgtt ggtggcaaaa   1260
tcaatgactt cttttttgctg agagatgcca ccaacctact aagtatcatc atcttattgg   1320
ttgatacctt tagcagcacc tcgagtggtt cttttttatct gatatggaac catcttaatc   1380
ttgcatgaaa aacaaacttc gcaaaatttt cttttaaaat ctaatatcta atattatact   1440
tttattaaaa tttaattatg attattttaa gaataaaaaa tttaaatttt gaaatcctca   1500
caaggctggc caagagataa tgaccatcat cctagtcggt ttgacgtagg acatccaaag   1560
atcaactata attcaagcat catattgaga tgctaggata taatcgatgg tgaaatttaa   1620
tgatgctcga ctgatcaaga tgggggccgg cccgatggcc tgttcaacaa tcattgatca   1680
aaatttttta accaaggtct atcaagatca ttaaaaagtc tttctaagat ctataaattg   1740
taataaagag acacaatcta gagagagaca cttttttacat aaagaaagta gaaattttag   1800
ggagagaaat tagagagaaa ggggaaagag agaggaagct gagaggaaga aagaaaagag   1860
aaagactctc tctctttttc ttttctttct tttctttctt ttcttttttct tttctttttt   1920
tcttccttttt ctttctttct ttctttggct cattagaaaa ataggggacc tattgatccc   1980
cttgttttcct aaatagggga ggaatctcat cttggtagct atggccggcg atgtgagcca   2040
aagtggcaaa atcatgaatc tcccaacttg cagccgacat tgacttttgg cactggaaaa   2100
tcaaagaaat ttgacaaaaa atgggaaaaa attgaaacca aaatagggac caaaatccgg   2160
taatagctag ccaaaaatcc ttgatctttg ctcatggagg ataggaaaaa agattattca   2220
agagattaag ggaatcttat ctcattttttt tgctgtgctt cggccatggt ggttgcagaa   2280
atcgtttgtg aaagctcgac aaactctgca atttcctcgg gcttgggcct cgatctttaa   2340
taggagaaga gagaagtcct ctttctttta aatagagtcg gagggaagga gtttgatttc   2400
ctccttatgg tggtttcaaa ctctgatcgg aagtccattg gaaaagaaga ctcccattag   2460
ttttaaaatc taataagatt tattgattag aaaattgata aaaaatgatt attaaaaaag   2520
tagcataatt atttaaatca atgatgctta gattgttgga ggtaaatagt aataaaatca   2580
aaaaattaaa attcatggga ccaaaaaata atgaacaaga tttgaaagaa atgtctataa   2640
ataagaattt atgaaacagg ggaacattga tcaaggtgt gttaaatagt gtccttaaag    2700
tgttattgtc cctctcacgt agactttgtg tgttgggaga gaacatagta attctctcaa   2760
cctatgcaac ctaaatcttt tgaaaagaaa tttaaaatta tagaaaaatt ggcaaactag   2820
aattttggtc attttctttta ttagtaaaaa atatactaag ttatatgtct ttatttatac   2880
tagtgaggtc tatctttgca caattcagac caaatttata ttctagttaa aagaggtata   2940
gattttttaa aatagatata actagtggaa atagtcatag aaaagttaaa aatcaatgaa   3000
aggtagattt cacttctata ttggctttat ttgtggtcac tttatctaat tcttttttttt   3060
```

```
gatggagcaa tataccctgt taaaatcttc tcgattttt  tttcacttta agcaacctat   3120
ttcgatgcct aaacaatgga atttagttta accacttaat atgctacact tttaaaagga   3180
gcaccatatt gtagggcttg aaaagttact tgatttaaaa aaagagcatc ttaattggac   3240
atcatacaag taagttatga cctctgaaaa tttgatacat gatttatcat cttgatatgg   3300
taaatcttgt taagatttcc tcatggtgtc taaagtggcc ggttcatact gagtttggtg   3360
attcttctgg tcaatggtta attgctcgaa tattttaag atataactaa tctccaactc    3420
tgccgactcc ttagtagtat gagcacatgg aaagcttgac ctaattgatt tcttaaattg   3480
cttgaaatca gtacttagaa aatatgcaaa atggatgaaa tgtttattgc agcgagagct   3540
ttctgatctg tacgaccgag agcttactag ttttttatga gctatacgtt ttgcacttaa   3600
gcctaattta aatagtgaaa tagttttgca acaattcaaa acaattaaaa tcaaaagaca   3660
agctgctatg catgttcaac tgactcggct ttcaatcgca atatgtcaca taggctggcc   3720
tagaatgcag atgcgtgcgt ggtgagcatc ctaaaaacct acatatccaa taaattccca   3780
ctagttggtg aagtattaaa tgtaactcgt attaactttt taatgtagga ctaaagttta   3840
ttcgactaat taagaactaa atactttaat aattgaactt ttccaaccag aaatcagaaa   3900
atatttaagt aattaaatat tacataataa ctagatcaaa atatcatggt tcctctctcg   3960
ctcgagatca attgggatgt tggtttatct tggtcatcca tcgagatgac tctatcttag   4020
cctttcaaaa cggcgcggta ccacgggtct caccgcttcg ttacatcgaa tgccaccatc   4080
ccttttttt  tttttttat  ttatttatgc tttcttgctc ctagattggt gcggcctcat   4140
tacaactcca ctgctacttg atgcttccct ctagcatctc ctttgcagct ctctcacttc   4200
caccactctt cggcctaatg ttgggaaacg acgaaggggc cttacaaaaa tgtcatccat   4260
gatggcagtg gagaagaaaa catcgctggg gctttccttc gatatccttc gcagccaaag   4320
ctcttatagg gttatatggg agaacgctgc attatttggg tgatcttttt ggatggtgtt   4380
gttgactgat gctagttttg cttcatgaat tgaatattta cacaagatga gaatacaatc   4440
tagtacaatt ggtaccaatt acctgggttt gactcctgct cgcatctgat tgaagcttgg   4500
ttaatgtgca tctcaattaa ttcagaaaga tcatcggact tcatgtgaat tattttgact   4560
agcatgaata gggctaaata aggctgaaat atgtgttaaa tttttaaaat tataacttga   4620
tcatatgatg tccaattgag atgttttcaa atcaaaaatt ttttcgaga  tttatcactt   4680
aatgttaaac tcttagaagg tcgaaacaga ctgaaagttt tcttttcaag atgtattttg   4740
accgagtata taacttgatg atcatatgat gcccaattga gatgttttca atgaaaatt   4800
tttttgaga  tttatgactt aatgttaaac tcttaaaagg tcgaaacaga ctgaaagttt   4860
tcttttcaag atgtattttg accaaatata tctcataatc tataaagaat atatttcata   4920
atctatgaat aattagatag agcgacagaa gataatgcta atgtaaaaat cacgatctat   4980
tttttataaa atttaatatt tttatataat cacttttact atagtcatat ttatttaaa   5040
aaatttagtt atatttaaaa tatcaaaaaa atttgacttg aattatataa gaaaggatct   5100
tcctactatt atagatagaa gctttatatc atagtttaca gtgtatggat catcaatgaa   5160
agaaagaggg atgtaaacct tacttttgaa attttttctat ttgtttctaa attttttaaa  5220
ggatccaagt tgagaattga gagaattctt tctttctgca aatcaaatca ttagtataat   5280
ccacatggag acgttgtaat agaaagtaga aactatattt tatgaataat agaaagggag   5340
ttgatttacg ccaagccttt tgtttgcttg attaattatt tatttttatg gtgttagctg   5400
gaccccatga atagcaacca tcgttgggtc agggtcgtgt atttgttttg gggtcttcat   5460
``` ta 5462

<210> SEQ ID NO 66
<211> LENGTH: 8953
<212> TYPE: DNA
<213> ORGANISM: Artificial Sequence
<220> FEATURE:
<223> OTHER INFORMATION: synthetic

<400> SEQUENCE: 66

```
caagtactcc agaatcaaaa ttgtgaaaga aaaataggat aaatctggtt aagctgtaat      60
ttatttactt actttctatc tatattaaaa ttattcagat tattttgcaa atttatggat     120
atgcttgaat cacgtatctg atactttctc ttcatctgga tggcagtacc atgtgatcac     180
cacgcagacg gatacctaca agaaaaaggc aaggctaaca tgctttctta ccatcattct     240
ttacggtctt tgatccggtt ttgcgtgtcc acttcttacg tagtcttttt caaacattcc     300
tatctaagac tgaaggtaat gatttgcaaa ggaatagctt tactgttttc ctctaagtag     360
atgaaatatt actcacgtag aaaggagcca tcataattgc agaaagaata aaactgaatg     420
gaatatgagt agaattgtca aaatcttggt ttaagggttt taatagccag atgagaaagc     480
aacctacttt tcttgaacaa cttgtttgtg actgtcttgt tgctcccatc ttgcatctat     540
gattagcaaa atatatgata aatagatatt cagatttgat cgaaaagaag gaagattttc     600
tttaatccat ttaatttgaa tctcacaaaa aaaagtaga agatttggac acgatcgctg     660
ggggcagcac gctcttaata gaatggtgtc acgttgcaga tctcgaaaaa ttattcaatt     720
tttttttaaaa aaaagagtc attgaaatta gacgttgtat gaccatgtta tgatctctga     780
aagtttgact tctgactcaa cttcccaatg tagcagattt tactcctgaa ccatgtttaa     840
cctcctgact catagtggcc aaagtatcta catcgagttc actggtcttc ttggatcaca     900
ttcataagaa tacttcccat aattttgctc aacgttgttt ttctcatcaa ccaaaggtat     960
atgctttta aaattgaaat gcccatgaat attatggcat tctttatttt gacattttgg    1020
ttgatcctat attgtttgtt tggcattcaa cacttcttca tgggaacctt tgaaatgagg    1080
taggtgctag gattttttctt tttacctatc catatcatat ttccaatgtc ttcttttaca    1140
ttaggttctt tagtgacaat aggggaaacg acccaatata ataccttga aaatttgggc     1200
aatatctact aaaactaact tgaataaaat attaacataa aaagggattt agtaacataa    1260
aagcataact caaaatcact caccttgtgt gccacgttct cattgccctt attattttg    1320
cattgtgaat tgtgtccccc aataaagcaa cgtgaatggt ggaagagagt tgaatggctt    1380
tgttgagtaa ttgtttgag ttactatagc attgctctac taaaattgaa atcttgctgt    1440
gaggctatgt atgagaagca agttcatgct ttttgactgt tgggatggaa gtatgagcaa    1500
tcttttaat agaaatgga cgaatcatga agttttcct tttattgaa aaagatgatc    1560
gaaaatatg tgcaagatag aaaaacactg aaaagataaa atgagaagta aaagtggaag    1620
tctaggagaa gaaaatttaa gagaaatatc ttcaatgaga ggatgtgtgc accaacaaag    1680
ccaactttca ctaagaatg taatgactca cctctacttt cttcgaataa ggggttccca    1740
gttgtggaaa gtatatagaa tcttctgaaa gactgagtaa atggagcaat tccttctaag    1800
aaatattatg gcatttctct cccacgaaat ttcaaagcaa agagcagcta gtagttgatc    1860
ctctaatctc ttaattgaag tttgaattt ctcttgcctc tatttggccc aaaggtcatg    1920
aagatctacc ggccaacctc ttaagttgaa ttagatctta atagaagtcc aaatgcttct    1980
```

```
tgtagaagaa catctaataa ataaatgagt gatagattct aatccagaga caaagagcac   2040
acctcgaatt cacttgccat ccttttctag ctagaacttc tctagcatga aacttgttcc   2100
ttaaggcaag ccaaataaat actcacattt taggaatgac tgccttccaa ataattttat   2160
aatatggaca aattagacca ccattattga taaacttgca atgaacaatt ataaatgagt   2220
tttcaggttg gcacattagc aatataggat ggtttgatta ttaaaaggat gatatgaagg   2280
gtttcaaggt ggtttgcctc gttcaaatca aaggattttg aagattaata ttccaagata   2340
aggttctcca actccattag gaaagtgtct tcatgtcatc ttagagaagc agctcgtacc   2400
aaacttgaca gatgttttat ttatttagag tgacacagat acccttggc aatactctcc   2460 atccttgtcc gaacaacttc taatcacacc tcacttatct tgcatctaac tcagaggcta   2520
caagttacac ctttcaacaa acctttttcgg tttgaaaatt tgtgattca ttatttagag   2580 ttcgaagagc atatcaagta ttggtcggag ttggcaccca aagcaaacga aacagttact   2640
gacatggtcc aaaagctgag atttctaaga tcccaactta agcactgaat aaagccatta   2700
tgggaaatat cattttaacg aaagaggaat ttagagtaag aattgattct cttgataccg   2760
aagaagaact aatacagctt tcatcacttc aaaatgatga acagatgcat ctcaagtcag   2820
cactagacca tcttctaaaa taggaagatc tatggaagca cactcccaa atgcagtggc   2880 ttcaaaatgg ggattgcaat acgaagttta tccatgtttg ggcaagtaac aggaaaaaaa   2940
gaatactatc actgaactct agcaaggcga tcagaagatt atcgaatagc agcaaatcca   3000
atccacattc tacaactttt tttctaccct actaggctcg actgaggaat gactcatcca   3060
agctgattgg aagattcttt atccagaagg acctctggat cttgctgaca ttgagtatcc   3120
atttatggag aaagaaatcc atgatacagt gtatgacttg gctttggaaa agtcacccgg   3180
atgatatttt cccattctcc ttctataagc acttctagtg tatcatcaaa catgacctga   3240
tgaacctact gtaaaatcag ctaatgtaga ccatctgaac tacttgttca tcaccctttat   3300 cccaaaaaaa aattggtgtg tattcagtta gagacttcag gccaataagc ctgattaatg   3360
gagtaataaa aaatatttca aaaactctat cgaaaaggct cccacagaaa atgaatttgt   3420
taattttatc cacagagctt gctttcaaca gaggaagaaa tatctctgaa tattttgtaa   3480
tgactatgga aactatacac ttctgcaaag ctgaagtaca caaggatctc aattataaag   3540
tcgacttcga gaaagctttt gacaatgtgg attggagctt tctattgaaa ttgctatcca   3600
gcacggggct ttgattcgag gtggtgtcaa tggatagaat atctgattta tacagctaaa   3660
ttctcagtcc ttattaatgg tgataaaggt aaacttttta aattgaggaa agatctcagg   3720
caaggagatc ctctattcgc ctagctcttt ctcttagttg ttgatataga atgatcaagg   3780
gagcaagtag gttcaatctt tttgttggaa ttggatcata taatatcatg ggataacttc   3840
aaagctttta gttcactgat gacacactta tattttgcag atatgatcta aaatacatca   3900
aaactcttaa attttactc tatagttatg agctactgat gggtctcaaa attaactttg   3960
aaaaattcca attttttggc ttgagaattg caaagatgtc agtacagcaa gttgcatcta   4020
tcctagaaag caaggtggct acattttcca ttacttattt gggtctccca ctccatcatt   4080
ctaaactgag gaaacttat tggaatccac tccttgagaa ggttcagaag aaattgatcg   4140
ggtagaaagg taaacttctt aacctctagg gtaggcttat actaactaat gcagtgctta   4200
cagggatccc actactctgg agggatacat tccttctccc tcaattcatt atcaaataaa   4260
ttgataaaat ccatcgatca ttcatttgga gaggaaacga ggagtataac taagggcact   4320
ctagaatatg ttggtcgaat atttgtcgat caaaaaaatt tggaggactg ggggttcctc   4380
```

```
aatctaaaaa ttttcaatac aattcttctt tgtaaatggt ggtggaagct ctactctaat    4440
gctggtgacc cgtggtgtag ttttattgcc actgtccacc caacttcaca ctagagatct    4500
aaaggtatac acaaatcaac ctcttcattt tggaatggtt tacagcacac atgaaatatt    4560
tctactccta atccactttc aagttagcaa ctagtatatt tttggaaaga tagttggtta    4620
cataatcatc cactgaagga tcgatttcct cacctttaca caatagcatt gaagtgcaac    4680
aactcagtgg caaggtatt aagcaatcta cttgataata gctcttttag tactcctctt    4740
cctcaaagat accaagaaga ttttcagagt ctataggaaa gcattgaaca aattacatta    4800
acggaacgac ctgatactat acaatggaaa tggtttagta gcaatatttt tttggcatga    4860
aggatctact attttctgca agatggagga gtttggcctc tactgagtaa tattatataa    4920
aaactcctaa taccaagaaa agccaagtta tttgcttggc taagtgctca caacaaaatc    4980
ccaatgaaag ctaatcttct taatagagga ataattggaa ctgattactg tacactttgc    5040
gatgacttat cagaaactaa tgatcatcta atgctcatct atactttttc aaaagcaatt    5100
tggaatcaag tactttcaga cctgcaattg tcgaaacttt tatgcatgct taacacccta    5160
tgggatactt ggagactcat caatatgcaa cacgatagaa gacctaaaact agctgctcta    5220 ttcgtaattg gtcaatggtg tctttggaag gaaagaaata aaagattatt cgacttctat    5280 acttttatc cacgatcgat tgctgaaact gtgtcacttt ttctttcttg ggcatcacac    5340
ctaacaacgg agcaactaaa gatgttagct cctgttcgag aagttctctt atctaagaat    5400
gaaaacacac aatctttagt gagaattaca gatgctaaca ggcgcagatg aatgttttat    5460
gagcattttt atagctgcag cttatatgtg atctatggtg caaggagtta attataacca    5520
tggatattag ttaggttgac tatcagaaat catctccaat acattctatg taaccactga    5580
tcaattccat gttcaactag ataggaacct gcctatatac aggtatgtcc ctgatgtaac    5640
tatagtatac tattattcat aaataaataa cgaaggtttt accttcttct cataaaaaaa    5700
aagtatcttc atgtcatcct atatgtcatg catctccttt gctacttctt ttatttactt    5760
cttaaacttg gttctaccat atattatcag cccctttaa atttgcttt ggatattgca    5820 tattccactc ttcaatcacc tcatgccaag caaaacattt attcacactt gaaaaccaat    5880
ataagaatac caaagaattt atccatgaaa ttctagaaac tttggtttta ctcctttctc    5940
catcattcaa aaaggttcaa aatgatgata actctatata gcttatttat caaatttacg    6000
aggttggtgt tcaatgtttt tgtgaaaaaa atatcttgct atccacatag tttgaatcca    6060 tactttgct atcttgagtt tcaaaaattt taatttgcta caattgttg ctattagcat    6120 atgactactt ttaagaagat aagccaatat actattttcc taagaattta aaaaatcaaa    6180
aataaaaatt tttatttaag atttttttaag ggttgttttc caaatgtgca atggggctta    6240
atcttggcat cattttctaa cttgtagaat tttgacccaa gtaacatttg tccaatcact    6300
tagaacttct ataacttcgt acaatcattt gttaatgttg ttcatctatt tatctatatt    6360
atctatctgg aatatagttg ctcttaatta tttttatata tcgcctatta tccacccctaa    6420 gctttcatgt tcatcctcat gttgttggag gtgcatgtct tattccaaac tatttaccat    6480
tgctgtagat tttaaaaaat ttgctagttt aggacttttt aatcttttga tatcatgttg    6540
atgtaagcta accctctaag gctagtcata atacatttta aggatttatg ttatatgaga    6600
ccaaaatttt aacaaaatga agtgttggaa attggtagaa tggaagtgta aagatgctta    6660
gagacataga actagccctg ggccatgtaa atcttccaaa agaagaagaa aataataaaa    6720
```

| | |
|---|---|
| ttaagatcat attcaatctc tacagaaaag ttggtctttg ttgtataata agccatctta | 6780 |
| acatatgatg gacaataaaa tatataaact tatgagtttt aatacttaga tggaagaaaa | 6840 |
| gggacagata tgtcacaccc catcctacta gcatgagtag gcacatgata cacggttgca | 6900 |
| tgccctgcag agtttgactc atgaggcatg caaggtattg aatagtagtc taggtaaaat | 6960 |
| taaaaaactt ggagcattct aaaaataaat caagttcatt ttataaaatc aatatttatt | 7020 |
| atggactcca tcaaatatta tgcgcataac atttttatttg caaatagaag aagataagtc | 7080 |
| ctagatccta agtctcctac tcttagtctc ataattcatc caagctatcc accaaatatc | 7140 |
| taaaacgaaa aagaaaaacg atagtatgct aatagctttg taagtcacct tttatctcta | 7200 |
| attagatcaa gcatattaga tataaaacaa taattttcaa agtatatgat ttgcaattag | 7260 |
| gaataaatat ttgataaata cagaataaat tttcataaag catatttact aacattattt | 7320 |
| ataaaatata taatgcttat atcaataaat taatttctaa atcaatatat ataaactatc | 7380 |
| cattctgtct tagccttaca actattgcta ccattccctg tagcatggtt aggaagagac | 7440 |
| tagctcttga atactcatgt catttatcaa catatgcgaa tgatcattcg actaatatag | 7500 |
| tcaaaaaaaa attactctga tttatataaa ttaaaaatta gtaaataata tatgctagta | 7560 |
| atcaccttac cagctaagct ctaaagaaaa ttagcttttg aatatacatc atgctattga | 7620 |
| ttattatatg tcagtgcttg tctcattttg tggcatgcaa aagactaga tcctaaactt | 7680 |
| atatgcatag tcagattaaa gagcaaatgt tgcatctgat tatatgaaca tctattatga | 7740 |
| tgtagagttt gtatcatgta tatttaattt aaacacaaat ataattatac ataaataata | 7800 |
| ttcatatttt aaatttttaaa tatttagata attattctag tgcaggtata aaaataagca | 7860 |
| atataaaatt ttaaatcgat ttatataaca tgcataataa aaaaaattaa ggatagaggt | 7920 |
| acttactgct caactcataa aacataagaa atctctttaa ctaactttag tgcaacctag | 7980 |
| atagaacata ttaatgatta agttttcatc taaaataaac atagatatca ttttaaaatc | 8040 |
| ttaggcattt aaatggtctc atgatttgtg aggcttttctt cagattctac aattttgaaa | 8100 |
| ttttttcaaa ttataatttt tttaccttga ttgataacaa agccaataat acacctcaaa | 8160 |
| tccaaatgta ttcctaatag ttttcaataa atctaatatc aataaatcat aattaagata | 8220 |
| tcaatccatt ctatgaattt gaccataaat cctacttgtt tctctgacct tcactataaa | 8280 |
| ttaatcatca aactaaataa gtgaggggat cataattctt ttacgacaat ccaagaattc | 8340 |
| aagtctagca tccacattag atggcttcct gtccagatat ttgcgcctct ccaaaattga | 8400 |
| gattatcaga ttaagaaaaa taaaataaga gagagggtta aaggacaatg ccttctaggt | 8460 |
| agtgatgtcc gacatcataa ttttgatcaa atctatgggg caaccaataa tattagggaa | 8520 |
| agaggattgg atttgagcaa gaatagcaaa gtcattgtca tcaatggcct gattcattga | 8580 |
| gttcaatgaa ggattggtgg ttgagtggtg gaggtggcat ctaggaagga gagagaaaga | 8640 |
| aaaagataga gagaaagaga taagaaaaat agagagaagg tggcagttaa gatcccttttt | 8700 |
| tgtgattaat atatagccgt aagatactca aagatctcac cttatcgacc tcaaacacta | 8760 |
| agggaggtgg aaggagggac tactacccat gaagctagag aaagggatga tgatgattgg | 8820 |
| aggaaggaag aaggaaaaat agtagactcg atgatgataa gactaaaaga aaagggtttg | 8880 |
| acttagccac ttggtatata atgaggtttg gtatggagtc aatagcttga gtaatagcat | 8940 |
| ggaaagagag aag | 8953 |

```
<210> SEQ ID NO 67
<211> LENGTH: 6021
```

```
<212> TYPE: DNA
<213> ORGANISM: Artificial Sequence
<220> FEATURE:
<223> OTHER INFORMATION: synthetic

<400> SEQUENCE: 67
aaatatctaa aacgaaaaag aaaaacgata gtatgctaat agctttgtaa gtcaccttt      60
atctctaatt agatcaagca tattagatat aaaacaataa ttttcaaagt atatgatttg    120
caattaggaa taaatatttg ataaatacag aataaatttt cataaagcat atttactaac    180
attatttata aaatatataa tgcttatatc aataaattaa tttctaaatc aatatatata    240
aactatccat tctgtcttag ccttacaact attgctacca ttccctgtag catggttagg    300
aagagactag ctcttgaata ctcatgtcat ttatcaacat atgcgaatga tcattcgact    360
aatatagtca aaaaaaaatt actctgattt atataaatta aaaattagta aataatatat    420
gctagtaatc accttaccag ctaagctcta aagaaaatta gcttttgaat atacatcatg    480
ctattgatta ttatatgtca gtgcttgtct cattttgtgg catgcaagaa gactagatcc    540
taaacttata tgcatagtca gattaaagag caaatgttgc atctgattat atgaacatct    600
attatgatgt agagtttgta tcatgtatat ttaatttaaa cacaaatata attatacata    660
aataatattc atattttaaa ttttaaatat ttagataatt attctagtgc aggtataaaa    720
ataagcaata taaattttta aatcgattta tataacatgc ataataaaaa aaattaagga    780
tagaggtact tactgctcaa ctcataaaac ataagaaatc tctttaacta actttagtgc    840
aacctagata gaacatatta atgattaagt tttcatctaa aataaacata gatatcattt    900
taaaatctta ggcatttaaa tggtctcatg atttgtgagg ctttcttcag attctacaat    960
tttgaaattt tttcaaatta taatttttt accttgattg ataacaaagc caataataca   1020
cctcaaatcc aaatgtattc ctaatagttt tcaataaatc taatatcaat aaatcataat   1080
taagatatca atccattcta tgaatttgac cataaatcct acttgtttct ctgaccttca   1140
ctataaatta atcatcaaac taaataagtg aggggatcat aattctttta cgacaatcca   1200
agaattcaag tctagcatcc acattagatg gcttcctgtc cagatatttg cgcctctcca   1260
aaattgagat tatcagatta agaaaaataa aataagagag agggttaaag gacaatgcct   1320
tctaggtagt gatgtccgac atcataattt tgatcaaatc tatggggcaa ccaataatat   1380
tagggaaaga ggattggatt tgagcaagaa tagcaaagtc attgtcatca atggcctgat   1440
tcattgagtt caatgaagga ttggtggttg agtggtggag gtggcatcta ggaaggagag   1500
agaaagaaaa agatagagag aaagagataa gaaaaataga gagaaggtgg cagttaagat   1560
cccttttttgt gattaatata tagccgtaag atactcaaag atctcacctt atcgacctca   1620
aacactaagg gaggtggaag gagggactac tacccatgaa gctagagaaa gggatgatga   1680
tgattggagg aaggaagaag gaaaaatagt agactcgatg atgataagac taaagaaaa    1740
gggtttgact tagccacttg gtatataatg aggtttggta tggagtcaat agcttgagta   1800
atagcatgga aagagagaag gagctgaaga gagtactaag tcttattaga ataaagaaag   1860
atagaatctt agcgaaaaat agggcctcaa atctttcagg tagaggaaaa agagggatca   1920
acgaatgaaa gactaaggaa aaggtgtgga gtaggatata ctctcgatta gtctctcaat   1980
catggattct agtagggctt cgtcagctgc tcaatcatgg attctgatag ctcaaatggt   2040
ggtaagtaga aagagagaga tctaaagaga ttgatagtgg ccttaaaacc agcacggtca   2100
aggataggca tgccttagag agaggaaaag agagagagat taatgaaat aagcgagaaa    2160
```

-continued

```
aatatattct tagagaatag attggcgata agaagaggag gtggttgggg catgcttaaa    2220
gaaataaaga aaattgagta ggcggaaagt ggtgatgctt ggcgatgaga agatttgaga    2280
gagagagcaa aaaaatgtgg atgatggtca taggataggg aaaggaaaga acaaagaagg    2340
gggtgctaag ctaactcttt ctaccttcct cacaccctga agcaaaggat ttggccaagg    2400
atggacaaat gggcgagggc tttggtggat ccatgcctac cctttctccc tctcacgatg    2460
attctagtca agctatctat ctttgatagc ttgagccaag ccaattgact tgatccaatc    2520
tctctaaatc catacaaact taagagagtg tattgattca cttattctct tctaagttga    2580
taagaaacat aattaagtgg agctcattaa gtatttcagg tagttgctaa cttggcaaaa    2640
tggaagcaat aataaatctt aaaagactat agcttggtat aatctcaacc atccatgatt    2700
tagaaagatc ttcagactca atatagatta ctttggctac tacaggtaag agctaaatag    2760
gatccaaaag taagatccat cacattagta agtcaaatta tatgtcaaat tttagtaggt    2820
atacttagtc ctacgatgcc taattaaaat gatcatcatt tgaaccttaa aatggactag    2880
tcaactaaaa tttttctttt tgaagaagat ttagaccata aaatatcttc taatctgtga    2940
agaattagat agagcgagga atataaaatt gatgtagaaa tcaagatcta tcatatatac    3000
aattttaata tttttttcat aatttttaaa tatttatctt cttttttat aggtctagtc    3060
ctatttaaac taggaagagg agtccaactt gacttatgca ataggggatg tccttctaga    3120
agataagaat aatttgatca gaattatata agagcaaacc tcattattat aaataggggc    3180
tatatacatc aatttatgag atagagaatc aatgaaacaa agtagactt aagttttatt     3240
ttcataattc ttctatcttc tacttttttt ctaggagatt caagttgagt ggattgaaga    3300
aaatctttca tcttctcgat cggatcatat tggtattaga gcgttggtct tctatattta    3360
tggagagctt taatgtattg tttaaatacg tgaacaatac aaacaatcaa gagaagtgct    3420
atccatgctt caaatacatc gaaatataaa agcaaatatg gctactaatt ctttttcaat    3480
ggacaatgag ataaaaggat gtcttacaca actcaaggag aagattgtgc aactcatgaa    3540
gattgtctcc agattgaaga taatttcaat acaagcacaa acaccagcaa ctcatgttgt    3600
gaaactgttt cctatgtttg gagatgaaga tcttctatct agtgaggaga ttgaattacc    3660
taaaagtatg aaaaatcttt cttcaatcat tgaaagttaa agcttgaatt gagatcccca    3720
tatataatgg aaccattgat gaaaaaaagc tagataattg gctaaactaa ttacaaacct    3780
attttattat ctatagatat tatggcatct agaagatagc ttttacttat ctcaagcttt    3840
ctagccatgc tcttatctga tgaaattcat atatgagaaa taataatatt tttaatatgg    3900
tgcagagcca attcaaaggt ttaatcaaga agtaatttta tctaattggc cataaggaag    3960
atcggtggat caaatgataa tacttatgat agaaacataa tcaatccact taggactata    4020
ccaccaagtt ccacaaacag gcaatctgcc ttggaatctt tatcaacaat tatacaattt    4080
ttataaagta tgttgaaagt cttcatgaga gcatctaaaa aaagatgaaa ctctttaagg    4140
ttgatgatat cagtaaagct aacatgaaag tcatagagat tgaggagaaa aatcaaatta    4200
gagaagataa ggaaggcaaa aagcatatca acataactca aaaaaaaaaa ttatgatcat    4260
tgaaatcttt gaaatacat caaggagaag tattgaaagt ttcatcctga attggagcta     4320
aagtagaaga agcccaagga tgataatttt aagaaaaata aaaagtggtc ctcaattcta    4380
tagagattga ggagctatct gaacttgagt aagcaaactt caaattgagc ttgatggtga    4440
gaaaacctaa tacaacaatt aaaacggatc tagaggtaca tgacaactca cccacttaaa    4500
gattcaagtg aagcagagta tcattaaggc tattataaat ctttgaagct agaagaacct    4560
```

```
cattttccaa tatttggttc agaaatcgag gttgtagatc aagcctcatc catatcctta    4620
tcctcttagt tggattcaga aggatgtcaa gttaaaaatt atgagatagt gtaccttcaa    4680
gttagccatc actgagaggt ttatttgtga ggtaactttt gaaatagttt ctttggatat    4740
ttgtcaagtt atccttagaa atgtgtacct ttagaatcaa gatgcaattt tctatagacg    4800
atagagaaag tatcatctta taagggatga gaaaagttc atgatcaaca cctcaagaac     4860
ataaggtaac tttgaccttg caactgttgc ccaagtgaag tgatttgtta atgtttgtga    4920
tgagtgcatg atgatggtat aaagaaccga tatcactcat gagaggtcaa ggccttgtcc    4980
tttggttcca tcaatcgatc aatagagatt gagattaagg aggagtcact atagtccttg    5040
tcgatgagga aggatgacaa caagcattcc taccatgaag tctagatttg agagcaaatg    5100
aaagtaatcc actgagacct gagagcaaaa aaggcgaga ccaaaaatca tcttcaagta     5160
aagtcaaatg gttcaaccat gagatgggga agtaagtatt ttcccacctt caattctaac    5220
tttgtagaaa ctaaatccct taaacagggg agccctaatt taagaggatc ctcagattca    5280
ttgtggacta ctttggctat tacaataaga gctggatagg aatcgaaagc aaaattcacc    5340
acattaggaa gccaaattgt atggcaaact tcaagagacc ataacttgat cacatgaaat    5400
ccaattaaga tgattttatt tttgaatttg aatatttttt tgagatctat aactttagat    5460
ctaaatcaag ctaaaatttt attgcttatg ccttcaaaat aggctagtca atcaaaact     5520 tttcttttca aaaagactt tgactgaaag atatctttca atctatgaag aatcaagtag     5580
agtgatgaaa gataaagttg atataaaaat tgagatctat ctcttataaa attttagtaa    5640
ttttattttt tttaatattt atctttattt agagatctat tcctatttaa actagaaaga    5700
attgtccaac ctaacttgtt caatgatcaa catcctccta aaagataaaa agaagaatct    5760
gactcaaatt ataaagggc ggacctttt tttttgatgaa aagggaggaa aaaaatccat     5820
caaaatttat taagaaaaaa agagtacaag aaaagaagga tatgaaagag taagagaagc    5880
cccacaacat ccatcaatat ttaaaattta aatttaaatc tcccccatca ttctatcaat    5940
atttgatatt caaatttaaa ttcttcgcag catcccacca acatttgaaa ttcaaatcct    6000
ttcatacaaa caaaataata t                                              6021
```

<210> SEQ ID NO 68
<211> LENGTH: 5329
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4258)..(4985)
<223> OTHER INFORMATION: n is a, c, g, or t

<400> SEQUENCE: 68

```
atattttcgt agtctctaaa ggcttcttcc agattggcaa tatactgatc tgactcagta     60
ttttttacta atatatcatc aacataaact ttgatattaa tttcaatttg ttacttaaaa    120
atcttattaa tcaagtatta gtatgtagca cctacatttt taagatcaaa agacatcatt    180
ttataacaat gcaaatcttt ttcagtgatg aaggccatat tttcttcatc ctcaagtgcc    240
attttgatct gatataacca gaaaagtat ccataaagct tagtaatttg tgtcttgaag     300
tagcatcaac aagctgatca attttgaga gagaaaaact atcttttagg caagctttat     360
tgagatcggt ataatcaaca tagatccttc attttttcatt agcctttta accatgacaa    420
```

```
catttacaat ccactttgga tattatgctt ctctgatgaa tttgtctttc aagagtttgt        480
cgacttcctc atctattatt ttttatcttt tcggggtgaa acttcttttc ttctgttgca        540
ttggtttatg ctttggatca acattcagct tatgtacaat aagatcagtt aaaatctcag        600
gcatattaga gactgactaa acaaagacat cggcattcat ccgaagaaaa gatattaatt        660
tctccctcag atcaggcttc aatagagatc caatttggac agttttttt ggatcatcac         720 acaaaagaac aataataagt ttctcgactg gttctcctcg attttgatg atatcaactt         780 tactttcttg atcaagtatt ttaattggta gagcttccac agaccttttc attttacag         840 ctatcagaaa atactactta gcaagtatct gatttcctca tatttctcca actccatact        900
tagtttggaa ttggattagt aaatgataag tgaagactat agccttaagg gcgttgagcc        960
taggtcggtc aagaatagca ttataagctg atggtatttt gacaataaaa aaagtgagtc       1020
ttacagttga ctggcatggt tctatccctg cagtgacgga caaagtgacc tctccttcca       1080
cagctacagg atttctagaa aatccaatta cggggtacc aacctattta gctaatttat        1140
catattcatt ctttggaatg tatcatagaa caatatatta gcagagcttt cattatcaat       1200
aagtattctt tttatatcat atttggctat tgccataaag atgacaacag catcattacg       1260
aggagtttga actctaacat catcatcgaa aaatgaaatt atgtgatcca tgcactgatg       1320
ctttggaagg ctttcagtaa tctcagccac ctcctcagtt ccgtcgagat ctgagatcat       1380
attgatgact gcagcagtag acttgttgtg atcattctca ttgttgggct tctatcattg       1440
gtcagtagct tgacttgccc gatctcgaac atatttacta agtaacatt agtggatcaa        1500 tacttcaatt ttatcttta attatcgatg ctcctcagta tcatggccat agtctcgatg        1560
gaaatgacag tattttctct tatctctctt tgctggaggg gctttcatag gattaggttg       1620
gcgaatatat cctaaatcct cgatttctat cagtatctga gctcgaggag tagatagtga       1680
ggtatagatg tcgaatcacc gaggtgggct tttgaacttc agattcttct gaggtcgttc       1740
agagttatcc tgttggtttt tatgatcttc ttcctagggc cactttttc catctctttt        1800 tttcttcacc taacgaagta tgcatgctct ctttctttc agcttgagca tacttacaaa        1860
cctagatcaa tatttgttca taattgtttg ggtagttctt attaagagag aagatcaggc       1920
gattactctt gagtccttgc ttcaaagctg ccattgcaat ggactcattg aagttcttca       1980
ctttcagtat ggcggcatta aagcatgcca catattcttg aagagattca ccttcctact       2040
atttgatagt aaaaagattg ctagtatttt tcaaatgaat ccatttatta tcaaaatacg       2100
tgatgaatat ttgctaactg tgtgaaagat gaaatagatc atgtctggag gtcagagaac       2160
tagattcttg cagatgtttt gagagtgatt ggaaaagtga tgcaaaatag ggcattagat       2220
accccttgta gtcttataat ggctctgaag ccttcaagat gatttaaggg attgatggag       2280
ccatcgaatg tttccaatgt aggtatcttg aatcgaggag gaactgattt accaagaatt       2340
ttttgagaaa aaagagatcg taagttgaaa tctcttctac cttgagaatg gcttccaatc       2400
tatatctcca tcattttctt ctcaagattt tgaatctttt gtccaagacc ctcctccata       2460
catggcttct tatgtggagc agatttcact tcccaagagt gatcagtatg gtcaagaaga       2520
tgatcatgat gaagatcttg aggagttggt tgctaagtgt gatgtgattg gactacttgg       2580
ggggctactt tttgctaccg ttctgtcgta tactacagca gtaagagctt ggacctgctg       2640
aaccaagaga ctaaactatt gtggatcaat aataattgaa ggttaggtat tctcctgaac       2700
atcttcagga gaagatgaag taggtaaagg atgatttggt gccttcttgt tcaccatttc       2760
tactaaaata ttttaagtgc ccttcctcta acactaatct attactgcaa ggcttcaaaa       2820
```

```
gacaggcaac gagatgggtc ttgaatcgaa ctagaatgtt tcttggttga atttggcgaa    2880
gtctgtaaca aatcttgcaa agaaaatctc gaaacctacg ggtaccttct ggttcaagat    2940
cctctgatgg ataagttagg taaagtcttg agaataggtt gtgaaaatag aagaatagaa    3000
ggatgagaag agagattgtc ggtaaatgga gagatgactc ttatttcttt caatggggga    3060
gctgaaaata attcagcaga gtttccactc tatcaatcct gacttatttt gtggagggta    3120
ccttggcccc ttcatatata ggggatgaag aggcctggta aggttgttag actattagga    3180
gagtttgtta gatcgttaat ttattataat agaatgacca gctatataaa aatcatggag    3240
tatttaccca catggtgatt gactgtagta taactgaaag atagctaatg cttagctgga    3300
tgactgctgt tagataactg tctgcattct tacggtacat tgatattta ccaatgtgac    3360 atagcttaaa tcggcaactg gctgaactaa atattatgta tccctttagt taacaatcat    3420
gtcggttaga gatcaatgta attcgcagca gatcgatcat aagctgagat gagtatcata    3480
ttttaagaac aacgctgggc gagttaggcc gatcaaatgt cagactgaaa aagcagatca    3540
ataaacctct gatgtgatct gaaagaatat ttatgattta aataataatc tatcaccacg    3600
tatccagata atgaggtcat ataacatgta ccaacagtgc attttttccat ctagttaaga    3660 ggttggttag tggcatttgt cttcgatatg taatgttcac ataactaatg tgcttagtag    3720
cattcttttg taaggttaaa tcttcaatga tcttaagttc acataattgc ctttgtgccc    3780
tattagttta tagttgacct tttaattcaa gagacagtca ccttagcaat cgatgtctgc    3840
ttagattggg ccaattaggt actcacatta atatattgaa tcatgtttga atataaagga    3900
ttagattgat ttataagttt cctttttattg tttacatact gatacttaga ttgacttact    3960
acattatttg atatgttatg ttctaatttt tggattaaaa ttgttgtttc tgatttctcc    4020
ttacatctaa tactttgtat aatttattat ttttagcat gattgagtgt agaggattag    4080
attgattttt aagtttattt tgattattta catgcccata cttaaattga cttactacat    4140
tattcaatat gttatgtttc aattattgag ttaaaatttt tatttctgat ttctactgat    4200
gtccagtgtg tgtgtgtgta cgtatgtgtg tatatattta tttacatata tatgtatnnn    4260
nnnnnnnnnn nnnnnnnnnn nnnnnnnnnn nnnnnnnnnn nnnnnnnnnn nnnnnnnnnn    4320
nnnnnnnnnn nnnnnnnnnn nnnnnnnnnn nnnnnnnnnn nnnnnnnnnn nnnnnnnnnn    4380
nnnnnnnnnn nnnnnnnnnn nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nnnnnnnnnn    4500
nnnnnnnnnn nnnnnnnnnn nnnnnnnnnn nnnnnnnnnn nnnnnnnnnn nnnnnnnnnn    4560
nnnnnnnnnn nnnnnnnnnn nnnnnnnnnn nnnnnnnnnn nnnnnnnnnn nnnnnnnnnn    4620
nnnnnnnnnn nnnnnnnnnn nnnnnnnnnn nnnnnnnnnn nnnnnnnnnn nnnnnnnnnn    4680
nnnnnnnnnn nnnnnnnnnn nnnnnnnnnn nnnnnnnnnn nnnnnnnnnn nnnnnnnnnn    4740
nnnnnnnnnn nnnnnnnnnn nnnnnnnnnn nnnnnnnnnn nnnnnnnnnn nnnnnnnnnn    4800
nnnnnnnnnn nnnnnnnnnn nnnnnnnnnn nnnnnnnnnn nnnnnnnnnn nnnnnnnnnn    4860
nnnnnnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnatgta tacatataca tgtatacata catatataga tatatatata tacatatatg    5040
tatatatata tatatatata cacatatata ggttatttgg aacctaagaa acttgcaaag    5100
ttactagatg caatgttcgg aaaccatgga ccgtaacaac tggagtagta tttgggtcat    5160
```

```
gaattcatgg ctagatcatg aattgagtgg gagtcaaccg aagtagggcc agctcagaca    5220
cttgtattta ggtcccatgc ttgcgtgcat tctcttccct gatatccttt ggctttgctg    5280
cctcaaatcc tcgagctatc ttatcatcat cgcattgagc tccatacct               5329
```

<210> SEQ ID NO 69
<211> LENGTH: 6061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5947)..(6061)
<223> OTHER INFORMATION: n is a, c, g, or t

<400> SEQUENCE: 69

```
cagtttggac ttcaatgtta acccaatatt gattttaaat ccaacattgg tccacttaga      60
cttatttatt tatttttatc aatttaatat aaaaaagatc taaacctcat aagtcataaa     120
ttttggattt atttttgaac atgtacaaaa taaaacagaa aaagaaaaa attacttatc      180 taaaagtaac tatatctgaa aactttcact ttagaattgt cttaaattaa tgtacttcca    240
tcaacaattc aatgttaata ttttatgaa tccaaatgga tgatagagta ttttttagaa     300
tgaagtattg aagtctaaat gacatcgtcc caaaataaaa gtgaatttat gaaatactac     360
atctgtcgga ttcggtttca tacgattaa aagtgtagga atagaatccg attataaata     420 attattttt tataaattct aattcaattt tattcgattt atatttttta accggtcaaa    480
attaatattt attaagtagg attggatgga tttattcgta tctcgattat ttgctcagcc    540
cattgccaaa tctaaactct tttcagatag gttccatgtg aacatgatac atgagatgca    600
gtgtgatagt acacaccatt gctaagaaaa ctttggagtt tgcgtaacaa tatctgttta    660
ccatttaaaa aatggcagtt tgaatttta acacgctctc ctccagattc agcttatgaa    720
cttttcgaat aaaaatacc ctggactatt ttccaaaaaa gtaccagcat cttttgaact     780
tgaatggaaa ttcggccaat aaaatgtttt catttattga agaaataaac agggtaacgc    840
agtagctcta tttcctctgc ttttcttttc tatattaata acatgattat tcatctctct    900
cggatcacaa aaaattaag ctattcaagc tttatttata tttcattttt aaattttta     960 cttaaataca aaatctccca tcccactact acggcagcat gttttctatg tatgattatt    1020
ttcattcaaa tgatatcatt ttttataatt tatattgtat gtaattaatt catttatagt    1080
tcttacattt tcctgtttct agtagataca ataaagcggt tttggactag tagcttgttc    1140
tctgtatcga gtttaacta aagctttgac aataatatat gaatccatat cactgggtag     1200
gagaggaata tgttgggtat aaaggattta aggaattaga tattttcata caattgtatt    1260
gcattgcaga cagtaattag attactatgc aattattctc tctctccatg tttgttgcag    1320
ttgaagaact ctaatgaagc tcacaaaaat ttactgcatg aacttgtaag tggaattaga    1380
cgactccgtt gtcctccatt ttcttttatt ttctttaaaa tcatctgcca ttcaaataga    1440
cagaaaaaaa aggattgatt agctattgga tgcctcttga attcaggaaa tgaaggacga    1500
gcacccagtt tatggttttg tggatgatga ccctagcaac tacgcaggtg cactagctct    1560
tgccaatggg gcttcccaca tgtatgcttt ccgtgttcag ccgagccagc cgaatctcca    1620
tcgaatgggg tttggctccc atgacctgcg ccttgcttga ttttattgta gcttaaagac    1680
cttacaactt ccagagtggt gttatatatt agtatcttaa gctatgacag tggtaagcct    1740
ctctatccgc tacttgttat cctttaggta ctttgcatgt ggtgcaaggt tataattgcc    1800
```

```
ttgtgtttct attgtcttcc tcatggtact tactggactg atgatgtcaa gtgaaatgga    1860
gttgtttgaa tcctgactga aatttctctt ggtccatcaa gtgcaagagt aagtttagac    1920
atcactcgca agcttttgct aggaaataag tagtttcatt gcactaatga tttcgaattt    1980
ttgttttcgg gttagagaaa cctagattaa tgctgttatt ggatgctggc agtcagatga    2040
agattatgtt tgattgtacc tcgttggaca gatgctcatg cgtagatcca taactctatt    2100
tcatttcatt tccctgtaca caattgaaac agggcatata tgaataggta tagaacagat    2160
gattcctgca atattggagg tggctagctc agcttagact aaagttggtc tagctgggat    2220
attctgaaca cctgagatgt tcaaataatg tgggataact tggcccaact caactaaaca    2280
ttggctcaaa gcatagtcaa ggtaaagctt gagcaagctc ttttgagctt ggttcgagtc    2340
cgagctgagc ccgggccgct tgtttagctg atgaactgaa ttcaaatagc cggtactcag    2400
cttggctcca ctcgattcat gagttcgaat cccctcaagt tcaacctcga acttgacggt    2460
gtagtcccac aaccatggcc acctataat gtgggacggc cattatgcat tcctctagtg    2520
cctgctccat atgactttg ttctcattat accatgcacc taaatgagtg ctcatagtga    2580
caatgtttag cctccacgta taatgtgtgc cagctaacta aagcctaaa ctttggtgaa    2640 atttctgcaa tgttgtggtt gtaaaacgct cctacgttga gacatgatgg tatctaagat    2700
tatagacaaa ctatcatgct gaatcaaccc aaatccaagg tgaataaaac ttgatacaaa    2760
gccgagctcc attgaaatag tacaatggat tctgcacttg aagaacatta caaaatcatt    2820
ttttcccaaa aagaaacatt gcgaacagac caaagcgtaa agaaattaca tgattcaact    2880
aattcaagct ttccatgatg taggcactcg ctagatgtag tagggtgata acttgctttg    2940
tgagggtgga tcataagctt aacctcaatc tatcccaatc tatcctttcc cttgacctat    3000
ccatgccaat ctaggccatt tctgcataaa tataacttaa tcccagtgga tccggcctag    3060
tttcactcac tccaacacat tcctactcaa tggtagccaa tcctttcttt agccctcaaa    3120
tataatccta atctagcata gccaaccatc aatcatgcct aataaagccc gactacacca    3180
acccgatcat tcctgatcgt acacaatcaa gacttatcct aattgatcct agctttttt    3240 aggcctctct tatagaacct gtgccaattc tggacaagct aatccaatct tagcagccaa    3300
aaatattaca tgtttaatta gccaaatcga acctatcata aacccaatat ataatcggac    3360
cataccaaga tcatcatcct atatttcctt ctcttgttat aactacacct aaaaaggaat    3420
ttcttcatac ttatgagggg tatattatga taaaaattcc ttcattttag ccctccatcc    3480
ttgtctattt ttgggaccac tagccaagta acaccttaag agccctccat cttaatattc    3540
cctctaacta gctcgatttc ttcttcattc tttctttgcg atgtgtcccc tccaatttaa    3600
ttcttacatg ttgggatttg agtactgaaa aataatagat aaagagaaag taaaactat    3660 gctaatgata ataccaaagg cataaagaaa tcacagcagt cgcaaaaaca tcaaattttt    3720
ttatggttcg gcctaagcct atatctacat agggacgaga gtaagaagaa gcttccacta    3780
taataatagt ttagagtaca aaaacttctc tgacaccatg tagggaacat cgcttctaat    3840
acaagaaaga agaaatccaa gattaaacaa acctctagaa aaattcttct cgatggaata    3900
actctaatct gagattgaac aatcttctcc aatcgatgat ctccaatctt cttttcttaa    3960
atgaagcacc cttcaagcct ctcttctttt ctctcttcct atcctctttt gtggctcaca    4020
acctcctctc cttttatgt tctatgttcc tcacatcaca tccacagact cattttttata    4080 gataaaaaat tagagtctat ttcggactcc ttttccacac acaagatggc ttcccacgcc    4140
```

```
attggttccg tgcgcatgac ttttttcatg ccacaaagga ttccgtgctg caaaagtttt    4200
ccatatccat gcagtttcca cacaccacaa aaactttcgc acacttctcg aaggcttttc    4260
atgctcgacc cttttggtt ttcaattaaa ttgatggatc ccatatgagg agggaccaca    4320
ccaataaatc tcctccttct aactcatatg gtaggttcca tcaagcctgt agcaccttg    4380 cattttatca gttttgttcc tgaagccggc ttcatcaata tattagaact attttcttca    4440
gtgtcaactt ttttaagctt gaaccacttc atctctagca tattgacatg cttttggaaa    4500
gtatgtcaaa ttgctcaaaa ttaatcttac ggttctcttt ttcgttagat tctagtgcat    4560
attacgcact ttaacataag atctaaggaa ggaagaggac tgaggtaagg tgaagtgatt    4620 tttttgagt tggtaatggt acaaaagtta tactagaccg tgggtaccta atctcggaga    4680
ttaccattta gatttggttc ttgatcattt gtatagtgat gcatttaaaa aattatttga    4740
gcaaaacagt gaatgccatt gggtctgaga gatccaaaac caaataaccct aaagtatata    4800 gatggttcct ttagctagat catgtatgag aaaaaatgat ctgccgactg gaaaaaatag    4860
atctttgagc tcattgattg ttaagtcata tctagtctgt gaatcatctc tttgaggatt    4920
aatgatcaag ctatcttta tgggttaaaa gaataggatc actgaaatac ttatcctagt    4980
atacatataa tgtgcatggc ctatttgatg agtcagacta gaaggttatc actacttcat    5040 caccttact gatgagcaat catgatatag atatgtatgt gagatacaaa tctaaaagat    5100
tttgaatggt tcaaagaatt cagatatgaa gtagaaaaga taaatcaaaa aattttaaa    5160 ggtacttgat cggatctaga atgcaatacc aaataaaaaa tttgttgatt atctaaaaaa    5220
agtgatatag tttcatgatg gaattcttct tgtacacctc agctcaacgg tatatatatg    5280
aggagcaata gcactatatg agatatggtc cggtccatca tgaatatcac taatttaatt    5340
attatttatt taagagcaag atttaatttt taaaatttaa attagatttt ttctaaaatt    5400
ggtttcaccg caccatatga gatatgattt ggtggataag ttagaggata ggtctgtgag    5460
aactcattta tagggtatcc caaaaggtat ttaaaatatt acttttctt tctagtagtt    5520 gacaatatga ttgtgagcaa tcatactgtt ttcttaaaaa cagtggaagg atgaactcaa    5580
aaagaaagtc tctaaagaac aacgagtcac aagacctata caacctattt aagatgagcc    5640
agtatatgta gtacttcctt cacctcatca atttagtagg atctcctatc ctttagaaag    5700
atactcggta ttcttacaaa ggatttagag aaagtgtttc ttgagggaga ttgagaatat    5760
agggatgatc tcaaaaccta caatgacata atataaggaa tcatgtagtt acatgaaggt    5820
cagtgggagg gttccatact gacatcgatt atgatgtggt tacatataga atttttttt    5880 caaagatcta gatcaaacat tctgaaaata aaaggtctat agagataaat ccgaaaagga    5940
tgtttgnnnn nnnnnnnnnn nnnnnnnnnn nnnnnnnnnn nnnnnnnnnn nnnnnnnnnn    6000
nnnnnnnnnn nnnnnnnnnn nnnnnnnnnn nnnnnnnnnn nnnnnnnnnn nnnnnnnnnn    6060 n                                                                   6061
```

<210> SEQ ID NO 70
<211> LENGTH: 14226
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1949)..(2907)
<223> OTHER INFORMATION: n is a, c, g, or t
<220> FEATURE:
<221> NAME/KEY: misc_feature
<222> LOCATION: (3857)..(4532)
<223> OTHER INFORMATION: n is a, c, g, or t

<400> SEQUENCE: 70

```
atcctcttttt gtggctcaca acctcctctc cttttttatgt tctatgttcc tcacatcaca      60
tccacagact cattttttata gataaaaaat tagagtctat ttcggactcc ttttccacac     120
acaagatggc ttcccacgcc attggttccg tgcgcatgac tttttttcatg ccacaaagga    180
ttccgtgctg caaaagtttt ccatatccat gcagtttcca cacaccacaa aaactttcgc     240
acacttctcg aaggcttttc atgctcgacc cttttttggtt ttcaattaaa ttgatggatc     300
ccatatgagg agggaccaca ccaataaatc tcctccttct aactcatatg gtaggttcca     360
tcaagcctgt agcacctttg cattttatca gttttgttcc tgaagccggc ttcatcaata     420
tattagaact attttcttca gtgtcaactt ttttaagctt gaaccacttc atctctagca     480
tattgacatg cttttggaaa gtatgtcaaa ttgctcaaaa ttaatcttac ggttctcttt     540
ttcgttagat tctagtgcat attacgcact ttaacataag atctaaggaa ggaagaggac     600
tgaggtaagg tgaagtgatt ttttttttgag ttggtaatgg tacaaaagtt atactagacc    660
gtgggtacct aatctcggag attaccattt agatttggtt cttgatcatt tgtatagtga     720
tgcatttaaa aaattatttg agcaaaacag tgaatgccat tgggtctgag agatccaaaa     780
tcaaataacc taaagtatat agatggttcc tttagctagg tcatgtatga gaaaaaatga    840
tctgccgact ggagaaaata gatctttgag ctcattgact gttaagtcat atctagtctg     900
tgaatcatct ctttgaggat taatgatcaa gctatccttt atgggttaaa agaataggat     960
cactgaaata cttatcctag tatacatata atgtgcatgg cctatttgat gagtcagact    1020
agaaggttat cactacttca tcacctttac tgatgagcaa tcatgatatg gatatgtatg    1080
tgagatacaa atctaaaaga ttttgaatgg ttcaaagaat tcagatatga agtagaaaag    1140
ataaatcaaa aaattttttaa aggtacttga tcggatctag aatgcaatac caaataaaaa    1200
atttgttgat tatctaaaaa aagtgatata gtttcatgat ggaattcttc ttgtacacct    1260
cagctcaacg gtatatatat gaggagcaat agcactatat gagatatggt ccggtccatc    1320
atgaatatca ctaatttaat tattatttat ttaagagcaa gatttaattt ttaaaattta    1380
aattagattt tttctaaaat tggtttcacc gcaccatatg agatatgatt tggtggataa    1440
gttagaggat agatctgtga gaactcattt ataggggtatc ccaaaaggta tttaaaatat    1500
tacttttttct ttccagtagt tgacaatatg attgtgagca atcatactgt tttcttaaaa    1560
atagtggaag gatgaactca aaagaaagt ctctaaagaa caacgagtca caagacctat     1620
acaacctatt taagatgagc cagtatatgt agtacttcct tcacctcatc aatttagtag    1680
gatctcctat cttttagaaa gatactcggt attcttacaa aggatttaga gaaagtgttt    1740
cttgagggag attgagaata tagggatgat ctcaaaacct acaatgacat aatataagga    1800
atcatgtagt tacatgaagg tcagtgggag ggttccatac tgcatcgat tatgatgtgg      1860
ttacatatag aatttttttt tcaaagatct agatcaaaca ttctgaaaat aaaaggtcta    1920
tagagataaa tccgaaaagg atgtttgann nnnnnnnnnn nnnnnnnnnn nnnnnnnnnn      1980
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
```

```
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnnnn nnnnnnnnnn nnnnnnnnnn nnnnnnnnnn nnnnnnnnnn nnnnnnnnnn    2580
nnnnnnnnnn nnnnnnnnnn nnnnnnnnnn nnnnnnnnnn nnnnnnnnnn nnnnnnnnnn    2640
nnnnnnnnnn nnnnnnnnnn nnnnnnnnnn nnnnnnnnnn nnnnnnnnnn nnnnnnnnnn    2700
nnnnnnnnnn nnnnnnnnnn nnnnnnnnnn nnnnnnnnnn nnnnnnnnnn nnnnnnnnnn    2760
nnnnnnnnnn nnnnnnnnnn nnnnnnnnnn nnnnnnnnnn nnnnnnnnnn nnnnnnnnnn    2820
nnnnnnnnnn nnnnnnnnnn nnnnnnnnnn nnnnnnnnnn nnnnnnnnnn nnnnnnnnnn    2880
nnnnnnnnnn nnnnnnnnnn nnnnnnnact atgtatgttg gctatgtagg ttccgattcg    2940
ctgtttggaa tatgatatac ctagatgaaa tctatcgatc ttgatagaaa agagaagtc     3000 ctatgtgatt cgtaagactg agttcagaaa aatctctgac cagagtaagt gtgaatattg    3060
aaaaattttt tttacgaaat tcacaaatga actcgagtcg agccaatgta gcatatgact    3120
gatgatagag tttgacgagt tctcaatgac ctccgtcaaa ttgggactct cgatagaggg    3180
attgtatcac acgataactg cacctaggga ttcacttttc tattttgcta gcttgccact    3240
atatgttgct agacgtcact ggtggatcgt gagaactcac taaaatcatt ttcggatcaa    3300
cgatctttgc tgaggtaagt tggaatcgtt tcagtccatc gaaaagagtt tcgatgatac    3360
tgtgatggag atcacgatat gtctcactat caaacagaat agaacctgag gagtcacata    3420
caaaaagagc ttaacctgat caatggcttg gattatattt gaattatcaa ttagattgat    3480
agtttgaata ttagaaactg ctaatttgta accgttacag ttttgacaac tactaattgt    3540
tagcgcaagg acttaattgc aagtattata attttttga ggctgattaa attataaatt     3600 aaatttaat taatttaatt cagatttaat ttaattagac ttaatttaat ttaatattaa     3660
ttggattcaa ttatccaaat cagatttgga tttcaagcct gattggatca ggcttgacag    3720
ccttttcgaa tttggctcat tttagactcg atttgaatcc gtttgaggtt ctatttggat    3780
cagataaacc atgacttaga gagctcaagt tttttgggac tctctttaga aatcatgtca    3840
aaaggagaag tagagcnnnn nnnnnnnnnn nnnnnnnnnn nnnnnnnnnn nnnnnnnnnn    3900
nnnnnnnnnn nnnnnnnnnn nnnnnnnnnn nnnnnnnnnn nnnnnnnnnn nnnnnnnnnn    3960
nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn nnnnnnnnnn nnnnnnnnnn    4080
nnnnnnnnnn nnnnnnnnnn nnnnnnnnnn nnnnnnnnnn nnnnnnnnnn nnnnnnnnnn    4140
nnnnnnnnnn nnnnnnnnnn nnnnnnnnnn nnnnnnnnnn nnnnnnnnnn nnnnnnnnnn    4200
nnnnnnnnnn nnnnnnnnnn nnnnnnnnnn nnnnnnnnnn nnnnnnnnnn nnnnnnnnnn    4260
nnnnnnnnnn nnnnnnnnnn nnnnnnnnnn nnnnnnnnnn nnnnnnnnnn nnnnnnnnnn    4320
nnnnnnnnnn nnnnnnnnnn nnnnnnnnnn nnnnnnnnnn nnnnnnnnnn nnnnnnnnnn    4380
nnnnnnnnnn nnnnnnnnnn nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nnnnnnnnnn    4500
nnnnnnnnnn nnnnnnnnnn nnnnnnnnnn nnccccatcg aaaagagttt cgatgatact    4560
gtgatggaga tcacgatatg tctcactatc aaacagaata gaacctgagg agtcatatac    4620
```

```
aaaaggagct taacctgatc aatggcttgg attatatttg aattatcaat tagattgata    4680
gtttgaatat tagaaactgc taatttgtaa ccgttacagt tttgacaact actaattgtt    4740
agcgcaagga cttaattgca agtattgtat tttttttgag gctgattaaa ttataaatta    4800
aattttaatt aatttaattc agatttaatt taattagact taatttaatt taatattaat    4860
taggttcaat tatccaaatc agatttggat ttcaagcctg attggatcag gcttgacagt    4920
cttttcgaat ttggctcatt ttagactcga tttgaatccg tttgaggttc tatttggatc    4980
agatgaacca tgacttagag agctcaagtt ttttgggact ctctctagaa atcatgtcaa    5040
aaggagaagt agagtattat ttttttcatc cttctttctt cacacgcatg aaggagagg    5100 gggcaccaat agttggtgcc ctgccttatc tggatgtctt tttcatccaa tttttttttt    5160
aattgaattt gatttaaaat agaatagaaa tatcttagat taaggtatag aagtactttt    5220
tttatgtgat aaaaaaaata gagaaagagg acgtgcgcta attattggcg tgagacatct    5280
ttccttcttt cttcccttat ctcaacgcac atctatcctt tgatttgttt ttgaacacct    5340
tggattaaaa gagatgagat ctcttgggca ttaagaagga gttgtgcgtg ggatttgaga    5400
tgtggtgcga caaaaaatta aaagaggatg catgaaggga ggtggcgtgc gttagatgcg    5460
agaggcttct ttcttacatc tttctctcct ccccaatgcc tcttccttcc ttctccactt    5520
cacgtccatg cccagattca ataaagatca gatctaagaa aagaaaagag agagaaaaag    5580
agaagaagaa gggttcttct tttcttcatg gtgatctggt atagatcctg ttggatttgt    5640
gcgaaagagt ttgagcaacg atctgcttct ttaagatctg aaagaaaaga tcaagatcca    5700
tggatgaaga gtgagatctg caaggtgcta gcacaccagt gatctcggtg ctccgatcaa    5760
atggctccgt gtggatatca gctgaggtcg aacgcgtgca tggctacgat cagaatctgc    5820
gatatctgca ggatccgaga tatggagatt cgatctccat tttattttc taacagttta    5880 tttttctatt tcagatatca gatcgtgggt acatatttgt atcaagatct ttactatggt    5940
tttcagatct gatttgatac gtaaataaat taaaattatt ttaatttatt tattttcact    6000
gtgtagatgt ctagaaaaaa ttttaaaacta cacgtacgaa atcgaagcat tttctaacaa    6060
ctctgactat caccatagac gacgtatatc tcttgcttcc caccaaactt ctttaataag    6120
ttctttagcc atagcatttc tttatcgacc tttgttatgg tgatgtattc aacctccatc    6180
gacgataatg tgacactttt atgactttga ttgccacaac accgctccct ctgagaatat    6240
catcagataa tctgacgtgg atttctgtat gtccacatca tcgatcatgt ccgtatctgt    6300
gtaagcctgt agcataggat ctccactatc atggcataaa tatatcctgg atatctattt    6360
aagatatctt attttccact tcattgcttt ccggtgctcc tttccaaagt tgaaagaaa    6420 ccgattgacc ataccatcca cttgagcaat attagacctg gtgtacacca tagcatacat    6480
aagactcccc accacttagt ccttctcact cttttctgctt tgctctttaa tcaatgtaaa    6540
gtgtcctaca agcagacacc accggcttca ctctactcat gttgaatcaa tccagcacct    6600
tctcaacata ggcctcctat gacaaccata ggacctggat ctcctatctc tagcaattct    6660
tatccttaat atcattttga cctatcccaa gtcttccgtc ataaatgttc gatccaactt    6720
taccttcaaa tcattgattt tggtaatgtg gcatcccaca atcagcatgt catcaacata    6780
tagcaaaaat ttgataaaat tattgtcaaa atatttttc atgaacatgc aatggtcaga    6840
acttactttc ttatatccat tctccattat gatggaatca aacttcttgt actactatca    6900
tggtgcctgc ttcagttcat aaagattttt cttcaagcaa cacactatgt tctcattaac    6960
```

-continued

```
ctttcatttc aaactcttct agttactcta tatattctcc tcctccaagt cgccatgaag    7020
gaatgccatc ttcacatcaa attgttccac ctcaacatct aaacagccag cgagatcgag    7080
gataactcga gtagacgtga gctttacaac gattgagaaa atctcttcaa aatcgatact    7140
ttttctctga ccaaaatctt tcacaactaa tctcatcttg taccttggtt ataaactatt    7200
ctcctatggc ttcaatctga acatctattt attttttgagt gcttgctttt tcttaggtat    7260
attcaccaac tcatatgtat tattttttcta taaagaattc atctcctctt tcattgcctt    7320
catccactcc tcactatgct ggagctctat ggcttcagag taggactcaa gctcttccac    7380
atctgttaat agcacataat cctatggtgg atatcttatg gatggcgtcc actctcttgt    7440
gaatctctgg acctcttatg caggtggttc aacatgcaac tcaatttgaa caccatccgc    7500
actctcctca gcctcatgac tatcatatgt accgtcatct gtagttgctc tcctgttatc    7560
aagacttctc gaagaggtat ctgggcataa gtctataggg ctgctcgggg ttgacttcgg    7620
cttcttaggc ttcttaaaat catcgatcgt ctgatcctcc aaaaaaataa tgtcatagtt    7680
gcacacgatc ttccactcca tagaatccca caatcgatag ttgaactctc cgtcctcact    7740
atagctcagg aatatgcact gcttcacctt gacatctagt ttggatctct catctttagg    7800
aatatgcacg aatgtcctgc atccaaagat tttcaaataa tcataagaaa tatctttctc    7860
caacaatatt ctctatagtg tatcacactt aagagtataa gaaaaaaaaa gattaatgct    7920
atggatcaca gtcatcaatg cctccctcca gaatgccttc gatagtttag cataagagcg    7980
catgctcccg atcctctcgc aaatcatcct gttcaccctc tcaacaatct cattttgttg    8040
tggcatctta ggcactgtct tctctagtct gatgccattt cattgatagt attttttgaa    8100 agaaccccctg tattcacccc tgttgtccgt ccaaatatac ttcagcttttt gcccagtctt    8160 tctttcaaca gagatgtcaa attacttgaa tattatcgag cacttgatcc ttcattttta    8220
aaatatatgt ccaaatttttt tagaagtgat catcaataaa agtcatgaag taagaacatc    8280
cataaaaaat tttatcactc agagaacaaa catcactgtg aataagatct aatgcaccaa    8340
tttttctttt agaaaaaaat tctaaaaaga aacttggatt tgcttaccca tcaagcaact    8400
ttcatatatc ttcaatccaa aactatgaat aggaagagca ttcttcttag tcaaaattga    8460
cattcctttt tggcttatat gtcccagtcg tcaatgccat aattctaagg tagaagattc    8520
ttccactaca ttcacctccc ctttaccgag cttggcttgt atgaagtaga gaaagccttg    8580
cttgatactt ttggctacta ctagcgattt tttggttagc ttctatttgc tgtctccaaa    8640
tatattgtag tagtcctcct catctaatac ccctatcgat aacaagttca gatgaatatc    8700
tagtacatgt cgaatatttt tcaaaaatag cctgtaccccc aagctcgtga tcagcataat    8760
atctccaata tcaaggattt ttaattctcc atcattctcc atctttattg tcccaaagtt    8820
actgaaatga caagatgaga ataattttca cctcactgta acatgatacg aagtggccaa    8880
atcgatcacc cagatagagt ctcaaccaat agtacttgca agatcatcat tgttgtgcc    8940 acaagcaacg atcatctctc catccgtagc tactgctatc atcttattgt tcgagctgga    9000
gtcatcactt gattatttttt tgacttctcc ttttttagta atcggtagtc tttcttaaag    9060
tgatcctttt tgccgtagtt gtaatatcta tcacttcgag acttggatct cttccgtaat    9120
ttagtggggc catcattcaa gttagattgg gagtccttgt gcttgtttct tccctttctt    9180
tctatgatga gagcctcatg gtggctcgag acaccttgct cctttctcct agcctcctca    9240
ttaagcatat agtctttcac cattgccaag gctatcgaac tatctggtga agaattgctt    9300
agagacacca ccaaagtctc ctaactatcg agtaagaaac ttaacaatag taaagcctag    9360
```

```
agctcctcat ctaacagcat cttcatcaca gtaagctggt tcaccacgtt ctaaaagttg    9420
cttagatgct ccaccatata agctccctcc ttatatttca tatttatcag tttgtgaatt    9480
aggaacacct tgttctatac catctctctt gtatagactt tttagtttca accaaaggcc    9540
atgagcatta acctccattg aaatatggtg aagatgcta tcatcaatcc actgttggat     9600
aatcccaacg attttatgat tcaatttctc ccattcttta tttgacatct tatcaaactg    9660
aataataaca tcctcgattg gatcatgaaa atcttagcag taaaggaggt cttccatgta    9720
aggattccag attgagtagt tagttaatgt cagcttgatc gtagtgcccg acgaagattg    9780
gttctccatc tattagcatc ttaatttctt tttgaatact ttagattttg taaaattttgg   9840 ctctgatacc acttattggg atttgagtac taaaagataa tagaaaaagc aaaagcaaaa    9900
atcacgccaa cgataatacc aaaggcacaa agaatcatag caatcgcaag agcactagaa    9960
ttttttatgg ctcgatcaaa gtctatgtct gcacagggat gaaaataaaa agaaactttt    10020
actataataa tagtttagag tataaaaact tctctgacac tacgccgaca atactacttc    10080
taatacaaga aagaagaaat tcaagattaa acaaacctcc agaagaatcc tttttgatgg    10140
aatatgaaag aataatattc tacaagtcaa tcgcatgagt aatgcaataa gatattgttc    10200
tatattttat cttccaaatt catatatttg atattaatta ttaataaaat tagatatttt    10260
atttcattat atgctgcatt ttaatacttg tttaaaatta taatgaactc cataggttag    10320
gacaataatt ttaaggtcat gatgagatca taccagtgag atttaaatct tgataaccct    10380
taatctaaaa tattctcaat agtaggatca ttaagtcaaa aatcaatgat actgataaaa    10440
ctggtacatc ctatatattc tcgacagaga gggtggttga tgtcataatc acttgtgtgg    10500
agacactaat acgaagatgt ggtgctcatt agagaataag ttcattgaat ttactgatcg    10560
agagaatata tgatgcaagt gatcctttga cctaagatca ccatggtgcc ttgtatatat    10620
gaatctatgt tttggttcat tctttagctt cattttttga gccttgtgtg gggtgctccg    10680
gacatggtgc agtatgtatg gaggttgtga gtggtcaaca aaaaatcaat cactccttgt    10740
aaaaggagcg aatatcttat gtgatcttat aggttgatcc aaaaaatctt tgaccaaagc    10800
agaatgataa ttagaaagag ttttttaatat atcattaact gaatcaatat cttctgatcg    10860
agatacatat aaataagtat ttgaatttga catgatttta tatccataac taatctgaaa    10920
tattgtatga ttgaagaatt gaattgtaca attttttacc attgaaaaaa attttttgata   10980 ttttttttca aatttaatat cttttttgata gtcatgacat gttgctagac atcaatcttg    11040
acttgtgggc tcacaaaaat taaaaagatt ttatttgaaa gttaattaga aagtattctg    11100
attaattgat gtatttggac tgacctaatc taattggatt gatttaggtc atgagcttga    11160
gcccactgct ggctagatga tcgctgtcgt aggcagtcaa gaataaaaat caactcaaac    11220
tatatagata gggtgagtag ggatcatttc tatggagatc taggatgatt atctttttttt   11280 ttaagaaaaa ataaaaagag aattgattgt agaagaatta aaagaaatag aatagcaaga    11340
attaaattaa aagtatgaat taatttatga aaaaaaataa gtcagagaaa taactcagaa    11400
attttgaatc caccatgcaa attagattta ttttcttctt ttttttatgt tgcaacatta    11460
attcttgtga ttaaggtatt agtatagctt atctctaaga gatacggact gtatcagtag    11520
attacaactc gtcctgttga agtataaact atctaaattc aattacaaaa tataagattc    11580
aatctaacat actacgatct atctctccaa agcacgtatc gtatctaggg atcacgatac    11640
gtcaatagag ggtataagcc gtgtaggctg gatcaatacc tcaaaaaaaa ataaaaagat    11700
```

-continued

| | |
|---|---|
| atgaaataaa agtataattt tattacataa aaatttaata taaaaaaaaa ccgtttacag | 11760 |
| gctttatcat atttctggat tgaagagatt tagccacgca tcaagctctc tagctccata | 11820 |
| atctctcaat aattgatccc taaagctctt taattttttt tttattatt tttttgtttt | 11880 |
| ttctttaatt tttttctctt cttattttg ctgccatctg ctgcctctgt tttctctgct | 11940 |
| cctgctgcct cctttatag agcacagctt cttcgaatta taagcatcta tggactttca | 12000 |
| attcccacta tcttttattt tgattgggat tttaaaactt tatccgcatc ccagcatctt | 12060 |
| gtttcacgcg agatcctagc gtccacatgt gttttgaatt cctatgggc cacagaccat | 12120 |
| ttaaaccacc aaagaccact ttactatttt gatttgaatc ccatggaagc cggctgcctc | 12180 |
| tggtctcatt caccctcca gtgcttcaca tgggtcccat taatttgaat tcctatgagc | 12240 |
| cacatccaag cttttgaatc caagccttcc ttattttta aatcaattaa aactttgctt | 12300 |
| taaatgcctt gtagaccctc ctatttgcat gctacgtgag aacattgtta agctcctctt | 12360 |
| ggcccactta agaacttcta tgggctacat gcttttggct agcttaaaa tggttttggg | 12420 |
| cctaactttg gatcaccatt cgaagtccat tttgaattca atttattttt attttttttt | 12480 |
| ttaacctaca aatcgagctc ttttattggt gatcattttt cctataaaac aaaaacaaaa | 12540 |
| agcatcaagt cttaagaaat aaaagttaat taatatatat tttgatactt ttattgggat | 12600 |
| atttaatgta cttatcacta gatatgaaat ccaatgggtc acacactttg aaatttgatc | 12660 |
| ttagtctaat ctaactagga tttattataa atcttatggg ttaaatttac atgctagcac | 12720 |
| atgaattaac tcaagttttc aattggattt agttctaagg tgtttgagct aaccctatcc | 12780 |
| tgatacctta aacctaatta gattagattt gaacctatgg ttttcttgat gccttatgct | 12840 |
| tattacatga aagagtttca tgtgacttaa attcctccat gccaccacat cttcatccat | 12900 |
| gccaaattaa tatggaacac cccatttaat tgtgcattta agaaggaata gtccttctta | 12960 |
| aacactcctc ttaatttccc acactttcct ttgttctaca caccatcaaa tggcttttgg | 13020 |
| aaatatgcgg gcgcagaagt ggaggtgtcc tatatgaagg ctcttccaca ttataagtta | 13080 |
| tcacatggtg aattaaatta ttgtgtgaga aaatcatgcg ccaagagttg cacccttg | 13140 |
| ggagttttag gcactccttc ttatcctata aataagggc acccacatatg gataaataca | 13200 |
| agggaattca gtttaggca tgagattgag aggagaaaaa gacacaaaaa tctgaaaaaa | 13260 |
| agataagaaa aaaaagaga gaaaatagaa agaaaagac gagagaaaac gaaaggcaag | 13320 |
| ggttgctaat cctagggttc aatttttcaa tagttggatt tctgaatcaa tttggggtgg | 13380 |
| tgagattttt tgagaaaaag tttctgatgt ggccctagta gaagattgaa ggcattcaga | 13440 |
| tgatggtgca atccgttttt gaaaagaaa agtgagtagt atacttgtga agaaagctgc | 13500 |
| aacactacat caaattggaa aggaccttga tcaaacccat atggatcacc gttgcaggat | 13560 |
| atctactttg gtatcttgtg aaggttattt tttttatcag atcatcatct tcaaaaaggt | 13620 |
| ataattttct acctaatatg catgcttgat ttgtttgatt aaaatctata aagtgttcat | 13680 |
| aaggtttgtg ttctgattgt attgttttaa gtattaaaac ttactttaaa aatataaaaa | 13740 |
| aatttgaaaa ctatcttcta ctgtgcaact aaaatccaac agaataaccc taatatgaga | 13800 |
| ttgagcgatc tccgtcaacc gatgttctct gatcttcttt tcttgaatga agcctcttca | 13860 |
| agcctttctt cttctctctc tctccctatc ttcttttgtg gcccacggcc tcctcttctt | 13920 |
| tttatgtttt gtatttctca tgtcacatcc ataaactccc ttttatagat aaaaaattag | 13980 |
| agtccatttt ggactccttt tccatgcttc ccacgccatt ggttctgtgc acacgacttt | 14040 |
| ttccatgcta caaaagtttt tcatgtctca cgtagtttcc atgcgccata aaattttgca | 14100 |

```
tacttctcca agacttttta tgctcgaccc tttttggttt tcatttaaat cagtgggtcc    14160
catatgacga gggatcacac caacatcata tgctctcctc accataccaa atggtatccc    14220
caacta                                                                14226

<210> SEQ ID NO 71
<211> LENGTH: 61
<212> TYPE: DNA
<213> ORGANISM: Artificial Sequence
<220> FEATURE:
<223> OTHER INFORMATION: synthetic

<400> SEQUENCE: 71
tttgggtcaa gctttaggct taggtcacat atacccaaaa tcatttggat gcatcaggtg     60
t                                                                     61

<210> SEQ ID NO 72
<211> LENGTH: 61
<212> TYPE: DNA
<213> ORGANISM: Artificial Sequence
<220> FEATURE:
<223> OTHER INFORMATION: synthetic

<400> SEQUENCE: 72
ttggctttgc tgcctcaaat cctcgagcta tcttatcatc atcgcattga gctccatacc     60
t                                                                     61

<210> SEQ ID NO 73
<211> LENGTH: 4061
<212> TYPE: DNA
<213> ORGANISM: Artificial Sequence
<220> FEATURE:
<223> OTHER INFORMATION: synthetic

<400> SEQUENCE: 73
atcaaatcat atgatccatc ttaaatttt aactcaaaaa attaatattg caaactagct     60
caaaataatt ttgatcacta catttctgct gtgcattcta atttaaaccg ttcacatttt    120
ttagattcat gaaataattt tgaccaaagt attactccat actatagtca aaaaagatta    180
aaatattaga ttctaattaa agccaaagat aaactttga ttctcatcct taattttgcc     240
taaagtataa ttattttgat taaccccttaa gcgcaataac acattcaaaa ccaacagata    300
ggtttactat aatccaaatg aattaaatct taattctttt atcaattcat ttagacaatt    360
tcaaatcaaa attctataag taatatcaat aaaaaaaatt tttgatgctc caataagtta    420
gaacttaaat caaaatatat aagtaaaatt gatttaatca tctcttctaa agtttcttct    480
attaagatct ttaatatcta tcaaatacat tccacaataa tcatgcaaac cttttaaaaa    540
ttaaattctc aatgccttta ctacatttta acaccaagct cgataatagt gataaagaaa    600
catctagatc agctttataa tcaaaaattt tgacttacaa ttttacgtgt gtctcaaaat    660
cttgaataaa tataaataag atcttttatc ttgatccaaa aatagtaatc aaggatttca    720
ttagtaactt caacaacaat ggtaaaaaaa ttttctatcc attgataaac ccaaattttg    780
aattgaagtt tcatgcatac catatagcct ttaataagat ctattatttg gatctaaaga    840
tagtaattaa aattgttaat gattccacta agatgaatac tttacaatct cataattaat    900
ttcttcaata aaaatagact tcttgataat gtctccaatt gtatatttt ttttatttct    960 acaagaaaac ttcatacatt ttttacgttc caatataaat cttaaaaagt tattccaatc   1020
```

| | | | | | |
|---|---|---|---|---|---|
| aaatatcata | aaagatcttc | ttagtccaac | cttaaataac | ttttatgaat | gaatctttat | 1080 |
| cttgccacta | aataatgaat | tttaaaatca | agagcaacat | cacagcattc | tgtcatgtca | 1140 |
| aatttgtgtt | agatgtatgt | cctagaaatc | aattagattg | acaatgtaaa | ttttttaagg | 1200 |
| atataattta | tatattttga | tttattaata | aaataaaatt | taaattaatt | tttattcata | 1260 |
| ttttttatc | tatgaatcat | ctaaagaatt | aataagatga | tgatacatat | tcttaagagt | 1320 |
| tcaaaatttg | aaatatatgt | cattgatgat | taatttctga | atactttga | attcttaaga | 1380 |
| gtttagaaga | tcttgaccca | agtagtgtga | atagtgaaaa | aaagttttca | catacttcac | 1440 |
| atcaaaaatt | taagttgaat | aaattgtaca | tatgacaggt | attatagttt | gacgagtaat | 1500 |
| ctataacctc | tatcttatca | aaattctgat | agaaagattg | tattgtatga | taactgtact | 1560 |
| tagaggttca | ccttttattt | tactggatta | ccactacatg | ttgctagatg | tcactggtgg | 1620 |
| attgtgagat | ctacgaagat | tatcttgatg | atcgataatt | ctcattgaaa | agattgaaac | 1680 |
| tattttaatg | atgttgtgat | agagatcata | atatatctta | ttatcagaca | gaatagaatt | 1740 |
| ctatgggatc | atacacaata | ggagattaag | actgatcaaa | tagttgaatg | atgattaaga | 1800 |
| atcattacgg | agttcagatt | atcaatataa | ttgataatta | gactaactta | taattgttac | 1860 |
| aagtagcaag | gacttaactg | ctaaaggtta | ataggttcaa | aaagaactta | tgtataaatg | 1920 |
| ttgtgcatct | taatttgatt | ggatcaaatt | agttatggct | gaattcaaga | tgaatcaaat | 1980 |
| aggaatttgg | ttcaattgaa | tttgggtcaa | gctttaggct | taggtcacat | atacccaaaa | 2040 |
| tcatttggat | gcatcaggtg | tgtgacacct | gaatcaggcc | tttctaaact | attttgagta | 2100 |
| agtttgatca | agtcaaaagg | atccacaccc | taaggtttct | tgaataaaac | cttaggcacc | 2160 |
| acattgagga | cctataggaa | actttgaccc | tctctcatat | ggggtggcac | actgaggttt | 2220 |
| tataaaaacc | ttaggcaccc | attttagcca | taaaaaaaaa | gctccaaggg | atggggcagt | 2280 |
| agccatgaag | aatccttggc | tgtcaggact | ctattcaaaa | gagttctcaa | ggttttggac | 2340 |
| tcttatggag | ccctaggatt | tgtttgccta | taaatagatg | gccacccaa | ggctttagat | 2400 |
| aatgttagag | acttgtgaag | ctctccctt | tctcttggtt | gccggcccac | cctctctcct | 2460 |
| ctctcttcca | tgccccaaga | cttctttctt | gtctccatca | tcttgctgaa | atttagattt | 2520 |
| cagcaagaaa | agtcaagtag | aagtcaaagt | tctaatgtag | ctcacaagat | gttgagaact | 2580 |
| tcctccatct | ggcaaaggtt | ctgcaagaga | gctagcatcc | tgagaaacaa | aaagattgct | 2640 |
| gatcagccct | catctccata | tggatatttg | tagagatcaa | atgcatgcat | agctagaaga | 2700 |
| gaatcttatc | acgatcatca | ctcgtgaaga | tcatctacct | gtgcaaaggt | atgagataag | 2760 |
| aaaaatattt | ttttttatcat | aattcatgaa | tcctttgctt | atattatact | gagattcttg | 2820 |
| gaatggattt | tttctctagt | aaaactctag | agatcagatc | tcaaagtctt | cttcacataa | 2880 |
| aggttttgaa | agttctttat | atttccgctg | ctttgattca | aaataaatta | gatctatttt | 2940 |
| gcctttcaac | ctttctcata | tttattgaca | tataaagctt | taattaatga | gattaatgaa | 3000 |
| aagcatgtgc | gaaatactga | gaaaatccta | acagtgatat | cagagctact | tttgtacata | 3060 |
| agaaaaggat | tcaagttaaa | taaaatatgt | ttgatttaag | taaatgaatc | aatcaaaatt | 3120 |
| tatcctaaca | taagtttgtc | ctggtataat | ggtcaagacc | attatgttga | aaggttatcc | 3180 |
| taggacaaaa | agtctaagta | aaatctatt | tatttaagta | aatgaatcaa | ttaaagttta | 3240 |
| ttctaatata | agattgcctt | agcataatgg | tgaagaccct | tatgttgaaa | ggttgtccta | 3300 |
| ggatggaaag | tgattgatga | gacaaatata | tcatgaaagt | attttcaca | gatggaataa | 3360 |
| aatatatata | ttttgtttgt | gaaaatgaga | tttcatgaat | gtgtttgtca | ttcaatatgt | 3420 |

```
gtggtgatca tcttgaattg ccacaaatcc ttttggatt agggttgtat catgactcac    3480
aaatcctgat ggtttgcaaa attttgcatt ctgtagtgat agaaaccaaa agttaatcca    3540
attttggaat aagattgatc aattggtatc taaggcaagt attttataat ggtggttact    3600
taattagtta taaaagtacg aagagtctcc taccaatctt acacttatct agccaatttg    3660
gttgattgaa ttctgaattt gggttgctta agtgttaagt tcactacaaa tatattgcaa    3720
ccatgattcc gacttagtca accaagccta gatctcttga atagattcat gttaattatg    3780
gatttacata ggatataaat aaataattaa aacttgaaga gatctaaatg aaaccttctc    3840
gtacatatta aatcgaatga tcttccatca ttgtagatat acggatactc tactgatgtt    3900
gatgattttc gactagatat agtactttgg ttgcatcgaa aaagtacaac cactttataa    3960
catgagatgt tgcagggtag agatgggggtt gggcccaata attgttaggt gaggatccaa    4020
atgatggctg cacttgcgtg tgaatggcga gtctgactta a                        4061
```

<210> SEQ ID NO 74
<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (990)..(1717)
<223> OTHER INFORMATION: n is a, c, g, or t

<400> SEQUENCE: 74

```
tataactgaa agatagctaa tgcttagctg gatgactgct gttagataac tgtctgcatt      60
cttacggtac attgatattt taccaatgtg acatagctta aatcggcaac tggctgaact     120
aaatattatg tatcccttta gttaacaatc atgtcggtta gagatcaatg taattcgcag     180
cagatcgatc ataagctgag atgagtatca tattttaaga acaacgctgg gcgagttagg     240
ccgatcaaat gtcagactga aaaagcagat caataaacct ctgatgtgat ctgaaagaat     300
atttatgatt taaataataa tctatcacca cgtatccaga taatgaggtc atataacatg     360
taccaacagt gcattttttcc atctagttaa gaggttggtt agtggcattt gtcttcgata     420
tgtaatgttc acataactaa tgtgcttagt agcattcttt tgtaaggtta aatcttcaat     480
gatcttaagt tcacataatt gcctttgtgc cctattagtt tatagttgac cttttaattc     540
aagagacagt caccttagca atcgatgtct gcttagattg ggccaattag gtactcacat     600
taatatattg aatcatgttt gaatataaag gattagattt atttataagt ttccttttat     660
tgtttacata ctgatactta gattgactta ctacattatt tgatatgtta tgttctaatt     720
tttggattaa aattgttgtt tctgatttct ccttacatct aatactttgt ataatttatt     780 atttttttagc atgattgagt gtagaggatt agattgattt ttaagtttat tttgattatt     840
tacatgccca tacttaaatt gacttactac attattcaat atgttatgtt tcaattattg     900
agttaaaatt tttatttctg atttctactg atgtccagtg tgtgtgtgtg tacgtatgtg     960
tgtatatatt tatttacata tatatgtatn nnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
```

```
nnnnnnnnnn nnnnnnnnnn nnnnnnnnnn nnnnnnnnnn nnnnnnnnnn nnnnnnnnnn      1320
nnnnnnnnnn nnnnnnnnnn nnnnnnnnnn nnnnnnnnnn nnnnnnnnnn nnnnnnnnnn      1380
nnnnnnnnnn nnnnnnnnnn nnnnnnnnnn nnnnnnnnnn nnnnnnnnnn nnnnnnnnnn      1440
nnnnnnnnnn nnnnnnnnnn nnnnnnnnnn nnnnnnnnnn nnnnnnnnnn nnnnnnnnnn      1500
nnnnnnnnnn nnnnnnnnnn nnnnnnnnnn nnnnnnnnnn nnnnnnnnnn nnnnnnnnnn      1560
nnnnnnnnnn nnnnnnnnnn nnnnnnnnnn nnnnnnnnnn nnnnnnnnnn nnnnnnnnnn      1620
nnnnnnnnnn nnnnnnnnnn nnnnnnnnnn nnnnnnnnnn nnnnnnnnnn nnnnnnnnnn      1680
nnnnnnnnnn nnnnnnnnnn nnnnnnnnnn nnnnnnnatg tatacatata catgtataca      1740
tacatatata gatatatata tatacatata tgtatatata tatatatata tacacatata      1800
taggttattt ggaacctaag aaacttgcaa agttactaga tgcaatgttc ggaaaccatg      1860
gaccgtaaca actggagtag tatttgggtc atgaattcat ggctagatca tgaattgagt      1920
gggagtcaac cgaagtaggg ccagctcaga cacttgtatt taggtcccat gcttgcgtgc      1980
attctcttcc ctgatatcct ttggcttttgc tgcctcaaat cctcgagcta tcttatcatc      2040
atcgcattga gctccatacc ttgctctttc ctaactgccc ccatcaaacc tccggagatc      2100
ctctttcttc tccaatgttg agatttgttg gagtcttccc accttctcac ttcaatgggt      2160
ggcaatttca agtgccagtt cccttatttg tcccagctat attgacaatg gggcttattc      2220
tagggtttct catggacata gtgataataa taatcaaggg accaagagag aaaaatcttt      2280
ctagtctgtg ttctttaagt ttgagagata ggcagcacat ttttttaata agcctttttc      2340
actcatcgga tcctgatttt cagttgttcg acctgaacag ttcaagcaat tgaactgctt      2400
gggtcactat tttggacgat tttcagccat ttttaagtat tgtttgactg gatccacgct      2460
gcgtagtggg cattgcgttg atcaagtaga cctgtaaggg tcaacaaggt ctgagaacac      2520
tgaatggatg ctccataatc ctcttgttat ctgtcaacca tttggaatct tttaaaacaa      2580
catgtggtga taatatatat gataaactgt gatagattca tgtatagatt atacatatga      2640
aaatgtagag tgcttagtaa aagtgatgaa gagcaatgcg ttagaatgtg ctagcctttg      2700
acctaaaaat tggaatgccc aatgatgagt tatgataaaa ttgtgacgtg atttatgaag      2760
tctaatgttt agttggcttg cagtttcaga tgcgataaag aattttatga tttagctctt      2820
tggtttttta acatgcaaac atttaattgt actgaaaaac atttatttcg aaacatgtag      2880
gagactattg gatattgaaa ttaaaattga ctttttggtg tttcacaata tttcttaata      2940
aacactacga ctatgtaaat aggtggtgga tcaaagggaa agaaatgttt ggtgattatt      3000
tttagaaaag acaagaagta tttgataaat ggttattttt caaccgatta atgagagaat      3060
gactatgaac ctatgaggtg cacctcttat gatgttgcat ggatgaagca tctaatccat      3120
gggtacaatt tactaaaata taggcccaat tctgagacag gaacatttac aactcatgta      3180
caaagaagaa acttaaagta tcatggatgc cgggatattt ccttcttcaa atctttcaaa      3240
agctgtagtt ttcattataa ggaaaaatga ttataactaa catcttctat aggtgatgag      3300
tggacactag aaggctttcc tataataaca gtagagagag tagaaaagcc tgtcagcatg      3360
cggtccataa gtatatatac atattttcag cgcttaaagt aaattttctt gtaccaaaaa      3420
aagataaatt ttcaaaataa aaactaaaat caactgaaat gtttgaaatc tgattcgtag      3480
gtacatggag aagagtgtaa gacagcaaat atcataaagg cagaataaga gctggtaatc      3540
ttgtaacctg gcgcaactat gttatgcatg tctatatgtg tgcatgttta tgtataacaa      3600
gtaatatttc ttttcttatt tactcacttc agttaggaag tcaatccaat ctcccttttgc      3660
```

```
ttgggtgtgt tcagattatc aagggccata acagtagtgc tggtaagcac ctgtttaatg    3720
gataaatggc gacaaattct ctccccttct gctcactcta ttatcatacc ttccgtctta    3780
cccatctgct atatcttata aggaacataa ggatcgacat agcttcatgc tatcacatta    3840
caagctaaga tcggaataat acctaatctt ttcgatctac tattaggtat tactataggg    3900
ttgtaaattg ggtttaggtt ttgaactata ttatattttg gtgtaagaat atagtgccac    3960
actatcttga accagactag ctgttgcact tttttgcag gcatcaatat tttgttcatc     4020
caaaaaaaaa tattgcacat gcacagatga agtatgaggg c                       4061
```

<210> SEQ ID NO 75
<211> LENGTH: 680
<212> TYPE: DNA
<213> ORGANISM: Artificial Sequence
<220> FEATURE:
<223> OTHER INFORMATION: synthetic

<400> SEQUENCE: 75

```
atggggaggg ggaagataga gatcaagaag atagagaatc ctacaaacag gcaggtgacc      60
tactccaaga ggaggacggg gatcatgaag aaggctaagg aactgacggt gctttgcgat     120
gctgaggtct cgcttatcat gttctccagc accggcaagt tctccgagta ttgcagcccc     180
ctttccgaca ccaagaccat atttgatcgc taccagcagg tgtcagggat caacctgtgg     240
agcgcccaat acgagaaaat gcaaaacact ttgaaccatc tgagggagat caaccagaac     300
ctccgcagag aaataaggca gcggatgggt gaagatctcg acagtttggg catccatgaa     360
ctgcgcggtc ttgagcaaaa tttagatgag gctttgaagg ttgttcgtca gaaaaatac     420 catgtgatca ccacgcagac ggataccta aagaaaaagg caaggctaac atgctttctt     480
accatcattc tttacggtct ttgatccggt tttgcgtgtc acttcttac gtagtctttt     540 tcaaacattc ctatctaaga ctgaaggtaa tgatttgcaa aggaatagct ttactgtttt     600
cctctaagta gatgaaatat tactcacgta gaaaggagcc atcataattg cagaaagaat     660
aaaactgaat ggaatatgag                                                680
```

<210> SEQ ID NO 76
<211> LENGTH: 167
<212> TYPE: PRT
<213> ORGANISM: Artificial Sequence
<220> FEATURE:
<223> OTHER INFORMATION: synthetic predicted sequence of tDEF1

<400> SEQUENCE: 76

```
Met Gly Arg Gly Lys Ile Glu Ile Lys Lys Ile Glu Asn Pro Thr Asn
1               5                   10                  15

Arg Gln Val Thr Tyr Ser Lys Arg Arg Thr Gly Ile Met Lys Lys Ala
            20                  25                  30

Lys Glu Leu Thr Val Leu Cys Asp Ala Glu Val Ser Leu Ile Met Phe
        35                  40                  45

Ser Ser Thr Gly Lys Phe Ser Glu Tyr Cys Ser Pro Leu Ser Asp Thr
    50                  55                  60

Lys Thr Ile Phe Asp Arg Tyr Gln Gln Val Ser Gly Ile Asn Leu Trp
65                  70                  75                  80

Ser Ala Gln Tyr Glu Lys Met Gln Asn Thr Leu Asn His Leu Arg Glu
                85                  90                  95

Ile Asn Gln Asn Leu Arg Arg Glu Ile Arg Gln Arg Met Gly Glu Asp
            100                 105                 110
```

```
Leu Asp Ser Leu Gly Ile His Glu Leu Arg Gly Leu Glu Gln Asn Leu
        115                 120                 125

Asp Glu Ala Leu Lys Val Val Arg His Arg Lys Tyr His Val Ile Thr
    130                 135                 140

Thr Gln Thr Asp Thr Tyr Lys Lys Lys Ala Arg Leu Thr Cys Phe Leu
145                 150                 155                 160

Thr Ile Ile Leu Tyr Gly Leu
                165
```

<210> SEQ ID NO 77
<211> LENGTH: 1850
<212> TYPE: DNA
<213> ORGANISM: Elaeis guineensis

<400> SEQUENCE: 77

| | | | | | |
|---|---|---|---|---|---|
| aaatcagcta | atgtagacca | tctgaactac | ttgttcatca | cccttatccc | aaaaaaaaat | 60 |
| tggtgtgtat | tcagttagag | acttcaggcc | aataagcctg | attaatggag | taataaaaaa | 120 |
| tatttcaaaa | actctatcga | aaaggctctc | acagaaaatg | aatttgttaa | ttttatccac | 180 |
| agagcttgct | ttcaacaaag | gaagaaatat | ctctgaatat | tttgtaatga | ctatggaaac | 240 |
| tatacacttc | tgcaaagctg | aagtacacaa | ggatctcaat | tataaagtcg | acttcgagaa | 300 |
| agcttttgac | aatgtggatt | ggagcttttct | attgaaattg | ctatccagca | cggggctttg | 360 |
| attcgaggtg | gtgtcaatgg | atagaatatc | tgatttatac | agctaaattc | tcagtcctta | 420 |
| ttaatggtga | taaaggtaaa | cttttttaaat | tgaggaaaga | tctcaggcaa | ggagatcctc | 480 |
| tattcgccta | gctctttctc | ttagttgttg | atatagaatg | atcaagggag | caagtaggtt | 540 |
| caatcttttt | gttggaattg | gatcatataa | tatcatggga | taacttcaaa | gcttttagtt | 600 |
| cactgatgac | acacttatat | tttgcagata | tgatctaaaa | tacatcaaaa | ctcttaaatt | 660 |
| tttactctat | agttatgagc | tactgatggg | tctcaaaatt | aactttgaaa | aattccaatt | 720 |
| ttttggcttg | agaattgcaa | agatgtcagt | acagcaagtt | gcatctatcc | tagaaagcaa | 780 |
| ggtggctaca | ttttccatta | cttatttggg | tctcccactc | catcattcta | aactgaggaa | 840 |
| aacttattgg | aatccactcc | ttgagaaggt | tcagaagaaa | ttgatcgggt | agaaaggtaa | 900 |
| acttcttaac | ctctagggta | ggcttatact | aactaatgca | gtgcttacag | ggatcccact | 960 |
| actctggagg | gatacattcc | ttctccctca | attcattatc | aaataaattg | ataaaatcca | 1020 |
| tcgatcattc | atttggagag | gaaacgagga | gtataactaa | gggcactcta | gaatatgttg | 1080 |
| gtcgaatatt | tgtcgatcaa | aaaaatttgg | aggactgggg | gttcctcaat | ctaaaaattt | 1140 |
| tcaatacaat | tcttctttgt | aaatggtggt | ggaagctcta | ctctaatgct | ggtgacccgt | 1200 |
| ggtgtagttt | tattgccact | atccacccaa | cttcacacta | gagatctaaa | ggtatacaca | 1260 |
| aatcaacctc | ttcattttgg | aatggtttac | agcacacatg | aaatatttct | actcctaatc | 1320 |
| cactttcaag | ttagcaacta | gtattatttt | ggaaagatag | ttggttacat | aatcatccac | 1380 |
| tgaaggatcg | atttcctcac | ctttacacaa | tagcattgaa | gtgcaacaac | tcagtggcaa | 1440 |
| aggtattaag | caatctactt | gataatagct | cttttagtac | tcctcttcct | caaagatacc | 1500 |
| aagaagattt | tcagagtcta | taggaaagca | ttgaacaaat | tacattaacg | gaacgacctg | 1560 |
| atactataca | atggaaatgg | tttagtagca | atattttttt | ggcatgaagg | atctactatt | 1620 |
| ttctgcaaga | tggaggagtt | tggcctctac | tgagtaatat | tatataaaaa | ctcctaatac | 1680 |
| caaagaaagc | caagttattt | gcttggctaa | gtgctcacaa | caaaatccca | atgaaagcta | 1740 |

```
atcttcttaa tagaggaata attggaactg attactgtac actttgcgat gacttatcag    1800
aaactaatga tcatctaatg ctcatctata cttttcaaa agcaatttgg                1850
```

<210> SEQ ID NO 78
<211> LENGTH: 498
<212> TYPE: DNA
<213> ORGANISM: Artificial Sequence
<220> FEATURE:
<223> OTHER INFORMATION: synthetic

<400> SEQUENCE: 78

```
atggggaggg ggaagataga gatcaagaag atagagaatc ctaccaacag gcaggtgacc     60
tactccaaga ggaggacggg gatcatgaag aaggctaagg agctgacggt gctttgcgat    120
gctgaggtct cgcttatcat gttctccagc accggcaagt tctccgagta ttgcagcccc    180
ctttccgaca ccaagaccat atttgatcgc taccagcagg tgtcagggat caacctgtgg    240
agcgcccaat acgagaaaat gcaaaacact ttgaaccatc tgagggagat caaccagaac    300
ctccgcagag aaataaggca gcggatgggt gaagatctcg acagtttggg catccatgaa    360
ctgcgcggtc ttgagcaaaa tttagatgag gctttgaagg ttgttcgtca cagaaaatac    420
catgtgatca ccacgcagac ggatacctac aagaaaaaga tgcatctcaa gtcagcacta    480
gaccatcttc taaaatag                                                  498
```

<210> SEQ ID NO 79
<211> LENGTH: 165
<212> TYPE: PRT
<213> ORGANISM: Artificial Sequence
<220> FEATURE:
<223> OTHER INFORMATION: synthetic

<400> SEQUENCE: 79

```
Met Gly Arg Gly Lys Ile Glu Ile Lys Lys Ile Glu Asn Pro Thr Asn
1               5                   10                  15

Arg Gln Val Thr Tyr Ser Lys Arg Arg Thr Gly Ile Met Lys Lys Ala
            20                  25                  30

Lys Glu Leu Thr Val Leu Cys Asp Ala Glu Val Ser Leu Ile Met Phe
        35                  40                  45

Ser Ser Thr Gly Lys Phe Ser Glu Tyr Cys Ser Pro Leu Ser Asp Thr
    50                  55                  60

Lys Thr Ile Phe Asp Arg Tyr Gln Gln Val Ser Gly Ile Asn Leu Trp
65                  70                  75                  80

Ser Ala Gln Tyr Glu Lys Met Gln Asn Thr Leu Asn His Leu Arg Glu
                85                  90                  95

Ile Asn Gln Asn Leu Arg Arg Glu Ile Arg Gln Arg Met Gly Glu Asp
            100                 105                 110

Leu Asp Ser Leu Gly Ile His Glu Leu Arg Gly Leu Glu Gln Asn Leu
        115                 120                 125

Asp Glu Ala Leu Lys Val Val Arg His Arg Lys Tyr His Val Ile Thr
    130                 135                 140

Thr Gln Thr Asp Thr Tyr Lys Lys Lys Met His Leu Lys Ser Ala Leu
145                 150                 155                 160

Asp His Leu Leu Lys
                165
```

<210> SEQ ID NO 80
<211> LENGTH: 459
<212> TYPE: DNA

<213> ORGANISM: Artificial Sequence
<220> FEATURE:
<223> OTHER INFORMATION: synthetic

<400> SEQUENCE: 80

```
atggggaggg ggaagataga gatcaagaag atagagaatc ctacaaacag gcaggtgacc    60
tactccaaga ggaggacggg gatcatgaag aaggctaagg aactgacggt gctttgcgat   120
gctgaggtct cgcttatcat gttctccagc accggcaagt tctccgagta ttgcagcccc   180
ctttccgaca ccaagaccat atttgatcgc taccagcagg tgtcagggat caacctgtgg   240
agcgcccaat acgagaaaat gcaaaacact ttgaaccatc tgaggagat caaccagaac   300
ctccgcagag aaataaggca gcggatgggt gaagatctcg acagtttggg catccatgaa   360
ctgcgcggtc ttgagcaaaa tttagatgag gctttgaagg ttgttcgtca cagaaaatac   420
catgtgatca ccacgcagac ggatacctac aagaaaaag                          459
```

<210> SEQ ID NO 81
<211> LENGTH: 153
<212> TYPE: PRT
<213> ORGANISM: Artificial Sequence
<220> FEATURE:
<223> OTHER INFORMATION: synthetic

<400> SEQUENCE: 81

```
Met Gly Arg Gly Lys Ile Glu Ile Lys Lys Ile Glu Asn Pro Thr Asn
1               5                   10                  15

Arg Gln Val Thr Tyr Ser Lys Arg Arg Thr Gly Ile Met Lys Lys Ala
            20                  25                  30

Lys Glu Leu Thr Val Leu Cys Asp Ala Glu Val Ser Leu Ile Met Phe
        35                  40                  45

Ser Ser Thr Gly Lys Phe Ser Glu Tyr Cys Ser Pro Leu Ser Asp Thr
    50                  55                  60

Lys Thr Ile Phe Asp Arg Tyr Gln Gln Val Ser Gly Ile Asn Leu Trp
65                  70                  75                  80

Ser Ala Gln Tyr Glu Lys Met Gln Asn Thr Leu Asn His Leu Arg Glu
                85                  90                  95

Ile Asn Gln Asn Leu Arg Arg Glu Ile Arg Gln Arg Met Gly Glu Asp
            100                 105                 110

Leu Asp Ser Leu Gly Ile His Glu Leu Arg Gly Leu Glu Gln Asn Leu
        115                 120                 125

Asp Glu Ala Leu Lys Val Val Arg His Arg Lys Tyr His Val Ile Thr
    130                 135                 140

Thr Gln Thr Asp Thr Tyr Lys Lys Lys
145                 150
```

<210> SEQ ID NO 82
<211> LENGTH: 21
<212> TYPE: DNA
<213> ORGANISM: Artificial Sequence
<220> FEATURE:
<223> OTHER INFORMATION: synthetic

<400> SEQUENCE: 82

```
tgatatgaag ggtttcaagg t                                              21
```

<210> SEQ ID NO 83
<211> LENGTH: 25
<212> TYPE: DNA
<213> ORGANISM: Artificial Sequence
<220> FEATURE:
<223> OTHER INFORMATION: synthetic

<400> SEQUENCE: 83
tcctatttta gaagatggtc tagtg                                          25

<210> SEQ ID NO 84
<211> LENGTH: 576
<212> TYPE: DNA
<213> ORGANISM: Artificial Sequence
<220> FEATURE:
<223> OTHER INFORMATION: synthetic

<400> SEQUENCE: 84
tgatatgaag ggtttcaagg tggtttgcct cgttcaaatc aaaggatttt gaagattaat      60
attccaagat aaggttctcc aactccatta ggaaagtgtc ttcatgtcat cttagagaag     120
cagctcgtac caaacttgac agatgtttta tttatttaga gtgacacaga tacccttggg     180
caatactctc catccttgtc cgaacaactt ctaatcacac ctcacttatc ttgcatctaa     240
ctcagaggct acaagttaca cctttcaaca aaccttttcg gtttgaaaat ttgtgatttc     300
attatttaga gttcgaagag catatcaagt attggtcgga gttggcaccc aaagcaaacg     360
aaacagttac tgacatggtc caaaagctga gatttctaag atcccaactt aagcactgaa     420
taaagccatt atgggaaata tcattttaac gaaagaggaa tttagagtaa gaattgattc     480
tcttgatacc gaagaagaac taatacagct ttcatcactt caaaatgatg aacagatgca     540
tctcaagtca gcactagacc atcttctaaa atagga                              576

<210> SEQ ID NO 85
<211> LENGTH: 22
<212> TYPE: DNA
<213> ORGANISM: Artificial Sequence
<220> FEATURE:
<223> OTHER INFORMATION: synthetic

<400> SEQUENCE: 85
agaattgatt ctcttgatac cg                                             22

<210> SEQ ID NO 86
<211> LENGTH: 24
<212> TYPE: DNA
<213> ORGANISM: Artificial Sequence
<220> FEATURE:
<223> OTHER INFORMATION: synthetic

<400> SEQUENCE: 86
ttttattact ccattaatca ggct                                           24

<210> SEQ ID NO 87
<211> LENGTH: 633
<212> TYPE: DNA
<213> ORGANISM: Artificial Sequence
<220> FEATURE:
<223> OTHER INFORMATION: synthetic

<400> SEQUENCE: 87
agaattgatt ctcttgatac cgaagaagaa ctaatacagc tttcatcact tcaaaatgat      60
gaacagatgc atctcaagtc agcactagac catcttctaa aataggaaga tctatggaag     120
caacactccc aaatgcagtg gcttcaaaat ggggattgca atacgaagtt tatccatgtt     180
tgggcaagta acaggaaaaa aagaatacta tcactgaact ctagcaaggc gatcagaaga     240

-continued

```
ttatcgaata gcagcaaatc caatccacat tctacaactt tttttctacc ctactaggct      300
cgactgagga atgactcatc caagctgatt ggaagattct ttatccagaa ggacctctgg      360
atcttgctga cattgagtat ccatttatgg agaaagaaat ccatgataca gtgtatgact      420
tggctttgga aaagtcaccc ggatgatatt ttcccattct ccttctataa gcacttctag      480
tgtatcatca acatgacct gatgaaccta ctgtaaaatc agctaatgta gaccatctga       540
actacttgtt catcaccctt atcccaaaaa aaaattggtg tgtattcagt tagagacttc      600
aggccaataa gcctgattaa tggagtaata aaa                                   633
```

<210> SEQ ID NO 88
<211> LENGTH: 20
<212> TYPE: DNA
<213> ORGANISM: Artificial Sequence
<220> FEATURE:
<223> OTHER INFORMATION: synthetic

<400> SEQUENCE: 88

```
gcaaggagat cctctattcg                                                   20
```

<210> SEQ ID NO 89
<211> LENGTH: 20
<212> TYPE: DNA
<213> ORGANISM: Artificial Sequence
<220> FEATURE:
<223> OTHER INFORMATION: synthetic

<400> SEQUENCE: 89

```
gatcgacaaa tattcgacca                                                   20
```

<210> SEQ ID NO 90
<211> LENGTH: 632
<212> TYPE: DNA
<213> ORGANISM: Artificial Sequence
<220> FEATURE:
<223> OTHER INFORMATION: synthetic

<400> SEQUENCE: 90

```
gcaaggagat cctctattcg cctagctctt tctcttagtt gttgatatag aatgatcaag      60
ggagcaagta ggttcaatct ttttgttgga attggatcat ataatatcat gggataactt      120
caaagctttt agttcactga tgacacactt atattttgca gatatgatct aaaatacatc      180
aaaactctta aatttttact ctatagttat gagctactga tgggtctcaa aattaacttt      240
gaaaaattcc aatttttttgg cttgagaatt gcaaagatgt cagtacagca agttgcatct      300
atcctagaaa gcaaggtggc tacatttttcc attacttatt tgggtctccc actccatcat      360
tctaaactga ggaaaactta ttggaatcca ctccttgaga aggttcagaa gaaattgatc      420
gggtagaaag gtaaacttct taacctctag ggtaggctta tactaactaa tgcagtgctt      480
acagggatcc cactactctg gagggataca ttccttctcc ctcaattcat tatcaaataa      540
attgataaaa tccatcgatc attcatttgg agaggaaacg aggagtataa ctaagggcac      600
tctagaatat gttggtcgaa tatttgtcga tc                                    632
```

<210> SEQ ID NO 91
<211> LENGTH: 24
<212> TYPE: DNA
<213> ORGANISM: Elaeis guineensis

<400> SEQUENCE: 91

```
ctctagcaag gcgatcagaa gatt                                              24
```

<210> SEQ ID NO 92
<211> LENGTH: 24
<212> TYPE: DNA
<213> ORGANISM: Elaeis guineensis

<400> SEQUENCE: 92
tcaggtgtta tgtcagtttg gact                                         24

<210> SEQ ID NO 93
<211> LENGTH: 24
<212> TYPE: DNA
<213> ORGANISM: Elaeis guineensis

<400> SEQUENCE: 93
aagtctccac tctatctatc ccga                                         24

<210> SEQ ID NO 94
<211> LENGTH: 24
<212> TYPE: DNA
<213> ORGANISM: Elaeis guineensis

<400> SEQUENCE: 94
gggtcaacaa ggtctgagaa cact                                         24

<210> SEQ ID NO 95
<211> LENGTH: 24
<212> TYPE: DNA
<213> ORGANISM: Elaeis guineensis

<400> SEQUENCE: 95
cgcaatcaga atcaactggc caat                                         24

<210> SEQ ID NO 96
<211> LENGTH: 24
<212> TYPE: DNA
<213> ORGANISM: Elaeis guineensis

<400> SEQUENCE: 96
atgatacacg gttgcatgcc ctgc                                         24

<210> SEQ ID NO 97
<211> LENGTH: 24
<212> TYPE: DNA
<213> ORGANISM: Elaeis guineensis

<400> SEQUENCE: 97
gatctatggt gcaaggagtt aatt                                         24

<210> SEQ ID NO 98
<211> LENGTH: 24
<212> TYPE: DNA
<213> ORGANISM: Elaeis guineensis

<400> SEQUENCE: 98
agagagaggg ttaaaggaca atgc                                         24

<210> SEQ ID NO 99
<211> LENGTH: 24
<212> TYPE: DNA
<213> ORGANISM: Elaeis guineensis

<400> SEQUENCE: 99 ataggagaa tagcttggct tcga 24

<210> SEQ ID NO 100
<211> LENGTH: 24
<212> TYPE: DNA
<213> ORGANISM: Elaeis guineensis

<400> SEQUENCE: 100
tcgggttctt ttattcgtgg attt 24

<210> SEQ ID NO 101
<211> LENGTH: 24
<212> TYPE: DNA
<213> ORGANISM: Elaeis guineensis

<400> SEQUENCE: 101
aggggagatt gttggcttag cttg 24

<210> SEQ ID NO 102
<211> LENGTH: 24
<212> TYPE: DNA
<213> ORGANISM: Elaeis guineensis

<400> SEQUENCE: 102
agtagactcg atgatgataa gact 24

<210> SEQ ID NO 103
<211> LENGTH: 24
<212> TYPE: DNA
<213> ORGANISM: Elaeis guineensis

<400> SEQUENCE: 103
accagcacgg tcaaggatag gcat 24

<210> SEQ ID NO 104
<211> LENGTH: 24
<212> TYPE: DNA
<213> ORGANISM: Elaeis guineensis

<400> SEQUENCE: 104
atagtagact cgatgatgat aaga 24

<210> SEQ ID NO 105
<211> LENGTH: 24
<212> TYPE: DNA
<213> ORGANISM: Elaeis guineensis

<400> SEQUENCE: 105
cctccaacat cggccaagtt agtt 24

<210> SEQ ID NO 106
<211> LENGTH: 24
<212> TYPE: DNA
<213> ORGANISM: Elaeis guineensis

<400> SEQUENCE: 106
aaatcctact tgtttctctg acct 24

<210> SEQ ID NO 107
<211> LENGTH: 24
<212> TYPE: DNA
<213> ORGANISM: Elaeis guineensis

<400> SEQUENCE: 107

```
catgaggcat gcaaggtatt gaat                                          24

<210> SEQ ID NO 108
<211> LENGTH: 24
<212> TYPE: DNA
<213> ORGANISM: Elaeis guineensis

<400> SEQUENCE: 108
aaggctggct aactcaaaga agag                                          24

<210> SEQ ID NO 109
<211> LENGTH: 24
<212> TYPE: DNA
<213> ORGANISM: Elaeis guineensis

<400> SEQUENCE: 109
aatgatcgag aagggctgga gaca                                          24

<210> SEQ ID NO 110
<211> LENGTH: 24
<212> TYPE: DNA
<213> ORGANISM: Elaeis guineensis

<400> SEQUENCE: 110
tgacccacca tcgagaagga ccga                                          24

<210> SEQ ID NO 111
<211> LENGTH: 24
<212> TYPE: DNA
<213> ORGANISM: Elaeis guineensis

<400> SEQUENCE: 111
ataactgaca agtggcattg atct                                          24

<210> SEQ ID NO 112
<211> LENGTH: 24
<212> TYPE: DNA
<213> ORGANISM: Elaeis guineensis

<400> SEQUENCE: 112
agaaggatga gaagagagat tgtc                                          24

<210> SEQ ID NO 113
<211> LENGTH: 24
<212> TYPE: DNA
<213> ORGANISM: Elaeis guineensis

<400> SEQUENCE: 113
aaagatgtta gctcctgttc gaga                                          24

<210> SEQ ID NO 114
<211> LENGTH: 24
<212> TYPE: DNA
<213> ORGANISM: Elaeis guineensis

<400> SEQUENCE: 114
aaaggctggc taactcaaag aaga                                          24

<210> SEQ ID NO 115
<211> LENGTH: 24
<212> TYPE: DNA
<213> ORGANISM: Elaeis guineensis
```

```
<400> SEQUENCE: 115
agagattgtg aacaaatgga gaga                                              24

<210> SEQ ID NO 116
<211> LENGTH: 24
<212> TYPE: DNA
<213> ORGANISM: Elaeis guineensis

<400> SEQUENCE: 116
atattgtctg ctcttcacca aaga                                              24

<210> SEQ ID NO 117
<211> LENGTH: 24
<212> TYPE: DNA
<213> ORGANISM: Elaeis guineensis

<400> SEQUENCE: 117
ctcgtaaggc ccaagggtag tcat                                              24

<210> SEQ ID NO 118
<211> LENGTH: 24
<212> TYPE: DNA
<213> ORGANISM: Elaeis guineensis

<400> SEQUENCE: 118
aaaatagctt gacccaccat cgag                                              24

<210> SEQ ID NO 119
<211> LENGTH: 24
<212> TYPE: DNA
<213> ORGANISM: Elaeis guineensis

<400> SEQUENCE: 119
atagaatagg gagaatagct tggc                                              24

<210> SEQ ID NO 120
<211> LENGTH: 24
<212> TYPE: DNA
<213> ORGANISM: Elaeis guineensis

<400> SEQUENCE: 120
tcctgtccag atatttgcgc ctct                                              24

<210> SEQ ID NO 121
<211> LENGTH: 24
<212> TYPE: DNA
<213> ORGANISM: Elaeis guineensis

<400> SEQUENCE: 121
acaactagcc aatgatcgag aagg                                              24

<210> SEQ ID NO 122
<211> LENGTH: 24
<212> TYPE: DNA
<213> ORGANISM: Elaeis guineensis

<400> SEQUENCE: 122
aacacactgc tgaaaggac tagg                                               24

<210> SEQ ID NO 123
<211> LENGTH: 24
<212> TYPE: DNA
<213> ORGANISM: Elaeis guineensis
```

<400> SEQUENCE: 123
aaactcatgg tgtcaaggga cgtg					24

<210> SEQ ID NO 124
<211> LENGTH: 24
<212> TYPE: DNA
<213> ORGANISM: Elaeis guineensis

<400> SEQUENCE: 124
gctacacagg cacaatctcg attt					24

<210> SEQ ID NO 125
<211> LENGTH: 19
<212> TYPE: DNA
<213> ORGANISM: Artificial Sequence
<220> FEATURE:
<223> OTHER INFORMATION: synthetic

<400> SEQUENCE: 125
ctttccgaca ccaagacca					19

<210> SEQ ID NO 126
<211> LENGTH: 24
<212> TYPE: DNA
<213> ORGANISM: Artificial Sequence
<220> FEATURE:
<223> OTHER INFORMATION: synthetic

<400> SEQUENCE: 126
caagtagcgg atagagaggc ttac					24

<210> SEQ ID NO 127
<211> LENGTH: 23
<212> TYPE: DNA
<213> ORGANISM: Artificial Sequence
<220> FEATURE:
<223> OTHER INFORMATION: synthetic

<400> SEQUENCE: 127
gttcgtcaca gaaaatacca tgt					23

<210> SEQ ID NO 128
<211> LENGTH: 21
<212> TYPE: DNA
<213> ORGANISM: Artificial Sequence
<220> FEATURE:
<223> OTHER INFORMATION: synthetic

<400> SEQUENCE: 128
tcttctgatc gccttgctag a					21

<210> SEQ ID NO 129
<211> LENGTH: 21
<212> TYPE: DNA
<213> ORGANISM: Artificial Sequence
<220> FEATURE:
<223> OTHER INFORMATION: synthetic

<400> SEQUENCE: 129
accggatcaa agaccgtaaa g					21

<210> SEQ ID NO 130
<211> LENGTH: 24
<212> TYPE: DNA

```
<213> ORGANISM: Elaeis guineensis

<400> SEQUENCE: 130
aaattcttac ttctgagcat actt                                          24

<210> SEQ ID NO 131
<211> LENGTH: 24
<212> TYPE: DNA
<213> ORGANISM: Elaeis guineensis

<400> SEQUENCE: 131
cgaggtggtg tcaatggata gaat                                          24

<210> SEQ ID NO 132
<211> LENGTH: 24
<212> TYPE: DNA
<213> ORGANISM: Elaeis guineensis

<400> SEQUENCE: 132
ctctttgtta tacaatcacg gtgt                                          24

<210> SEQ ID NO 133
<211> LENGTH: 24
<212> TYPE: DNA
<213> ORGANISM: Elaeis guineensis

<400> SEQUENCE: 133
caaggcgatc agaagattat cgaa                                          24

<210> SEQ ID NO 134
<211> LENGTH: 24
<212> TYPE: DNA
<213> ORGANISM: Elaeis guineensis

<400> SEQUENCE: 134
gtgccatatg tcatagtcaa ctgt                                          24

<210> SEQ ID NO 135
<211> LENGTH: 24
<212> TYPE: DNA
<213> ORGANISM: Elaeis guineensis

<400> SEQUENCE: 135
aatctgatat tggcatccac atga                                          24

<210> SEQ ID NO 136
<211> LENGTH: 24
<212> TYPE: DNA
<213> ORGANISM: Elaeis guineensis

<400> SEQUENCE: 136
cctgactttc ggttggctgt ctct                                          24

<210> SEQ ID NO 137
<211> LENGTH: 24
<212> TYPE: DNA
<213> ORGANISM: Elaeis guineensis

<400> SEQUENCE: 137
aatcctactt gtttctctga cctt                                          24

<210> SEQ ID NO 138
<211> LENGTH: 24
```

```
<212> TYPE: DNA
<213> ORGANISM: Elaeis guineensis

<400> SEQUENCE: 138
ctctagcaag gcgatcagaa gatt                                          24

<210> SEQ ID NO 139
<211> LENGTH: 24
<212> TYPE: DNA
<213> ORGANISM: Elaeis guineensis

<400> SEQUENCE: 139
aaatggcata ctctggcaat tcga                                          24

<210> SEQ ID NO 140
<211> LENGTH: 24
<212> TYPE: DNA
<213> ORGANISM: Elaeis guineensis

<400> SEQUENCE: 140
tctatctcat ccctctcaac caat                                          24

<210> SEQ ID NO 141
<211> LENGTH: 24
<212> TYPE: DNA
<213> ORGANISM: Elaeis guineensis

<400> SEQUENCE: 141
gtagcccatg tctttgtttt ccct                                          24

<210> SEQ ID NO 142
<211> LENGTH: 24
<212> TYPE: DNA
<213> ORGANISM: Elaeis guineensis

<400> SEQUENCE: 142
tgtggatggc taacgatatg gact                                          24

<210> SEQ ID NO 143
<211> LENGTH: 24
<212> TYPE: DNA
<213> ORGANISM: Elaeis guineensis

<400> SEQUENCE: 143
actagcacca tgtgtcgtta tggg                                          24

<210> SEQ ID NO 144
<211> LENGTH: 24
<212> TYPE: DNA
<213> ORGANISM: Elaeis guineensis

<400> SEQUENCE: 144
ttcagtcaga gacttcaggc caat                                          24

<210> SEQ ID NO 145
<211> LENGTH: 24
<212> TYPE: DNA
<213> ORGANISM: Elaeis guineensis

<400> SEQUENCE: 145
aggctctcac agaaaatgaa tttg                                          24

<210> SEQ ID NO 146
```

```
<211> LENGTH: 24
<212> TYPE: DNA
<213> ORGANISM: Elaeis guineensis

<400> SEQUENCE: 146
ttatacagct aaattctcag tcct                                              24

<210> SEQ ID NO 147
<211> LENGTH: 24
<212> TYPE: DNA
<213> ORGANISM: Elaeis guineensis

<400> SEQUENCE: 147
tatacagcta aattctcagt cctt                                              24

<210> SEQ ID NO 148
<211> LENGTH: 24
<212> TYPE: DNA
<213> ORGANISM: Elaeis guineensis

<400> SEQUENCE: 148
acagctaaat tctcagtcct tatt                                              24

<210> SEQ ID NO 149
<211> LENGTH: 24
<212> TYPE: DNA
<213> ORGANISM: Elaeis guineensis

<400> SEQUENCE: 149
gctaaattct cagtccttat taat                                              24

<210> SEQ ID NO 150
<211> LENGTH: 24
<212> TYPE: DNA
<213> ORGANISM: Elaeis guineensis

<400> SEQUENCE: 150
cattctaaac tgaggaaaac ttat                                              24

<210> SEQ ID NO 151
<211> LENGTH: 24
<212> TYPE: DNA
<213> ORGANISM: Elaeis guineensis

<400> SEQUENCE: 151
aggttcagaa gaaattgatc gggt                                              24

<210> SEQ ID NO 152
<211> LENGTH: 24
<212> TYPE: DNA
<213> ORGANISM: Elaeis guineensis

<400> SEQUENCE: 152
attgatcggg tagaaaggta aact                                              24

<210> SEQ ID NO 153
<211> LENGTH: 24
<212> TYPE: DNA
<213> ORGANISM: Elaeis guineensis

<400> SEQUENCE: 153
tgcagtgctt acagggatcc cact                                              24
```

```
<210> SEQ ID NO 154
<211> LENGTH: 24
<212> TYPE: DNA
<213> ORGANISM: Elaeis guineensis

<400> SEQUENCE: 154
acgaggagta taactaaggg cact                                              24

<210> SEQ ID NO 155
<211> LENGTH: 24
<212> TYPE: DNA
<213> ORGANISM: Elaeis guineensis

<400> SEQUENCE: 155
aagggcactc tagaatatgt tggt                                              24

<210> SEQ ID NO 156
<211> LENGTH: 24
<212> TYPE: DNA
<213> ORGANISM: Elaeis guineensis

<400> SEQUENCE: 156
aagggcactt tagaatatgt tggt                                              24

<210> SEQ ID NO 157
<211> LENGTH: 24
<212> TYPE: DNA
<213> ORGANISM: Elaeis guineensis

<400> SEQUENCE: 157
tggtttacag cacacatgaa atat                                              24

<210> SEQ ID NO 158
<211> LENGTH: 24
<212> TYPE: DNA
<213> ORGANISM: Elaeis guineensis

<400> SEQUENCE: 158
ggcatgaagg atctactatt ttct                                              24

<210> SEQ ID NO 159
<211> LENGTH: 24
<212> TYPE: DNA
<213> ORGANISM: Elaeis guineensis

<400> SEQUENCE: 159
ggcatgaagg atctactatt ttct                                              24

<210> SEQ ID NO 160
<211> LENGTH: 24
<212> TYPE: DNA
<213> ORGANISM: Elaeis guineensis

<400> SEQUENCE: 160
acttttatgc atgcttaaca ccct                                              24

<210> SEQ ID NO 161
<211> LENGTH: 24
<212> TYPE: DNA
<213> ORGANISM: Elaeis guineensis

<400> SEQUENCE: 161
atgcatgctt aacaccctat ggga                                              24
```